United States Patent
Sakamoto et al.

(10) Patent No.: US 10,173,992 B2
(45) Date of Patent: *Jan. 8, 2019

(54) POLYMERIZABLE COMPOUND, POLYMERIZABLE COMPOSITION, POLYMER, OPTICALLY ANISOTROPIC BODY, AND METHOD FOR PRODUCING POLYMERIZABLE COMPOUND

(71) Applicant: ZEON CORPORATION, Tokyo (JP)

(72) Inventors: Kei Sakamoto, Tokyo (JP); Satoshi Kiriki, Tokyo (JP); Kumi Okuyama, Tokyo (JP); Kanako Taira, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 130 days.

This patent is subject to a terminal disclaimer.

(21) Appl. No.: 15/179,145

(22) Filed: Jun. 10, 2016

(65) Prior Publication Data
US 2016/0280672 A1    Sep. 29, 2016

Related U.S. Application Data

(62) Division of application No. 14/413,787, filed as application No. PCT/JP2013/065040 on May 30, 2013, now Pat. No. 9,586,917.

(30) Foreign Application Priority Data

Jul. 9, 2012  (JP) ................................. 2012-153914
Oct. 19, 2012 (JP) ................................. 2012-232316
(Continued)

(51) Int. Cl.
*C07C 251/86* (2006.01)
*G02F 1/137* (2006.01)
(Continued)

(52) U.S. Cl.
CPC .......... *C07D 277/82* (2013.01); *C07C 69/753* (2013.01); *C07D 277/84* (2013.01);
(Continued)

(58) Field of Classification Search
None
See application file for complete search history.

(56) References Cited

U.S. PATENT DOCUMENTS

| | | | |
|---|---|---|---|
| 4,476,137 A | 10/1984 | Haviv et al. | |
| 5,567,349 A | 10/1996 | Kelly et al. | |
| 5,863,457 A | 1/1999 | Hasebe et al. | |
| 6,139,771 A | 10/2000 | Walba et al. | |
| 6,203,724 B1 | 3/2001 | Reiffenrath et al. | |
| 2002/0159005 A1 | 10/2002 | Arakawa et al. | |
| 2003/0102458 A1 | 6/2003 | Nishikawa et al. | |
| 2007/0176145 A1 | 8/2007 | Nishikawa et al. | |
| 2007/0298191 A1 | 12/2007 | Yamahara et al. | |
| 2009/0072194 A1 | 3/2009 | Yamahara et al. | |
| 2009/0189120 A1 | 7/2009 | Takeuchi | |
| 2010/0201920 A1 | 8/2010 | Adlem et al. | |
| 2010/0258764 A1 | 10/2010 | Sakamoto et al. | |
| 2010/0301271 A1 | 12/2010 | Adlem et al. | |
| 2015/0277007 A1 | 10/2015 | Matsuyama et al. | |
| 2016/0108315 A1 | 4/2016 | Matsuyama et al. | |
| 2016/0257659 A1 | 9/2016 | Sakamoto et al. | |

FOREIGN PATENT DOCUMENTS

| | | |
|---|---|---|
| EP | 2 910 986 A1 | 8/2015 |
| JP | 07-294735 A | 11/1995 |

(Continued)

OTHER PUBLICATIONS

Jul. 25, 2016 Office Action Issued in U.S. Appl. No. 14/413,787.
(Continued)

*Primary Examiner* — Richard A Huhn
(74) *Attorney, Agent, or Firm* — Oliff PLC

(57) ABSTRACT

A polymerizable compound has a practical low melting point, excellent solubility in a general-purpose solvent, and can produce an optical film at low cost, exhibits low reflected luminance, and achieves uniform conversion of polarized light over a wide wavelength band, an optically anisotropic article. A carbonyl compound is useful as a raw material for producing the polymerizable compound. (In the formula (I), $Y^1$ to $Y^8$ represent —C(=O)—O—, $G^1$ and $G^2$ represent a $C_{1-20}$ divalent linear aliphatic group, $Z^1$ and $Z^2$ represent a $C_{2-10}$ alkenyl group that is unsubstituted, or substituted with a halogen atom, $A^x$ represents a $C_{2-30}$ organic group with at least one aromatic ring, $A^y$ represents a hydrogen atom or $C_{1-20}$ alkyl group, $A^1$ represents a trivalent aromatic group, $A^2$ and $A^3$ represent a $C_{3-30}$ divalent alicyclic hydrocarbon group, $A^4$ and $A^5$ represent a $C_{6-30}$ divalent aromatic group or the like, and $Q^1$ represents a hydrogen atom.)

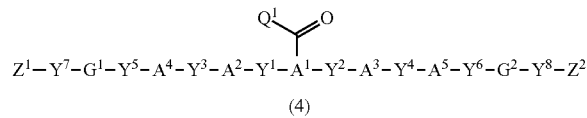

(4)

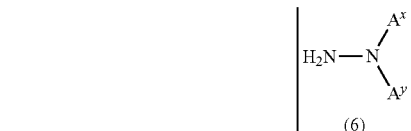

(6)

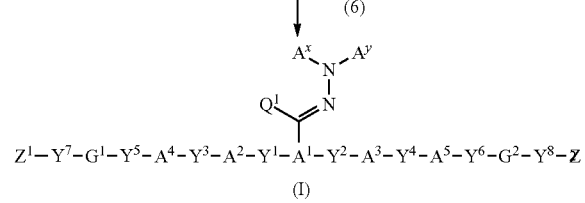

(I)

7 Claims, No Drawings

| (30) | Foreign Application Priority Data | | (56) | References Cited | |
|---|---|---|---|---|---|
| Mar. 26, 2013 | (JP) ................................ | 2013-064874 | | FOREIGN PATENT DOCUMENTS | |
| Mar. 29, 2013 | (JP) ................................ | 2013-075379 | | | |

FOREIGN PATENT DOCUMENTS

| JP | 2000-284126 A | 10/2000 |
|---|---|---|
| JP | 2001-004837 A | 1/2001 |
| JP | 2001-234154 A | 8/2001 |
| JP | 2002-267838 A | 9/2002 |
| JP | 2003-160540 A | 6/2003 |
| JP | 2005-208414 A | 8/2005 |
| JP | 2005-208415 A | 8/2005 |
| JP | 2005-208416 A | 8/2005 |
| JP | 2005-289980 A | 10/2005 |
| JP | 2006-330710 A | 12/2006 |
| JP | 2008-291218 A | 12/2008 |
| JP | 2009-179563 A | 8/2009 |
| JP | 2010-001284 A | 1/2010 |
| JP | 2010-031223 A | 2/2010 |
| JP | 2010-070505 A | 4/2010 |
| JP | 2010-537954 A | 12/2010 |
| JP | 2010-537955 A | 12/2010 |
| JP | 2011-006360 A | 1/2011 |
| JP | 2011-006361 A | 1/2011 |
| JP | 2011-042606 A | 3/2011 |
| WO | 00/026705 A1 | 5/2000 |
| WO | 2006/052001 A1 | 5/2006 |
| WO | 2012/141245 A1 | 10/2012 |
| WO | 2012/147904 A1 | 11/2012 |
| WO | 2012/176679 A1 | 12/2012 |
| WO | 2014/132978 A1 | 9/2014 |
| WO | 2015064698 A1 | 5/2015 |
| WO | 2015141784 A1 | 9/2015 |
| WO | 2016056542 A1 | 4/2016 |
| WO | 2016088749 A1 | 6/2016 |

(51) Int. Cl.

| C07D 277/82 | (2006.01) |
|---|---|
| C07D 417/12 | (2006.01) |
| C07D 277/84 | (2006.01) |
| C07D 513/04 | (2006.01) |
| C08F 20/36 | (2006.01) |
| C07C 69/753 | (2006.01) |
| C08F 22/24 | (2006.01) |
| C09K 19/04 | (2006.01) |
| C08F 28/06 | (2006.01) |
| C08F 22/10 | (2006.01) |
| C08F 22/14 | (2006.01) |
| C08F 22/20 | (2006.01) |
| C08F 20/68 | (2006.01) |
| C08F 22/26 | (2006.01) |
| C08F 22/22 | (2006.01) |
| C08F 26/06 | (2006.01) |
| G02B 5/30 | (2006.01) |

(52) U.S. Cl.
CPC ......... *C07D 417/12* (2013.01); *C07D 513/04* (2013.01); *C08F 20/36* (2013.01); *C08F 22/24* (2013.01); *C09K 19/0403* (2013.01); *C07C 251/86* (2013.01); *C07C 2601/14* (2017.05); *C08F 20/68* (2013.01); *C08F 22/105* (2013.01); *C08F 22/14* (2013.01); *C08F 22/20* (2013.01); *C08F 22/22* (2013.01); *C08F 22/26* (2013.01); *C08F 26/06* (2013.01); *C08F 28/06* (2013.01); *C08F 2500/26* (2013.01); *C09K 2019/0414* (2013.01); *C09K 2019/0481* (2013.01); *G02B 5/30* (2013.01); *G02F 1/137* (2013.01); *G02F 2202/022* (2013.01); *G02F 2202/40* (2013.01)

OTHER PUBLICATIONS

Sep. 1, 2016 Office Action Issued in U.S. Appl. No. 14/413,787.
Jul. 16, 2013 Search Report issued in International Application No. PCT/JP2013/065040.
Jul. 16, 2013 Written Opinion issued in International Application No. PCT/2013/065040.
Nov. 5, 2015 Supplementary Search Report issued in European Patent Application No. 13 81 6607.
Nov. 9, 2016 Office Action issued in European Application No. 13 816 607.9.

ns. The disclosures of
POLYMERIZABLE COMPOUND, POLYMERIZABLE COMPOSITION, POLYMER, OPTICALLY ANISOTROPIC BODY, AND METHOD FOR PRODUCING POLYMERIZABLE COMPOUND This is a Division of U.S. application Ser. No. 14/413,787 filed Jan. 9, 2015, which in turn is a National Stage Application of PCT/JP2013/065040 filed May 30, 2013, which claims the benefit of Japanese Application No. 2013-075379 (filed Mar. 29, 2013), Japanese Application No. 2013-064874 (filed Mar. 26, 2013), Japanese Application No. 2012-232316 (filed Oct. 19, 2012), and Japanese Application No. 2012-153914 (filed Jul. 9, 2012). The disclosures of the prior applications are hereby incorporated by reference herein in their entireties.

TECHNICAL FIELD

The invention relates to a polymerizable compound, a polymerizable composition, and a polymer that may produce an optical film that achieves uniform conversion of polarized light over a wide wavelength band, an optically anisotropic article, a carbonyl compound that is useful as a raw material for producing the polymerizable compound, a method for producing the polymerizable compound using the carbonyl compound, and a method for using the carbonyl compound as a raw material for producing the polymerizable compound.

A flat panel display (FPD) that utilizes an optical film (e.g., polarizer and retardation film) can achieve high-resolution display, and has been widely used as a display device (e.g., TV) that exhibits excellent performance.

Examples of the retardation film include a quarter-wave plate that converts linearly polarized light into circularly polarized light, a half-wave plate that converts the plane of vibration of linearly polarized light by 90°, and the like. These retardation films can achieve accurate conversion of specific monochromatic light so that ¼λ or ½λ retardation occurs.

However, known retardation films have a problem in that polarized light that passes through is converted into colored polarized light. Specifically, since a material that forms the retardation film has wavelength dispersion with respect to retardation, and a polarization state distribution corresponding to each wavelength occurs with respect to white light that includes different light beams in the visible region, it is impossible to achieve accurate ¼λ or ½λ retardation over the entire wavelength band.

In order to solve the above problem, various wideband retardation films that can achieve uniform retardation with respect to light over a wide wavelength band (i.e., retardation films having reverse wavelength dispersion) have been studied (see Patent Documents 1 to 6, for example).

It has been desired to reduce the thickness of the flat panel display as much as possible along with an improvement in performance and widespread use of mobile information terminals (e.g., mobile personal computer and mobile phone). Therefore, a reduction in thickness of the retardation film has also been desired.

It has been considered that it is most effective to produce a retardation film by applying a polymerizable composition that includes a low-molecular-weight polymerizable compound to a film substrate in order to reduce the thickness of the retardation film. Various low-molecular-weight polymerizable compounds having excellent wavelength dispersion, and various polymerizable compositions using such polymerizable compounds have been developed (see Patent Documents 7 to 24, for example).

However, the low-molecular-weight polymerizable compounds or the polymerizable compositions disclosed in Patent Documents 7 to 24 have a number of problems in that it may be difficult to apply the low-molecular-weight polymerizable compound or the polymerizable composition to a film due to a high melting point that is not suitable for an industrial process, or the temperature range in which liquid crystallinity is obtained may be very narrow, or solubility in a solvent generally used for an industrial process may be low, or a polymer film obtained by polymerizing the low-molecular-weight polymerizable compound or the polymerizable composition may has insufficient reverse wavelength dispersion. Moreover, since the above low-molecular-weight polymerizable compounds and the like are synthesized by performing a plurality of steps using a synthesis method that utilizes an expensive reagent, the production cost increases.

RELATED-ART DOCUMENT

Patent Document

Patent Document 1: JP-A-10-68816
Patent Document 2: JP-A-10-90521
Patent Document 3: JP-A-11-52131
Patent Document 4: JP-A-2000-284126 (US20020159005A1)
Patent Document 5: JP-A-2001-4837
Patent Document 6: WO2000/026705
Patent Document 7: JP-A-2002-267838
Patent Document 8: JP-A-2003-160540 (US20030102458A1)
Patent Document 9: JP-A-2005-208414
Patent Document 10: JP-A-2005-208415
Patent Document 11: JP-A-2005-208416
Patent Document 12: JP-A-2005-289980 (US20070176145A1)
Patent Document 13: JP-A-2006-330710 (US20090072194A1)
Patent Document 14: JP-A-2009-179563 (US20090189120A1)
Patent Document 15: JP-A-2010-31223
Patent Document 16: JP-A-2011-6360
Patent Document 17: JP-A-2011-6361
Patent Document 18: JP-A-2011-42606
Patent Document 19: JP-T-2010-537954 (US20100201920A1)
Patent Document 20: JP-T-2010-537955 (US20100301271A1)
Patent Document 21: WO2006/052001 (US20070298191A1)
Patent Document 22: U.S. Pat. No. 6,139,771
Patent Document 23: U.S. Pat. No. 6,203,724
Patent Document 24: U.S. Pat. No. 5,567,349

SUMMARY OF THE INVENTION

Technical Problem

The invention was conceived in view of the above situation. An object of the invention is to provide a polymerizable compound, a polymerizable composition, and a polymer that have a practical low melting point, exhibit excellent solubility in a general-purpose solvent, and can produce an optical film that can be produced at low cost, exhibits low reflected luminance, and achieves uniform conversion of polarized light over a wide wavelength band, an optically anisotropic article, a carbonyl compound that is useful as a raw material for producing the polymerizable compound, a method for producing the polymerizable compound using the carbonyl compound, and a method for using the carbonyl compound as a raw material for producing the polymerizable compound.

Solution to Problem

The inventors of the invention conducted extensive studies in order to achieve the above object. As a result, the inventors found that an optical film that achieves uniform conversion of polarized light over a wide wavelength band can be produced at low cost by utilizing an optically anisotropic article that is produced using a polymer obtained by polymerizing a polymerizable compound represented by the following formula (I), or a polymerizable composition that includes the polymerizable compound and an initiator. This finding has led to the completion of the invention.

Several aspects of the invention provide the following polymerizable compound (see (1) to (7)), polymerizable composition (see (8) and (9)), polymer (see (10) and (11)), optically anisotropic article (see (12)), carbonyl compound (see (13) to (16)), method for producing the polymerizable compound (see (17)), and method for using the carbonyl compound as a raw material for producing the polymerizable compound (see (18)).

(1) A polymerizable compound represented by the following formula (I), substituted or unsubstituted alkynyl group having 2 to 20 carbon atoms, a substituted or unsubstituted cycloalkyl group having 3 to 12 carbon atoms, —C(=O)—R$^3$, —SO$_2$—R$^4$, —C(=S)NH—R$^9$, or an organic group having 2 to 30 carbon atoms that includes at least one aromatic ring selected from the group consisting of an aromatic hydrocarbon ring and a heteroaromatic ring, R$^3$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or an aromatic hydrocarbon group having 5 to 12 carbon atoms, R$^4$ is an alkyl group having 1 to 20 carbon atoms, an alkenyl group having 2 to 20 carbon atoms, a phenyl group, or a 4-methylphenyl group, R$^9$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or a substituted or unsubstituted aromatic group having 5 to 20 carbon atoms, provided that the aromatic ring included in A$^x$ and A$^y$ is substituted or unsubstituted, and A$^x$ and A$^y$ are optionally bonded to each other to form a ring, A$^1$ is a substituted or unsubstituted trivalent aromatic group,
A$^2$ and A$^3$ are independently a substituted or unsubstituted divalent alicyclic hydrocarbon group having 3 to 30 carbon atoms,
A$^4$ and A$^5$ are independently a substituted or unsubstituted divalent aromatic group having 6 to 30 carbon atoms, and
Q$^1$ is a hydrogen atom, or a substituted or unsubstituted alkyl group having 1 to 6 carbon atoms.

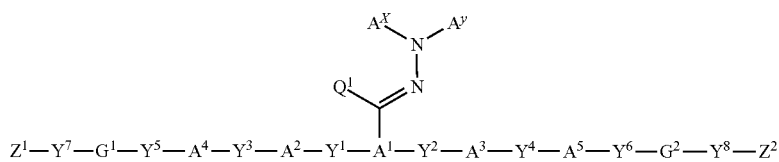

(I)

wherein Y$^1$ to Y$^8$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ is a hydrogen atom or an alkyl group having 1 to 6 carbon atoms, G$^1$ and G$^2$ are independently a substituted or unsubstituted divalent linear aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the linear aliphatic group includes two or more contiguous —O— or —S— is excluded, R$^2$ is a hydrogen atom or an alkyl group having 1 to 6 carbon atoms, Z$^1$ and Z$^2$ are independently an alkenyl group having 2 to 10 carbon atoms that is substituted with a halogen atom, or unsubstituted, A$^x$ is an organic group having 2 to 30 carbon atoms that includes at least one aromatic ring selected from the group consisting of an aromatic hydrocarbon ring and a heteroaromatic ring, A$^y$ is a hydrogen atom, a substituted or unsubstituted alkyl group having 1 to 20 carbon atoms, a substituted or unsubstituted alkenyl group having 2 to 20 carbon atoms, a (2) The polymerizable compound according to (1), wherein the total number of π electrons included in A$^x$ and A$^y$ is 4 to 24.

(3) The polymerizable compound according to (1) or (2), wherein A$^1$ is a substituted or unsubstituted trivalent benzene ring group, or a substituted or unsubstituted trivalent naphthalene ring group.

(4) The polymerizable compound according to any one of (1) to (3), wherein Y$^1$ to Y$^8$ are independently a chemical single bond, —O—, —O—C(=O)—, —C(=O)—O—, or —O—C(=O)—O—.

(5) The polymerizable compound according to any one of (1) to (4), wherein Z$^1$ and Z$^2$ are independently CH$_2$=CH—, CH$_2$=C(CH$_3$)—, or CH$_2$=C(Cl)—.

(6) The polymerizable compound according to any one of (1) to (5), wherein G$^1$ and G$^2$ are independently a substituted or unsubstituted divalent aliphatic group having 1 to 20 carbon atoms that optionally includes —O—, —O—C(=O)—, —C(=O)—O—, or —C(=O)—, provided that a case where the aliphatic group includes two or more contiguous —O— is excluded.

(7) The polymerizable compound according to any one of (1) to (6), wherein G$^1$ and G$^2$ are independently an alkylene group having 1 to 12 carbon atoms.

(8) A polymerizable composition including at least one type of the polymerizable compound according to any one of (1) to (7).

(9) A polymerizable composition including at least one type of the polymerizable compound according to any one of (1) to (7), and an initiator.
(10) A polymer obtained by polymerizing the polymerizable compound according to any one of (1) to (7), or the polymerizable composition according to (8) or (9).
(11) The polymer according to (10), the polymer being a liquid crystalline polymer.
(12) An optically anisotropic article including the polymer according to (11).
(13) A carbonyl compound represented by the following formula (4),

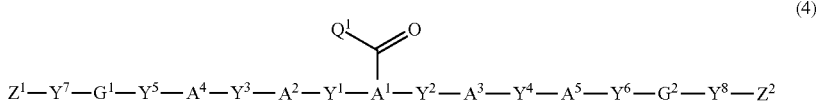

(4)

wherein $Y^1$ to $Y^8$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms,
$G^1$ and $G^2$ are independently a substituted or unsubstituted divalent linear aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more contiguous —O— or —S— is excluded, $R^2$ is a hydrogen atom or an alkyl group having 1 to 6 carbon atoms,
$Z^1$ and $Z^2$ are independently an alkenyl group having 2 to 10 carbon atoms that is unsubstituted, or substituted with a halogen atom,
$A^1$ is a substituted or unsubstituted trivalent aromatic group,
$A^2$ and $A^3$ are independently a substituted or unsubstituted divalent alicyclic hydrocarbon group having 3 to 30 carbon atoms,
$A^4$ and $A^5$ are independently a substituted or unsubstituted divalent aromatic group having 6 to 30 carbon atoms, and
$Q^1$ is a hydrogen atom, or a substituted or unsubstituted alkyl group having 1 to 6 carbon atoms.
(14) The carbonyl compound according to (13), wherein $A^1$ is a substituted or unsubstituted trivalent benzene ring group, or a substituted or unsubstituted trivalent naphthalene ring group.
(15) The carbonyl compound according to (13) or (14), wherein $A^2$ and $A^3$ are independently a substituted or unsubstituted divalent cyclohexyl group.
(16) The carbonyl compound according to any one of (13) to (15), wherein $Z^1$ and $Z^2$ are independently CH$_2$=CH—, CH$_2$=C(CH$_3$)—, or CH$_2$=C(Cl)—.

(17) A method for producing a polymerizable compound represented by the following formula (I), the method including reacting the carbonyl compound according to any one of (13) to (16) with a hydrazine compound represented by the following formula,

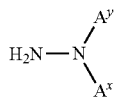

wherein $A^x$ is an organic group having 2 to 30 carbon atoms that includes at least one aromatic ring selected from the group consisting of an aromatic hydrocarbon ring and a heteroaromatic ring,
$A^y$ is a hydrogen atom, a substituted or unsubstituted alkyl group having 1 to 20 carbon atoms, a substituted or unsubstituted alkenyl group having 2 to 20 carbon atoms, a substituted or unsubstituted alkynyl group having 1 to 20 carbon atoms, a substituted or unsubstituted cycloalkyl group having 3 to 12 carbon atoms, —C(=O)—R$^3$, —SO$_2$—R$^4$, —C(=S)NH—R$^9$, or an organic group having 2 to 30 carbon atoms that includes at least one aromatic ring selected from the group consisting of an aromatic hydrocarbon ring and a heteroaromatic ring, $R^3$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or an aromatic hydrocarbon group having 5 to 12 carbon atoms, $R^4$ is an alkyl group having 1 to 20 carbon atoms, an alkenyl group having 2 to 20 carbon atoms, a phenyl group, or a 4-methylphenyl group, $R^9$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or a substituted or unsubstituted aromatic group having 5 to 20 carbon atoms, provided that the aromatic ring included in $A^x$ and $A^y$ is substituted or unsubstituted, and $A^x$ and $A^y$ are optionally bonded to each other to form a ring,

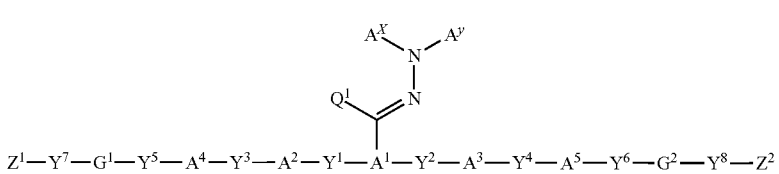

(I)

wherein $A^x$, $A^y$, $Y^1$ to $Y^8$, $Z^1$, $Z^2$, $G^1$, $G^2$, $A^1$ to $A^5$, and $Q^1$ are the same as defined above.
(18) A method for using the carbonyl compound according to any one of (13) to (16) as a raw material for producing a polymerizable compound represented by the following formula (I),

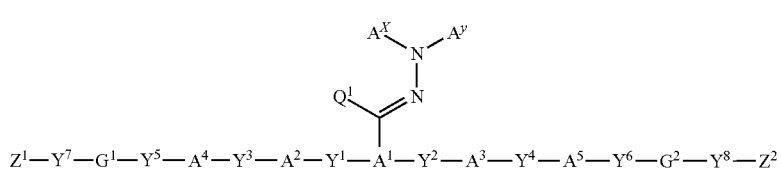

(I)

wherein $A^x$, $A^y$, $Y^1$ to $Y^8$, $Z^1$, $Z^2$, $G^1$, $G^2$, $A^1$ to $A^5$, and $Q^1$ are the same as defined above.

Advantageous Effects of the Invention

The polymerizable compound, the polymerizable composition, and the polymer according to the aspects of the invention have a practical low melting point, exhibit excellent solubility in a general-purpose solvent, and can produce an optical film that can be produced at low cost, exhibits low reflected luminance, and achieves uniform conversion of polarized light over a wide wavelength band.

Since the optically anisotropic article according to the aspect of the invention is produced using the polymer according to the aspect of the invention, the optically anisotropic article can be produced at low cost, exhibits low reflected luminance, and achieves uniform conversion of polarized light over a wide wavelength band.

An antireflective film may be produced by combining the film-like optically anisotropic article according to the aspect of the invention with a polarizer. The antireflective film may suitably be used to prevent reflection from a touch panel, an organic electroluminescence device, and the like.

The carbonyl compound according to the aspect of the invention is useful as an intermediate for producing the polymerizable compound according to the aspect of the invention.

The method for producing a polymerizable compound according to the aspect of the invention can efficiently produce the polymerizable compound according to the aspect of the invention.

It is possible to easily produce the polymerizable compound according to the aspect of the invention in high yield by utilizing the carbonyl compound according to the aspect of the invention as a raw material.

DESCRIPTION OF EMBODIMENTS

A polymerizable compound, a polymerizable composition, a polymer, an optically anisotropic article, a carbonyl compound, a method for producing a polymerizable compound, and a method for using a carbonyl compound as a raw material for producing a polymerizable compound according to exemplary embodiments of the invention are described in detail below. Note that the expression "substituted or unsubstituted" used herein in connection with a group or the like means that the group or the like is unsubstituted, or substituted with a substituent.

1) Polymerizable Compound

A polymerizable compound according to one embodiment of the invention is a compound represented by the formula (I).

$Y^1$ to $Y^8$ in the formula (1) are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—.

$R^1$ is a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that $Y^1$ to $Y^6$ included in the polymerizable compound according to one embodiment of the invention be independently a chemical single bond, —O—, —O—C(=O)—, —C(=O)—O—, or —O—C(=O)—O—.

$G^1$ and $G^2$ are independently a substituted or unsubstituted divalent aliphatic group having 1 to 20 carbon atoms.

Examples of the divalent aliphatic group having 1 to 20 carbon atoms include divalent aliphatic groups having a linear structure, such as an alkylene group having 1 to 20 carbon atoms and an alkenylene group having 2 to 20 carbon atoms; divalent aliphatic groups such as a cycloalkanediyl group having 3 to 20 carbon atoms, a cycloalkenediyl group having 4 to 20 carbon atoms, and a divalent fused alicyclic group having 10 to 30 carbon atoms; and the like.

Examples of a substituent that may substitute the divalent aliphatic group represented by $G^1$ and $G^2$ include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The aliphatic group optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more contiguous —O— or —S— is excluded. $R^2$ is a hydrogen atom or an alkyl group having 1 to 6 carbon atoms similar to that represented by $R^1$, and is preferably a hydrogen atom or a methyl group.

—O—, —O—C(=O)—, —C(=O)—O—, and —C(=O)— are preferable as the group that is optionally included in the aliphatic group.

Specific examples of the aliphatic group that includes the above group include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—CH$_2$—O—C(=O)—O—CH$_2$—CH$_2$—, —CH$_2$—CH$_2$—NR$^2$—C(=O)—CH$_2$—CH$_2$—, —CH$_2$—CH$_2$—C(=O)—NR$^2$—CH$_2$—, —CH$_2$—NR$^2$—CH$_2$—CH$_2$—, —CH$_2$—C(=O)—CH$_2$—, and the like.

It is preferable that $G^1$ and $G^2$ be independently a divalent aliphatic group having a linear structure (e.g., an alkylene group having 1 to 20 carbon atoms or an alkenylene group having 2 to 20 carbon atoms), more preferably an alkylene group having 1 to 12 carbon atoms (e.g., methylene group, ethylene group, trimethylene group, propylene group, tetramethylene group, pentamethylene group, hexamethylene group, octamethylene group, or decamethylene group (—$(CH_2)_{10}$—)), and particularly preferably a tetramethylene group (—$(CH_2)_4$—), a hexamethylene group (—$(CH_2)_6$—), an octamethylene group (—$(CH_2)_8$—), or a decamethylene group (—$(CH_2)_{10}$—), in order to more advantageously achieve the intended effects of the invention.

$Z^1$ and $Z^2$ are independently an alkenyl group having 2 to 10 carbon atoms that is unsubstituted, or substituted with a halogen atom.

The number of carbon atoms of the alkenyl group is preferably 2 to 6. Examples of the halogen atom that may substitute the alkenyl group represented by $Z^1$ and $Z^2$ include a fluorine atom, a chlorine atom, a bromine atom, and the like. Among these, a chlorine atom is preferable, Specific examples of the alkenyl group having 2 to 10 carbon atoms represented by $Z^1$ and $Z^2$ include $CH_2$=CH—, $CH_2$=$C(CH_3)$—, $CH_2$=CH—$CH_2$—, $CH_3$—CH=CH—, $CH_2$=CH—$CH_2$—$CH_2$—, $CH_2$=C($CH_3$)—$CH_2$—$CH_2$—, $(CH_3)_2$C=CH—$CH_2$—, $(CH_3)_2$C=CH—$CH_2$—$CH_2$—, $CH_2$=C(Cl)—, $CH_2$=C($CH_3$)—$CH_2$—, $CH_3$—CH=CH—$CH_2$—, and the like.

It is preferable that $Z^1$ and $Z^2$ be independently $CH_2$=CH—, $CH_2$=C($CH_3$)—, $CH_2$=C(Cl)—, $CH_2$=CH—$CH_2$—, $CH_2$=C($CH_3$)—$CH_2$—, or $CH_2$=C($CH_3$)—$CH_2$—$CH_2$—, more preferably $CH_2$=CH—, $CH_2$=C($CH_3$)—, or $CH_2$=C(Cl)—, and still more preferably $CH_2$=CH—, in order to more advantageously achieve the intended effects of the invention.

$A^x$ is an organic group having 2 to 30 carbon atoms that includes at least one aromatic ring selected from the group consisting of an aromatic hydrocarbon ring and a heteroaromatic ring.

The term "aromatic ring" used herein refers to a cyclic structure that exhibits aromaticity in a broad sense according to Huckel's rule (i.e., a cyclic conjugated structure that includes (4n+2) π electrons, and a structure that exhibits aromaticity in which lone pairs of heteroatoms (e.g., sulfur, oxygen, or nitrogen) are involved in the n electron system (e.g., thiophene, furan, and benzothiazole).

The organic group having 2 to 30 carbon atoms represented by $A^x$ that includes at least one aromatic ring selected from the group consisting of an aromatic hydrocarbon ring and a heteroaromatic ring, may include a plurality of aromatic rings, and may include an aromatic hydrocarbon ring and a heteroaromatic ring.

Examples of the aromatic hydrocarbon ring include a benzene ring, a naphthalene ring, an anthracene ring, and the like. Examples of the heteroaromatic ring include monocyclic heteroaromatic rings such as a pyrrole ring, a furan ring, a thiophene ring, a pyridine ring, a pyridazine ring, a pyrimidine ring, a pyrazine ring, a pyrazole ring, an imidazole ring, an oxazole ring, and a thiazole ring; fused heteroaromatic rings such as a benzothiazole ring, a benzoxazole ring, a quinoline ring, a phthalazine ring, a benzimidazole ring, a benzopyrazole ring, a benzofuran ring, a benzothiophene ring, a thiazolopyridine ring, an oxazolopyridine ring, a thiazolopyrazine ring, an oxazolopyrazine ring, a thiazolopyridazine ring, an oxazolopyridazine ring, a thiazolopyrimidine ring, and an oxazolopyrimidine ring; and the like.

The aromatic ring included in $A^x$ may be substituted with a substituent. Examples of the substituent include halogen atoms such as a fluorine atom and a chlorine atom; a cyano group; alkyl groups having 1 to 6 carbon atoms such as a methyl group, an ethyl group, and a propyl group; alkenyl groups having 2 to 6 carbon atoms such as a vinyl group and an allyl group; alkyl halide groups having 1 to 6 carbon atoms such as a trifluoromethyl group; substituted amino groups such as a dimethylamino group; alkoxy groups having 1 to 6 carbon atoms such as a methoxy group, an ethoxy group, and an isopropoxy group; a nitro group; aryl groups such as a phenyl group and a naphthyl group; —C(=O)—$R^5$; —C(=O)—$OR^5$; —$SO_2R^6$; and the like. $R^5$ is an alkyl group having 1 to 20 carbon atoms, an alkenyl group having 2 to 20 carbon atoms, or a cycloalkyl group having 3 to 12 carbon atoms, and $R^6$ is an alkyl group having 1 to 20 carbon atoms, an alkenyl group having 2 to 20 carbon atoms, a phenyl group, or a 4-methylphenyl group similar to that represented by $R^4$.

The aromatic ring included in $A^x$ may be substituted with a plurality of identical or different substituents, and two adjacent substituents may be bonded to each other to form a ring. A ring formed by two adjacent substituents may be either a monocyclic ring or a fused polycyclic ring, and may be either an unsaturated ring or a saturated ring.

Note that the number of carbon atoms (i.e., 2 to 30) of the organic group represented by $A^x$ refers to the total number of carbon atoms of the organic group excluding the number of carbon atoms of a substituent. This also applies to the number of carbon atoms of the organic group represented by $A^y$.

Examples of the organic group having 2 to 30 carbon atoms represented by $A^x$ that includes at least one aromatic ring selected from the group consisting of an aromatic hydrocarbon ring and a heteroaromatic ring, include aromatic cyclic hydrocarbon groups; heteroaromatic ring groups; alkyl groups having 3 to 30 carbon atoms that include at least one aromatic ring selected from the group consisting of an aromatic hydrocarbon ring and a heteroaromatic ring; alkenyl groups having 4 to 30 carbon atoms that include at least one aromatic ring selected from the group consisting of an aromatic hydrocarbon ring and a heteroaromatic ring; alkynyl groups having 4 to 30 carbon atoms that include at least one aromatic ring selected from the group consisting of an aromatic hydrocarbon ring and a heteroaromatic ring; and the like.

Specific examples of the organic group represented by $A^x$ are shown below. Note that the organic group represented by $A^x$ is not limited to the following groups. "-" in the following formulas is a bond that extends from an arbitrary position of the ring (hereinafter the same).

(1) Aromatic hydrocarbon ring group

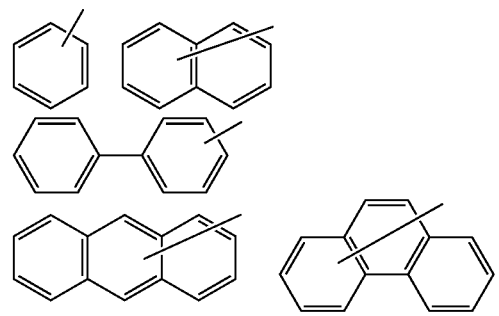

-continued

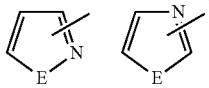

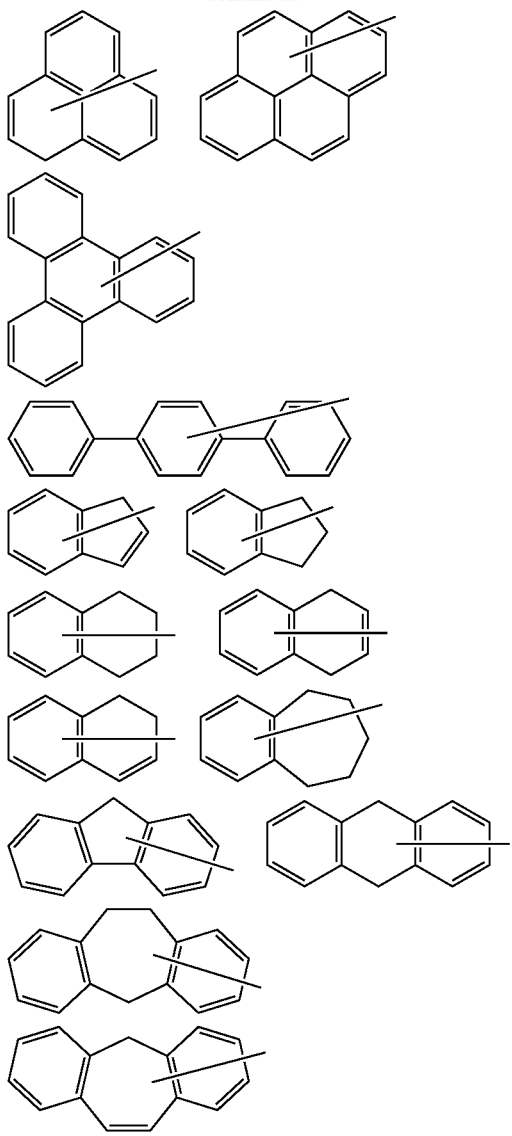

wherein E is NR[6], an oxygen atom, or a sulfur atom, and R[6] is a hydrogen atom, or an alkyl group having 1 to 6 carbon atoms (e.g., methyl group, ethyl group, or propyl group).

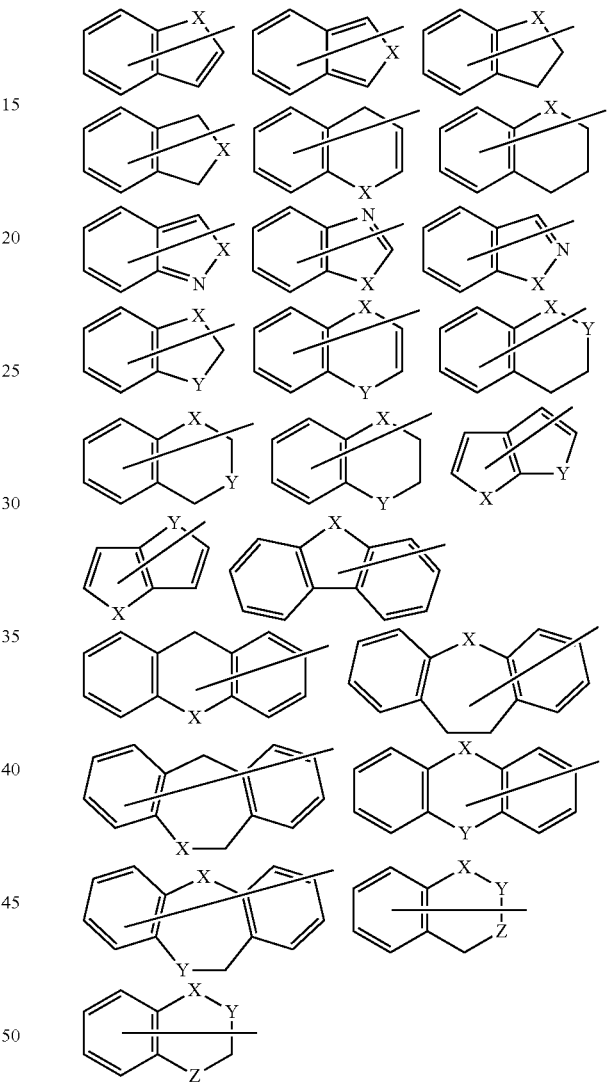

wherein X, Y, and Z are independently NR[7], an oxygen atom, a sulfur atom, —SO—, or —SO$_2$—, provided that a case where two or more oxygen atoms, sulfur atoms, —SO—, or —SO$_2$— are situated at contiguous positions is excluded, and R[7] is a hydrogen atom, or an alkyl group having 1 to 6 carbon atoms (e.g., methyl group, ethyl group, or propyl group) similar to that represented by R[6].

(2) Heteroaromatic ring group

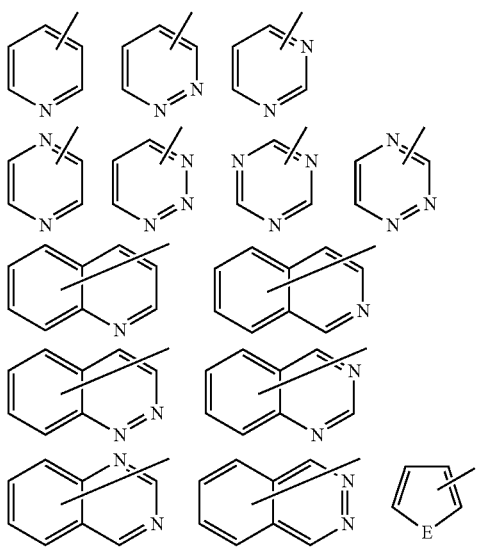

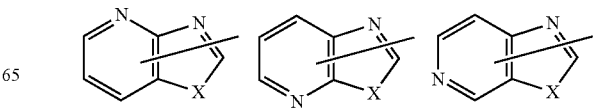

-continued

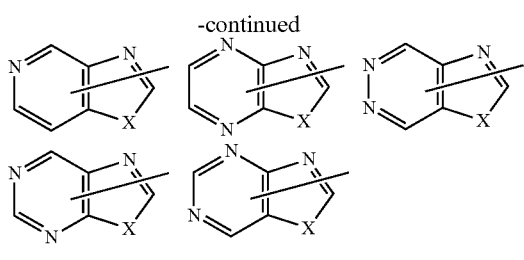

wherein X is the same as defined above.

(3) Alkyl group that includes at least one aromatic ring selected from the group consisting of an aromatic hydrocarbon ring group and a heteroaromatic ring group

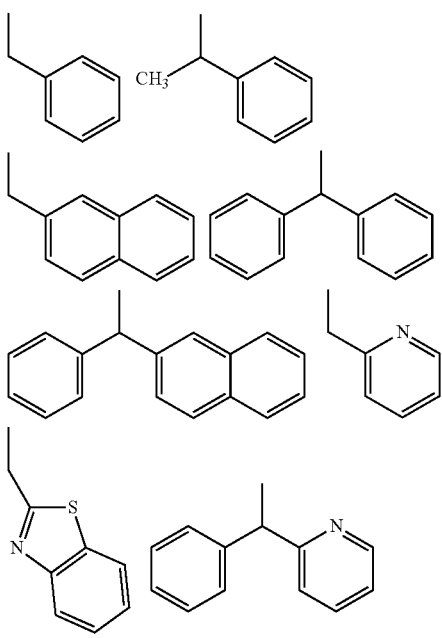

(4) Alkenyl group that includes at least one aromatic ring selected from the group consisting of an aromatic hydrocarbon ring group and a heteroaromatic ring group

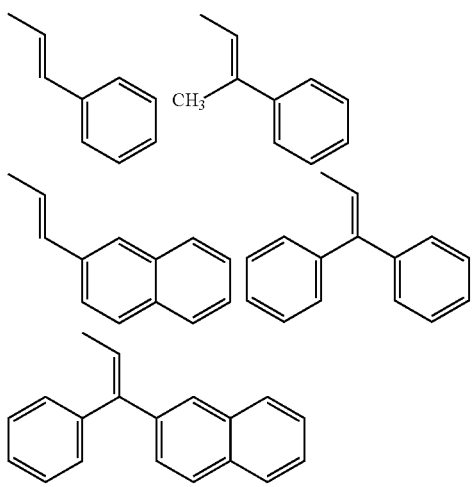

(5) Alkynyl group that includes at least one aromatic ring selected from the group consisting of an aromatic hydrocarbon ring group and a heteroaromatic ring group

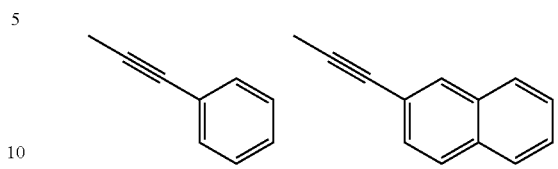

$A^x$ is preferably an aromatic hydrocarbon group having 6 to 30 carbon atoms or a heteroaromatic ring group having 4 to 30 carbon atoms. $A^x$ is more preferably a group among the groups shown below.

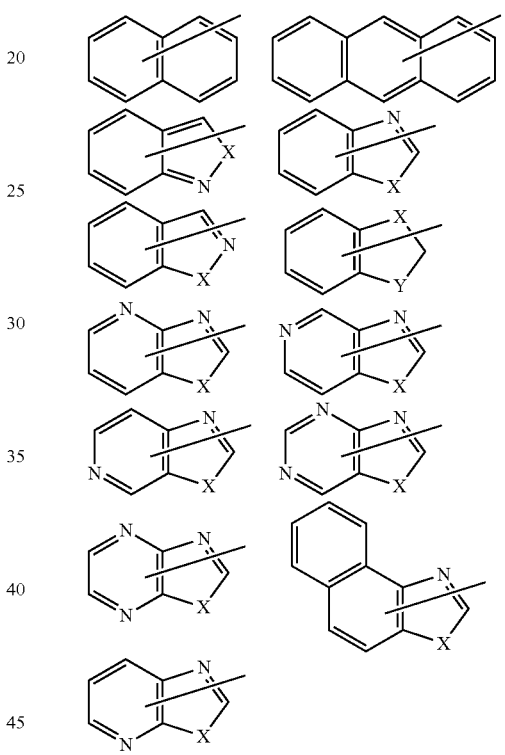

$A^x$ is still more preferably a group among the groups shown below.

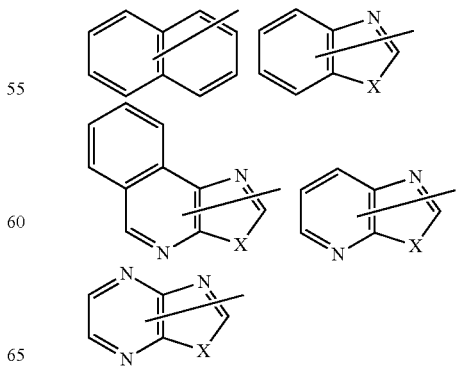

The ring included in $A^x$ may be substituted with a substituent. Examples of the substituent include halogen atoms such as a fluorine atom and a chlorine atom; a cyano group; alkyl groups having 1 to 6 carbon atoms such as a methyl group, an ethyl group, and a propyl group; alkenyl groups having 2 to 6 carbon atoms such as a vinyl group and an allyl group; alkyl halide groups having 1 to 6 carbon atoms such as a trifluoromethyl group; substituted amino groups such as a dimethylamino group; alkoxy groups having 1 to 6 carbon atoms such as a methoxy group, an ethoxy group, and an isopropoxy group; a nitro group; aryl groups such as a phenyl group and a naphthyl group; $—C(=O)—R^8$; $—C(=O)—OR^8$; $—SO_2R^6$; and the like. $R^8$ is an alkyl group having 1 to 6 carbon atoms (e.g., methyl group or ethyl group), or an aryl group having 6 to 14 carbon atoms (e.g., phenyl group). The substituent is preferably a halogen atom, a cyano group, an alkyl group having 1 to 6 carbon atoms, or an alkoxy group having 1 to 6 carbon atoms.

The ring included in $A^x$ may be substituted with a plurality of identical or different substituents, and two adjacent substituents may be bonded to each other to form a ring. A ring formed by two adjacent substituents may be either a monocyclic ring or a fused polycyclic ring.

Note that the number of carbon atoms (i.e., 2 to 30) of the organic group represented by $A^x$ refers to the total number of carbon atoms of the organic group excluding the number of carbon atoms of a substituent. This also applies to the number of carbon atoms of the organic group represented by $A^y$.

$A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, $—C(=O)—R^3$, $—SO_2—R^4$, $—C(=S)NH—R^9$, or an organic group having 2 to 30 carbon atoms that includes at least one aromatic ring selected from the group consisting of aromatic hydrocarbon rings and heteroaromatic rings. $R^3$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or an aromatic hydrocarbon group having 5 to 12 carbon atoms, $R^4$ is an alkyl group having 1 to 20 carbon atoms, an alkenyl group having 2 to 20 carbon atoms, a phenyl group, or a 4-methylphenyl group, and $R^9$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or a substituted or unsubstituted aromatic group having 5 to 20 carbon atoms.

Examples of the (unsubstituted) alkyl group having 1 to 20 carbon atoms represented by $A^y$ include a methyl group, an ethyl group, an n-propyl group, an isopropyl group, an n-butyl group, an isobutyl group, a 1-methylpentyl group, a 1-ethylpentyl group, a sec-butyl group, a t-butyl group, an n-pentyl group, an isopentyl group, a neopentyl group, an n-hexyl group, an isohexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, and the like. The number of carbon atoms of the substituted or unsubstituted alkyl group having 1 to 20 carbon atoms is preferably 1 to 12, and more preferably 4 to 10.

Examples of the (unsubstituted) alkenyl group having 2 to 20 carbon atoms represented by $A^y$ include a vinyl group, a propenyl group, an isopropenyl group, a butenyl group, an isobutenyl group, a pentenyl group, a hexenyl group, a heptenyl group, an octenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, and the like.

The number of carbon atoms of the substituted or unsubstituted alkenyl group having 2 to 20 carbon atoms is preferably 2 to 12.

Examples of the (unsubstituted) cycloalkyl group having 3 to 12 carbon atoms represented by $A^y$ include a cyclopropyl group, a cyclobutyl group, a cyclopentyl group, a cyclohexyl group, a cyclooctyl group, and the like.

Examples of the (unsubstituted) alkynyl group having 2 to 20 carbon atoms represented by $A^y$ include an ethynyl group, a propynyl group, a 2-propynyl group (propargyl group), a butynyl group, a 2-butynyl group, a 3-butynyl group, a pentynyl group, a 2-pentynyl group, a hexynyl group, a 5-hexynyl group, a heptynyl group, an octynyl group, a 2-octynyl group, a nonanyl group, a decanyl group, a 7-decanyl group, and the like.

Examples of a substituent that may substitute the substituted or unsubstituted alkyl group having 1 to 20 carbon atoms and the substituted or unsubstituted alkenyl group having 2 to 20 carbon atoms represented by $A^y$ include halogen atoms such as a fluorine atom and a chlorine atom; a cyano group; substituted amino groups such as a dimethylamino group; alkoxy groups having 1 to 20 carbon atoms, such as a methoxy group, an ethoxy group, an isopropoxy group, and a butoxy group; alkoxy groups having 1 to 12 carbon atoms that are substituted with an alkoxy group having 1 to 12 carbon atoms, such as a methoxymethoxy group and a methoxyethoxy group; a nitro group; aryl groups such as a phenyl group and a naphthyl group; cycloalkyl groups having 3 to 8 carbon atoms, such as a cyclopropyl group, a cyclopentyl group, and a cyclohexyl group; cycloalkyloxy groups having 3 to 8 carbon atoms, such as a cyclopentyloxy group and a cyclohexyloxy group; cyclic ether groups having 2 to 12 carbon atoms, such as a tetrahydrofuranyl group, a tetrahydropyranyl group, a dioxoranyl group, and a dioxanyl group; aryloxy groups having 6 to 14 carbon atoms, such as a phenoxy group and a naphthoxy group; fluoroalkoxy group having 1 to 12 carbon atoms in which at least one hydrogen atom is substituted with a fluorine atom, such as a trifluoromethyl group, a pentafluoroethyl group, and $—CH_2CF_3$; a benzofuryl group; a benzopyranyl group; a benzodioxolyl group; a benzodioxanyl group; $—C(=O)—R^7$; $—C(=O)—OR^7$; $—SO_2R^8$; $—SR^{10}$; alkoxy groups having 1 to 12 carbon atoms that are substituted with $—SR^{10}$; a hydroxyl group; and the like. $R^7$ and $R^{10}$ are independently an alkyl group having 1 to 20 carbon atoms, an alkenyl group having 2 to 20 carbon atoms, a cycloalkyl group having 3 to 12 carbon atoms, or an aromatic hydrocarbon group having 6 to 20 carbon atoms, and $R^6$ is an alkyl group having 1 to 20 carbon atoms, an alkenyl group having 2 to 20 carbon atoms, a phenyl group, or a 4-methylphenyl group similar to that represented by $R^4$.

Examples of a substituent that may substitute the substituted or unsubstituted cycloalkyl group having 3 to 12 carbon atoms represented by $A^y$ include halogen atoms such as a fluorine atom and a chlorine atom; a cyano group; substituted amino groups such as a dimethylamino group; alkyl groups having 1 to 6 carbon atoms, such as a methyl group, an ethyl group, and a propyl group; alkoxy groups having 1 to 6 carbon atoms, such as a methoxy group, an ethoxy group, and an isopropoxy group; a nitro group; aryl groups such as a phenyl group and a naphthyl group; cycloalkyl groups having 3 to 8 carbon atoms, such as a cyclopropyl group, a cyclopentyl group, and a cyclohexyl group; —C(=O)—$R^7$; —C(=O)—$OR^7$; —$SO_2R^4$; a hydroxyl group; and the like. $R^7$ and $R^8$ are the same as defined above.

Examples of a substituent that may substitute the substituted or unsubstituted alkynyl group having 2 to 20 carbon atoms represented by $A^y$ include those mentioned above in connection with the substituted or unsubstituted alkyl group having 1 to 20 carbon atoms, and the substituted or unsubstituted alkenyl group having 2 to 20 carbon atoms.

$R^3$ included in the group represented by —C(=O)—$R^3$ that may be represented by $A^y$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or an aromatic hydrocarbon group having 5 to 12 carbon atoms. Specific examples of these groups include those mentioned above in connection with the substituted or unsubstituted alkyl group having 1 to 20 carbon atoms, the substituted or unsubstituted alkenyl group having 2 to 20 carbon atoms, and the substituted or unsubstituted cycloalkyl group having 3 to 12 carbon atoms represented by $A^y$.

$R^4$ included in the group represented by —$SO_2$—$R^4$ that may be represented by $A^y$ is an alkyl group having 1 to 20 carbon atoms, an alkenyl group having 2 to 20 carbon atoms, a phenyl group, or a 4-methylphenyl group.

Specific examples of the alkyl group having 1 to 20 carbon atoms and the alkenyl group having 2 to 20 carbon atoms represented by $R^4$ include those mentioned above in connection with the alkyl group having 1 to 20 carbon atoms and the alkenyl group having 2 to 20 carbon atoms represented by $A^y$.

Examples of the organic group having 2 to 30 carbon atoms represented by $A^y$ that includes at least one aromatic ring selected from the group consisting of an aromatic hydrocarbon ring and a heteroaromatic ring, include those mentioned above in connection with $A^x$.

$A^y$ is preferably a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, —C(=O)—$R^3$, —$SO_2$—$R^4$, or an organic group having 2 to 30 carbon atoms that includes at least one aromatic ring selected from the group consisting of an aromatic hydrocarbon ring and a heteroaromatic ring, and more preferably a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, a substituted or unsubstituted aromatic hydrocarbon group having 6 to 12 carbon atoms, a substituted or unsubstituted heteroaromatic ring group having 3 to 9 carbon atoms, —C(=O)—$R^3$, or —$SO_2$—$R^4$. Note that $R^3$ and $R^4$ are the same as defined above.

Examples of a preferable substituent that may substitute the substituted or unsubstituted alkyl group having 1 to 20 carbon atoms, the substituted or unsubstituted alkenyl group having 2 to 20 carbon atoms, or the substituted or unsubstituted alkynyl group having 2 to 20 carbon atoms represented by $A^y$, include halogen atoms, a cyano group, alkoxy groups having 1 to 20 carbon atoms, alkoxy groups having 1 to 12 carbon atoms that are substituted with an alkoxy group having 1 to 12 carbon atoms, a phenyl group, a cyclohexyl group, cyclic ether groups having 2 to 12 carbon atoms, aryloxy groups having 6 to 14 carbon atoms, a hydroxyl group, a benzodioxanyl group, a phenylsulfonyl group, a 4-methylphenylsulfonyl group, a benzoyl group, and —$SR^{10}$. Note that $R^{10}$ is the same as defined above.

Examples of a preferable substituent that may substitute the substituted or unsubstituted cycloalkyl group having 3 to 12 carbon atoms, the substituted or unsubstituted aromatic hydrocarbon group having 6 to 12 carbon atoms, or the substituted or unsubstituted heteroaromatic ring group having 3 to 9 carbon atoms represented by $A^y$, include a fluorine atom, alkyl groups having 1 to 6 carbon atoms, alkoxy groups having 1 to 6 carbon atoms, and a cyano group.

$A^x$ and $A^y$ are optionally bonded to each other to form a ring. Examples of such a ring include a substituted or unsubstituted unsaturated hetero ring having 4 to 30 carbon atoms, and a substituted or unsubstituted unsaturated carbon ring having 6 to 30 carbon atoms.

The unsaturated hetero ring having 4 to 30 carbon atoms and the unsaturated carbon ring having 6 to 30 carbon atoms are not particularly limited, and may or may not have aromaticity. Examples of the unsaturated hetero ring having 4 to 30 carbon atoms and the unsaturated carbon ring having 6 to 30 carbon atoms are shown below.

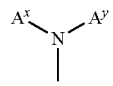

Note that the rings shown below correspond to the above part in the formula (I).

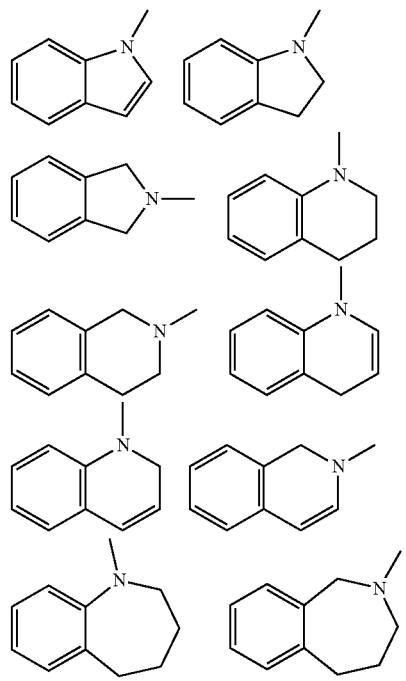

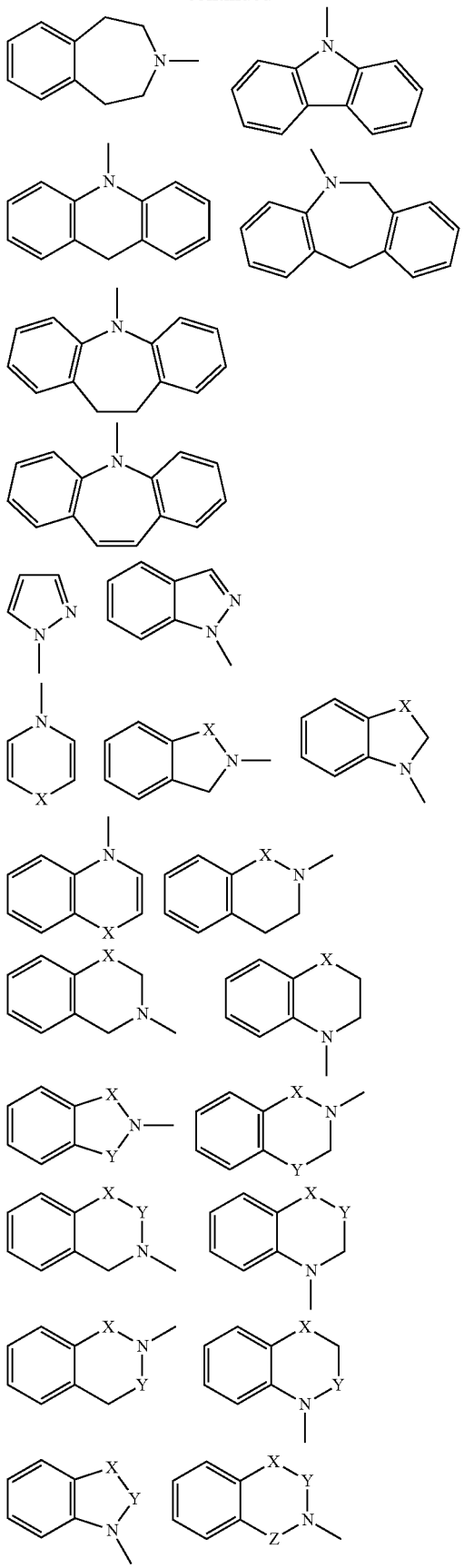
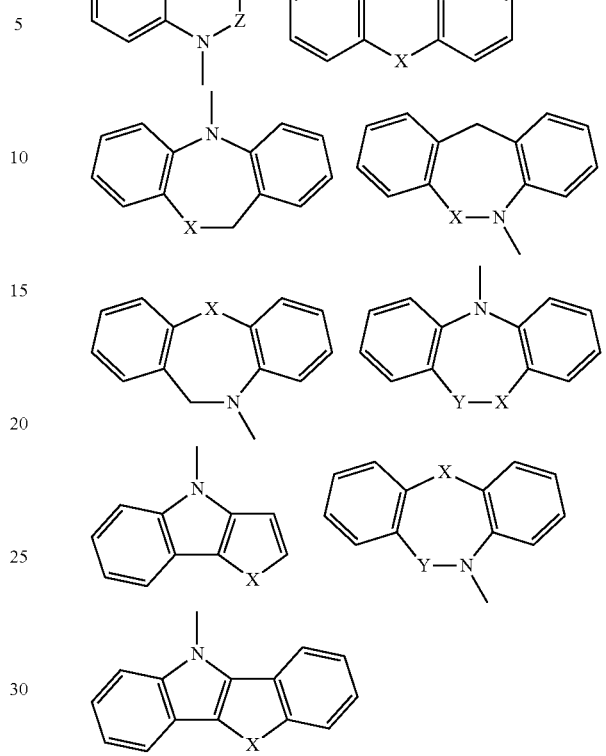

wherein X, Y, and Z are the same as defined above.

These rings may be substituted with a substituent. Examples of the substituent include those mentioned above in connection with a substituent that may substitute the aromatic ring included in $A^x$.

The total number of π electrons included in $A^x$ and $A^y$ is preferably 4 to 24, more preferably 6 to 20, and still more preferably 6 to 18, in order to more advantageously achieve the intended effects of the invention.

Examples of a preferable combination of $A^x$ and $A^y$ include (α) a combination wherein $A^x$ is an aromatic hydrocarbon group or a heteroaromatic ring group having 4 to 30 carbon atoms, and $A^y$ is a hydrogen atom, a cycloalkyl group having 3 to 8 carbon atoms, an aromatic hydrocarbon group having 6 to 12 carbon atoms that is optionally substituted with a halogen atom, a cyano group, an alkyl group having 1 to 6 carbon atoms, an alkoxy group having 1 to 6 carbon atoms, or a cycloalkyl group having 3 to 8 carbon atoms, a heteroaromatic ring group having 3 to 9 carbon atoms that is optionally substituted with a halogen atom, an alkyl group having 1 to 6 carbon atoms, an alkoxy group having 1 to 6 carbon atoms, or a cyano group, a substituted or unsubstituted alkyl group having 1 to 20 carbon atoms, a substituted or unsubstituted alkenyl group having 2 to 20 carbon atoms, or a substituted or unsubstituted alkynyl group having 2 to 20 carbon atoms, wherein a substituent that may substitute the alkyl group, the alkenyl group, or the alkynyl group is a halogen atom, a cyano group, an alkoxy group having 1 to 20 carbon atoms, an alkoxy group having 1 to 12 carbon atoms that is substituted with an alkoxy group having 1 to 12 carbon atoms, a phenyl group, a cyclohexyl group, a cyclic ether group having 2 to 12 carbon atoms, an aryloxy group having 6 to 14 carbon atoms, a hydroxyl group, a benzodioxanyl group, a benzenesulfonyl group, a benzoyl group, or —$SR^{10}$, and (β) $A^x$ and $A^y$ are bonded to each other to form an unsaturated heterocyclic ring or an unsaturated carbon ring. Note that $R^{10}$ is the same as defined above.

Examples of a more preferable combination of $A^x$ and $A^y$ include (γ) a combination wherein $A^x$ is a group among the groups respectively having the following structures, and $A^y$ is a hydrogen atom, a cycloalkyl group having 3 to 8 carbon atoms, an aromatic hydrocarbon group having 6 to 12 carbon atoms that is optionally substituted with a halogen atom, a cyano group, an alkyl group having 1 to 6 carbon atoms, an alkoxy group having 1 to 6 carbon atoms, or a cycloalkyl group having 3 to 8 carbon atoms, a heteroaromatic ring group having 3 to 9 carbon atoms that is optionally substituted with a halogen atom, an alkyl group having 1 to 6 carbon atoms, an alkoxy group having 1 to 6 carbon atoms, or a cyano group, a substituted or unsubstituted alkyl group having 1 to 20 carbon atoms, a substituted or unsubstituted alkenyl group having 2 to 20 carbon atoms, or a substituted or unsubstituted alkynyl group having 2 to 20 carbon atoms, wherein a substituent that may substitute the alkyl group, the alkenyl group, or the alkynyl group is a halogen atom, a cyano group, an alkoxy group having 1 to 20 carbon atoms, an alkoxy group having 1 to 12 carbon atoms that is substituted with an alkoxy group having 1 to 12 carbon atoms, a phenyl group, a cyclohexyl group, a cyclic ether group having 2 to 12 carbon atoms, an aryloxy group having 6 to 14 carbon atoms, a hydroxyl group, a benzodioxanyl group, a benzenesulfonyl group, a benzoyl group, or —$SR^{10}$. Note that $R^{10}$ is the same as defined above.

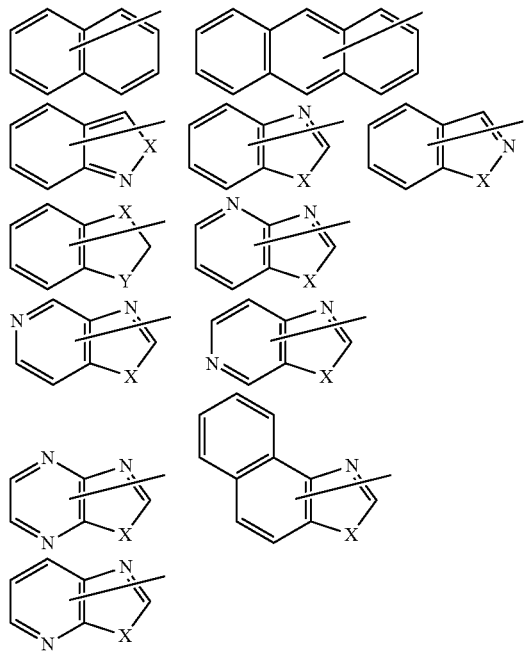

wherein X and Y are the same as defined above.

Examples of a particularly preferable combination of $A^x$ and $A^y$ include (δ) a combination wherein $A^x$ is a group among the groups respectively having the following structures, and $A^y$ is a hydrogen atom, a cycloalkyl group having 3 to 8 carbon atoms, an aromatic hydrocarbon group having 6 to 12 carbon atoms that is optionally substituted with a halogen atom, a cyano group, an alkyl group having 1 to 6 carbon atoms, an alkoxy group having 1 to 6 carbon atoms, or a cycloalkyl group having 3 to 8 carbon atoms, a heteroaromatic ring group having 3 to 9 carbon atoms that is optionally substituted with a halogen atom, an alkyl group having 1 to 6 carbon atoms, an alkoxy group having 1 to 6 carbon atoms, or a cyano group, a substituted or unsubstituted alkyl group having 1 to 20 carbon atoms, a substituted or unsubstituted alkenyl group having 2 to 20 carbon atoms, or a substituted or unsubstituted alkynyl group having 2 to 20 carbon atoms, wherein a substituent that may substitute the alkyl group, the alkenyl group, or the alkynyl group is a halogen atom, a cyano group, an alkoxy group having 1 to 20 carbon atoms, an alkoxy group having 1 to 12 carbon atoms that is substituted with an alkoxy group having 1 to 12 carbon atoms, a phenyl group, a cyclohexyl group, a cyclic ether group having 2 to 12 carbon atoms, an aryloxy group having 6 to 14 carbon atoms, a hydroxyl group, a benzodioxanyl group, a benzenesulfonyl group, a benzoyl group, or —$SR^{10}$. Note that X is the same as defined above, and $R^{10}$ is the same as defined above.

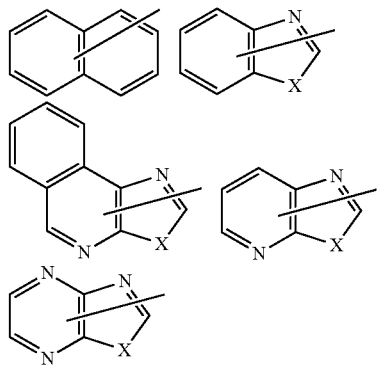

$A^1$ is a substituted or unsubstituted trivalent aromatic group. The trivalent aromatic group may be a trivalent carbocyclic aromatic group, or may be a trivalent heterocyclic aromatic group. It is preferable that the trivalent aromatic group be a trivalent carbocyclic aromatic group, more preferably a trivalent benzene ring group or a trivalent naphthalene ring group, and still more preferably a trivalent benzene ring group or a trivalent naphthalene ring group represented by the following formulas, in order to more advantageously achieve the intended effects of the invention.

Note that the substituents $Y^1$ and $Y^2$ are also included in the following formulas so that the bonding state can be easily understood ($Y^1$ and $Y^2$ are the same as defined above; hereinafter the same).

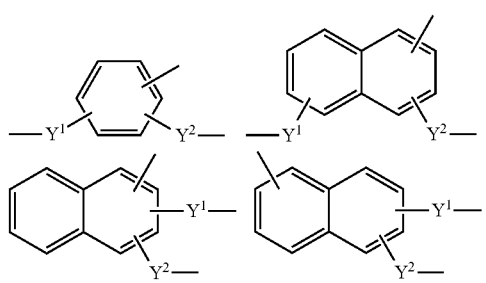

$A^1$ is more preferably a group among groups respectively represented by the following formulas (A11) to (A25), still more preferably a group among the groups respectively represented by the formulas (A11), (A13), (A15), (A19), and (A23), and particularly preferably the group represented by the formula (A11) or the group represented by the formula (A23).

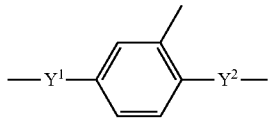
(A11)

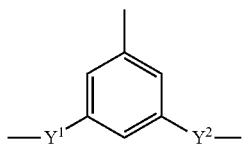
(A12)

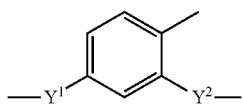
(A13)

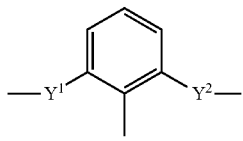
(A14)

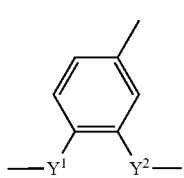
(A15)

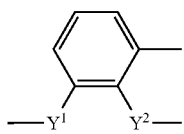
(A16)

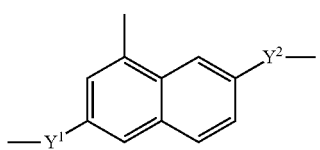
(A17)

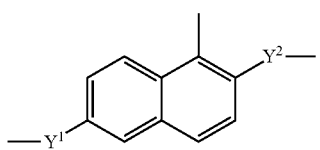
(A18)

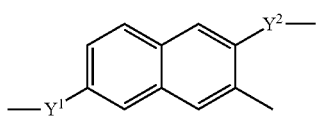
(A19)

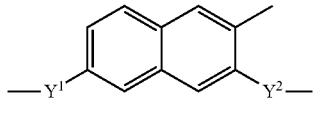
(A20)

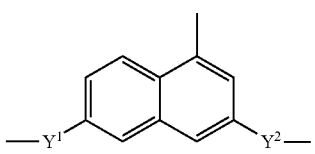
(A21)

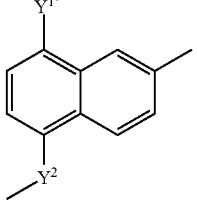
(A22)

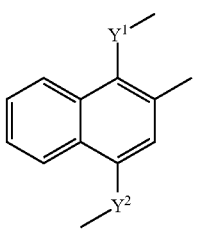
(A23)

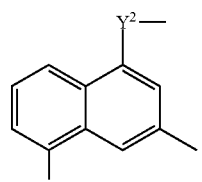
(A24)

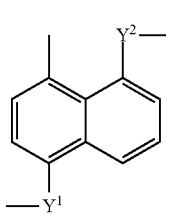
(A25)

Examples of a substituent that may substitute the trivalent aromatic group represented by $A^1$ include those mentioned above in connection with a substituent that may substitute the aromatic ring included in $A^x$. It is preferable that $A^1$ be unsubstituted.

$A^2$ and $A^3$ are independently a substituted or unsubstituted divalent alicyclic hydrocarbon group having 3 to 30 carbon atoms.

Examples of the divalent alicyclic hydrocarbon group having 3 to 30 carbon atoms include cycloalkanediyl groups having 3 to 30 carbon atoms, divalent fused alicyclic groups having 10 to 30 carbon atoms, and the like.

Examples of the cycloalkanediyl group having 3 to 30 carbon atoms include a cyclopropanediyl group; a cyclobutanediyl group such as a cyclobutane-1,2-diyl group and a cyclobutane-1,3-diyl group; a cyclopentanediyl group such as a cyclopentane-1,2-diyl group and a cyclopentane-1,3-diyl group; a cyclohexanediyl group such as a cyclohexane-1,2-diyl group, a cyclohexane-1,3-diyl group, and a cyclohexane-1,4-diyl group; a cycloheptanediyl group such as a cycloheptane-1,2-diyl group, a cycloheptane-1,3-diyl group, and a cycloheptane-1,4-diyl group; a cyclooctanediyl group such as a cyclooctane-1,2-diyl group, a cyclooctane-1,3-diyl group, a cyclooctane-1,4-diyl group, and a cyclooctane-1,5-diyl group; a cyclodecanediyl group such as a cyclodecane-1,2-diyl group, a cyclodecane-1,3-diyl group, a cyclodecane-1,4-diyl group, and a cyclodecane-1,5-diyl group; a cyclododecanediyl group such as a cyclododecane-1,2-diyl group, a cyclododecane-1,3-diyl group, a cyclododecane-1,4-diyl group, and a cyclododecane-1,5-diyl group; a cyclotetradecanediyl group such as a cyclotetradecane-1,2-diyl group, a cyclotetradecane-1,3-diyl group, a cyclotetradecane-1,4-diyl group, a cyclotetradecane-1,5-diyl group, and a cyclotetradecane-1,7-diyl group; a cycloeicosanediyl group such as a cycloeicosane-1,2-diyl group and a cycloeicosane-1,10-diyl group; and the like.

Examples of the divalent fused alicyclic group having 10 to 30 carbon atoms include a decalindiyl group such as a decalin-2,5-diyl group and a decalin-2,7-diyl group; an adamantanediyl group such as an adamantane-1,2-diyl group and an adamantane-1,3-diyl group; a bicyclo[2.2.1]heptanediyl group such as a bicyclo[2.2.1]heptane-2,3-diyl group, a bicyclo[2.2.1]heptane-2,5-diyl group, and a bicyclo[2.2.1]heptane-2,6-diyl group; and the like.

These divalent alicyclic hydrocarbon groups may be substituted with a substituent at an arbitrary position. Examples of the substituent include those mentioned above in connection with a substituent that may substitute the aromatic ring included in $A^x$.

$A^2$ and $A^3$ are preferably a divalent alicyclic hydrocarbon group having 3 to 12 carbon atoms, more preferably a cycloalkanediyl group having 3 to 12 carbon atoms, still more preferably a group among the groups respectively represented by the following formulas (A31) to (A34), and particularly preferably the group represented by the formula (A32).

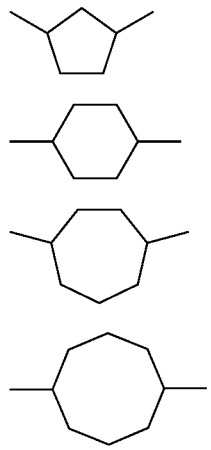

(A31)

(A32)

(A33)

(A34)

The divalent alicyclic hydrocarbon group having 3 to 30 carbon atoms is classified into a cis-stereoisomer and a trans-stereoisomer based on the difference in the steric configuration of the carbon atom bonded to $Y^1$ and $Y^3$ (or $Y^2$ and $Y^4$). For example, a cyclohexane-1,4-diyl group is classified into a cis-isomer (A32a) and a trans-isomer (A32b) (see below).

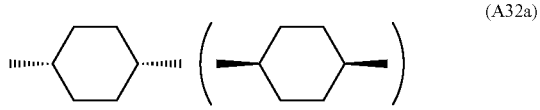

(A32a)

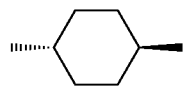

(A32b)

The divalent alicyclic hydrocarbon group having 3 to 30 carbon atoms may be a cis-isomer, a trans-isomer, or a mixture of a cis-isomer and a trans-isomer. Note that it is preferable that the divalent alicyclic hydrocarbon group having 3 to 30 carbon atoms be a trans-isomer or a cis-isomer, and more preferably a trans-isomer, since an excellent alignment capability can be obtained.

$A^4$ and $A^5$ are independently a substituted or unsubstituted divalent aromatic group having 6 to 30 carbon atoms.

The aromatic group represented by $A^4$ and $A^5$ may be a monocyclic aromatic group, or may be a polycyclic aromatic group.

Specific examples of a preferable aromatic group represented by $A^4$ and $A^5$ include the following groups.

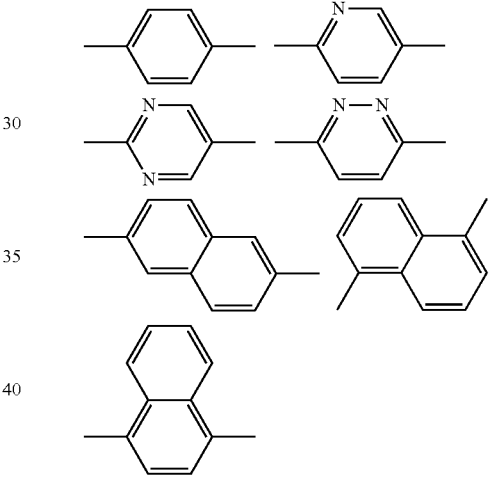

The divalent aromatic group represented by $A^4$ and $A^5$ may be substituted with a substituent at an arbitrary position. Examples of the substituent include halogen atoms, a cyano group, a hydroxyl group, alkyl groups having 1 to 6 carbon atoms, alkoxy groups having 1 to 6 carbon atoms, a nitro group, —C(=O)—OR$^8$, and the like. Note that $R^8$ is an alkyl group having 1 to 6 carbon atoms. Among these, a halogen atom, an alkyl group having 1 to 6 carbon atoms, and an alkoxy group having 1 to 6 carbon atoms are preferable as the substituent. A fluorine atom is preferable as the halogen atom. A methyl group, an ethyl group, and a propyl group are preferable as the alkyl group having 1 to 6 carbon atoms. A methoxy group and an ethoxy group are preferable as the alkoxy group having 1 to 6 carbon atoms.

It is preferable that $A^4$ and $A^5$ be independently a group among the groups respectively represented by the following formula (A41), (A42), and (A43) that are optionally substituted with a substituent, and particularly preferably the group represented by the formula (A41) that is optionally substituted with a substituent, in order to more advantageously achieve the intended effects of the invention.

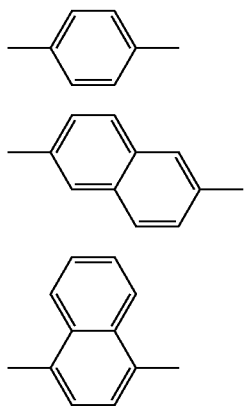

(A41)

(A42)

(A43)

$Q^1$ is a hydrogen atom, or a substituted or unsubstituted alkyl group having 1 to 6 carbon atoms.

Examples of the substituted or unsubstituted alkyl group having 1 to 6 carbon atoms include those mentioned above in connection with $A^x$.

$Q^1$ is preferably a hydrogen atom or an alkyl group having 1 to 6 carbon atoms, and more preferably a hydrogen atom or a methyl group.

The polymerizable compound according to one embodiment of the invention may be produced by effecting the following reaction, for example.

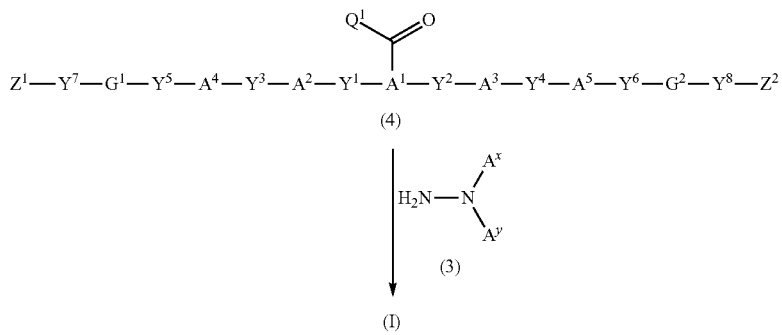

wherein $Y^1$ to $Y^8$, $G^1$, $G^2$, $Z^1$, $Z^2$, $A^x$, $A^y$, $A^1$ to $A^5$, and $Q^1$ are the same as defined above.

Specifically, the polymerizable compound represented by the formula (I) can be produced with high selectivity in high yield by reacting the hydrazine compound represented by the formula (3) (hydrazine compound (3)) with the carbonyl compound represented by the formula (4) (carbonyl compound (4)) in a molar ratio (hydrazine compound (3): carbonyl compound (4)) of 1:2 to 2:1 (preferably 1:1.5 to 1.5:1).

The above reaction may be effected in the presence of an acid catalyst such as an organic acid (e.g., (±)-10-camphorsulfonic acid or p-toluenesulfonic acid), or an inorganic acid (e.g., hydrochloric acid or sulfuric acid). The addition of the acid catalyst may reduce the reaction time, and improve the yield. The acid catalyst is normally added in an amount of 0.001 to 1 mol based on 1 mol of the carbonyl compound (4). The acid catalyst may be added directly, or a solution prepared by dissolving the acid catalyst in an appropriate solvent may be added.

The solvent used for the above reaction is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, and t-butyl alcohol; ether-based solvents such as diethyl ether, tetrahydrofuran, 1,2-dimethoxyethane, 1,4-dioxane, and cyclopentyl methyl ether; ester-based solvents such as ethyl acetate, propyl acetate, and methyl propionate; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents including two or more solvents among these solvents; and the like.

Among these, alcohol-based solvents, ether-based solvents, and mixed solvents of an alcohol-based solvent and an ether-based solvent are preferable.

The solvent may be used in an appropriate amount taking account of the type of each compound, the reaction scale, and the like. The solvent is normally used in an amount of 1 to 100 g per gram of the hydrazine compound (3).

The reaction proceeds smoothly when the reaction temperature is within the range from −10° C. to the boiling point of the solvent. The reaction time is determined taking account of the reaction scale, but is normally several minutes to several hours.

The hydrazine compound (3) may be produced as shown below.

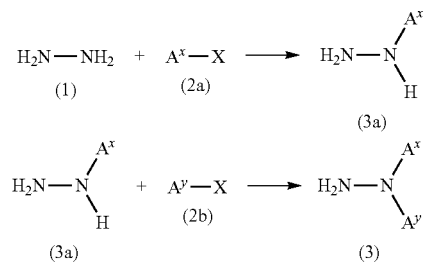

wherein $A^x$ and $A^y$ are the same as defined above, and X is a leaving group (e.g., halogen atom, methanesulfonyloxy group, or p-toluenesulfonyloxy group).

Specifically, the compound represented by the formula (2a) is reacted with the hydrazine (1) in an appropriate solvent in a molar ratio (compound (2a):hydrazine (1)) of 1:1 to 1:20 (preferably 1:2 to 1:10) to obtain the corresponding hydrazine compound (3a), and the hydrazine compound (3a) is reacted with the compound represented by the formula (2b) to obtain the hydrazine compound (3).

Hydrazine monohydrate is normally used as the hydrazine (1). A commercially available product may be used directly as the hydrazine (1).

The solvent used for the above reaction is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, and t-butyl alcohol; ether-based solvents such as diethyl ether, tetrahydrofuran, 1,2-dimethoxyethane, 1,4-dioxane, and cyclopentyl methyl ether; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents including two or more solvents among these solvents; and the like.

Among these, alcohol-based solvents, ether-based solvents, and mixed solvents of an alcohol-based solvent and an ether-based solvent are preferable.

The solvent may be used in an appropriate amount taking account of the type of each compound, the reaction scale, and the like. The solvent is normally used in an amount of 1 to 100 g per gram of hydrazine.

The reaction proceeds smoothly when the reaction temperature is within the range from −10° C. to the boiling point of the solvent. The reaction time is determined taking account of the reaction scale, but is normally several minutes to several hours.

The hydrazine compound (3) may also be produced by reducing the diazonium salt (5) (see below) using a known method.

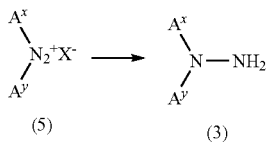

wherein $A^x$ and $A^y$ are the same as defined above, and $X^-$ is an anion that is a counter ion for diazonium. Examples of the anion represented by $X^-$ include inorganic anions such as a hexafluorophosphoric acid ion, a fluoroboric acid ion, a chloride ion, and a sulfuric acid ion; organic anions such as a polyfluoroalkylcarboxylic acid ion, a polyfluoroalkylsulfonic acid ion, a tetraphenylboric acid ion, an aromatic carboxylic acid ion, and an aromatic sulfonic acid ion; and the like.

Examples of a reducing agent used for the above reaction include a metal salt reducing agent.

The term "metal salt reducing agent" normally refers to a compound that includes a metal having a small valence, or a compound that includes a metal ion and a hydrido source (see "Yuki Gosei Jikkenhou Handbook (Handbook of Organic Synthesis Experiments)", 1990, edited by The Society of Synthetic Organic Chemistry, Japan, published by Maruzen Co., Ltd., p. 810).

Examples of the metal salt reducing agent include $NaAlH_4$, $NaAlH_p(Or)_q$ (wherein p and q are independently an integer from 1 to 3, provided that p+q=4, and r is an alkyl group having 1 to 6 carbon atoms), $LiAlH_4$, $iBu_2AlH$, $LiBH_4$, $NaBH_4$, $SnCl_2$, $CrCl_2$, $TiCl_3$, and the like.

The reduction reaction may be effected under known reaction conditions. For example, the reduction reaction may be effected under the reaction conditions described in JP-A-2005-336103, "Shin-Jikken Kagaku Koza (New Experimental Chemistry Course)", 1978, Vol. 14, published by Maruzen Co., Ltd., "Jikken Kagaku Koza (Experimental Chemistry Course)", 1992, Vol. 20, published by Maruzen Co., Ltd., or the like.

The diazonium salt (5) may be produced from aniline or the like using a known method.

The carbonyl compound (4) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)—NH— or —NH—C(=O)—)-forming reaction.

An ether linkage may be formed as described below.

(i) A compound represented by D1-hal (wherein Hal is a halogen atom (hereinafter the same)) and a compound represented by D2-OMet (wherein Met is an alkali metal (mainly sodium) (hereinafter the same)) are mixed and condensed (Williamson synthesis). Note that D1 and D2 are an arbitrary organic group (hereinafter the same).

(ii) A compound represented by D1-hal and a compound represented by D2-OH are mixed and condensed in the presence of a base (e.g., sodium hydroxide or potassium hydroxide).

(iii) A compound represented by D1-J (wherein J is an epoxy group) and a compound represented by D2-OH are mixed and condensed in the presence of a base (e.g., sodium hydroxide or potassium hydroxide).

(iv) A compound represented by D1-OFN (wherein OFN is a group that includes an unsaturated bond) and a compound represented by D2-OMet are mixed and subjected to an addition reaction in the presence of a base (e.g., sodium hydroxide or potassium hydroxide).

(v) A compound represented by D1-hal and a compound represented by D2-OMet are mixed and condensed in the presence of copper or cuprous chloride (Ullmann condensation).

An ester linkage and an amide linkage may be formed as described below.

(vi) A compound represented by D1-COOH and a compound represented by D2-OH or D2-NH$_2$ are subjected to dehydration and condensation in the presence of a dehydration-condensation agent (e.g., N,N-dicyclohexylcarbodiimide).

(vii) A compound represented by D1-COOH is reacted with a halogenating agent to obtain a compound represented by D1-CO-hal, and the compound represented by D1-CO-hal is reacted with a compound represented by D2-OH or D2-NH$_2$ in the presence of a base.

(viii) A compound represented by D1-COOH is reacted with an acid anhydride to obtain a mixed acid anhydride, and the mixed acid anhydride is reacted with a compound represented by D2-OH or D2-NH$_2$.

(ix) A compound represented by D1-COOH and a compound represented by D2-OH or D2-NH$_2$ are subjected to dehydration and condensation in the presence of an acid catalyst or a base catalyst.

More specifically, the carbonyl compound (4) according to one embodiment of the invention may be produced using the following method (see the following reaction formula).

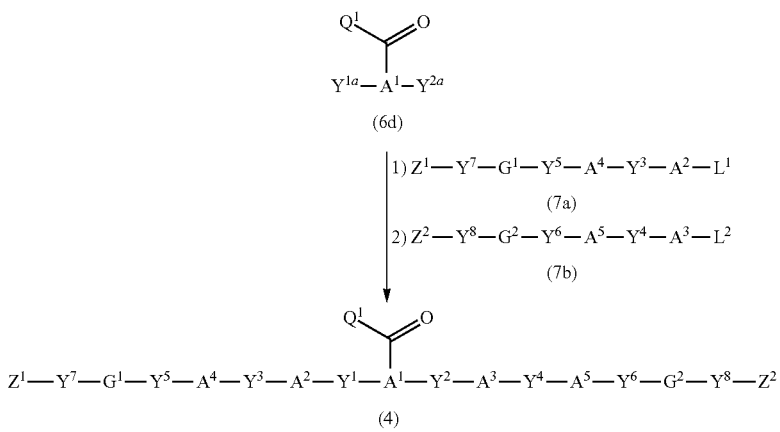

wherein $Y^1$ to $Y^8$, $G^1$, $G^2$, $Z^1$, $Z^2$, $A^1$ to $A^5$, and $Q^1$ are the same as defined above, $L^1$ and $L^2$ are a leaving group (e.g., hydroxyl group, halogen atom, methanesulfonyloxy group, or p-toluenesulfonyloxy group), —$Y^{1a}$ is a group that reacts with -$L^1$ to form —$Y^1$—, and —$Y^{2a}$ is a group that reacts with -$L^2$ to form —$Y^2$—.

Specifically, the carbonyl compound (4) according to one embodiment of the invention may be produced by sequentially reacting the compound represented by the formula (7a) and the compound represented by the formula (7b) with the compound represented by the formula (6d) using an ether linkage (—O—)-forming reaction, an ester linkage (—C(=O)—O— or —O—C(=O)—)-forming reaction, or a carbonate linkage (—O—C(=O)—O—)-forming reaction known in the art.

The carbonyl compound (4) wherein $Y^1$ is a group represented by $Y^{11}$—C(=O)—O—, and the group represented by $Z^2$—Y-$G^2$-$Y^6$-$A^5$-$Y^4$-$A^3$-$Y^2$— is identical with the group represented by $Z^1$-$Y^7$-$G^1$-$Y^5$-$A^4$-$Y^3$-$A^2$-$Y^1$— (hereinafter referred to as "compound (4')") may be produced as shown below.

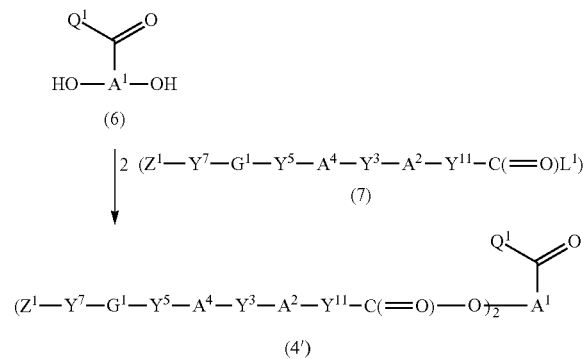

wherein $Y^3$, $Y^5$, $Y^7$, $G^1$, $Z^1$, $A^1$, $A^2$, $A^4$, $Q^1$, and $L^1$ are the same as defined above, $Y^{11}$ is a group whereby $Y^1$ is $Y^{11}$—C(=O)—O—, and $Y^1$ is the same as defined above.

Specifically, the dihydroxy compound represented by the formula (6) (compound (6)) is reacted with the compound represented by the formula (7) (compound (7)) in a molar ratio (compound (6):compound (7)) of 1:2 to 1:4 (preferably 1:2 to 1:3) to produce the target compound (4') with high selectivity in high yield.

When the compound (7) is a compound (carboxylic acid) represented by the formula (7) wherein $L^1$ is a hydroxyl group, the target product may be obtained by effecting the reaction in the presence of a dehydration-condensation agent (e.g., 1-ethyl-3-(3-dimethylaminopropyl)carbodiimide hydrochloride or dicyclohexylcarbodiimide).

The dehydration-condensation agent is normally used in an amount of 1 to 3 mol based on 1 mol of the compound (7).

When the compound (7) is a compound (carboxylic acid) represented by the formula (7) wherein $L^1$ is a hydroxyl group, the target product may also be obtained by effecting the reaction in the presence of a sulfonyl halide (e.g., methanesulfonyl chloride or p-toluenesulfonyl chloride) and a base (e.g., triethylamine, diisopropylethylamine, pyridine, or 4-(dimethylamino)pyridine).

The sulfonyl halide is normally used in an amount of 1 to 3 mol based on 1 mol of the compound (7).

The base is normally used in an amount of 1 to 3 mol based on 1 mol of the compound (7).

In this case, a compound (mixed acid anhydride) represented by the formula (7) wherein $L^1$ is a sulfonyloxy group may be isolated, and subjected to the subsequent reaction.

When the compound (7) is a compound (acid halide) represented by the formula (7) wherein $L^1$ is a halogen atom, the target product may be obtained by effecting the reaction in the presence of a base.

Examples of the base include organic bases such as triethylamine and pyridine; and inorganic bases such as sodium hydroxide, sodium carbonate, and sodium hydrogen carbonate.

The base is normally used in an amount of 1 to 3 mol based on 1 mol of the compound (7).

Examples of the solvent used for the above reaction include chlorine-based solvents such as chloroform and methylene chloride; amide-based solvents such as N-methylpyrrolidone, N,N-dimethylformamide, N,N-dimethylacetamide, and hexamethylphosphoric triamide; ether-based solvents such as 1,4-dioxane, cyclopentyl methyl ether, tetrahydrofuran, tetrahydropyran, and 1,3-dioxolane; sulfur-containing solvents such as dimethyl sulfoxide and sulfolane; aromatic hydrocarbon-based solvents such as benzene, toluene, and xylene; aliphatic hydrocarbon-based solvents such as n-pentane, n-hexane, and n-octane; alicyclic hydrocarbon-based solvents such as cyclopentane and cyclohexane; mixed solvents of two or more solvents among these solvents; and the like.

The solvent may be used in an appropriate amount taking account of the type of each compound, the reaction scale, and the like. The solvent is normally used in an amount of 1 to 50 g per gram of the hydroxy compound (6).

Many of the compounds (6) are known compounds, and may be produced using a known method.

For example, the compound (6) may be produced using the following method (see the following reaction formula) (see WO2009/042544 and The Journal of Organic Chemistry, 2011, 76, 8082-8087). A commercially available product may be used as the compound (6) optionally after purification.

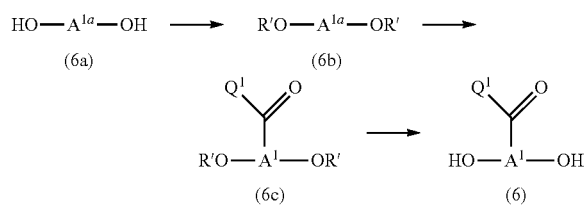

wherein $A^1$ and $Q^1$ are the same as defined above, $A^{1a}$ is a divalent aromatic group that forms $A^1$ through formylation or acylation, and R' is a protecting group for a hydroxyl group, such as an alkyl group having 1 to 6 carbon atoms (e.g., methyl group or ethyl group), or an alkoxyalkyl group having 2 to 6 carbon atoms (e.g., methoxymethyl group).

Specifically, the target compound (6) may be produced by alkylating the hydroxyl groups of the dihydroxy compound represented by the formula (6a) (e.g., 1,4-dihydroxybenzene or 1,4-dihydroxynaphthalene) to obtain the compound represented by the formula (6b), effecting formylation or acylation at the ortho position with respect to the OR' group using a known method to obtain the compound represented by the formula (6c), and deprotecting (dealkylating) the compound represented by the formula (6c).

A commercially available product may be used as the compound (6) either directly or after purification.

Most of the compounds (7) are known compounds. The carbonyl compound (7) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)—NH— or —NH—C(=O)—)-forming reaction.

For example, when the compound (7) is a compound represented by the following formula (7') (compound (7')), the compound (7) may be produced as shown below using a dicarboxylic acid represented by the formula (9') (compound (9')).

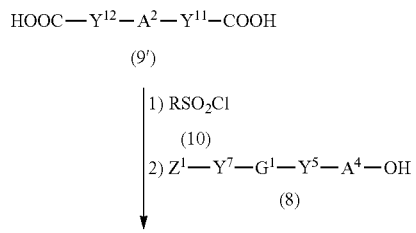

-continued

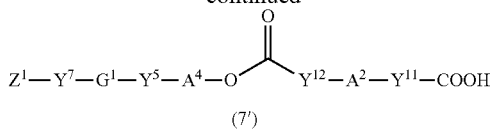

wherein $Y^5$, $Y^7$, $G^1$, $Z^1$, $A^2$, $A^4$, and $Y^{11}$ are the same as defined above, $Y^{12}$ is a group whereby —O—C(=O)—$Y^{12}$ is $Y^3$, and R is an alkyl group such as a methyl group or an ethyl group, or a substituted or unsubstituted aryl group such as a phenyl group or a p-methylphenyl group.

Specifically, the sulfonyl chloride represented by the formula (10) is reacted with the compound (9') in the presence of a base (e.g., triethylamine or 4-(dimethylamino)pyridine).

The compound (8) and a base (e.g., triethylamine or 4-(dimethylamino)pyridine) are added to the reaction mixture to effect a reaction.

Sulfonyl chloride is normally used in an amount of 0.5 to 0.7 equivalents based on 1 equivalent of the compound (9').

The compound (8) is normally used in an amount of 0.5 to 0.6 equivalents based on 1 equivalent of the compound (9').

The base is normally used in an amount of 0.5 to 0.7 equivalents based on 1 equivalent of the compound (9').

The reaction temperature is 20 to 30° C. The reaction time is determined taking account of the reaction scale and the like, but is normally several minutes to several hours.

Examples of a solvent used for the above reaction include those mentioned above in connection with the solvent that may be used when producing the compound (4'). It is preferable to use an ether as the solvent.

The solvent may be used in an appropriate amount taking account of the type of each compound, the reaction scale, and the like. The solvent is normally used in an amount of 1 to 50 g per gram of the compound (9').

After completion of the reaction, a post-treatment operation normally employed in synthetic organic chemistry is performed, optionally followed by a known separation/purification means such as column chromatography, recrystallization, or distillation to isolate the target product.

The structure of the target product may be identified by measurement (e.g., NMR spectrometry, IR spectrometry, or mass spectrometry), elemental analysis, or the like.

2) Polymerizable Composition

A polymerizable composition according to one embodiment of the invention includes the polymerizable compound according to one embodiment of the invention, and an initiator. The initiator is used to more efficiently polymerize the polymerizable composition according to one embodiment of the invention.

The initiator may be appropriately selected taking account of the type of polymerizable group included in the polymerizable compound. For example, a radical initiator may be used when the polymerizable group is a radically polymerizable group. An anionic initiator may be used when the polymerizable group is an anionically polymerizable group. A cationic initiator may be used when the polymerizable group is a cationically polymerizable group.

Examples of the radical initiator include a thermal radical generator that is a compound that generates active species that initiate polymerization of the polymerizable compound upon heating, and a photo-radical generator that is a compound that generates active species that initiate polymerization of the polymerizable compound upon exposure to exposure light (e.g., visible rays, ultraviolet rays (e.g., i-line), deep ultraviolet rays, electron beams, or X-rays). It is preferable to use the photo-radical generator.

Examples of the photo-radical generator include acetophenone-based compounds, biimidazole-based compounds, triazine-based compounds, O-acyloxime-based compounds, onium salt-based compounds, benzoin-based compounds, benzophenone-based compounds, α-diketone-based compounds, polynuclear quinone-based compounds, xanthone-based compounds, diazo-based compounds, imide sulfonate-based compounds, and the like. These compounds generate active radicals and/or an active acid upon exposure. These photo-radical generators may be used either alone or in combination.

Specific examples of the acetophenone-based compounds include 2-hydroxy-2-methyl-1-phenylpropan-1-one, 2-methyl-1-[4-(methylthio)phenyl]-2-morpholinopropan-1-one, 2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione, 2-benzyl-2-dimethylamino-4'-morpholinobutyrophenone, and the like, Specific examples of the biimidazole-based compounds include 2,2'-bis(2-chlorophenyl)-4,4',5,5'-tetrakis(4-ethoxycarbonylphenyl)-1,2'-biimidazole, 2,2'-bis(2-bromophenyl)-4,4',5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound since sensitivity can be further improved.

The term "hydrogen donor" used herein refers to a compound that can donate a hydrogen atom to radicals generated by the biimidazole-based compound upon exposure. A mercaptan-based compound, an amine-based compound, and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis (dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compounds include triazine-based compounds that include a halomethyl group, such as 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl) ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine.

Specific examples of the O-acyloxime-based compounds include 1-[4-(phenylthio)phenyl]-heptane-1,2-dione-2-(O-benzoyloxime), 1-[4-(phenylthio)phenyl]-octane-1,2-dione-2-(O-benzoyloxime), 1-[4-(benzoyl)phenyl]-octane-1,2-dione-2-(O-benzoyloxime), 1-[9-ethyl-6-(2-methylbenzoyl)-9h-carbazol-3-yl]-ethanone-1-(O-acetyloxime), 1-[9-ethyl-6-(3-methylbenzoyl)-9h-carbazol-3-yl]-ethanone-1-(O-acetyloxime), 1-(9-ethyl-6-benzoyl-9h-carbazol-3-yl)-ethanone-1-(O-acetyloxime), ethanone-1-[9-ethyl-6-(2-methyl-4-tetrahydrofuranylbenzoyl)-9H-carbazol-3-yl]-1-(O-acetyloxime), ethanone-1-[9-ethyl-6-(2-methyl-4-tetrahydropyranylbenzoyl)-9H-carbazol-3-yl]-1-(O-acetyloxime), ethanone-1-[9-ethyl-6-(2-methyl-5-tetrahydrofuranylbenzoyl)-9H-carbazol-3-yl]-1-(O-acetyloxime), ethanone-1-[9-ethyl-6-(2-methyl-5-tetrahydropyranylbenzoyl)-9H-carbazol-3-yl]-1-(O-acetyloxime), ethanone-1-[9-ethyl-6-{2-methyl-4-(2,2-dimethyl-1,3-dioxolanyl)benzoyl}-9H-carbazol-3-yl]-1-(O-acetyloxime), ethanone-1-[9-ethyl-6-(2-methyl-4-tetrahydrofuranylmethoxybenzoyl)-9-carbazol-3-yl]-1-(O-acetyloxime), ethanone-1-[9-ethyl-6-(2-methyl-4-tetrahydropyranylmethoxybenzoyl)-9H-carbazol-3-yl]-1-(O-acetyloxime), ethanone-1-[9-ethyl-6-(2-methyl-5-tetrahydrofuranylmethoxybenzoyl)-9H-carbazol-3-yl]-1-(O-acetyloxime), ethanone-1-[9-ethyl-6-(2-methylbenzoyl)-9h-carbazol-3-yl]-1-(O-acetyloxime), ethanone-1-[9-ethyl-6-(2-methyl-5-tetrahydropyranylmethoxybenzoyl)-9H-carbazol-3-yl]-1-(O-acetyloxime), ethanone-1-[9-ethyl-6-{2-methyl-4-(2,2-dimethyl-1,3-dioxolanyl) methoxybenzoyl}-9H-carbazol-3-yl]-1-(O-acetyloxime), and the like.

A commercially available product may be used directly as the photo-radical generator. Specific examples of a commercially available photo-radical generator include Irgacure 907, Irgacure 184, Irgacure 369, Irgacure 651, Irgacure 819, Irgacure 907, Irgacure OXE02 (manufactured by BASF); Adekaoptomer N1919 (manufactured by Adeka Corporation); and the like.

Examples of the anionic initiator include alkyllithium compounds; monolithium salts or monosodium salts of biphenyl, naphthalene, pyrene, and the like; polyfunctional initiators such as dilithiums and trilithium salts; and the like.

Examples of the cationic initiator include proton acids such as sulfuric acid, phosphoric acid, perchloric acid, and trifluoromethanesulfonic acid; Lewis acids such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally used to prepare the polymerizable composition according to one embodiment of the invention in an amount of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust surface tension. The surfactant is not particularly limited, but is preferably a nonionic surfactant. A commercially available product may be used as the nonionic surfactant. Examples of the nonionic surfactant include a nonionic surfactant that is an oligomer having a molecular weight of about several thousand (e.g., "KH-40" manufactured by AGC Seimi Chemical Co., Ltd.), and the like. The surfactant is normally added to the polymerizable composition according to one embodiment of the invention in an amount of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, or a metal oxide (e.g., titanium oxide). Each additive is normally added to the polymerizable composition according to one embodiment of the invention in an amount of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate organic solvent.

Examples of the organic solvent include ketones such as cyclopentanone, cyclohexanone, and methyl ethyl ketone; acetates such as butyl acetate and amyl acetate; halogenated hydrocarbons such as chloroform, dichloromethane, and dichloroethane; ethers such as 1,4-dioxane, cyclopentyl methyl ether, tetrahydrofuran, tetrahydropyran, and 1,3-dioxolane; and the like.

The polymerizable composition thus obtained is useful as a raw material for producing a polymer according to one embodiment of the invention or an optically anisotropic article according to one embodiment of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compound according to one embodiment of the invention, or a copolymer of the polymerizable compound according to one embodiment of the invention and an additional copolymerizable monomer.

Examples of the additional copolymerizable monomer include, but are not limited to, 4'-methoxyphenyl 4-(2-methacryloyloxyethyloxy)benzoate, biphenyl 4-(6-methacryloyloxyhexyloxy)benzoate, 4'-cyanobiphenyl 4-(2-acryloyloxyethyloxy)benzoate, 4'-cyanobiphenyl 4-(2-methacryloyloxyethyloxy)benzoate, 3',4'-difluorophenyl 4-(2-methacryloyloxyethyloxy)benzoate, naphthyl 4-(2-methacryloyloxyethyloxy)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amyltolan, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like.

Examples of a commercially available product of the additional copolymerizable monomer include LC-242 (manufactured by BASF) and the like. The compounds disclosed in JP-A-2007-002208, JP-A-2009-173893, JP-A-2009-274984, JP-A-2010-030979, JP-A-2010-031223, JP-A-2011-006360, and the like may also be used as the additional copolymerizable monomer.

A polyfunctional monomer that includes a plurality of polymerizable unsaturated groups (e.g., acryloyl group, methacryloyl group, vinyl group, and allyl group) may also be used as the additional copolymerizable monomer.

Examples of such a polyfunctional monomer include alkanediol diacrylates such as 1,2-butanediol diacrylate, 1,4-butanediol diacrylate, 1,3-butanediol diacrylate, neopentanediol diacrylate, and 1,6-hexanediol diacrylate, alkanediol dimethacrylates such as 1,2-butanediol dimethacrylate, 1,3-butanediol dimethacrylate, 1,4-butanediol dimethacrylate, neopentanediol dimethacrylate, and 1,6-hexanediol dimethacrylate, polyethylene glycol diacrylates such as ethylene glycol diacrylate, diethylene glycol diacrylate, triethylene glycol diacrylate, and tetraethylene glycol diacrylate, polypropylene glycol diacrylates such as propylene glycol diacrylate, dipropylene glycol diacrylate, tripropylene glycol diacrylate, and tetrapropylene glycol diacrylate, polyethylene glycol dimethacrylates such as ethylene glycol dimethacrylate, diethylene glycol dimethacrylate, triethylene glycol dimethacrylate, and tetraethylene glycol dimethacrylate, polypropylene glycol dimethacrylates such as propylene glycol dimethacrylate, dipropylene glycol dimethacrylate, tripropylene glycol dimethacrylate, and tetrapropylene glycol dimethacrylate, polyethylene glycol divinyl ethers such as ethylene glycol divinyl ether, diethylene glycol divinyl ether, triethylene glycol divinyl ether, and tetraethylene glycol divinyl ether, polyethylene glycol diallyl ethers such as ethylene glycol diallyl ether, diethylene glycol diallyl ether, triethylene glycol diallyl ether, and tetraethylene glycol diallyl ether, bisphenol F ethoxylate diacrylate, bisphenol F ethoxylate dimethacrylate, bisphenol A ethoxylate diacrylate, bisphenol A ethoxylate dimethacrylate, trimethylolpropane triacrylate, trimethylolpropane trimethacrylate, trimethylolpropane ethoxylate triacrylate, trimethylolpropane ethoxylate trimethacrylate, trimethylolpropane propoxylate triacrylate, trimethylolpropane propoxylate trimethacrylate, isocyanuric acid ethoxylate triacrylate, glycerol ethoxylate triacrylate, glycerol propoxylate triacrylate, pentaerythritol ethoxylate tetraacrylate, ditrimethylolpropane ethoxylate tetraacrylate, dipentaerythritol ethoxylate hexacrylate, and the like.

The polymerizable compound according to one embodiment of the invention may be (co)polymerized optionally together with the additional copolymerizable monomer in the presence of an appropriate initiator. The initiator may be used in an amount similar to that of the initiator included in the polymerizable composition.

When the polymer according to one embodiment of the invention is a copolymer of the polymerizable compound according to one embodiment of the invention and the additional copolymerizable monomer, the content of structural units derived from the polymerizable compound according to one embodiment of the invention is not particularly limited, but is preferably 50 wt % or more, and more preferably 70 wt % or more, based on the total structural units. When the content of structural units derived from the polymerizable compound is within the above range, a polymer that has a high glass transition temperature (Tg) and high hardness can be obtained.

The polymer (1) may be produced by (A) (co)polymerizing the polymerizable compound optionally together with the additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound in an organic solvent optionally together with the additional copolymerizable monomer to a substrate using a known coating method, removing the solvent, and effecting polymerization by applying heat or activated energy rays, for example.

Examples of the initiator include those mentioned above in connection with the initiator included in the polymerizable composition.

The organic solvent used for polymerization when using the method (A) is not particularly limited as long as the organic solvent is inert. Examples of the organic solvent include aromatic hydrocarbons such as toluene, xylene, and mesitylene; ketones such as cyclohexanone, cyclopentanone, and methyl ethyl ketone; acetates such as butyl acetate and amyl acetate; halogenated hydrocarbons such as chloroform, dichloromethane, and dichloroethane; ethers such as cyclopentyl methyl ether, tetrahydrofuran, and tetrahydropyran; and the like. Among these, it is preferable to use a compound having a boiling point of 60 to 250° C., and preferably 60 to 150° C., from the viewpoint of handling capability.

Examples of the organic solvent used to dissolve the polymer in the method (A) and the organic solvent used for the method (B) include ketone-based solvents such as acetone, methyl ethyl ketone, methyl isobutyl ketone, cyclopentanone, and cyclohexanone; ester-based solvents such as butyl acetate and amyl acetate; halogenated hydrocarbon-based solvents such as dichloromethane, chloroform, and dichloroethane; ether-based solvents such as tetrahydrofuran, tetrahydropyran, 1,2-dimethoxyethane, 1,4-dioxane, cyclopentyl methyl ether, 1,3-dioxolane; aprotic polar solvents such as N,N-dimethylformamide, N,N-dimethylacetamide, dimethyl sulfoxide, γ-butyrolactone, and N-methylpyrrolidone; and the like. Among these, it is preferable to use a compound having a boiling point of 60 to 200° C. from the viewpoint of handling capability. These solvents may be used either alone or in combination.

A substrate formed of a known organic or inorganic material may be used as the substrate. Examples of the organic material include polycycloolefins (e.g., Zeonex and Zeonor (registered trademark; manufactured by Zeon Corporation); Arton (registered trademark; manufactured by JSR Corporation); and Apel (registered trademark; manufactured by Mitsui Chemicals Inc.)), polyethylene terephthalate, polycarbonate, polyimide, polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use an organic material.

The substrate may be a single-layer substrate, or may be a laminate.

The substrate is preferably a substrate formed of an organic material, and more preferably a resin film formed of the organic material.

The polymer solution (method (A)) or the solution that is subjected to polymerization (method (B)) may be applied to the substrate using a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use the polymerizable composition that includes the initiator (particularly a photoinitiator) in order to implement more efficient polymerization.

Specifically, it is preferable to produce the polymer according to one embodiment of the invention using the method (B) that applies the polymerizable composition according to one embodiment of the invention to a substrate, and polymerizes the applied polymerizable composition. Examples of the substrate include a substrate used to produce an optically anisotropic article (described later), and the like.

The polymerizable composition according to one embodiment of the invention may be applied to the substrate using a known coating method (e.g., bar coating method, spin coating method, roll coating method, gravure coating method, spray coating method, die coating method, cap coating method, or dipping method). A known organic solvent may be added to the polymerizable composition according to one embodiment of the invention in order to improve the applicability of the polymerizable composition. In this case, it is preferable to remove the organic solvent by natural drying, drying by heating, drying under reduced pressure, drying by heating under reduced pressure, or the like after applying the polymerizable composition to the substrate.

The polymerizable compound according to one embodiment of the invention or the polymerizable composition according to one embodiment of the invention may be polymerized by applying activated energy rays, or utilizing a thermal polymerization method, for example. It is preferable to polymerize the polymerizable compound or the polymerizable composition by applying activated energy rays since heating is unnecessary (i.e., the reaction can be effected at room temperature). It is preferable to apply light (e.g., ultraviolet rays) to the polymerizable compound or the polymerizable composition from the viewpoint of convenience.

The temperature during application is preferably set to 30° C. or less. The dose is normally 1 W/m$^2$ to 10 kW/m$^2$, and preferably 5 W/m$^2$ to 2 kW/m$^2$.

A polymer obtained by polymerizing the polymerizable compound according to one embodiment of the invention or the polymerizable composition according to one embodiment of the invention may be removed from the substrate, and used alone, or may be used directly as an optical film organic material or the like without removing the polymer from the substrate.

The number average molecular weight of the polymer according to one embodiment of the invention thus obtained is preferably 500 to 500,000, and more preferably 5000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as a standard (eluant: tetrahydrofuran).

It is considered that the polymer according to one embodiment of the invention has a structure in which crosslinking points are uniformly present within the molecule, and exhibits a high crosslinking efficiency and excellent hardness.

The polymer according to one embodiment of the invention makes it possible to inexpensively produce an optical film that achieves uniform conversion of polarized light over a wide wavelength band, and exhibits satisfactory performance.

4) Optically Anisotropic Article

An optically anisotropic article according to one embodiment of the invention includes the polymer according to one embodiment of the invention.

The optically anisotropic article according to one embodiment of the invention may be obtained by forming an alignment film on a substrate, and forming a liquid crystal layer on the alignment film using the polymer according to one embodiment of the invention.

The alignment film is formed on the surface of the substrate in order to achieve in-plane alignment of an organic semiconductor compound in one direction.

The alignment film may be obtained by applying a solution (alignment film composition) that includes a polymer (e.g., polyimide, polyvinyl alcohol, polyester, polyallylate, polyamideimide, or polyetherimide) to the substrate to form a film, drying the film, and subjecting the film to a rubbing treatment in one direction, for example.

The thickness of the alignment film is preferably 0.001 to 5 µm, and more preferably 0.001 to 1 µm.

The rubbing treatment may be performed on the alignment film or the substrate. The rubbing treatment may be implemented using an arbitrary method. For example, the alignment film may be rubbed in a given direction using a roll around which a cloth or felt formed of synthetic fibers (e.g., nylon) or natural fibers (e.g., cotton) is wound. It is preferable to wash the alignment film with isopropyl alcohol or the like after the rubbing treatment in order to remove fine powder (foreign substances) formed during the rubbing treatment to clean the surface of the alignment film.

The alignment film may be provided with a function of achieving in-plane alignment in one direction by applying polarized UV rays to the surface of the alignment film.

The liquid crystal layer may be formed on the alignment film using the polymer according to one embodiment of the invention by utilizing the method described above in connection with the polymer according to one embodiment of the invention.

Since the optically anisotropic article according to one embodiment of the invention is produced using the polymer according to one embodiment of the invention, the optically anisotropic article can be produced at low cost, exhibits low reflected luminance, achieves uniform conversion of polarized light over a wide wavelength band, and shows satisfactory performance.

Examples of the optically anisotropic article according to one embodiment of the invention include a retardation film, an alignment film for liquid crystal display elements (liquid crystal displays), a polarizer, a viewing angle enhancement film, a color filter, a low-pass filter, an optical polarization prism, an optical filter, and the like.

5) Carbonyl Compound

A carbonyl compound according to one embodiment of the invention is a compound represented by the formula (4) (hereinafter may be referred to as "carbonyl compound (4)").

The carbonyl compound (4) according to one embodiment of the invention may suitably be used as an intermediate for producing the polymerizable compound (I) according to one embodiment of the invention. The method for producing the carbonyl compound (4) has been described in detail above in connection with the polymerizable compound (see "1) Polymerizable compound").

6) Method for Producing Polymerizable Compound, and Method for Using Carbonyl Compound as Raw Material for Producing Polymerizable Compound A method for producing a polymerizable compound according to one embodiment of the invention produces the polymerizable compound (I) according to one embodiment of the invention by reacting the carbonyl compound (4) according to one embodiment of the invention with the hydrazine compound represented by the formula (3). The details of the production method have been described above in connection with the polymerizable compound (see "1) Polymerizable compound").

The method for producing a polymerizable compound according to one embodiment of the invention can efficiently and easily produce the polymerizable compound (1) according to one embodiment of the invention.

A method for using a carbonyl compound as a raw material for producing a polymerizable compound uses the carbonyl compound (4) according to one embodiment of the invention as a raw material for producing the polymerizable compound (I) according to one embodiment of the invention. The details of the method have been described above in connection with the polymerizable compound (see "1) Polymerizable compound").

It is possible to easily produce the polymerizable compound (I) according to one embodiment of the invention in high yield by utilizing the carbonyl compound (4) according to one embodiment of the invention as a raw material.

EXAMPLES

The invention is further described below by way of examples. Note that the invention is not limited to the following examples.

Example 1: Synthesis of Compound 1

Compound 1

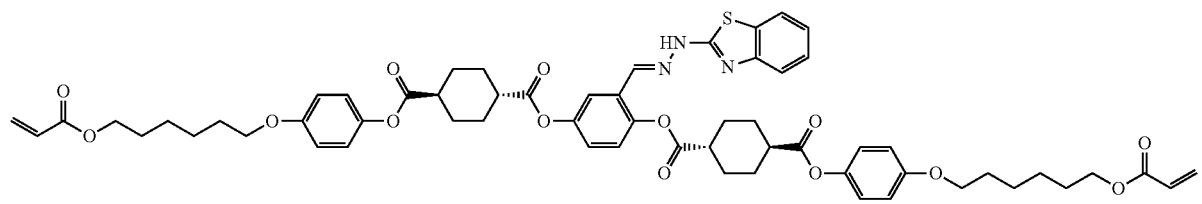

Step 1: Synthesis of Intermediate A

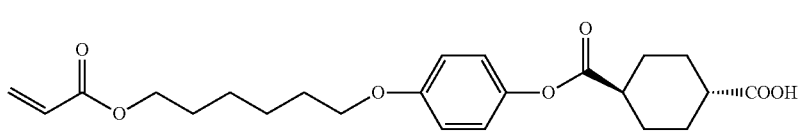

Intermediate A

A three-necked reactor equipped with a thermometer was charged with 17.98 g (104.42 mmol) of trans-1,4-cyclohexanedicarboxylic acid and 180 ml of tetrahydrofuran (THF) under a nitrogen stream. After the addition of 6.58 g (57.43 mmol) of methanesulfonyl chloride to the mixture, the reactor was immersed in a water bath to adjust the temperature of the reaction mixture to 20° C. 6.34 g (62.65 mmol) of triethylamine was added dropwise to the reaction mixture over 10 minutes while maintaining the temperature of the reaction mixture at 20 to 30° C. After the dropwise addition, the mixture was stirred at 25° C. for 2 hours.

After the addition of 0.64 g (5.22 mmol) of 4-(dimethylamino)pyridine and 13.80 g (52.21 mmol) of 4-(6-acryloyloxyhex-1-yloxy)phenol (manufactured by DKSH) to the reaction mixture, the reactor was immersed in a water bath to adjust the temperature of the reaction mixture to 15° C. 6.34 g (62.65 mmol) of triethylamine was added dropwise to the reaction mixture over 10 minutes while maintaining the temperature of the reaction mixture at 20 to 30° C. After the dropwise addition, the mixture was stirred at 25° C. for 2 hours. After completion of the reaction, 1000 ml of distilled water and 100 ml of a saturated sodium chloride solution were added to the reaction mixture, followed by extraction twice with 400 ml of ethyl acetate. The organic layer was collected, and dried over anhydrous sodium sulfate, and sodium sulfate was separated by filtration. The solvent was evaporated from the filtrate using a rotary evaporator, and the residue was purified by silica gel column chromatography (THF:toluene=1:9 (volume ratio (hereinafter the same)) to obtain 14.11 g of an intermediate A as a white solid (yield: 65%).

The structure of the target product was identified by $^1$H-NMR.

$^1$H-NMR (500 MHz, DMSO-$d_6$, TMS, δ ppm): 12.12 (s, 1H), 6.99 (d, 2H, J=9.0 Hz), 6.92 (d, 2H, J=9.0 Hz), 6.32 (dd, 1H, J=1.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.94 (t, 2H, J=6.5 Hz), 2.48-2.56 (m, 1H), 2.18-2.26 (m, 1H), 2.04-2.10 (m, 2H), 1.93-2.00 (m, 2H), 1.59-1.75 (m, 4H), 1.35-1.52 (m, 8H)

Step 2: Synthesis of Intermediate B

A three-necked reactor equipped with a thermometer was charged with 4.00 g (9.56 mmol) of the intermediate A synthesized in the step 1 and 60 ml of THF under a nitrogen stream to prepare a homogeneous solution. After the addition of 1.12 g (9.78 mmol) of methanesulfonyl chloride to the solution, the reactor was immersed in a water bath to adjust the temperature of the reaction mixture to 20° C. 1.01 g (9.99 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After the addition of 0.11 g (0.87 mmol) of 4-(dimethylamino)pyridine and 0.60 g (4.35 mmol) of 2,5-dihydroxybenzaldehyde to the reaction mixture, the reactor was immersed in a water bath to adjust the temperature of the reaction mixture to 15° C. 1.10 g (10.87 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After completion of the reaction, 400 ml of distilled water and 50 ml of a saturated sodium chloride solution were added to the reaction mixture, followed by extraction twice with 750 ml of ethyl acetate. The organic layer was collected, and dried over anhydrous sodium sulfate, and sodium sulfate was separated by filtration. The solvent was evaporated from the filtrate using a rotary evaporator, and the residue was dissolved in 100 ml of THF. 500 ml of methanol was added to the solution to precipitate crystals, which were filtered off. The crystals were washed with methanol, and dried under vacuum to obtain 2.51 g of an intermediate B as a white solid (yield: 62%).

The structure of the target product was identified by $^1$H-NMR.

$^1$H-NMR (500 MHz, DMSO-$d_6$, TMS, δ ppm): 10.02 (s, 1H), 7.67 (d, 1H, J=3.0 Hz), 7.55 (dd, 1H, J=3.0 Hz, 8.5 Hz), 7.38 (d, 1H, J=8.5 Hz), 6.99-7.04 (m, 4H), 6.91-6.96 (m, 4H), 6.32 (dd, 2H, J=1.5 Hz, 17.5 Hz), 6.17 (dd, 2H, J=10.0 Hz, 17.5 Hz), 5.93 (dd, 2H, J=1.5 Hz, 10.0 Hz), 4.11 (t, 4H, J=6.5 Hz), 3.95 (t, 4H, J=6.5 Hz), 2.56-2.81 (m, 4H), 2.10-2.26 (m, 8H), 1.50-1.76 (m, 16H), 1.33-1.49 (m, 8H)

Step 3: Synthesis of Compound 1

A three-necked reactor equipped with a thermometer was charged with 2.30 g (2.45 mmol) of the intermediate B synthesized in the step 2 and 25 ml of THF under a nitrogen stream to prepare a homogeneous solution. 0.49 ml (0.25

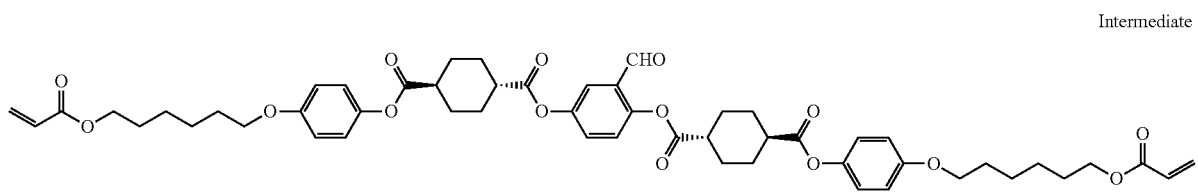

Intermediate B mmol) of concentrated hydrochloric acid was added to the solution. A solution prepared by dissolving 0.40 g (2.45 mol) of 2-hydrazinobenzothiazole in 5 ml of THF was added dropwise to the solution over 15 minutes. After the dropwise addition, the mixture was stirred at 25° C. for 1 hour. After completion of the reaction, the reaction mixture was added to 400 ml of methanol to precipitate a solid, which was filtered off. The solid was dried using a vacuum dryer to obtain 2.4 g of a compound 1 as a light yellow solid (yield: 90%).

The structure of the target product was identified by $^1$H-NMR.

$^1$H-NMR (500 MHz, DMSO-$d_6$, TMS, δ ppm): 12.63 (s, 1H), 8.10 (s, 1H), 7.80 (d, 1H, J=5.0 Hz), 7.60 (d, 1H, J=3.0 Hz), 7.48 (s, 1H), 7.21-7.35 (m, 3H), 7.14 (t, 1H, J=7.5 Hz), 6.98-7.05 (m, 4H), 6.91-6.97 (m, 4H), 6.32 (dd, 2H, J=1.5 Hz, 17.5 Hz), 6.18 (dd, 2H, J=10.0 Hz, 17.5 Hz), 5.93 (dd, 2H, J=1.5 Hz, 10.0 Hz), 4.12 (t, 4H, J=6.5 Hz), 3.95 (t, 4H, J=6.5 Hz), 2.56-2.83 (m, 4H), 2.11-2.30 (m, 8H), 1.52-1.80 (m, 16H), 1.33-1.49 (m, 8H)

Example 2: Synthesis of Compound 2

A three-necked reactor equipped with a thermometer was charged with 182.0 g (3635 mol) of hydrazine monohydrate, followed by heating to 40° C. under a nitrogen stream. A solution prepared by mixing 60.0 g (363.5 mmol) of 1-bromohexane and 60 ml of ethanol was added dropwise to the reactor over 4 hours using a dropping funnel. After the dropwise addition, the mixture was stirred at 40° C. for 1 hour. After cooling the reaction mixture to 25° C., 200 ml of distilled water was added to the reaction mixture, followed by extraction twice with 300 ml of chloroform. The organic layer was collected, and dried over anhydrous sodium sulfate, and sodium sulfate was separated by filtration. The filtrate was concentrated using a rotary evaporator, and the concentrate was distilled under reduced pressure to obtain 10.44 g of an intermediate D as a colorless transparent liquid (degree of vacuum: 3.0 kPa, boiling point: 90° C.) (yield: 25%).

Compound 2

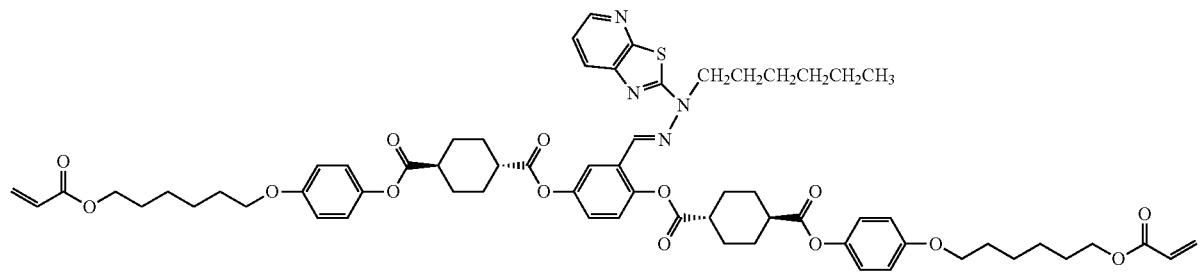

Step 1: Synthesis of Intermediate C

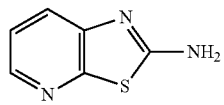

Intermediate C

A three-necked reactor equipped with a thermometer was charged with 9.00 g (70.01 mmol) of 3-amino-2-chloropyridine and 90 ml of concentrated hydrochloric acid under a nitrogen stream to prepare a homogeneous solution. After the addition of 10.21 g (105.01 mmol) of potassium thiocyanate to the solution, the mixture was stirred at 100° C. for 4 hours. After completion of the reaction, the reaction mixture was cooled to 20° C., followed by addition of 90 ml of water. The reaction mixture was added to 300 ml of a saturated sodium hydrogen carbonate aqueous solution while cooling the mixture with ice. The pH of the aqueous solution was adjusted to 8 by adding powdery sodium carbonate to precipitate crystals. The crystals were filtered off, washed with distilled water, and dried using a vacuum dryer to obtain 8.74 g of an intermediate C as a light yellow solid (yield: 83%).

The structure of the target product was identified by $^1$H-NMR.

$^1$H-NMR (500 MHz, DMSO-$d_6$, TMS, δ ppm): 8.11 (dd, 1H, J=1.5 Hz, 5.0 Hz), 7.82 (s, 2H), 7.63 (dd, 1H, J=1.5 Hz, 8.0 Hz), 7.25 (dd, 1H, J=5.0 Hz, 8.0 Hz)

Step 2: Synthesis of Intermediate D

 Intermediate D

The structure of the target product was identified by $^1$H-NMR.

$^1$H-NMR (500 MHz, DMSO-$d_6$, TMS, δ ppm): 3.02 (s, 3H), 2.76 (t, 2H, J=7.0 Hz), 1.44-1.53 (m, 2H), 1.24-1.37 (m, 6H), 0.89 (t, 3H, J=7.0 Hz)

Step 3: Synthesis of Intermediate E

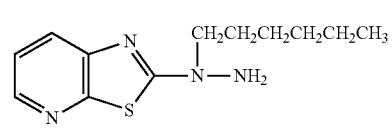

Intermediate E

A three-necked reactor equipped with a thermometer was charged with 2.70 g (17.86 mmol) of the intermediate C synthesized in the step 1, 10.38 g (89.29 mmol) of the intermediate D synthesized in the step 2, 1.49 ml (17.86 mmol) of concentrated hydrochloric acid, and 25 ml of ethylene glycol under a nitrogen stream to prepare a homogenous solution. The solution was stirred at 140° C. for 20 hours. After completion of the reaction, the reaction mixture was cooled to 20° C. 300 ml of distilled water and 50 ml of a saturated sodium chloride solution were added to the reaction mixture, followed by extraction with 500 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=1:9) to obtain 1.33 g of an intermediate E as a light yellow solid (yield: 30%).

The structure of the target product was identified by $^1$H-NMR.

$^1$H-NMR (500 MHz, DMSO-d$_6$, TMS, δ ppm): 8.07 (dd, 1H, J=1.5 Hz, 5.0 Hz), 7.62 (dd, 1H, J=1.5 Hz, 8.0 Hz), 7.22 (dd, 1H, J=5.0 Hz, 8.0 Hz), 5.46 (s, 2H), 3.70 (t, 2H, J=7.0 Hz), 1.64-1.73 (m, 2H), 1.22-1.35 (m, 6H), 0.86 (t, 3H, J=7.0 Hz)

Step 4: Synthesis of Compound 2

A three-necked reactor equipped with a thermometer was charged with 1.20 g (1.28 mmol) of the intermediate B synthesized in the step 2 of Example 1 and 30 ml of THF under a nitrogen stream to prepare a homogeneous solution. After the addition of 0.26 ml (0.26 mmol) of 1 N hydrochloric acid, a solution prepared by dissolving 0.48 g (1.92 mmol) of the intermediate E synthesized in the step 3 in 5 ml of THF was added dropwise to the mixture over 15 minutes. After the dropwise addition, the mixture was stirred at 25° C. for 5 hours. 250 ml of methanol was added to the reaction mixture to precipitate a solid, which was filtered off. The solid was purified by silica gel column chromatography (chloroform:THF=97:3) to obtain 1.25 g of a compound 2 as a light yellow solid (yield: 84%).

The structure of the target product was identified by $^1$H-NMR.

$^1$H-NMR (500 MHz, DMSO-d$_6$, TMS, δ ppm): 8.30 (dd, 1H, J=1.5 Hz, 5.0 Hz), 7.96 (dd, 1H, J=1.5 Hz, 8.0 Hz), 7.89 (s, 1H), 7.63 (d, 1H, J=3.0 Hz), 7.39 (dd, 1H, J=5.0 Hz, 8.0 Hz), 7.32 (d, 1H, J=8.5 Hz), 7.27 (dd, 1H, J=3.0 Hz, 8.5 Hz), 6.98-7.04 (m, 4H), 6.91-6.97 (m, 4H), 6.32 (dd, 2H, J=1.5 Hz, 17.5 Hz), 6.17 (dd, 2H, J=10.0 Hz, 17.5 Hz), 5.93 (dd, 2H, J=1.5 Hz, 10.0 Hz), 4.35 (t, 2H, J=7.0 Hz), 4.11 (t, 4H, J=6.5 Hz), 3.95 (t, 4H, J=6.5 Hz), 2.56-2.84 (m, 4H), 2.11-2.30 (m, 8H), 1.52-1.75 (m, 18H), 1.22-1.49 (m, 14H), 0.85 (t, 3H, J=7.0 Hz)

Example 3: Synthesis of Compound 3 the addition of 51.8 g (375 mmol) of potassium carbonate and 19.4 ml (312 mmol) of methyl iodide to the solution, the mixture was stirred at 25° C. for 20 hours. After completion of the reaction, the reaction mixture was filtered through celite. The filtrate was added to 500 ml of water, and extracted with 500 ml of ethyl acetate. The ethyl acetate layer was dried over anhydrous sodium sulfate, and sodium sulfate was separated by filtration. Ethyl acetate was evaporated from the filtrate under reduced pressure using a rotary evaporator to obtain a white solid. The white solid was recrystallized from n-hexane (125 ml) to obtain 20.3 g of an intermediate F as colorless crystals (yield: 86.3%).

The structure of the target product was identified by $^1$H-NMR.

$^1$H-NMR (500 MHz, CDCl$_3$, TMS, δ ppm): 8.19-8.22 (m, 2H), 7.52-7.48 (m, 2H), 6.69 (s, 2H), 3.95 (s, 6H)

Step 2: Synthesis of Intermediate G

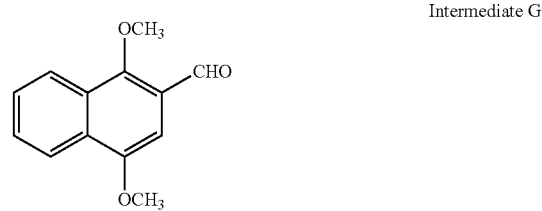 [SMILES: COc1cc(C=O)c(OC)c2ccccc12]

Intermediate G

A four-necked reactor equipped with a thermometer was charged with 15.0 g (79.7 mmol) of the intermediate F synthesized in the step 1 and 100 ml of dichloromethane under a nitrogen stream to prepare a homogeneous solution. After the addition of 91.7 g (91.7 mmol) of titanium tetrachloride (1.0 M dichloromethane solution) and 8.11 ml (91.7

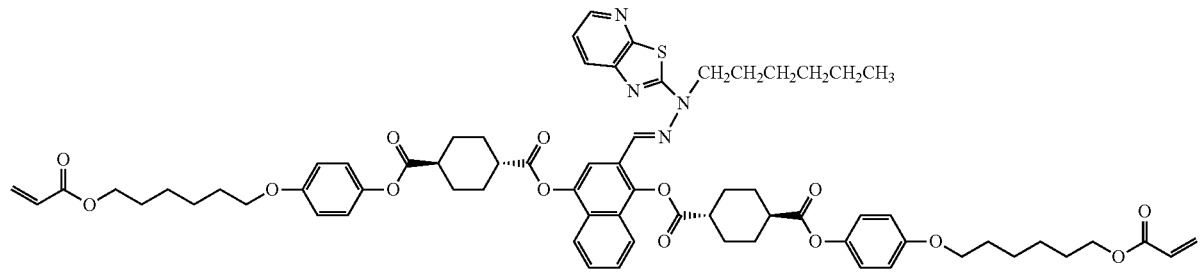

Compound 3

Step 1: Synthesis of Intermediate F

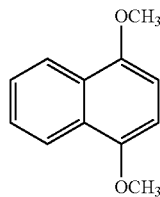

Intermediate F

A four-necked reactor equipped with a thermometer was charged with 20.0 g (125 mmol) of 1,4-dihydroxynaphthalene and 200 ml of N,N-dimethylformamide (DMF) under a nitrogen stream to prepare a homogeneous solution. After mmol) of dichloromethyl methyl ether dropwise to the solution, the mixture was stirred at 0° C. for 1 hour. After completion of the reaction, the reaction mixture was added to 300 ml of ice water, and extracted with 500 ml of ethyl acetate. After drying the ethyl acetate layer over anhydrous magnesium sulfate, magnesium sulfate was separated by filtration. Ethyl acetate was evaporated from the filtrate under reduced pressure using a rotary evaporator to obtain a white solid. The white solid was recrystallized from n-hexane (260 ml) to obtain 16.6 g of an intermediate G as colorless crystals (yield: 96.4%).

The structure of the target product was identified by $^1$H-NMR.

$^1$H-NMR (500 MHz, CDCl$_3$, TMS, δ ppm): 10.58 (s, 1H), 8.28-8.31 (m, 1H), 8.20-8.22 (m, 1H), 7.61-7.67 (m, 2H), 7.13 (s, 1H), 4.10 (s, 3H), 4.03 (s, 3H)

Step 3: Synthesis of Intermediate H

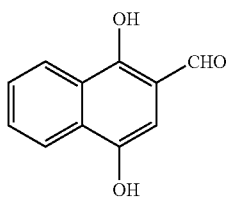

Intermediate H

A four-necked reactor equipped with a thermometer was charged with 16.6 g (76.8 mmol) of the intermediate G synthesized in the step 2 and 100 ml of dichloromethane under a nitrogen stream to prepare a homogeneous solution. The solution was cooled to −40° C. After the addition of 230 ml (230 mmol) of boron tribromide (17% dichloromethane solution) dropwise to the solution, the mixture was heated to 25° C., and stirred for 2 hours. After completion of the reaction, the reaction mixture was added to 500 ml of ice water, and extracted with 500 ml of dichloromethane. After drying the dichloromethane layer over anhydrous magnesium sulfate, magnesium sulfate was separated by filtration. Dichloromethane was evaporated from the filtrate under reduced pressure using a rotary evaporator to obtain a yellow solid. The yellow solid was purified by silica gel column chromatography (n-hexane:ethyl acetate=70:30) to obtain 12.7 g of an intermediate H as a yellow solid (yield: 87.9%).

The structure of the target product was identified by $^1$H-NMR.

$^1$H-NMR (500 M Hz, CDCl$_3$, TMS, δ ppm): 12.31 (s, 1H), 9.88 (s, 1H), 8.45 (d, 1H, J=8.5 Hz), 8.16 (d, 1H, J=8.5 Hz), 7.72 (dd, 1H, J=7.8 Hz, 8.5 Hz), 7.61 (dd, 1H, J=7.8 Hz, 8.5 Hz), 6.83 (s, 1H), 5.17 (s, 1H)

Step 4: Synthesis of Intermediate I

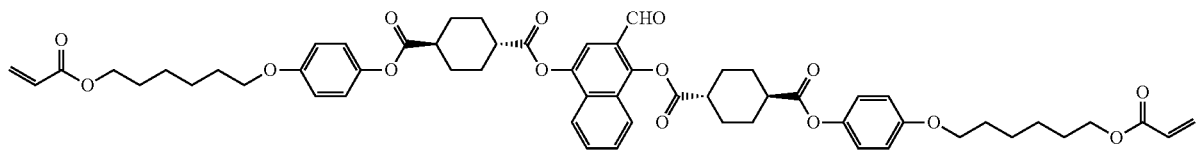

Intermediate I

A three-necked reactor equipped with a thermometer was charged with 3.19 g (7.61 mmol) of the intermediate A synthesized in the step 1 of Example 1 and 50 ml of THF under a nitrogen stream to prepare a homogeneous solution. After the addition of 0.91 g (7.93 mmol) of methanesulfonyl chloride to the solution, the reactor was immersed in a water bath to adjust the temperature of the reaction mixture to 20° C. 0.80 g (7.93 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After the addition of 0.08 g (0.63 mmol) of 4-(dimethylamino)pyridine and 0.60 g (3.17 mmol) of the intermediate H synthesized in the step 3 to the reaction mixture, the reactor was immersed in a water bath to adjust the temperature of the reaction mixture to 15° C. 0.80 g (7.93 mmol) of triethylamine was added dropwise to the reaction mixture over 5 minutes while maintaining the temperature of the reaction mixture at 20 to 30° C. After the dropwise addition, the mixture was stirred at 25° C. for 2 hours. 150 ml of distilled water and 50 ml of a saturated sodium chloride solution were added to the reaction mixture, followed by extraction twice with 300 ml of ethyl acetate. The organic layer was collected, and dried over anhydrous sodium sulfate, and sodium sulfate was separated by filtration. The filtrate was concentrated using a rotary evaporator, and the resulting solid was dissolved in 100 ml of THF. 500 ml of methanol was added to the solution to precipitate crystals, which were filtered off. The crystals were washed with methanol, and dried under vacuum to obtain 1.82 g of an intermediate I as a grayish white solid (yield; 58%).

The structure of the target product was identified by $^1$H-NMR.

1H-NMR (500 MHz, DMSO-d$_6$, TMS, δ ppm): 10.22 (s, 1H), 8.11 (d, 1H, J=8.5 Hz), 7.99 (d, 1H, J=8.5 Hz), 7.76-7.91 (m, 2H), 7.71 (s, 1H), 7.01-7.07 (m, 4H), 6.91-6.98 (m, 4H), 6.32 (dd, 2H, J=1.5 Hz, 17.5 Hz), 6.18 (dd, 2H, J=10.0 Hz, 17.5 Hz), 5.94 (dd, 2H, J=1.5 Hz, 10.0 Hz), 4.12 (t, 4H, J=6.5 Hz), 3.96 (t, 4H, J=6.5 Hz), 3.02-3.12 (m, 1H), 2.86-2.97 (m, 1H), 2.60-2.74 (m, 2H), 2.28-2.43 (m, 4H), 2.14-2.27 (m, 4H), 1.54-1.86 (m, 16H), 1.30-1.53 (m, 8H)

Step 5: Synthesis of Compound 3

A three-necked reactor equipped with a thermometer was charged with 1.67 g (1.69 mmol) of the intermediate I synthesized in the step 4 and 30 ml of THF under a nitrogen stream to prepare a homogeneous solution. After the addition of 0.34 ml (0.34 mmol) of 1 N hydrochloric acid to the solution, a solution prepared by dissolving 0.85 g (3.38 mol) of the intermediate E synthesized in the step 3 of Example 2 in 5 ml of THF was added dropwise to the mixture over 30 minutes. After the dropwise addition, the mixture was stirred at 25° C. for 5 hours. The reaction mixture was added to 250 ml of methanol to precipitate a solid, which was filtered off. The solid was purified by silica gel column chromatography (chloroform:THF=97:3) to obtain 1.61 g of a compound 3 as a light yellow solid (yield: 78%).

The structure of the target product was identified by $^1$H-NMR.

$^1$H-NMR (500 MHz, DMSO-d$_6$, TMS, δ ppm): 8.31 (dd, 1H, J=1.5 Hz, 5.0 Hz), 7.94-7.99 (m, 2H), 7.88-7.94 (m, 2H), 7.78 (s, 1H), 7.69-7.76 (m, 2H), 7.40 (dd, 1H, J=5.0 Hz, 8.0 Hz), 6.99-7.08 (m, 4H), 6.90-6.98 (m, 4H), 6.32 (dd, 2H, J=1.5 Hz, 17.5 Hz), 6.18 (dd, 2H, J=10.0 Hz, 17.5 Hz), 5.94 (dd, 2H, J=1.5 Hz, 10.0 Hz), 4.40 (t, 2H, J=7.0 Hz), 4.12 (t, 4H, J=6.5 Hz), 3.96 (t, 2H, J=6.5 Hz), 3.95 (t, 2H, J=6.5 Hz), 2.89-3.12 (m, 2H), 2.61-2.75 (m, 2H), 2.30-2.42 (m, 4H), 2.15-2.28 (m, 4H), 1.55-1.85 (m, 18H), 1.19-1.52 (m, 14H), 0.86 (t, 3H, J=7.0 Hz)

Example 4: Synthesis of Compound 4

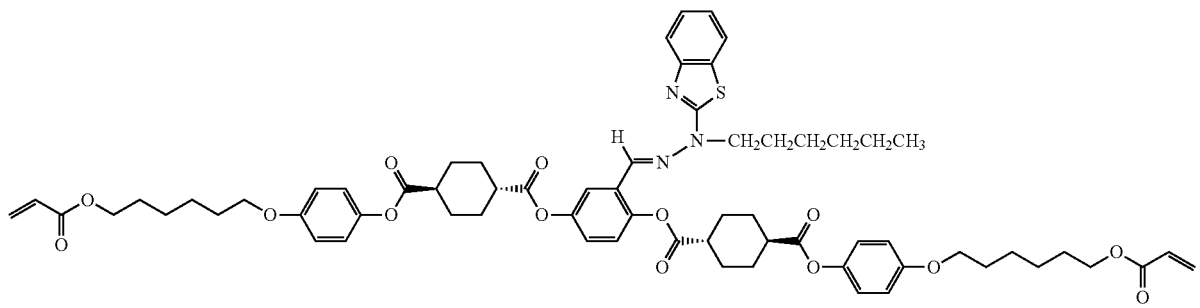

Compound 4

Step 1: Synthesis of Intermediate J

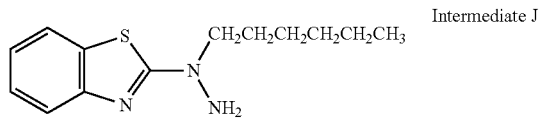

Intermediate J

A four-necked reactor equipped with a thermometer was charged with 2.00 g (12.1 mmol) of 2-hydrazinobenzothiazole and 20 ml of DMF under a nitrogen stream to prepare a homogeneous solution. After the addition of 8.36 g (60.5 mmol) of potassium carbonate and 3.08 g (14.5 mmol) of 1-iodohexane to the solution, the mixture was stirred at 50° C. for 7 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (hexane:ethyl acetate=75:25) to obtain 2.10 g of an intermediate J as a white solid (yield: 69.6%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 8.0 Hz, 8.0 Hz), 7.06 (ddd, 1H, J=1.0 Hz, 8.0 Hz, 8.0 Hz), 4.22 (s, 2H), 3.74 (t, 2H, J=7.5 Hz), 1.69-1.76 (m, 2H), 1.29-1.42 (m, 6H), 0.89 (t, 3H, J=7.0 Hz)

Step 2: Synthesis of Compound 4

A four-necked reactor equipped with a thermometer was charged with 697 mg (2.37 mmol) of the intermediate J synthesized in the step 1, 2.00 g (2.13 mmol) of the intermediate B synthesized in Example 1, 3 ml of ethanol, and 20 ml of THF under a nitrogen stream to prepare a homogeneous solution. After the addition of 55.1 mg (0.24 mmol) of (±)-10-camphorsulfonic acid to the solution, the mixture was stirred at 40° C. for 5 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a white solid. The white solid was purified by silica gel column chromatography (toluene:ethyl acetate=90:10) to obtain 2.24 g of a compound 4 as a white solid (yield: 86.4%).

The structure of the target product was identified by $^1$H-NMR.

$^1$H-NMR (400 MHz, CDCl$_3$, TMS, δ ppm): 7.75 (d, 1H, J=2.5 Hz), 7.67-7.70 (m, 3H), 7.34 (ddd, 1H, J=1.0 Hz, 7.0 Hz, 7.5 Hz), 7.17 (ddd, 1H, J=1.0 Hz, 7.5 Hz, 7.5 Hz), 7.12 (d, 1H, J=9.0 Hz), 7.10 (dd, 1H, J=2.5 Hz, 9.0 Hz), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.0 Hz), 6.13 (dd, 2H, J=10.5 Hz, 17.5 Hz), 5.82 (dd, 2H, J=1.5 Hz, 10.5 Hz), 4.30 (t, 2H, J=8.0 Hz), 4.18 (t, 4H, J=6.5 Hz), 3.95 (t, 4H, J=6.5 Hz), 2.58-2.70 (m, 4H), 2.31-2.35 (m, 8H), 1.66-1.82 (m, 18H), 1.31-1.54 (m, 14H), 0.90 (t, 3H, J=7.0 Hz)

Example 5: Synthesis of Compound 5

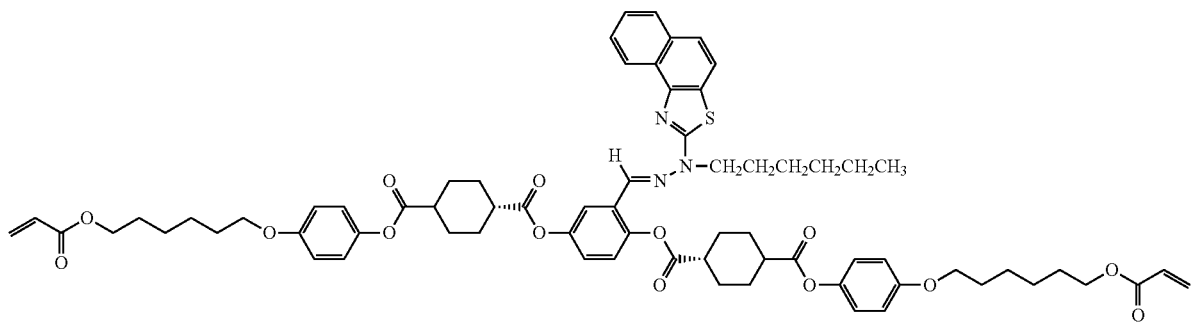

Compound 5

Step 1: Synthesis of Intermediate K

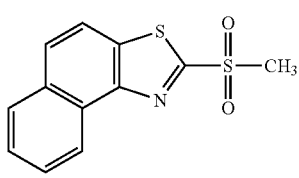

Intermediate K

A four-necked reactor equipped with a thermometer was charged with 1.50 g (6.48 mmol) of 2-(methylthio)naphtho[1,2d]thiazole and 15 ml of methylene chloride under a nitrogen stream to prepare a homogeneous solution. After the addition of 3.52 g (14.3 mmol) of 3-chloroperbenzoic acid (water content: about 30%) to the solution, the mixture was stirred at 25° C. for 8 hours. After completion of the reaction, the reaction mixture was added to 100 ml of saturated sodium bicarbonate water, and extracted twice with 200 ml of methylene chloride. After drying the methylene chloride layer over anhydrous magnesium sulfate, magnesium sulfate was separated by filtration. Methylene chloride was evaporated from the filtrate under reduced pressure using a rotary evaporator to obtain a white solid. The white solid was purified by silica gel column chromatography (toluene:ethyl acetate=90:10) to obtain 1.49 g of an intermediate K as a white solid (yield: 74.6%).

The structure of the target product was identified by $^1$H-NMR and $^{13}$C-NMR.

$^1$H-NMR (400 MHz, CDCl$_3$, TMS, δ ppm): 8.84 (d, 1H, J=7.6 Hz), 8.00 (d, 1H, J=8.0 Hz), 7.99 (d, 1H, J=9.2 Hz), 7.95 (d, 1H, J=9.2 Hz), 7.75 (dd, 1H, J=7.6 Hz, 8.0 Hz), 7.68 (dd, 1H, J=7.6 Hz, 7.6 Hz), 3.48 (s, 3H)

$^{13}$C-NMR (100 MHz, CDCl$_3$, TMS, δ ppm): 164.6, 149.7, 134.7, 132.3, 129.5, 129.2, 128.4, 128.1, 127.5, 124.0, 118.7, 42.8

Step 2: Synthesis of Intermediate L

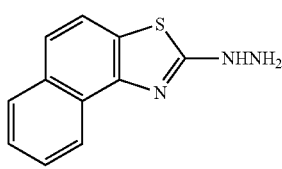

Intermediate L

A four-necked reactor equipped with a thermometer was charged with 1.49 g (4.83 mmol) of the intermediate K synthesized by the step 1, 1.2 ml (24.2 mmol) of hydrazine monohydrate, 10 ml of 1-propanol, and 5 ml of THF under a nitrogen stream to prepare a homogenous solution. The solution was stirred at 80° C. for 4 hours. After completion of the reaction, the reaction mixture was cooled to 20° C., followed by addition of 20 ml of water to precipitate a solid, which was filtered off. The solid was washed with water, and dried using a vacuum dryer to obtain 993 mg of an intermediate L as a light yellow solid (yield: 95.5%).

The structure of the target product was identified by $^1$H-NMR.

$^1$H-NMR (500 MHz, DMSO-d$_6$, TMS, δ ppm): 9.20 (s, 1H), 8.34 (d, 1H, J=8.0 Hz), 7.90 (d, 1H, J=8.0 Hz), 7.83 (d, 1H, J=8.5 Hz), 7.53 (d, 1H, J=8.5 Hz), 7.51 (dd, 1H, J=7.5 Hz, 8.0 Hz), 7.46 (dd, 1H, J=7.5 Hz, 8.0 Hz), 5.12 (s, 2H)

Step 3: Synthesis of Intermediate M

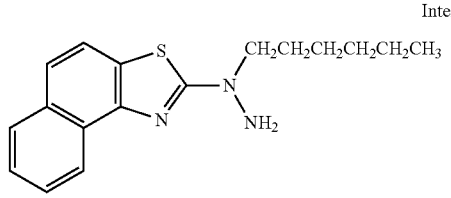

Intermediate M

A four-necked reactor equipped with a thermometer was charged with 993 mg (4.61 mmol) of the intermediate L synthesized in the step 2 and 10 ml of DMF under a nitrogen stream to prepare a homogeneous solution. After the addition of 3.00 g (9.22 mmol) of cesium carbonate and 1.17 g (5.53 mmol) of 1-iodohexane to the solution, the mixture was stirred at 25° C. for 5 hours. After completion of the reaction, the reaction mixture was added to 100 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a light yellow solid. The yellow solid was purified by silica gel column chromatography (hexane: ethyl acetate=90:10) to obtain 545 mg of an intermediate M as a white solid (yield: 39.4%).

The structure of the target product was identified by $^1$H-NMR.

$^1$H-NMR (500 MHz, CDCl$_3$, TMS, δ ppm): 8.57 (d, 1H, J=8.0 Hz), 7.85 (d, 1H, J=8.0 Hz), 7.69 (d, 1H, J=8.5 Hz), 7.532 (d, 1H, J=8.5 Hz), 7.531 (dd, 1H, J=7.5 Hz, 8.0 Hz), 7.46 (dd, 1H, J=7.5 Hz, 8.0 Hz), 4.27 (s, 2H), 3.83 (t, 2H, J=7.5 Hz), 1.76 (tt, 2H, J=7.5 Hz, 7.5 Hz), 1.34-1.45 (m, 6H), 0.90 (t, 3H, J=7.0 Hz)

Step 4: Synthesis of Intermediate N

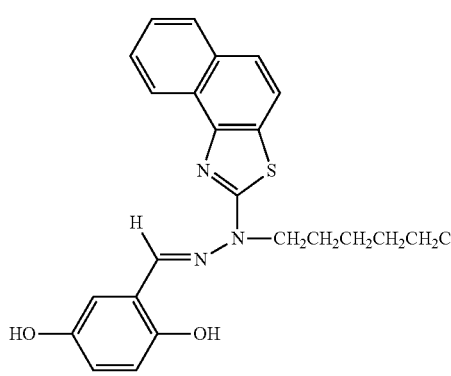

Intermediate N

A four-necked reactor equipped with a thermometer was charged with 545 mg (1.82 mmol) of 2,5-dihydroxybenzaldehyde, 1.40 g (1.40 mmol) of the intermediate M synthesized in the step 3, and 10 ml of 1-propanol under a nitrogen stream to prepare a homogenous solution. After the addition of 42.3 mg (0.18 mmol) of (±)-10-camphorsulfonic acid to the solution, the mixture was stirred at 25° C. for 4 hours. After completion of the reaction, 100 ml of water was added to the mixture to precipitate a solid, which was filtered off. The solid was washed with water, and dried using a vacuum dryer to obtain 588 mg of an intermediate N as a yellow solid (yield: 76.9%).

The structure of the target product was identified by ¹H-NMR.

¹H-NMR (500 MHz, DMSO-d₆, TMS, δ ppm): 9.42 (s, 1H), 8.99 (s, 1H), 8.51 (d, 1H, J=8.0 Hz), 8.19 (s, 1H), 7.98 (d, 1H, J=8.0 Hz), 7.96 (d, 1H, J=8.5 Hz), 7.70 (d, 1H, J=8.5 Hz), 7.61 (dd, 1H, J=7.5 Hz, 8.0 Hz), 7.54 (dd, 1H, J=7.5 Hz, 8.0 Hz), 7.22 (d, 1H, J=3.0 Hz), 6.78 (d, 1H, J=9.0 Hz), 6.71 (dd, 1H, J=3.0 Hz, 9.0 Hz), 4.47 (t, 2H, J=7.0 Hz), 1.75 (tt, 2H, J=7.0 Hz, 7.0 Hz), 1.38-1.46 (m, 4H), 1.26-1.33 (m, 2H), 0.86 (t, 3H, J=7.5 Hz)

Step 5: Synthesis of Compound 5

A four-necked reactor equipped with a thermometer was charged with 588 mg (1.40 mmol) of the intermediate N synthesized in the step 4, 1.47 g (3.50 mmol) of the intermediate A synthesized in Example 1, 85.5 mg (0.70 mmol) of 4-(dimethylamino)pyridine, and 15 ml of N-methylpyrrolidone under a nitrogen stream to prepare a homogeneous solution. After the addition of 805 mg (4.20 mmol) of 1-ethyl-3-(3-dimethylaminopropyl)carbodiimide hydrochloride (WSC) to the solution, the mixture was stirred at 25° C. for 5 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a white solid. The white solid was purified by silica gel column chromatography (toluene:ethyl acetate=90:10) to obtain 1.12 g of a compound 5 as a white solid (yield: 65.5%).

The structure of the target product was identified by ¹H-NMR.

1H-NMR (500 MHz, CDCl₃, TMS, δ ppm): 8.63 (d, 1H, J=8.0 Hz), 7.89 (d, 1H, J=8.0 Hz), 7.78 (d, 1H, J=2.5 Hz), 7.76 (d, 1H, J=8.5 Hz), 7.63 (d, 1H, J=8.5 Hz), 7.58 (dd, 1H, J=7.5 Hz, 8.0 Hz), 7.50 (dd, 1H, J=7.5 Hz, 8.0 Hz), 7.13 (d, 1H, J=9.0 Hz), 7.10 (dd, 1H, J=2.5 Hz, 9.0 Hz), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.0 Hz), 6.13 (dd, 2H, J=10.5 Hz, 17.0 Hz), 5.82 (dd, 2H, J=1.5 Hz, 10.5 Hz), 4.42 (t, 2H, J=7.5 Hz), 4.17 (t, 4H, J=6.5 Hz), 3.94 (t, 4H, J=6.0 Hz), 3.47 (d, 1H, J=4.5 Hz), 2.57-2.71 (m, 4H), 2.30-2.35 (m, 8H), 1.76-1.82 (m, 6H), 1.66-1.74 (m, 12H), 1.32-1.54 (m, 14H), 0.92 (t, 3H, J=7.5 Hz)

Example 6: Synthesis of Compound 6

Step 1: Synthesis of Intermediate O

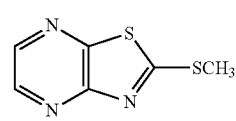

Intermediate O

A four-necked reactor equipped with a thermometer was charged with 3.46 g (26.7 mmol) of 2-amino-3-chloropyrazine, 8.56 g (53.4 mmol) of potassium ethylxanthate, and 30 ml of DMF under a nitrogen stream to prepare a homogeneous solution. The solution was refluxed with heating for 7 hours, and the reaction mixture was cooled to 0° C. After the addition of 3.3 ml (53.4 mmol) of methyl iodide, the mixture was stirred at 0° C. for 1 hour. After completion of the reaction, the reaction mixture was added to 300 ml of water, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 4.38 g of an intermediate O as a light yellow solid (yield: 89.5%).

The structure of the target product was identified by ¹H-NMR.

¹H-NMR (500 MHz, CDCl₃, TMS, δ ppm): 8.55 (d, 1H, J=2.5 Hz), 8.37 (d, 1H, J=2.5 Hz), 2.88 (s, 3H)

¹³C-NMR (125 MHz, CDCl₃, TMS, δ ppm): 175.2, 158.0, 153.3, 141.7, 139.4, 15.4

Step 2: Synthesis of Intermediate P

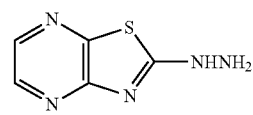

Intermediate P

A four-necked reactor equipped with a thermometer was charged with 1.50 g (8.19 mmol) of the intermediate O synthesized in the step 1, 4.0 ml (81.9 mmol) of hydrazine monohydrate, and 10 ml of ethanol under a nitrogen stream to prepare a homogenous solution. The solution was stirred at 25° C. for 5 hours. After completion of the reaction, the reaction mixture was added to 100 ml of water to precipitate a solid, which was filtered off. The solid was washed with Compound 6

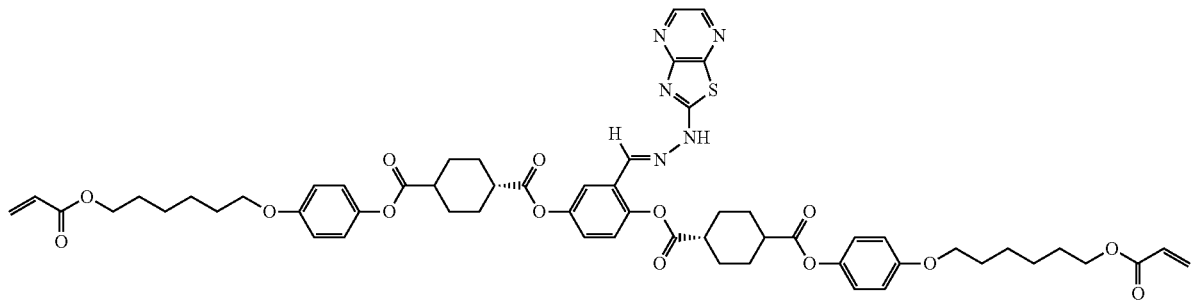

water, and dried using a vacuum dryer to obtain 1.15 g of an intermediate P as a yellow solid (yield: 84.0%).

The structure of the target product was identified by $^1$H-NMR and $^{13}$C-NMR.

$^1$H-NMR (400 MHz, DMSO-d$_6$, TMS, δ ppm): 9.99 (brs, 1H), 8.17 (d, 1H, J=2.6 Hz), 7.97 (d, 1H, J=2.6 Hz), 5.30 (s, 2H)

$^{13}$C-NMR (100 MHz, DMSO-d$_6$, TMS, δ ppm): 175.5, 160.4, 150.8, 140.7, 135.3

Step 3: Synthesis of Compound 6

A four-necked reactor equipped with a thermometer was charged with 390 mg (2.34 mmol) of the intermediate P synthesized in the step 2, 2.08 mg (2.22 mmol) of the intermediate B synthesized in Example 1, 3 ml of ethanol, and 15 ml of THF under a nitrogen stream to prepare a homogeneous solution. After the addition of 54.4 mg (0.23 mmol) of (±)-10-camphorsulfonic acid to the solution, the mixture was stirred at 40° C. for 5 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a light yellow solid. The light yellow solid was purified by silica gel column chromatography (chloroform:methanol=95:5) to obtain 1.82 g of a compound 6 as a light yellow solid (yield: 75.3%).

The structure of the target product was identified by $^1$H-NMR.

$^1$H-NMR (500 MHz, CDCl$_3$, TMS, δ ppm): 13.00 (brs, 1H), 8.84 (s, 1H), 8.33 (d, 1H, J=2.5 Hz), 8.22 (d, 1H, J=2.5 Hz), 7.71 (d, 1H, J=2.5 Hz), 7.19 (dd, 1H, J=2.5 Hz, 9.0 Hz), 7.14 (d, 1H, J=9.0 Hz), 6.99 (d, 2H, J=9.0 Hz), 6.96 (d, 2H, J=9.0 Hz), 6.88 (d, 2H, J=9.0 Hz), 6.86 (d, 2H, J=9.0 Hz), 6.403 (dd, 1H, J=1.5 Hz, 17.5 Hz), 6.398 (dd, 1H, J=1.5 Hz, 17.5 Hz), 6.13 (dd, 1H, J=10.5 Hz, 17.5 Hz), 6.12 (dd, 1H, J=10.5 Hz, 17.5 Hz), 5.822 (dd, 1H, J=1.5 Hz, 10.5 Hz), 5.817 (dd, 1H, J=1.5 Hz, 10.5 Hz), 4.18 (t, 2H, J=7.0 Hz), 4.17 (t, 2H, J=7.0 Hz), 3.95 (t, 2H, J=6.5 Hz), 3.93 (t, 2H, J=6.5 Hz), 2.59-2.66 (m, 3H), 2.46-2.52 (m, 1H), 2.17-2.34 (m, 8H), 1.41-1.82 (m, 24H)

Example 7: Synthesis of Compound 7

Step 1: Synthesis of Intermediate Q

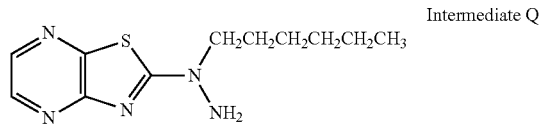

Intermediate Q

A four-necked reactor equipped with a thermometer was charged with 4.17 g (24.9 mmol) of the intermediate P synthesized in the step 2 of Example 6 and 30 ml of DMF under a nitrogen stream to prepare a homogeneous solution. After the addition of 16.2 g (49.8 mmol) of cesium carbonate and 4.4 ml (29.9 mmol) of 1-iodohexane to the solution, the mixture was stirred at 25° C. for 5 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a white solid. The white solid was purified by silica gel column chromatography (toluene:ethyl acetate=60:40) to obtain 1.69 g of an intermediate Q as a white solid (yield: 27.0%).

The structure of the target product was identified by $^1$H-NMR.

$^1$H-NMR (500 MHz, DMSO-d$_6$, TMS, δ ppm): 8.22 (d, 1H, J=3.0 Hz), 8.02 (d, 1H, J=3.0 Hz), 5.65 (s, 2H), 3.78 (t, 2H, J=7.0 Hz), 1.71 (tt, 2H, J=7.0 Hz, 7.0 Hz), 1.26-1.32 (m, 6H), 0.86 (t, 3H, J=7.0 Hz)

Step 2: Synthesis of Compound 7

A four-necked reactor equipped with a thermometer was charged with 338 mg (1.34 mmol) of the intermediate Q synthesized in the step 1, 1.20 g (1.28 mmol) of the intermediate B synthesized in Example 1, 3 ml of ethanol, and 10 ml of THF under a nitrogen stream to prepare a homogeneous solution. After the addition of 15.6 mg (0.13 mmol) of (±)-10-camphorsulfonic acid to the solution, the mixture was stirred at 40° C. for 5 hours. After completion of the reaction, the reaction mixture was added to 100 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a white solid. The white solid was purified by silica gel column chromatography (toluene:ethyl acetate=90:10) to obtain 1.21 g of a compound 7 as a white solid (yield: 79.4%).

The structure of the target product was identified by $^1$H-NMR.

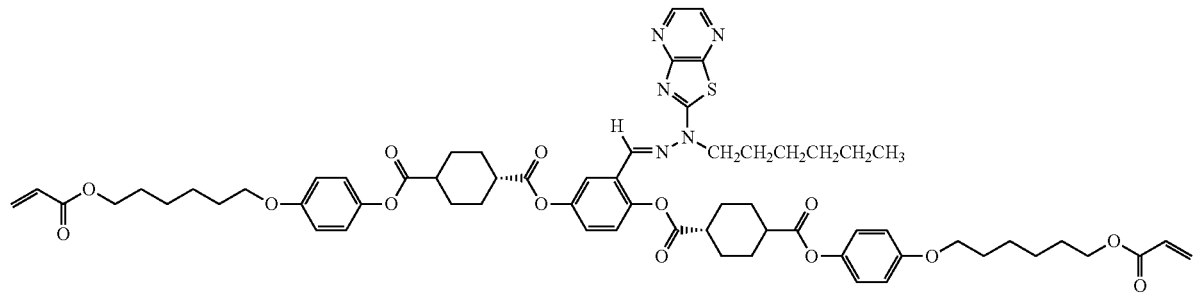

$^1$H-NMR (500 MHz, CDCl$_3$, TMS, δ ppm): 8.39 (d, 1H, J=2.5 Hz), 8.20 (d, 1H, J=2.5 Hz), 7.84 (s, 1H), 7.75 (d, 1H, J=2.0 Hz), 7.14-7.18 (m, 2H), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.36 (t, 2H, J=7.5 Hz), 4.18 (t, 4H, J=6.5 Hz), 3.95 (t, 4H, J=6.5 Hz), 2.56-2.72 (m, 4H), 2.25-2.36 (m, 8H), 1.69-1.83 (m, 18H), 1.41-1.54 (m, 10H), 1.30-1.39 (m, 4H), 0.90 (t, 3H, J=7.0 Hz)

Example 8: Synthesis of Compound 8

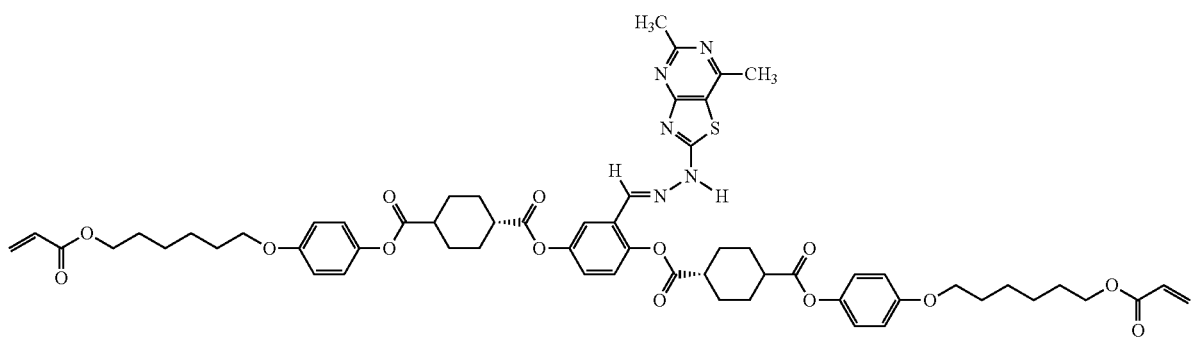

Compound 8

Step 1: Synthesis of Intermediate R

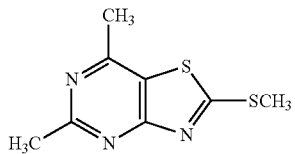

Intermediate R

A four-necked reactor equipped with a thermometer was charged with 8.89 g (56.4 mmol) of 4-amino-5-chloro-2,6-dimethylpyrimidine, 18.1 g (113 mmol) of potassium ethylxanthate, and 100 ml of DMF under a nitrogen stream to prepare a solution. The solution was refluxed with heating for 8 hours, and the reaction mixture was cooled to 0° C. After the addition of 7.0 ml (113 mmol) of methyl iodide, the mixture was stirred at 0° C. for 1 hour. After completion of the reaction, the reaction mixture was added to 500 ml of water, and extracted with 700 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=80:20) to obtain 6.88 g of an intermediate R as a light yellow solid (yield: 57.7%).

The structure of the target product was identified by $^1$H-NMR.

$^1$H-NMR (400 MHz, CDCl$_3$, TMS, δ ppm): 2.83 (s, 3H), 2.79 (s, 3H), 2.67 (s, 3H)

Step 2: Synthesis of Intermediate S

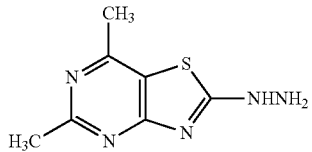

Intermediate S

A four-necked reactor equipped with a thermometer was charged with 4.54 g (21.5 mmol) of the intermediate R synthesized in the step 1, 10.0 ml (215 mmol) of hydrazine monohydrate, and 80 ml of ethanol under a nitrogen stream to prepare a solution. The solution was stirred at 25° C. for 2 hours. After completion of the reaction, the reaction mixture was added to 300 ml of water to precipitate a solid, which was filtered off. The solid was washed with water, and dried using a vacuum dryer to obtain 4.12 g of an intermediate S as a light yellow solid (yield: 98.1%).

The structure of the target product was identified by $^1$H-NMR and $^{13}$C-NMR.

$^1$H-NMR (500 MHz, DMSO-d$_6$, TMS, δ ppm): 10.08 (s, 1H), 5.36 (s, 2H), 2.48 (s, 3H), 2.45 (s, 3H)

$^{13}$C-NMR (125 MHz, DMSO-d$_6$, TMS, δ ppm): 178.2, 170.9, 167.8, 156.3, 118.0, 25.3, 23.2

Step 3: Synthesis of Compound 8

A four-necked reactor equipped with a thermometer was charged with 460 mg (2.36 mmol) of the intermediate S synthesized in the step 2, 2.00 g (2.12 mmol) of the intermediate B synthesized in Example 1, 3 ml of ethanol, and 20 ml of THF under a nitrogen stream to prepare a solution. After the addition of 54.8 mg (0.24 mmol) of (±)-10-camphorsulfonic acid to the solution, the mixture was stirred at 40° C. for 3 hours. After completion of the reaction, the reaction mixture was added to 150 ml of water, and extracted with 300 ml of ethyl acetate, After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.02 g of a compound 8 as a yellow solid (yield: 43.1%).

The structure of the target product was identified by $^1$H-NMR.

$^1$H-NMR (500 MHz, CDCl$_3$, TMS, δ ppm): 13.51 (brs, 1H), 8.85 (s, 1H), 7.72 (d, 1H, J=2.5 Hz), 7.18 (dd, 1H, J=2.5 Hz, 8.8 Hz), 7.13 (d, 1H, J=8.8 Hz), 6.98 (d, 2H, J=9.0 Hz), 6.95 (d, 2H, J=9.0 Hz), 6.88 (d, 2H, J=9.0 Hz), 6.87 (d, 2H, J=9.0 Hz), 6.41 (dd, 1H, J=1.5 Hz, 17.5 Hz), 6.40 (dd, 1H, J=1.5 Hz, 17.5 Hz), 6.14 (dd, 1H, J=10.5 Hz, 17.5 Hz), 6.11 (dd, 1H, J=10.5 Hz, 17.5 Hz), 5.83 (dd, 1H, J=1.5 Hz, 10.5 Hz), 5.82 (dd, 1H, J=1.5 Hz, 10.5 Hz), 4.18 (t, 2H, J=7.5 Hz), 4.17 (t, 2H, J=7.0 Hz), 3.95 (t, 2H, J=6.5 Hz), 3.93 (t, 2H, J=6.5 Hz), 2.75 (s, 3H), 2.62 (s, 3H), 2.58-2.60 (m, 2H), 2.38-2.51 (m, 2H), 2.26-2.34 (m, 4H), 2.07-2.14 (m, 4H), 1.63-1.82 (m, 10H), 1.41-1.53 (m, 14H)

Synthesis Example 1: Synthesis of Compound A

Compound A

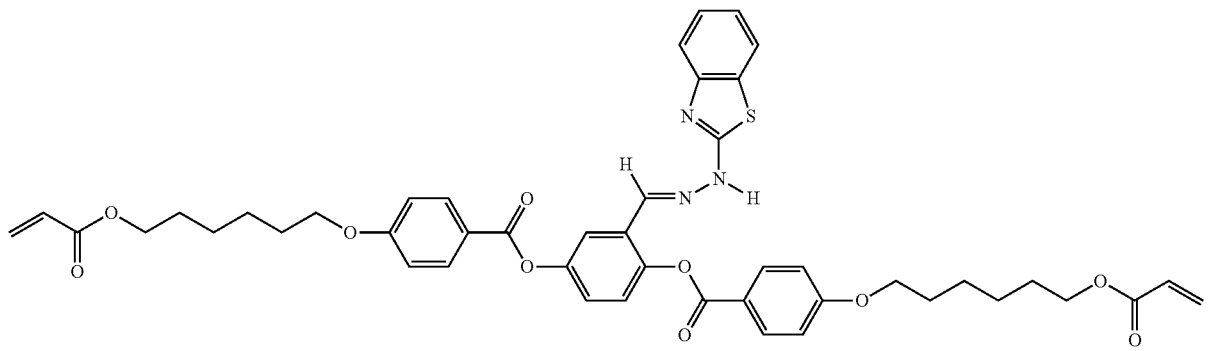

Step 1: Synthesis of Intermediate A

Compound α

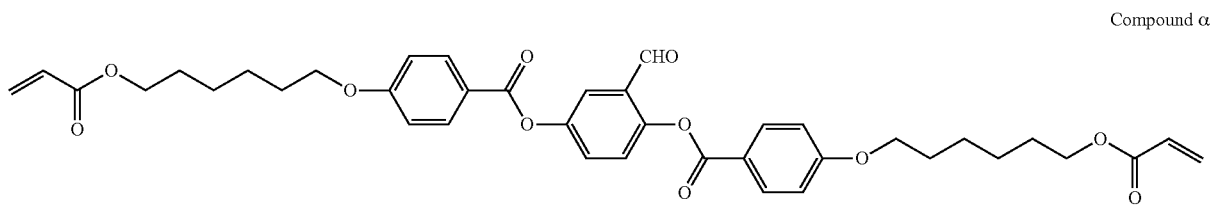 [SMILES: C=CC(=O)OCCCCCCOc1ccc(C(=O)Oc2ccc(OC(=O)c3ccc(OCCCCCCOC(=O)C=C)cc3)c(C=O)c2)cc1]

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream to prepare a homogeneous solution. After the addition of 83.3 g (434.4 mmol) of 1-ethyl-3-(3-dimethylaminopropyl)carbodiimide hydrochloride (WSC), the mixture was stirred at 25° C. for 12 hours. After completion of the reaction, the reaction mixture was added to 1.5 l of water, and extracted with 500 ml of ethyl acetate. The ethyl acetate layer was dried over anhydrous sodium sulfate, and sodium sulfate was separated by filtration. Ethyl acetate was evaporated from the filtrate under reduced pressure using a rotary evaporator to obtain a light yellow solid. The light yellow solid was purified by silica gel column chromatography (toluene:ethyl acetate=9:1) to obtain 75 g of an intermediate a as a white solid (yield: 75.4%).

The structure of the target product was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H)

Step 2: Synthesis of Compound A

A four-necked reactor equipped with a thermometer was charged with 10.5 g (15.3 mmol) of the intermediate a and 80 ml of THF under a nitrogen stream to prepare a homogeneous solution. 3.0 g (18.3 mol) of 2-hydrazinobenzothiazole was added to the solution to prepare a solution. After the addition of 18 mg (0.08 mmol) of (±)-10-camphorsulfonic acid, the mixture was stirred at 25° C. for 3 hours, After completion of the reaction, the reaction mixture was added to 800 ml of 10% sodium bicarbonate water, and extracted twice with 100 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a light yellow solid. The light yellow solid was purified by silica gel column chromatography (toluene:ethyl acetate=8:2) to obtain 8.0 g of a compound A as a light yellow solid (yield: 62.7%).

The structure of the target product was identified by $^1$H-NMR and mass spectroscopy.

$^1$H-NMR (500 MHz, DMSO-d$_6$, TMS, δ ppm): 12.30 (br, 1H), 8.19 (s, 1H), 8.17-8.12 (m, 4H), 7.76 (d, 1H, J=3.0 Hz), 7.68 (d, 1H, J=7.5 Hz), 7.45-7.39 (m, 3H), 7.28 (t, 1H, J=8.0 Hz), 7.18-7.14 (m, 4H), 7.09 (t, 1H, J=8.0 Hz), 6.33 (dd, 2H, J=1.5 Hz, 17.5 Hz), 6.18 (dd, 2H, J=10.5 Hz, 17.5 Hz), 5.944 (dd, 1H, J=1.5 Hz, 10.5 Hz), 5.941 (dd, 1H, J=1.5 Hz, 10.5 Hz), 4.14-4.10 (m, 8H), 1.80-1.75 (m, 4H), 1.69-1.63 (m, 4H), 1.53-1.38 (m, 8H)

LCMS (APCI) calcd for $C_{46}H_{47}N_3O_{10}S$: 833 [M$^+$]. Found: 833.

The phase transition temperature was measured by the following method using the compounds 1 to 8 obtained in Examples 1 to 8, the compound A obtained in Synthesis Example 1, the compound 1r of Reference Example 1 that was used in Comparative Example 1 ("K35" manufactured by Zeon Corporation), and the compound 2r of Reference Example 2 that was used in Comparative Example 2 ("LC242" manufactured by BASF).

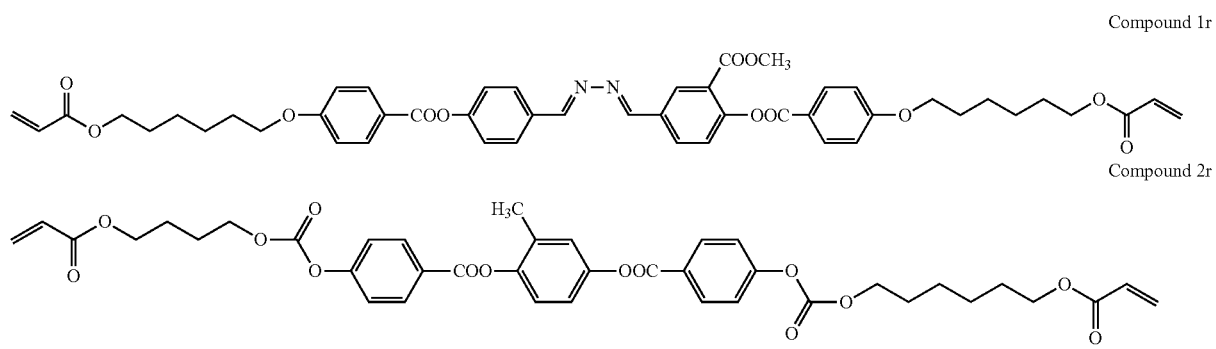

Phase Transition Temperature Measurement 1

10 mg of each compound (compounds 1 to 8, A, 1r, and 2r) was weighed, and placed in a solid state between two glass substrates provided with a polyimide alignment film subjected to a rubbing treatment (manufactured by E.H.C. Co. Ltd. (hereinafter the same)). The substrates were placed on a hot plate, heated from 40° C. to 200° C., and cooled to 40° C. A change in structure when the temperature was changed was observed using a polarizing microscope ("ECLIPSE LV100 POL" manufactured by Nikon Corporation (hereinafter the same)). Note that the phase transition temperature of the compounds 4 to 8 was measured within the range of 40° C. to 250° C., and the phase transition temperature of the compound A was measured within the range of 50° C. to 200° C.

The phase transition temperature measurement results are shown in Table 1.

In Table 1, "C" refers to "Crystal", "N" refers to "Nematic", and "I" refers to "Isotropic". The term "Crystal" means that the test compound was in a solid phase, the term "Nematic" means that the test compound was in a nematic liquid crystal phase, and the term "Isotropic" means that the test compound was in an isotropic liquid phase (hereinafter the same).

TABLE 1

| Compound No. | | Phase transition temperature |
|---|---|---|
| Example 1 | Compound 1 | C ⇌ (163° C. / 40° C. or less) N → (163° C. or more) I |
| Example 2 | Compound 2 | C ⇌ (118° C. / 64° C.) N → (163° C. or more) I |
| Example 3 | Compound 3 | C ⇌ (135° C. / 84° C.) N → (200° C. or more) I |
| Example 4 | Compound 4 | C ⇌ (96° C. / 40° C. or less) N → (250° C. or more) I |
| Example 5 | Compound 5 | C ⇌ (130° C. / 40° C. or less) N → (250° C. or more) I |
| Example 6 | Compound 6 | C ⇌ (230° C. / 40° C. or less) N → (250° C. or more) I |

TABLE 1-continued

| Compound No. | | Phase transition temperature |
|---|---|---|
| Example 7 | Compound 7 | C ⇌ (152° C. / 76° C.) N ⇌ (220° C. / 205° C.) I |
| Example 8 | Compound 8 | C ⇌ (230° C. / 40° C. or less) N → (250° C. or more) I |
| Synthesis Example 1 | Compound A | C ⇌ (102° C. / 50° C. 以下) N ⇌ (165° C. / 140° C.) I |
| Reference Example 1 | Compound 1r | C ⇌ (80° C. / 40° C. or less) N → (200° C. or more) I |
| Reference Example 2 | Compound 2r | C ⇌ (60° C. / 40° C. 以下) N ⇌ (123° C. / 122° C.) I |

Example 9 and Comparative Examples 1 and 2

1 g of each compound (compound 1 obtained in Example 1, compound 1r of Reference Example 1, and compound 2r of Reference Example 2), 30 mg of a photoinitiator A ("Adekaoptomer N-1919" manufactured by Adeka Corporation (hereinafter the same)), and 100 mg of a 1% cyclopentanone solution of a surfactant A ("KH-40" manufactured by AGC Seimi Chemical Co., Ltd. (hereinafter the same)) were dissolved in 2.3 g of cyclopentanone. The solution was filtered through a disposable filter having a pore size of 0.45 μm to obtain a polymerizable composition (polymerizable compositions 1, 1r, and 2r).

Examples 10 and 11

1.0 g of the compound 2 obtained in Example 2 or the compound 3 obtained in Example 3, 30 mg of the photoinitiator A, and 100 mg of a 1% cyclopentanone solution of the surfactant A were dissolved in 3.0 g of cyclopentanone and 0.25 g of dimethyl sulfoxide. The solution was filtered through a disposable filter having a pore size of 0.45 m to obtain a polymerizable composition (polymerizable compositions 1, 1r, and 2r).

Example 12

0.5 g of the compound 3 obtained in Example 3, 0.5 g of the compound A synthesized in Synthesis Example 1, 30 mg of the photoinitiator A, and 100 mg of a 1% cyclopentanone solution of the surfactant A were dissolved in 2.3 g of cyclopentanone. The solution was filtered through a disposable filter having a pore size of 0.45 µm to obtain a polymerizable composition 4.

Example 13

0.5 g of the compound 3 obtained in Example 3, 0.5 g of the compound 2r, 30 mg of the photoinitiator A, and 100 mg of a 1% cyclopentanone solution of the surfactant A were dissolved in 2.3 g of cyclopentanone. The solution was filtered through a disposable filter having a pore size of 0.45 µm to obtain a polymerizable composition 5.

Example 14

1.0 g of the compound 4 obtained in Example 4, 30 mg of the photoinitiator A, and 100 mg of a 1% cyclopentanone solution of the surfactant A were dissolved in 2.3 g of cyclopentanone. The solution was filtered through a disposable filter having a pore size of 0.45 µm to obtain a polymerizable composition 6.

Example 15

1.0 g of the compound 5 obtained in Example 5, 30 mg of the photoinitiator A, and 100 mg of a 1% cyclopentanone solution of the surfactant A were dissolved in 2.9 g of chloroform. The solution was filtered through a disposable filter having a pore size of 0.45 µm to obtain a polymerizable composition 7.

Example 16

0.5 g of the compound 5 obtained in Example 5, 0.5 g of the compound A, 30 mg of the photoinitiator A, and 100 mg of a 1% cyclopentanone solution of the surfactant A were dissolved in 2.2 g of cyclopentanone and 1.7 g of chloroform. The solution was filtered through a disposable filter having a pore size of 0.45 µm to obtain a polymerizable composition 8.

Example 17

1.0 g of the compound 6 obtained in Example 6, 30 mg of the photoinitiator A, and 100 mg of a 1% cyclopentanone solution of the surfactant A were dissolved in 5.3 g of chloroform. The solution was filtered through a disposable filter having a pore size of 0.45 µm to obtain a polymerizable composition 9.

Example 18

0.2 g of the compound 6 obtained in Example 6, 0.8 g of the compound A, 30 mg of the photoinitiator A, and 100 mg of a 1% cyclopentanone solution of the surfactant A were dissolved in 3.7 g of chloroform. The solution was filtered through a disposable filter having a pore size of 0.45 µm to obtain a polymerizable composition 10.

Example 19

0.5 g of the compound 7 obtained in Example 7, 0.5 g of the compound A, 30 mg of the photoinitiator A, and 100 mg of a 1% cyclopentanone solution of the surfactant A were dissolved in 2.2 g of cyclopentanone. The solution was filtered through a disposable filter having a pore size of 0.45 µm to obtain a polymerizable composition 11.

Example 20

0.2 g of the compound 7 obtained in Example 7, 0.8 g of the compound A, 30 mg of the photoinitiator A, and 100 mg of a 1% cyclopentanone solution of the surfactant A were dissolved in 2.2 g of cyclopentanone. The solution was filtered through a disposable filter having a pore size of 0.45 µm to obtain a polymerizable composition 12.

Example 21

0.5 g of the compound 8 obtained in Example 8, 0.5 g of the compound A, 30 mg of the photoinitiator A, and 100 mg of a 1% cyclopentanone solution of the surfactant A were dissolved in 8.0 g of chloroform. The solution was filtered through a disposable filter having a pore size of 0.45 µm to obtain a polymerizable composition 13.

The polymerizable compositions 1 to 13, 1r, and 2r were polymerized by the following method to obtain polymers. The retardation was measured, and the wavelength dispersion was evaluated using the resulting polymers.

Retardation Measurement and Wavelength Dispersion Evaluation I (i) Formation 1 of Liquid Crystal Layer Using Polymerizable Composition Each of the polymerizable compositions 1 to 8, 10 to 12, 1r, and 2r was applied to a transparent glass substrate provided with a polyimide alignment film subjected to a rubbing treatment (manufactured by E.H.C. Co. Ltd. (hereinafter the same)) using a #4 wire bar. The resulting film was dried for 1 minute at the temperature shown in Table 2, and subjected to an alignment treatment for 1 minute at the temperature shown in Table 2 to form a liquid crystal layer. UV rays were applied to the liquid crystal layer at a dose of 2000 mJ/cm$^2$ at the temperature shown in Table 2 to effect polymerization to prepare a wavelength dispersion measurement sample.

(ii) Formation 2 of Liquid Crystal Layer Using Polymerizable Composition

Each of the polymerizable compositions 9 and 13 was applied to a transparent glass substrate provided with a polyimide alignment film subjected to a rubbing treatment using a #6 wire bar. The resulting film was dried for 1 minute at the temperature shown in Table 2, and subjected to an alignment treatment for 1 minute at the temperature shown in Table 2 to form a liquid crystal layer. UV rays were applied to the liquid crystal layer at a dose of 2000 mJ/cm$^2$ at the temperature shown in Table 2 to effect polymerization to prepare a wavelength dispersion measurement sample.

(iii) Measurement of Retardation

The retardation between 400 nm and 800 nm was measured using the sample utilizing an ellipsometer ("M2000U" manufactured by J. A. Woollam).

(iv) Evaluation of Wavelength Dispersion

The wavelength dispersion was evaluated from the values α and β calculated by the following expressions using the measured retardation.

$$\alpha = \text{(retardation at 449.9 nm)/(retardation at 548.5 nm)}$$

$$\beta = \text{(retardation at 650.2 nm)/(retardation at 548.5 nm)}$$

The value α is smaller than 1, and the value β is larger than 1 when ideal wideband wavelength dispersion (reverse wavelength dispersion) is achieved. The values α and β are almost identical when flat wavelength dispersion is achieved. The value α is larger than 1, and the value β is smaller than 1 when normal dispersion is achieved.

Flat wavelength dispersion that ensures that the values α and β are almost identical is preferable, and reverse wavelength dispersion that ensures that the value α is smaller than 1, and the value β is larger than 1, is particularly preferable.

Table 2 shows the thickness (μm) of the liquid crystal polymer films obtained by polymerizing the polymerizable compositions, the retardation (Re) at a wavelength of 548.5 nm, and the values α and β.

A three-necked reactor equipped with a thermometer was charged with 3.00 g (17.69 mmol) of 2-chlorobenzothiazole, 3.26 g (70.74 mmol) of methylhydrazine, and 10 ml of methanol under a nitrogen stream to prepare a solution. The solution was refluxed for 1 hour. After completion of the reaction, the reaction mixture was cooled to 25° C., and added to 300 ml of distilled water to precipitate crystals. The crystals were filtered off, washed with distilled water, and dried under vacuum to obtain 3.01 g of an intermediate T as a white solid (yield: 95%).

The structure of the target product was identified by $^1$H-NMR.

TABLE 2

| | Polymerizable composition | Polymerizable compound Type | Ratio (%) | Polymerizable compound Type | Ratio (%) | Drying temperature (° C.) | Alignment treatment temperature (° C.) | Exposure temperature (° C.) | Thickness (μm) | Re (548.5 nm) | α | β |
|---|---|---|---|---|---|---|---|---|---|---|---|---|
| Example 9 | 1 | Compound 1 | 100 | — | — | 195 | 23 | 23 | 1.570 | 93.58 | 0.798 | 1.047 |
| Example 10 | 2 | Compound 2 | 100 | — | — | 150 | 100 | 100 | 1.121 | 78.11 | 0.908 | 1.013 |
| Example 11 | 3 | Compound 3 | 100 | — | — | 150 | 100 | 100 | 1.182 | 63.49 | 0.618 | 1.104 |
| Example 12 | 4 | Compound 3 | 50 | Compound A | 50 | 120 | 23 | 23 | 1.543 | 123.32 | 0.755 | 1.024 |
| Example 13 | 5 | Compound 3 | 50 | Compound 2r | 50 | 120 | 23 | 23 | 1.321 | 145.55 | 0.940 | 1.004 |
| Example 14 | 6 | Compound 4 | 100 | — | — | 120 | 23 | 23 | 1.604 | 118.23 | 0.833 | 1.034 |
| Example 15 | 7 | Compound 5 | 100 | — | — | 120 | 23 | 23 | 1.778 | 107.68 | 0.492 | 1.099 |
| Example 16 | 8 | Compound 5 | 50 | Compound A | 50 | 120 | 23 | 23 | 1.024 | 59.15 | 0.515 | 1.094 |
| Example 17 | 9 | Compound 6 | 100 | — | — | 235 | 23 | 23 | 2.092 | 103.85 | 0.917 | 1.013 |
| Example 18 | 10 | Compound 6 | 20 | Compound A | 80 | 120 | 23 | 23 | 1.720 | 91.47 | 0.856 | 1.036 |
| Example 19 | 11 | Compound 7 | 50 | Compound A | 50 | 120 | 23 | 23 | 1.548 | 98.73 | 0.863 | 1.046 |
| Example 20 | 12 | Compound 7 | 20 | Compound A | 80 | 120 | 23 | 23 | 1.423 | 103.66 | 0.853 | 1.003 |
| Example 21 | 13 | Compound 8 | 50 | Compound A | 50 | 180 | 23 | 23 | 1.674 | 108.05 | 0.950 | 1.025 |
| Comparative Example 1 | 1r | Compound 1r | 100 | — | — | 90 | 23 | 23 | 1.509 | 355.97 | 1.193 | 0.918 |
| Comparative Example 2 | 2r | Compound 2r | 100 | — | — | 80 | 23 | 23 | 1.479 | 222.90 | 1.086 | 0.970 |

As is clear from the results shown in Table 2, it was confirmed that the polymers obtained in Examples 9 to 11 using the compounds 1 to 8 according to the invention were an optically anisotropic article. The optically anisotropic articles showed ideal wideband wavelength dispersion in which the value α was smaller than 1, and the value β was larger than 1.

Example 22: Synthesis of Compound 9

Step 1: Synthesis of Intermediate T

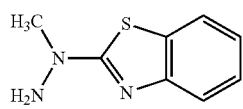

Intermediate T $^1$H-NMR (500 MHz, DMSO-d$_6$, TMS, δ ppm): 7.66 (dd, 1H, J=1.0 Hz, 8.0 Hz), 7.36 (dd, 1H, J=1.0 Hz, 8.0 Hz), 7.20 (dt, 1H, J=1.0 Hz, 7.5 Hz), 6.99 (dt, 1H, J=1.0 Hz, 7.5 Hz), 5.40 (s, 2H), 3.31 (s, 3H)

Step 2: Synthesis of Compound 9

A three-necked reactor equipped with a thermometer was charged with 0.70 g (0.75 mmol) of the intermediate B synthesized in the step 2 of Example 1 (see "Synthesis of compound 1") and 15 ml of THF under a nitrogen stream to Compound 9

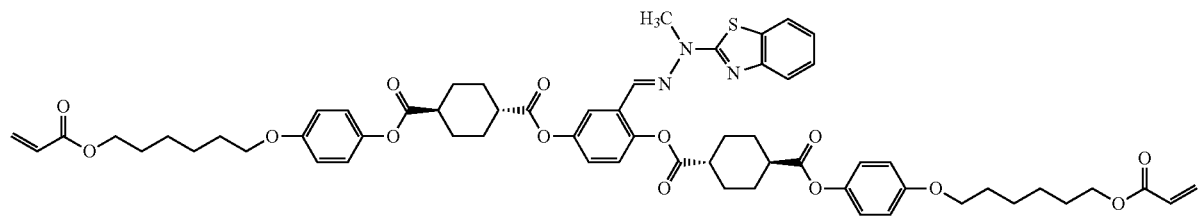

prepare a solution. After the addition of 0.15 ml (0.15 mmol) of 1 N hydrochloric acid and 0.27 g (1.49 mmol) of the intermediate T synthesized in the step 1 to the solution, the mixture was stirred at 40° C. for 10 hours. The reaction mixture was concentrated using a rotary evaporator, and the concentrate was purified by silica gel column chromatography (chloroform:THF=98:2) to obtain 0.70 g of a compound 9 as a light yellow solid (yield: 85%).

The structure of the target product was identified by ¹H-NMR.

¹H-NMR (500 MHz, CDCl₃, TMS, δ ppm): 7.74 (t, 1H, J=1.5 Hz), 7.66-7.71 (m, 2H), 7.64 (s, 1H), 7.35 (dt, 1H, J=1.0 Hz, 7.5 Hz), 7.18 (dt, 1H, J=1.0 Hz, 7.5 Hz), 7.11 (d, 2H, J=1.5 Hz), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.17 (t, 4H, J=6.5 Hz), 3.94 (t, 4H, J=6.5 Hz), 3.73 (s, 3H), 2.55-2.76 (m, 4H), 2.25-2.39 (m, 8H), 1.65-1.84 (m, 16H), 1.41-1.55 (m, 8H)

Example 23: Synthesis of Compound 10

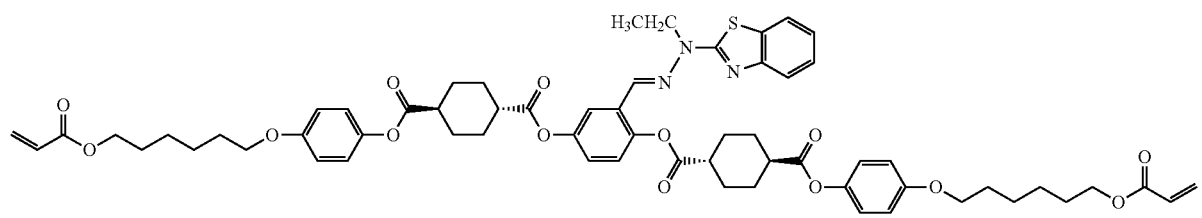

Compound 10

Step 1: Synthesis of Intermediate U

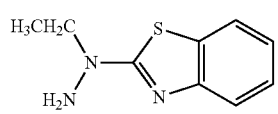

Intermediate U

A three-necked reactor equipped with a thermometer was charged with 3.00 g (18.16 mmol) of 2-hydrazinobenzothiazole and 70 ml of DMF under a nitrogen stream to prepare a solution. After the addition of 11.83 g (36.32 mmol) of cesium carbonate to the solution, the mixture was cooled to 0° C. After the addition of 3.12 g (19.97 mmol) of iodoethane dropwise to the mixture over 10 hours, the mixture was stirred at 0° C. for 2 hours, and stirred at 25° C. for 5 hours. After completion of the reaction, 600 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=1:9) to obtain 1.48 g of an intermediate U as a white solid (yield: 42%).

The structure of the target product was identified by ¹H-NMR.

¹H-NMR (500 MHz, DMSO-d₆, TMS, δ ppm): 7.65 (dd, 1H, J=1.0 Hz, 8.0 Hz), 7.35 (dd, 1H, J=1.0 Hz, 8.0 Hz), 7.20 (dt, 1H, J=1.0 Hz, 7.5 Hz), 6.98 (dt, 1H, J=1.0 Hz, 7.5 Hz), 5.34 (s, 2H), 3.73 (q, 2H, J=7.0 Hz), 1.20 (t, 3H, J=7.0 Hz)

Step 2: Synthesis of Compound 10

A three-necked reactor equipped with a thermometer was charged with 0.70 g (0.75 mmol) of the intermediate B synthesized in the step 2 of Example 1 (see "Synthesis of compound 1") and 15 ml of THF under a nitrogen stream to prepare a solution. After the addition of 0.15 ml (0.15 mmol) of 1 N hydrochloric acid and 0.29 g (1.49 mmol) of the intermediate U synthesized in the step 1 to the solution, the mixture was stirred at 40° C. for 10 hours. After completion of the reaction, the reaction mixture was concentrated using a rotary evaporator, and the concentrate was purified by silica gel column chromatography (chloroform:THF=98:2) to obtain 0.67 g of a compound 10 as a light yellow solid (yield: 81%).

The structure of the target product was identified by ¹H-NMR.

¹H-NMR (500 MHz, CDCl₃, TMS, δ ppm): 7.75 (dd, 1H, J=1.5 Hz, 2.0 Hz), 7.66-7.71 (m, 3H), 7.35 (dt, 1H, J=1.0 Hz, 7.5 Hz), 7.17 (dt, 1H, J=1.0 Hz, 7.5 Hz), 7.10-7.12 (m, 2H), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.38 (q, 2H, J=7.0 Hz), 4.18 (t, 4H, J=6.5 Hz), 3.95 (t, 4H, J=6.5 Hz), 2.55-2.76 (m, 4H), 2.26-2.40 (m, 8H), 1.65-1.84 (m, 16H), 1.41-1.55 (m, 8H), 1.34 (t, 3H, J=7.0 Hz)

Example 24: Synthesis of Compound 11

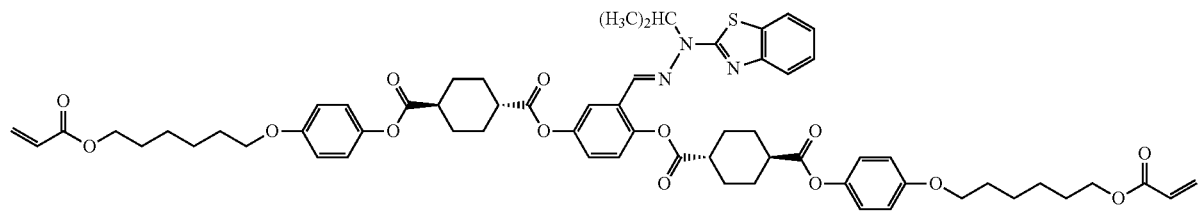

Compound 11

Step 1: Synthesis of Intermediate V

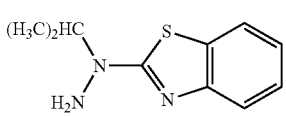

Intermediate V

A three-necked reactor equipped with a thermometer was charged with 3.00 g (18.16 mmol) of 2-hydrazinobenzothiazole and 70 ml of DMF under a nitrogen stream to prepare a solution, After the addition of 11.83 g (36.32 mmol) of cesium carbonate to the solution, the mixture was cooled to 0° C. After the addition of 3.33 g (27.23 mmol) of 2-bromopropane, the mixture was stirred at 0° C. for 1 hour, and stirred at 25° C. for 20 hours. 600 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=1:9) to obtain 1.11 g of an intermediate V as a white solid (yield: 29%).

The structure of the target product was identified by $^1$H-NMR.

$^1$H-NMR (500 MHz, DMSO-d$_6$, TMS, δ ppm): 7.65 (dd, 1H, J=1.0 Hz, 8.0 Hz), 7.35 (dd, 1H, J=1.0 Hz, 8.0 Hz), 7.20 (dt, 1H, J=1.0 Hz, 7.5 Hz), 6.98 (dt, 1H, J=1.0 Hz, 7.5 Hz), 5.10 (s, 2H), 4.61-4.72 (m, 1H), 1.17 (d, 6H, J=6.5 Hz)

Step 2: Synthesis of Compound 11

A three-necked reactor equipped with a thermometer was charged with 1.4 g (1.49 mmol) of the intermediate B synthesized in the step 2 of Example 1 (see "Synthesis of compound 1") and 30 ml of THF under a nitrogen stream to prepare a solution. After the addition of 0.30 ml (0.30 mmol) of 1 N hydrochloric acid and 0.62 g (2.98 mmol) of the intermediate V synthesized in the step 1 to the solution, the mixture was stirred at 40° C. for 10 hours. The reaction mixture was concentrated using a rotary evaporator, and the concentrate was purified by silica gel column chromatography (chloroform:THF=98:2) to obtain 1.40 g of a compound 11 as a light yellow solid (yield: 83%).

The structure of the target product was identified by $^1$H-NMR.

$^1$H-NMR (500 MHz, CDCl$_3$, TMS, δ ppm): 8.08 (s, 1H), 7.74 (d, 1H, J=2.5 Hz), 7.69 (dd, 1H, J=1.0 Hz, 8.0 Hz), 7.65 (d, 1H, J=8.0 Hz), 7.33 (dt, 1H, J=1.0 Hz, 7.5 Hz), 7.16 (dt, 1H, J=1.0 Hz, 7.5 Hz), 7.08-7.13 (m, 2H), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 5.29-5.39 (m, 1H), 4.17 (t, 4H, J=6.5 Hz), 3.94 (t, 4H, J=6.5 Hz), 2.54-2.74 (m, 4H), 2.25-2.39 (m, 8H), 1.65-1.84 (m, 16H), 1.62 (d, 6H, J=7.0 Hz), 1.41-1.55 (m, 8H)

Example 25: Synthesis of Compound 12

Step 1: Synthesis of Intermediate W

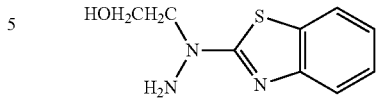

Intermediate W

A three-necked reactor equipped with a thermometer was charged with 3.00 g (17.69 mmol) of 2-chlorobenzothiazole, 5.38 g (70.74 mmol) of 2-hydrazinoethanol, and 10 ml of methanol under a nitrogen stream to prepare a solution. The solution was refluxed for 2 hours. The reaction mixture was cooled to 25° C., and added to 300 ml of distilled water to precipitate crystals. The crystals were filtered off, washed with distilled water, and dried under vacuum to obtain 3.27 g of an intermediate W as a white solid (yield: 88%).

The structure of the target product was identified by $^1$H-NMR.

$^1$H-NMR (500 MHz, DMSO-d$_6$, TMS, δ ppm): 7.66 (dd, 1H, J=1.0 Hz, 8.0 Hz), 7.35 (dd, 1H, J=1.0 Hz, 8.0 Hz), 7.20 (dt, 1H, J=1.0 Hz, 7.5 Hz), 6.98 (dt, 1H, J=1.0 Hz, 7.5 Hz), 5.37 (s, 2H), 4.86 (t, 1H, J=5.0 Hz), 3.69-3.81 (m, 4H)

Step 2: Synthesis of Compound 12

A three-necked reactor equipped with a thermometer was charged with 1.40 g (1.50 mmol) of the intermediate B synthesized in the step 2 of Example 1 (see "Synthesis of compound 1") and 30 ml of THF under a nitrogen stream to prepare a solution. After the addition of 0.30 ml (0.30 mmol) of 1 N hydrochloric acid and 0.62 g (2.98 mmol) of the intermediate W synthesized in the step 1 to the solution, the mixture was stirred at 40° C. for 8 hours. The reaction mixture was concentrated using a rotary evaporator, and the concentrate was purified by silica gel column chromatography (chloroform:THF=98:2) to obtain 1.32 g of a compound 12 as a light yellow solid (yield: 78%).

The structure of the target product was identified by $^1$H-NMR.

$^1$H-NMR (500 MHz, CDCl$_3$, TMS, δ ppm): 7.95 (s, 1H), 7.73-7.75 (m, 1H), 7.69 (dd, 1H, J=1.0 Hz, 8.0 Hz), 7.65 (d, 1H, J=8.0 Hz), 7.35 (dt, 1H, J=1.0 Hz, 7.5 Hz), 7.18 (dt, 1H, J=1.0 Hz, 7.5 Hz), 7.10-7.13 (m, 2H), 6.99 (d, 2H, J=9.0 Hz), 6.98 (d, 2H, J=9.0 Hz), 6.88 (d, 2H, J=9.0 Hz), 6.88 (d, 2H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.45 (t, 2H, J=5.0 Hz), 4.17 (t, 4H, J=6.5 Hz), 4.04 (q, 2H, J=5.0 Hz), 3.95 (t, 2H, J=6.5 Hz), 3.94 (t, 2H, J=6.5 Hz), 2.85 (t, 1H, J=5.0 Hz), 2.54-2.74 (m, 4H), 2.25-2.39 (m, 8H), 1.65-1.84 (m, 16H), 1.41-1.55 (m, 8H)

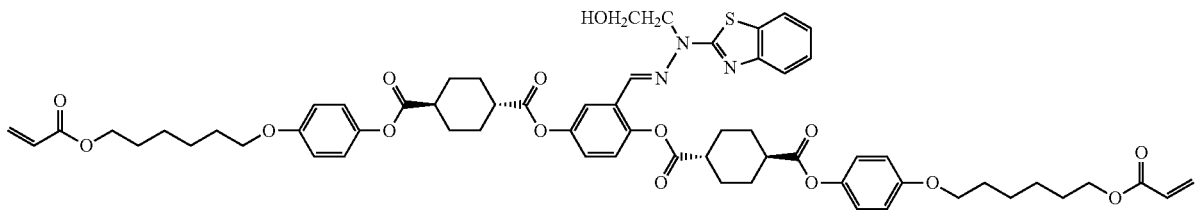

Compound 12

Example 26: Synthesis of Compound 13

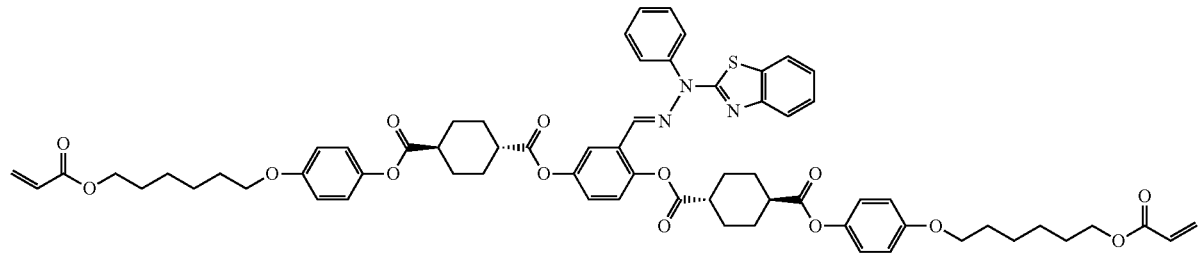

Compound 13

Step 1: Synthesis of Intermediate X

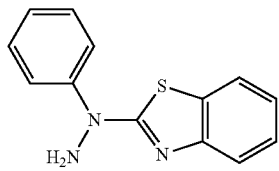

Intermediate X

A three-necked reactor equipped with a thermometer was charged with 3.00 g (17.69 mmol) of 2-chlorobenzothiazole, 7.65 g (70.74 mmol) of phenylhydrazine, and 30 ml of ethylene glycol under a nitrogen stream to prepare a solution. The solution was heated to 140° C., and stirred for 5 hours. After completion of the reaction, 300 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and 15 ml of THF was added to the concentrate to dissolve the concentrate. The solution was added to 300 ml of distilled water to precipitate a solid, which was filtered off. The solid was washed with distilled water, and dried under vacuum to obtain a yellow solid. A flask was charged with the yellow solid. After the addition of 50 ml of toluene, the mixture was stirred for 30 minutes, and filtered to remove a toluene-insoluble solid component. The filtrate was concentrated using a rotary evaporator, and the concentrate was purified by silica gel column chromatography (THF:toluene=2:50) to obtain 0.94 g of an intermediate X as a yellow oil (yield: 22%).

The structure of the target product was identified by $^1$H-NMR.

$^1$H-NMR (500 MHz, DMSO-$d_6$, TMS, δ ppm): 8.01 (dd, 2H, J=1.0 Hz, 9.0 Hz), 7.78 (dd, 1H, J=1.0 Hz, 8.0 Hz), 7.51 (dd, 1H, J=1.0 Hz, 8.0 Hz), 7.43 (dd, 2H, J=7.5 Hz, 8.5 Hz), 7.28 (dt, 1H, J=1.0 Hz, 7.5 Hz), 7.08-7.16 (m, 2H), 6.26 (s, 2H)

Step 2: Synthesis of Compound 13

A three-necked reactor equipped with a thermometer was charged with 1.00 g (1.06 mmol) of the intermediate B synthesized in the step 2 of Example 1 (see "Synthesis of compound 1") and 30 ml of THF under a nitrogen stream to prepare a solution. After the addition of 0.22 ml (0.22 mmol) of 1 N hydrochloric acid and 0.38 g (1.60 mmol) of the intermediate X synthesized in the step 1 to the solution, the mixture was stirred at 40° C. for 2 hours. After completion of the reaction, the reaction mixture was concentrated using a rotary evaporator, and the concentrate was purified by silica gel column chromatography (chloroform:THF=40:1) to obtain 1.14 g of a compound 13 as a light yellow solid (yield: 95%).

The structure of the target product was identified by $^1$H-NMR.

$^1$H-NMR (500 MHz, CDCl$_3$, TMS, δ ppm): 7.82 (d, 1H, J=2.5 Hz), 7.73 (dd, 1H, J=1.0 Hz, 8.0 Hz), 7.64-7.70 (m, 2H), 7.60 (d, 2H, J=7.5 Hz), 7.35-7.42 (m, 3H), 7.30 (dt, 1H, J=1.0 Hz, 7.5 Hz), 7.18 (dt, 1H, J=1.0 Hz, 7.5 Hz), 7.03-7.12 (m, 2H), 7.00 (d, 2H, J=9.0 Hz), 6.99 (d, 2H, J=9.0 Hz), 6.90 (d, 2H, J=9.0 Hz), 6.89 (d, 2H, J=9.0 Hz), 6.41 (dd, 1H, J=1.5 Hz, 17.5 Hz), 6.41 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.18 (t, 2H, J=6.5 Hz), 3.92-3.98 (m, 4H), 2.56-2.71 (m, 2H), 2.41-2.50 (m, 1H), 2.27-2.40 (m, 5H), 2.12-2.22 (m, 2H), 1.64-1.91 (m, 14H), 1.41-1.56 (m, 10H), 1.19-1.31 (m, 2H)

Example 27: Synthesis of Compound 14

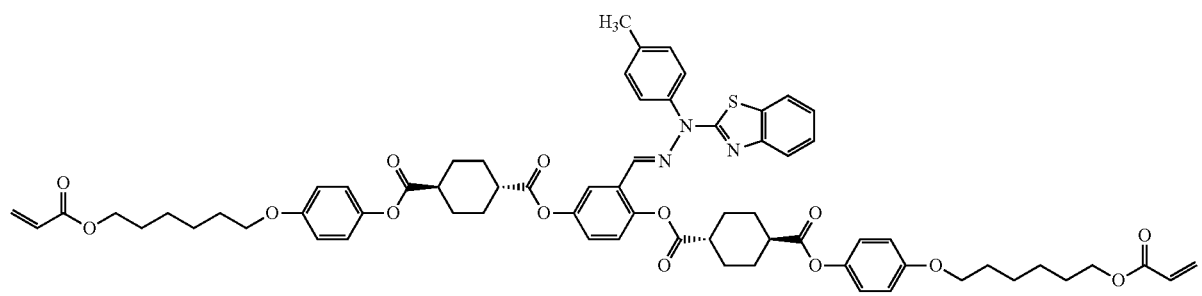

Compound 14

Step 1: Synthesis of Intermediate Y

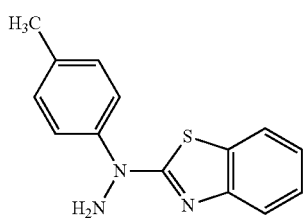

Intermediate Y

A three-necked reactor equipped with a thermometer was charged with 2.50 g (14.74 mmol) of 2-chlorobenzothiazole, 7.01 g (44.21 mmol) of p-tolylhydrazine hydrochloride, 7.62 g (58.95 mmol) of N,N-diisopropylethylamine, and 40 ml of ethylene glycol under a nitrogen stream to prepare a solution. The solution was stirred at 140° C. for 5 hours. 400 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator. After the addition of 50 ml of toluene to the concentrate, the mixture was stirred for 30 minutes. A toluene-insoluble solid component was removed by filtration, and the filtrate was concentrated using a rotary evaporator. The concentrate was purified by silica gel column chromatography (THF:toluene=5:95) to obtain 0.64 g of an intermediate Y as a light yellow solid (yield: 17%).

The structure of the target product was identified by $^1$H-NMR.

$^1$H-NMR (500 MHz, DMSO-$d_6$, TMS, δ ppm): 7.86 (d, 2H, J=8.5 Hz), 7.76 (dd, 1H, J=1.0 Hz, 8.0 Hz), 7.47 (dd, 1H, J=1.0 Hz, 8.0 Hz), 7.27 (dt, 1H, J=1.0 Hz, 7.5 Hz), 7.23 (d, 2H, J=8.5 Hz), 7.09 (dt, 1H, J=1.0 Hz, 7.5 Hz), 6.19 (s, 2H), 2.31 (s, 3H)

Step 2: Synthesis of Compound 14

A three-necked reactor equipped with a thermometer was charged with 1.00 g (1.06 mmol) of the intermediate B synthesized in the step 2 of Example 1 (see "Synthesis of compound 1") and 30 ml of THF under a nitrogen stream to prepare a solution. After the addition of 0.22 ml (0.22 mmol) of 1 N hydrochloric acid and 0.32 g (1.28 mmol) of the intermediate Y synthesized in the step 1 to the solution, the mixture was stirred at 40° C. for 1 hour. After completion of the reaction, the reaction mixture was concentrated using a rotary evaporator, and the concentrate was purified by silica gel column chromatography (chloroform:THF=40:1) to obtain 1.16 g of a compound 14 as a light yellow solid (yield: 93%).

The structure of the target product was identified by $^1$H-NMR.

$^1$H-NMR (500 MHz, CDCl$_3$, TMS, δ ppm): 7.82 (d, 1H, J=2.5 Hz), 7.72 (dd, 1H, J=1.0 Hz, 8.0 Hz), 7.61 (dd, 1H, J=1.0 Hz, 8.0 Hz), 7.46 (d, 2H, J=8.0 Hz), 7.40 (s, 1H), 7.25-7.32 (m, 3H), 7.17 (dt, 1H, J=1.0 Hz, 7.5 Hz), 7.04-7.12 (m, 2H), 6.96-7.01 (m, 4H), 6.86-6.92 (m, 4H), 6.41 (dd, 1H, J=1.5 Hz, 17.5 Hz), 6.41 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.18 (t, 2H, J=6.5 Hz), 3.95 (t, 2H, J=6.5 Hz), 3.95 (t, 2H, J=6.5 Hz), 2.55-2.72 (m, 2H), 2.50 (s, 3H), 2.41-2.50 (m, 1H), 2.27-2.41 (m, 5H), 2.14-2.22 (m, 2H), 1.65-1.95 (m, 14H), 1.41-1.60 (m, 10H), 1.22-1.34 (m, 2H)

Example 28: Synthesis of Compound 15

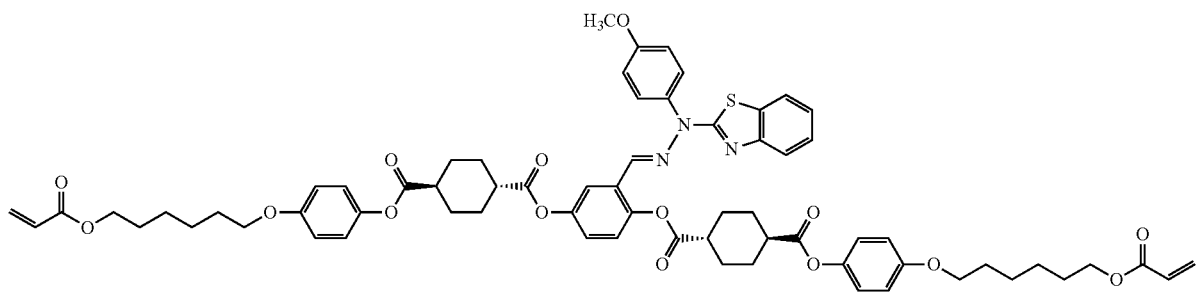

Compound 15

Step 1: Synthesis of Intermediate Z

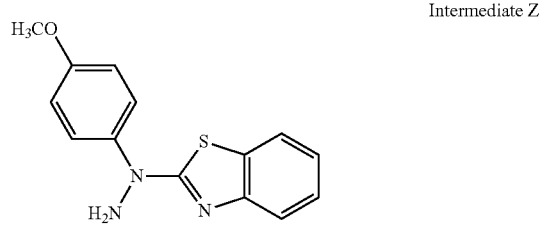 [SMILES: COc1ccc(N(N)c2nc3ccccc3s2)cc1]

Intermediate Z

A three-necked reactor equipped with a thermometer was charged with 2.50 g (14.74 mmol) of 2-chlorobenzothiazole, 7.72 g (44.21 mmol) of 4-methoxyphenylhydrazine hydrochloride, 7.62 g (58.95 mmol) of N,N-diisopropylethylamine, and 40 ml of ethylene glycol under a nitrogen stream to prepare a solution. The solution was stirred at 140° C. for 5 hours. 400 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator. After the addition of 50 ml of toluene to the concentrate, the mixture was stirred for 30 minutes. A toluene-insoluble solid component was removed by filtration. The filtrate was concentrated using a rotary evaporator, and the concentrate was purified by silica gel column chromatography (THF:toluene=5:95) to obtain 0.84 g of an intermediate Z as a white solid (yield: 21%).

The structure of the target product was identified by $^1$H-NMR.

$^1$H-NMR (500 MHz, DMSO-$d_6$, TMS, δ ppm): 7.82 (d, 2H, J=9.0 Hz), 7.75 (dd, 1H, J=1.0 Hz, 8.0 Hz), 7.43 (dd, 1H, J=1.0 Hz, 8.0 Hz), 7.25 (dt, 1H, J=1.0 Hz, 7.5 Hz), 7.07 (dt, 1H, J=1.0 Hz, 7.5 Hz), 7.01 (d, 2H, J=9.0 Hz), 6.15 (s, 2H), 3.78 (s, 3H)

Step 2: Synthesis of Compound 15

A three-necked reactor equipped with a thermometer was charged with 1.00 g (1.06 mmol) of the intermediate B synthesized in the step 2 of Example 1 (see "Synthesis of compound 1") and 30 ml of THF under a nitrogen stream to prepare a solution. After the addition of 0.22 ml (0.22 mmol) of 1 N hydrochloric acid and 0.34 g (1.28 mmol) of the intermediate Z synthesized in the step 1 to the solution, the mixture was stirred at 40° C. for 1 hour. After completion of the reaction, the reaction mixture was concentrated using a rotary evaporator, and the concentrate was purified by silica gel column chromatography (chloroform:THF=40:1) to obtain 1.18 g of a compound 15 as a light yellow solid (yield: 93%).

The structure of the target product was identified by $^1$H-NMR.

$^1$H-NMR (500 MHz, CDCl$_3$, TMS, δ ppm): 7.82 (d, 1H, J=2.5 Hz), 7.72 (dd, 1H, J=1.0 Hz, 8.0 Hz), 7.62 (dd, 1H, J=1.0 Hz, 8.0 Hz), 7.39 (s, 1H), 7.26-7.33 (m, 3H), 7.13-7.19 (m, 3H), 7.04-7.12 (m, 2H), 6.96-7.02 (m, 4H), 6.86-6.92 (m, 4H), 6.41 (dd, 1H, J=1.5 Hz, 17.5 Hz), 6.41 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.18 (t, 2H, J=6.5 Hz), 3.95 (t, 2H, J=6.5 Hz), 3.95 (t, 2H, J=6.5 Hz), 3.88 (s, 3H), 2.55-2.72 (m, 2H), 2.25-2.51 (m, 6H), 2.13-2.22 (m, 2H), 1.65-1.96 (m, 14H), 1.41-1.59 (m, 10H), 1.19-1.31 (m, 2H)

Example 29: Synthesis of Compound 16

Step 1: Synthesis of Intermediate A1

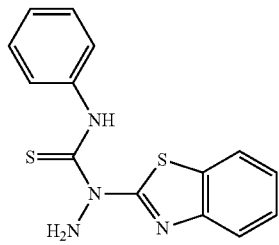

Intermediate A1

A three-necked reactor equipped with a thermometer was charged with 3.30 g (20.0 mmol) of 2-hydrazinobenzothiazole and 75 ml of ethanol under a nitrogen stream to prepare a solution. The solution was cooled to 0° C. After the addition of 2.70 g (20.0 mmol) of phenyl isothiocyanate over 30 minutes, the mixture was stirred at 0° C. for 3 hours, and stirred at 25° C. for 15 hours. After completion of the reaction, a solid that precipitated in the reactor was filtered off. The solid was washed with ethanol, and dried under vacuum to obtain 4.14 g of an intermediate A1 as a white solid (yield: 69%).

The structure of the target product was identified by $^1$H-NMR.

$^1$H-NMR (500 MHz, DMSO-$d_6$, TMS, δ ppm): 10.22 (s, 1H), 10.09 (s, 2H), 7.80 (d, 1H, J=7.5 Hz), 7.46-7.55 (m, 3H), 7.26-7.36 (m, 3H), 7.09-7.19 (m, 2H)

Step 2: Synthesis of Compound 16

A three-necked reactor equipped with a thermometer was charged with 2.50 g (2.66 mmol) of the intermediate B synthesized in the step 2 of Example 1 (see "Synthesis of compound 1") and 150 ml of THF under a nitrogen stream to prepare a solution. After the addition of 2.65 ml (2.65 mmol) of 1 N hydrochloric acid and 4.0 g (13.3 mmol) of the intermediate A1 synthesized in the step 1 to the solution, the mixture was stirred at 60° C. for 30 hours. After completion of the reaction, the reaction mixture was concentrated using a rotary evaporator, and the concentrate was purified by silica gel column chromatography (chloroform:THF=95:5) to obtain 1.40 g of a compound 16 as a light yellow solid (yield: 43%).

The structure of the target product was identified by $^1$H-NMR.

$^1$H-NMR (500 MHz, CDCl$_3$, TMS, δ ppm): 11.86 (s, 1H), 8.06 (s, 1H), 7.62-7.85 (m, 2H), 7.28-7.59 (m, 4H), 7.06-7.25 (m, 4H), 6.80-7.05 (m, 10H), 6.40 (dd, 1H, J=1.5 Hz, Compound 16

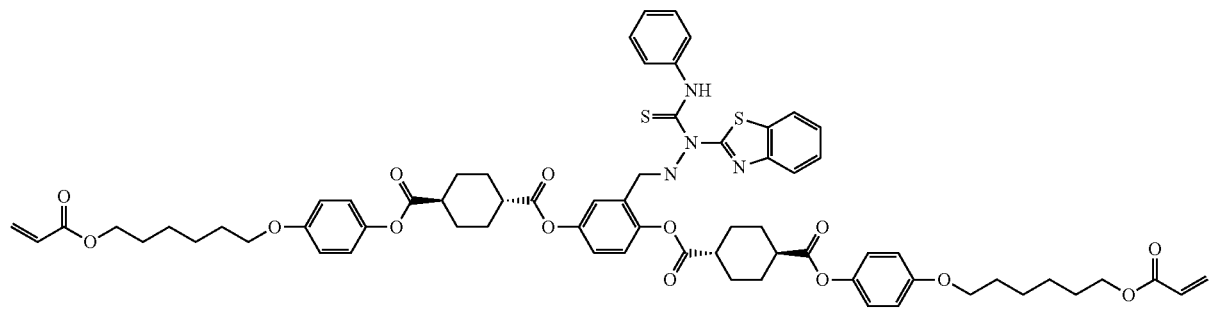

17.5 Hz), 6.40 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.17 (t, 2H, J=6.5 Hz), 3.89-3.98 (m, 4H), 2.50-2.76 (m, 2H), 2.21-2.48 (m, 6H), 1.99-2.16 (m, 2H), 1.35-1.85 (m, 26H)

Example 30: Synthesis of Compound 17

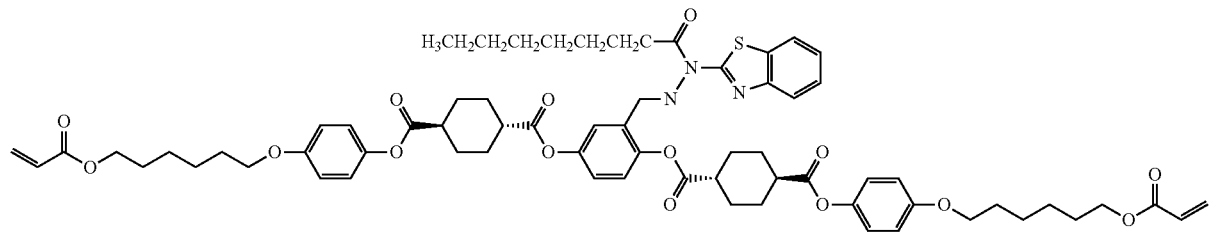

Compound 17

Step 1: Synthesis of Intermediate B1

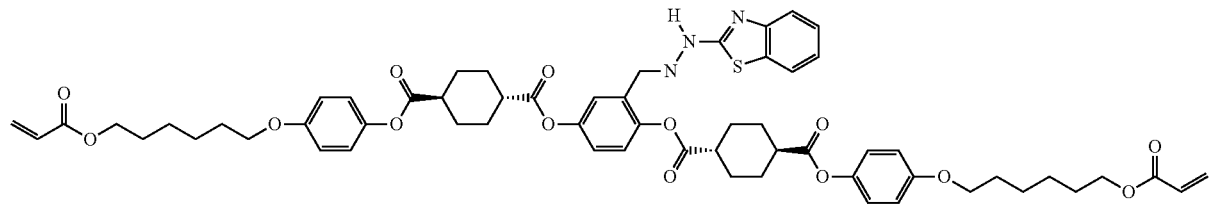

Compound B1

A three-necked reactor equipped with a thermometer was charged with 2.30 g (2.45 mmol) of the intermediate B synthesized in the step 2 of Example 1 (see "Synthesis of compound 1") and 25 ml of THF under a nitrogen stream to prepare a solution. After the addition of 0.49 ml (0.49 mmol) of 1 N hydrochloric acid to the solution, a solution prepared by dissolving 0.40 g (2.45 mol) of 2-hydrazinobenzothiazole in 5 ml of THF was added dropwise to the mixture over 15 minutes. After the dropwise addition, the mixture was stirred at 25° C. for 1 hour. After completion of the reaction, the reaction mixture was added to 400 ml of methanol to precipitate a solid, which was filtered off. The solid was dried using a vacuum dryer to obtain 2.4 g of an intermediate B1 as a light yellow solid (yield: 90%).

The structure of the target product was identified by $^1$H-NMR.

$^1$H-NMR (500 MHz, DMSO-$d_6$, TMS, δ ppm): 12.63 (s, 1H), 8.10 (s, 1H), 7.80 (d, 1H, J=5.0 Hz), 7.60 (d, 1H, J=3.0 Hz), 7.48 (s, 1H), 7.21-7.35 (m, 3H), 7.14 (t, 11, J=7.5 Hz), 6.98-7.05 (m, 4H), 6.91-6.97 (m, 4H), 6.32 (dd, 2H, J=1.5 Hz, 17.5 Hz), 6.18 (dd, 2H, J=10.0 Hz, 17.5 Hz), 5.93 (dd, 2H, J=1.5 Hz, 10.0 Hz), 4.12 (t, 4H, J=6.5 Hz), 3.95 (t, 4H, J=6.5 Hz), 2.56-2.83 (m, 4H), 2.11-2.30 (m, 8H), 1.52-1.80 (m, 16H), 1.33-1.49 (m, 8H)

Step 2: Synthesis of Compound 17

A three-necked reactor equipped with a thermometer was charged with 2.00 g (1.84 mmol) of the intermediate B1 synthesized in the step 1, 0.02 g (0.18 mmol) of 4-(dimethylamino)pyridine, and 100 ml of THF under a nitrogen stream to prepare a solution. After the addition of 0.33 g (2.03 mmol) of n-octanoyl chloride to the solution, the reactor was immersed in an ice bath to adjust the temperature of the reaction mixture to 10° C. After the addition of 0.22 g (2.21 mmol) of triethylamine dropwise to the reaction mixture over 10 minutes, the mixture was stirred at 25° C. for 2 hours. After completion of the reaction, 600 ml of distilled water and 10 ml of a saturated sodium chloride solution were added to the reaction mixture, followed by extraction twice with 200 ml of chloroform. The organic layer was dried over anhydrous sodium sulfate, and sodium sulfate was separated by filtration. The reaction mixture was concentrated using a rotary evaporator, and the concentrate was purified by silica gel column chromatography (chloroform:THF=40:2) to obtain 1.72 g of a compound 17 as a light yellow solid (yield: 77%).

The structure of the target product was identified by $^1$H-NMR.

$^1$H-NMR (500 MHz, CDCl$_3$, TMS, δ ppm): 8.89 (s, 1H), 7.89-7.98 (m, 2H), 7.78 (d, 1H, J=2.5 Hz), 7.53 (dt, 1H, J=1.0 Hz, 7.5 Hz), 7.42 (dt, 1H, J=1.0 Hz, 7.5 Hz), 7.20 (dd, 1H, J=2.5 Hz, 9.0 Hz), 7.14 (d, 1H, J=9.0 Hz), 6.98 (d, 2H, J=9.0 Hz), 6.96 (d, 2H, J=9.0 Hz), 6.89 (d, 2H, J=9.0 Hz), 6.88 (d, 2H, J=9.0 Hz), 6.40 (dd, 1H, J=1.5 Hz, 17.5 Hz), 6.40 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.17 (t, 2H, J=6.5 Hz), 3.92-3.98 (m, 4H), 3.01 (t, 2H, J=7.5 Hz), 2.54-2.70 (m, 2H), 2.39-2.48 (m, 1H), 2.23-2.37 (m, 5H), 1.91-2.06 (m, 4H), 1.62-1.86 (m, 14H), 1.26-1.56 (m, 20H), 0.90 (t, 3H, J=7.0 Hz)

Example 31: Synthesis of Compound 18

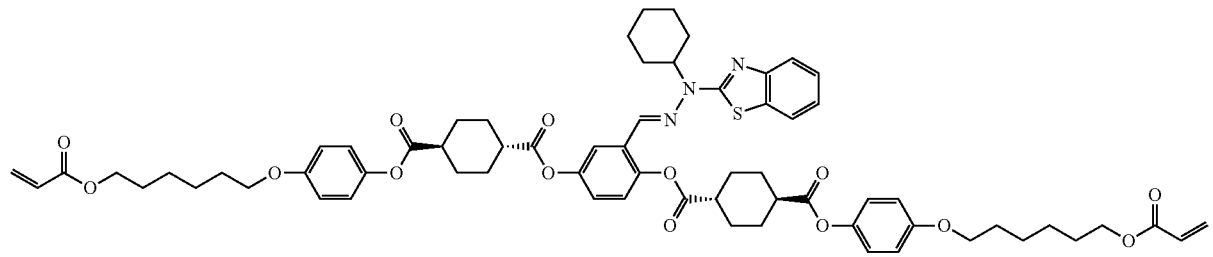

Compound 18

Step 1: Synthesis of Intermediate C1

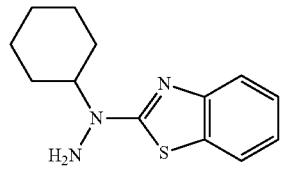

Intermediate C1

A four-necked reactor equipped with a thermometer was charged with 2.50 g (16.6 mmol) of cyclohexylhydrazine hydrochloride and 8 ml of triethylamine under a nitrogen stream to prepare a solution. After the addition of 5.63 g (33.2 mmol) of 2-chlorobenzothiazole to the solution, the mixture was stirred at 80° C. for 5 hours. After completion of the reaction, the reaction mixture was cooled to 20° C., added to 150 ml of a saturated sodium hydrogen carbonate aqueous solution, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (hexane:ethyl acetate=75:25) to obtain 1.02 g of an intermediate C1 as a white solid (yield: 22.3%).

The structure of the target product was identified by $^1$H-NMR.

synthesized in the step 1, 38.6 mg (0,166 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (chloroform:THF=97:3) to obtain 1.24 g of a compound 18 as a light yellow solid (yield: 71.4%).

The structure of the target product was identified by $^1$H-NMR, $^1$H-NMR (500 MHz, CDCl$_3$, TMS, δ ppm): 8.15 (s, 1H), 7.72 (d, 1H, J=1.5 Hz), 7.68 (dd, 1H, J=1.5 Hz, 8.0 Hz), 7.66 (dd, 1H, J=1.5 Hz, 8.0 Hz), 7.31-7.35 (m, 1H), 7.14-7.18 (m, 1H), 7.13 (d, 1H, J=9.0 Hz), 7.10 (dd, 1H, J=1.5 Hz, 9.0 Hz), 6.96-7.00 (m, 4H), 6.86-6.90 (m, 4H), 6.40 (dd, 2H, J=1.5 Hz, 17.0 Hz), 6.13 (dd, 2H, J=10.0 Hz, 17.0 Hz), 5.82 (dd, 2H, J=1.5 Hz, 10.0 Hz), 4.62-4.70 (m, 1H), 4.17 (t, 4H, J=6.5 Hz), 3.94 (t, 4H, J=6.5 Hz), 2.55-2.74 (m, 4H), 2.27-2.47 (m, 10H), 1.90-2.00 (m, 4H), 1.65-1.85 (m, 16H), 1.42-1.55 (m, 10H), 1.24-1.33 (m, 2H)

Example 32: Synthesis of Compound 19

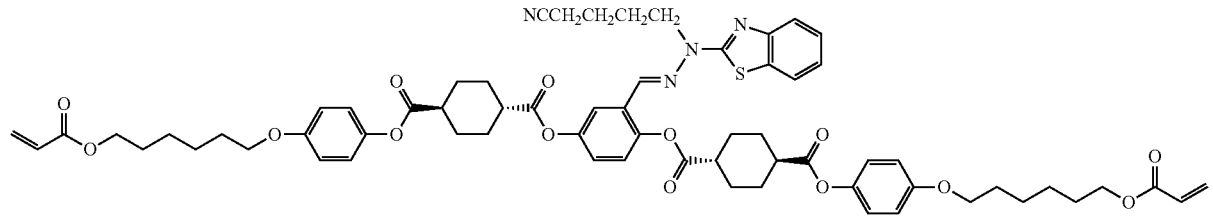

Compound 19

$^1$H-NMR (400 MHz, CDCl$_3$, TMS, δ ppm): 7.58 (d, 1H, J=7.8 Hz), 7.52 (d, 1H, J=8.2 Hz), 7.26 (dd, 1H, J=7.4 Hz, 8.2 Hz), 7.05 (dd, 1H, J=7.4 Hz, 7.8 Hz), 4.25-4.32 (m, 1H), 4.04 (s, 2H), 1.84-1.88 (m, 4H), 1.68-1.73 (m, 1H), 1.43-1.59 (m, 4H), 1.08-1.19 (m, 1H)

Step 2: Synthesis of Compound 18

A three-necked reactor equipped with a thermometer was charged with 1.04 g (1.49 mmol) of the intermediate B synthesized in the step 2 of Example 1 (see "Synthesis of compound 1"), 456 mg (1.84 mmol) of the intermediate C1

Step 1: Synthesis of Intermediate D1

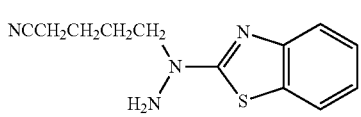

Intermediate D1

A four-necked reactor equipped with a thermometer was charged with 5.00 g (30.3 mmol) of 2-hydrazinobenzothiazole and 100 ml of DMF under a nitrogen stream to prepare a solution. After the addition of 20.9 g (152 mmol) of potassium carbonate and 5.17 g (30.3 mmol) of 5-bromovaleronitrile to the solution, the mixture was stirred at 60° C. for 8 hours. After completion of the reaction, the reaction mixture was cooled to 20° C., added to 500 ml of water, and extracted with 500 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (n-hexane:ethyl acetate=60:40) to obtain 3.41 g of an intermediate D1 as a white solid (yield: 45.7%).

The structure of the target product was identified by $^1$H-NMR.

$^1$H-NMR (400 MHz, CDCl$_3$, TMS, δ ppm): 7.60 (d, 1H, J=7.8 Hz), 7.51 (d, 1H, J=8.1 Hz), 7.28 (dd, 1H, J=7.3, 8.1 Hz), 7.07 (dd, 1H, J=7.3 Hz, 7.8 Hz), 4.23 (s, 2H), 3.81 (t, 2H, J=6.9 Hz), 2.46 (t, 2H, J=7.1 Hz), 1.88-1.95 (m, 2H), 1.71-1.79 (m, 2H)

Step 2: Synthesis of Compound 19

A three-necked reactor equipped with a thermometer was charged with 1.50 g (1.60 mmol) of the intermediate B synthesized in the step 2 of Example 1 (see "Synthesis of compound 1"), 438 mg (1.78 mmol) of the intermediate D1 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=85:15) to obtain 1.31 g of a compound 19 as a light yellow solid (yield: 70.2%).

The structure of the target product was identified by $^1$H-NMR.

$^1$H-NMR (500 MHz, CDCl$_3$, TMS, δ ppm): 7.74 (d, 1H, J=1.5 Hz), 7.64-7.72 (m, 3H), 7.35 (ddd, 1H, J=1.5 Hz, 8.0 Hz, 8.0 Hz), 7.19 (ddd, 1H, J=1.5 Hz, 8.0 Hz, 8.0 Hz), 7.10-7.14 (m, 2H), 6.96-7.01 (m, 4H), 6.86-6.91 (m, 4H), 6.40 (dd, 2H, J=1.5 Hz, 17.0 Hz), 6.12 (dd, 2H, J=10.5 Hz, 17.0 Hz), 5.82 (dd, 2H, J=1.5 Hz, 10.5 Hz), 4.22 (t, 2H, J=6.5 Hz), 4.18 (t, 4H, J=6.5 Hz), 3.95 (t, 4H, J=6.5 Hz), 2.58-2.75 (m, 4H), 2.55 (t, 2H, J=6.5 Hz), 2.26-2.40 (m, 8H), 1.96 (tt, 2H, J=6.5 Hz, 6.5 Hz), 1.66-1.83 (m, 18H), 1.42-1.55 (m, 8H)

Example 33: Synthesis of Compound 20

Step 1: Synthesis of Intermediate E1

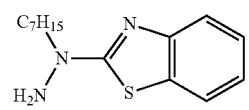

Intermediate E1

A three-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mol) of cesium carbonate to the solution, the mixture was cooled to 0° C. After the addition of 3.28 g (14.5 mmol) of iodineheptane to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (n-hexane:ethyl acetate=85:15) to obtain 1.81 g of an intermediate E1 as a white solid (yield: 56.9%).

The structure of the target product was identified by $^1$H-NMR.

$^1$H-NMR (500 MHz, CDCl$_3$, TMS, δ ppm): 7.59 (dd, 1H, J=1.5 Hz, 8.0 Hz), 7.53 (dd, 1H, J=1.5 Hz, 8.0 Hz), 7.06-7.28 (m, 2H), 4.22 (s, 2H), 3.75 (t, 2H, J=7.0 Hz), 1.29-1.38 (m, 10H), 0.88 (t, 3H, J=7.0 Hz)

Step 2: Synthesis of Compound 20

A three-necked reactor equipped with a thermometer was charged with 1.50 g (1.60 mmol) of the intermediate B synthesized in the step 2 of Example 1 (see "Synthesis of compound 1"), 468 mg (1.78 mmol) of the intermediate E1 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=9:1) to obtain 1.46 g of a compound 20 as a light yellow solid (yield: 77.5%).

The structure of the target product was identified by $^1$H-NMR.

$^1$H-NMR (500 MHz, CDCl$_3$, TMS, δ ppm): 7.75 (d, 1H, J=1.5 Hz), 7.66-7.70 (m, 3H), 7.34 (ddd, 1H, J=1.5 Hz, 8.0 Hz, 8.0 Hz), 7.17 (ddd, 1H, J=1.5 Hz, 8.0 Hz, 8.0 Hz), Compound 20

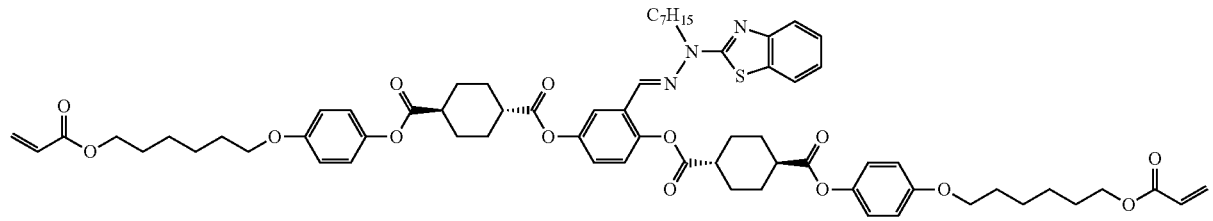

7.08-7.14 (m, 2H), 6.95-7.01 (m, 4H), 6.87-6.90 (m, 4H), 6.40 (dd, 2H, J=1.5 Hz, 17.5 Hz), 6.12 (dd, 2H, J=10.5 Hz, 17.5 Hz), 5.82 (dd, 2H, J=1.5 Hz, 10.5 Hz), 4.30 (t, 2H, J=7.0 Hz), 4.18 (t, 4H, J=7.0 Hz), 3.95 (t, 4H, J=7.0 Hz), 2.55-2.73 (m, 4H), 2.26-2.40 (m, 8H), 1.65-1.84 (m, 16H), 1.36-1.55 (m, 14H), 1.25-1.35 (m, 4H), 0.87 (t, 3H, J=7.0 Hz)

Example 34: Synthesis of Compound 21

Compound 21

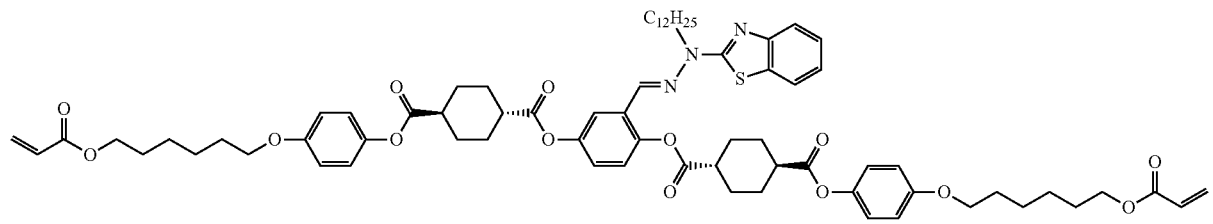

Step 1: Synthesis of Intermediate F1

Intermediate F1

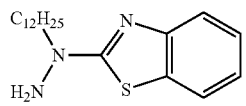

A four-necked reactor equipped with a thermometer was charged with 3.00 g (18.2 mmol) of 2-hydrazinobenzothiazole and 45 ml of DMF under a nitrogen stream to prepare a solution. After the addition of 11.9 g (36.4 mmol) of cesium carbonate and 6.45 g (21.8 mmol) of 1-iododecane to the solution, the mixture was stirred at 25° C. for 20 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=95:5) to obtain 2.93 g of an intermediate F1 as a white solid (yield: 48.3%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 7.5 Hz, 8.0 Hz), 7.06 (ddd, 1H, J=1.0 Hz, 7.5 Hz, 8.0 Hz), 4.22 (s, 2H), 3.74 (t, 2H, J=7.5 Hz), 1.73 (tt, 2H, J=7.5 Hz, 7.5 Hz), 1.41-1.25 (m, 18H), 0.88 (t, 3H, J=7.0 Hz)

Step 2: Synthesis of Compound 21

A three-necked reactor equipped with a thermometer was charged with 1.50 g (1.60 mmol) of the intermediate B synthesized in the step 2 of Example 1 (see "Synthesis of compound 1"), 592 mg (1.78 mmol) of the intermediate F1 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=9:1) to obtain 1.44 g of a compound 21 as a light yellow solid (yield: 71.9%).

The structure of the target product was identified by $^1$H-NMR.

$^1$H-NMR (500 MHz, CDCl$_3$, TMS, δ ppm): 7.74 (d, 1H, J=1.5 Hz), 7.66-7.70 (m, 3H), 7.34 (ddd, 1H, J=1:5 Hz, 7.5 Hz, 7.5 Hz), 7.17 (ddd, 1H, J=1.5 Hz, 7.5 Hz, 7.5 Hz), 7.08-7.14 (m, 2H), 6.95-7.01 (m, 4H), 6.86-6.91 (m, 4H), 6.41 (dd, 2H, J=1.5 Hz, 17.5 Hz), 6.12 (dd, 2H, J=10.5 Hz, 17.5 Hz), 5.82 (dd, 2H, J=1.5 Hz, 10.5 Hz), 4.30 (t, 2H, J=7.0 Hz), 4.18 (t, 4H, J=7.0 Hz), 3.94 (t, 4H, J=7.0 Hz), 2.56-2.73 (m, 4H), 2.28-2.39 (m, 8H), 1.66-1.84 (m, 18H), 1.35-1.55 (m, 10H), 1.19-1.33 (m, 16H), 0.86 (t, 3H, J=7.0 Hz)

Example 35: Synthesis of Compound 22

Compound 22

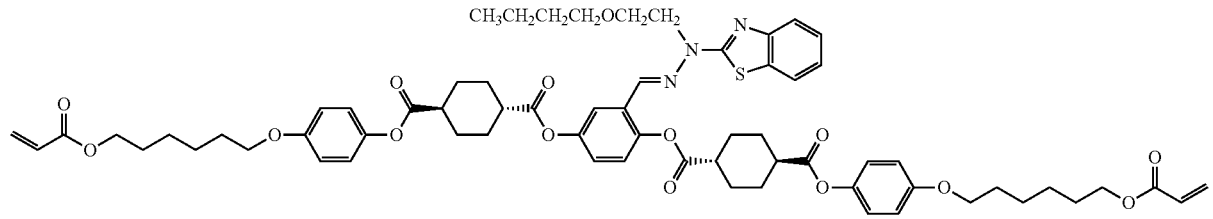

Step 1: Synthesis of Intermediate G1

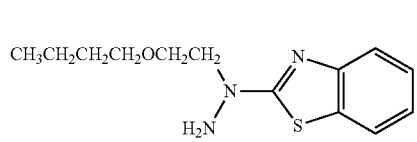
Intermediate G1

A three-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mol) of cesium carbonate to the solution, the mixture was cooled to 0° C. After the addition of 1.98 g (14.5 mmol) of butyl 2-chloroethyl ether to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (n-hexane:ethyl acetate=75:25) to obtain 1.70 g of an intermediate G1 as a white solid (yield: 53.0%).

The structure of the target product was identified by $^1$H-NMR.

$^1$H-NMR (500 MHz, CDCl$_3$, TMS, δ ppm): 7.61 (dd, 1H, J=1.0 Hz, 8.0 Hz), 7.50 (dd, 1H, J=1.0 Hz, 8.0 Hz), 7.27-7.29 (m, 1H), 7.04-7.08 (m, 1H), 4.70 (s, 2H), 4.01 (t, 2H, J=5.0 Hz), 3.82 (t, 2H, J=5.0 Hz), 3.44 (t, 2H, J=7.0 Hz), 1.52-1.57 (m, 2H), 1.31-1.39 (m, 2H), 0.90 (t, 3H, J=7.0 Hz)

Step 2: Synthesis of Compound 22

A three-necked reactor equipped with a thermometer was charged with 1.50 g (1.60 mmol) of the intermediate B synthesized in the step 2 of Example 1 (see "Synthesis of compound 1"), 396 mg (1.78 mmol) of the intermediate G1 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=9:1) to obtain 1.31 g of a compound 22 as a light yellow solid (yield: 69.4%).

The structure of the target product was identified by $^1$H-NMR.

$^1$H-NMR (500 MHz, CDCl$_3$, TMS, δ ppm): 8.03 (s, 1H), 7.76 (d, 1H, J=1.5 Hz), 7.65-7.71 (m, 2H), 7.34 (ddd, 1H, J=1.5 Hz, 8.0 Hz, 8.0 Hz), 7.17 (ddd, 1H, J=1.5 Hz, 8.0 Hz, 8.0 Hz), 7.09-7.12 (m, 2H), 6.96-7.00 (m, 4H), 6.87-6.90 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.45 (t, 2H, J=5.5 Hz), 4.18 (t, 4H, J=7.0 Hz), 3.95 (t, 4H, J=7.0 Hz), 3.79 (t, 2H, J=5.5 Hz), 3.44 (t, 2H, J=7.0 Hz), 2.55-2.74 (m, 4H), 2.28-2.40 (m, 8H), 1.65-1.83 (m, 16H), 1.42-1.55 (m, 10H), 1.25-1.34 (m, 2H), 0.85 (t, 3H, J=7.0 Hz)

Example 36: Synthesis of Compound 23

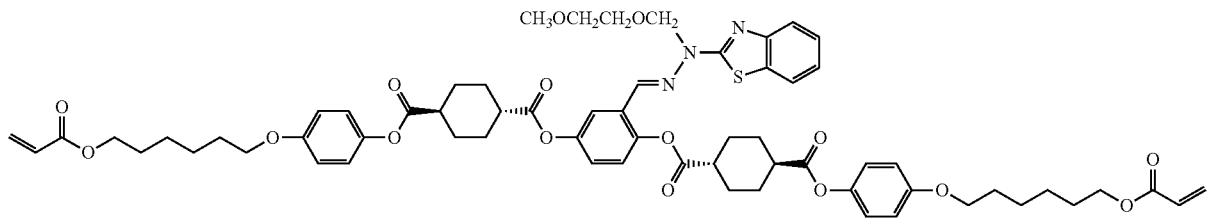
Compound 23

A three-necked reactor equipped with a thermometer was charged with 2.00 g (1.84 mmol) of the intermediate B1 synthesized in the step 1 of Example 30 (see "Synthesis of compound 17") and 20 ml of THF under a nitrogen stream to prepare a solution. The solution was cooled to 0° C. After the addition of 344 mg (2.76 mmol) of 2-methoxyethoxymethyl chloride to the solution, a solution prepared by dissolving 476 mg (3.68 mol) of N,N-diisopropylethylamine in 5 ml of THF was added dropwise to the mixture over 5 minutes. After the dropwise addition, the mixture was stirred at 25° C. for 20 hours. After completion of the reaction, the reaction mixture was added to 100 ml of water, and extracted with 200 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (chloroform:THF=95:5) to obtain 1.58 g of a compound 23 as a light yellow solid (yield: 73.0%).

The structure of the target product was identified by $^1$H-NMR.

$^1$H-NMR (500 MHz, DMSO-d$_6$, TMS, δ ppm): 8.31 (s, 1H), 7.62-7.71 (m, 2H), 7.32-7.42 (m, 2H), 7.25-7.29 (m, 2H), 7.15-7.19 (m, 1H), 7.00-7.04 (m, 4H), 6.92-6.96 (m, 4H), 6.32 (dd, 2H, J=1.5 Hz, 17.5 Hz), 6.17 (dd, 2H, J=10.5 Hz, 17.5 Hz), 5.93 (dd, 2H, J=1.5 Hz, 10.5 Hz), 5.60 (s, 2H), 4.12 (t, 4H, J=6.5 Hz), 3.95 (t, 4H, J=6.5 Hz), 3.71 (t, 2H, J=6.0 Hz), 3.46 (t, 2H, J=6.0 Hz), 3.20 (s, 3H), 2.60-2.85 (m, 4H), 2.11-2.28 (m, 8H), 1.55-1.75 (m, 16H), 1.35-1.50 (m, 8H)

Example 37: Synthesis of Compound 24

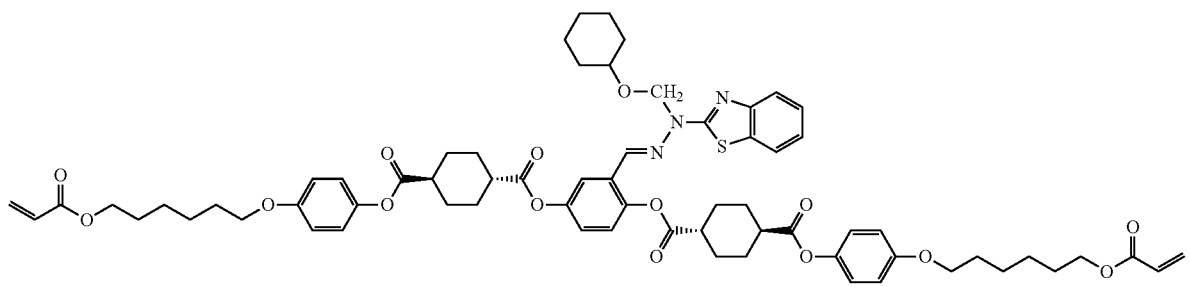

Step 1: Synthesis of Compound 24

A three-necked reactor equipped with a thermometer was charged with 2.00 g (1.84 mmol) of the intermediate B1 synthesized in the step 1 of Example 30 (see "Synthesis of compound 17") and 20 ml of THF under a nitrogen stream to prepare a solution. The solution was cooled to 0° C. After the addition of 412 mg (2.76 mmol) of chloromethyl cyclohexyl ether to the solution, a solution prepared by dissolving 476 mg (7.36 mol) of N,N-diisopropylethylamine in 5 ml of THF was added dropwise to the mixture over 5 minutes. After the dropwise addition, the mixture was stirred at 25° C. for 3 hours. After completion of the reaction, the reaction mixture was added to 100 ml of water, and extracted with 200 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=95:5) to obtain 1.54 g of a compound 24 as a light yellow solid (yield: 70.0%).

The structure of the target product was identified by $^1$H-NMR.

$^1$H-NMR (500 MHz, CDCl$_3$, TMS, δ ppm): 8.33 (s, 1H), 7.86 (d, 1H, J=2.0 Hz), 7.42 (d, 1H, J=7.5 Hz), 7.25-7.29 (m, 2H), 7.08-7.13 (m, 3H), 6.96-7.00 (m, 4H), 6.86-6.90 (m, 4H), 6.41 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 5.62 (s, 2H), 4.18 (t, 4H, J=6.5 Hz), 3.95 (t, 4H, J=6.5 Hz), 3.56-3.64 (m, 1H), 2.57-2.76 (m, 4H), 2.27-2.40 (m, 8H), 1.89-1.95 (m, 2H), 1.64-1.83 (m, 16H), 1.42-1.55 (m, 10H), 1.18-1.39 (m, 6H)

Example 38: Synthesis of Compound 25

Step 1: Synthesis of Intermediate H1

Intermediate H1

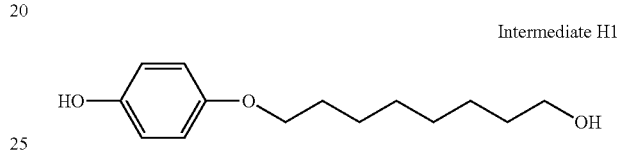

A three-necked reactor equipped with a thermometer was charged with 7.28 g (66.1 mmol) of hydroquinone, 2.38 g (59.5 mmol) of sodium hydroxide, and 50 ml of distilled water under a nitrogen stream. 9.90 g (60.1 mol) of 8-chloro-1-n-octanol was added dropwise to the solution over 30 minutes. After the dropwise addition, the mixture was refluxed for 5 hours. After completion of the reaction, the reaction mixture was cooled to 25° C. to precipitate a white solid, which was filtered off. The solid was recrystallized from 120 ml of toluene to obtain 7.93 g of an intermediate H1 as a white solid (yield: 56.1%).

The structure of the target product was identified by $^1$H-NMR.

$^1$H-NMR (500 MHz, DMSO-d$_6$, TMS, δ ppm): 8.86 (s, 1H), 6.72 (dd, 2H, J=2.5 Hz, 8.0 Hz), 6.65 (dd, 2H, J=2.5 Hz, 8.0 Hz), 4.33 (t, 1H, J=5.0 Hz), 3.82 (t, 2H, J=6.5 Hz), 3.37 (dt, 2H, J=5.0 Hz, 6.5 Hz), 1.65 (tt, 2H, J=6.5 Hz, 6.5 Hz), 1.28-1.42 (m, 10H)

Step 2: Synthesis of Intermediate I1

Intermediate I1

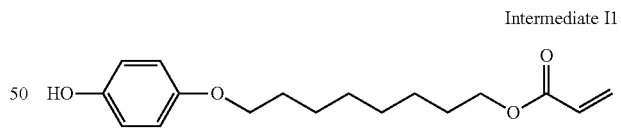

Compound 25

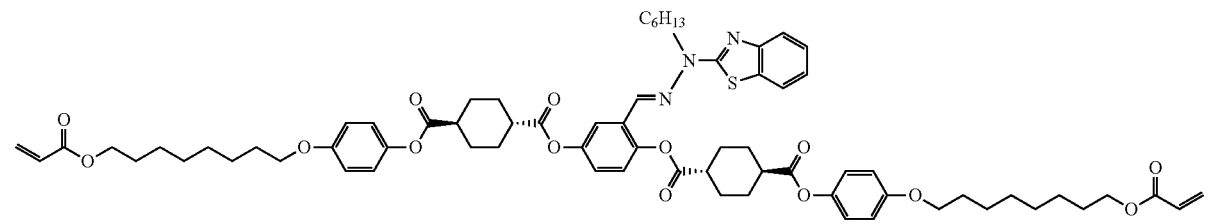

A three-necked reactor equipped with a thermometer was charged with 7.84 g (32.9 mmol) of the intermediate H1 synthesized by the step 1, 2.61 g (36.2 mmol) of acrylic acid, 40.8 mg (0.329 mmol) of 4-methoxyphenol, 316 mg (3.29 mmol) of methanesulfonic acid, and 40 ml of toluene under a nitrogen stream. The mixture was refluxed for 6 hours. After cooling the reaction mixture to 25° C., the reaction mixture was added to 200 ml of water, and extracted with 100 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a brown solid. The brown solid was purified by silica gel column chromatography (toluene:THF=95:5) to obtain 6.95 g of an intermediate 11 as a white solid (yield: 71.9%).

The structure of the target product was identified by $^1$H-NMR.

$^1$H-NMR (500 MHz, DMSO-$d_6$, TMS, δ ppm): 8.86 (s, 1H), 6.72 (dd, 2H, J=2.5 Hz, 9.0 Hz), 6.65 (dd, 2H, J=2.5 Hz, 8.0 Hz), 6.31 (dd, 1H, J=1.5 Hz, 17.5 Hz), 6.17 (dd, 1H, J=10.5 Hz, 17.5 Hz), 5.93 (dd, 1H, J=1.5 Hz, 10.5 Hz), 4.10 (t, 2H, J=6.5 Hz), 3.83 (t, 2H, J=6.5 Hz), 1.58-1.68 (m, 4H), 1.30-1.39 (m, 8H)

Step 3: Synthesis of Intermediate J1 over 5 minutes while maintaining the temperature of the reaction mixture at 20 to 30° C. After the dropwise addition, the mixture was stirred at 25° C. for 2 hours. After completion of the reaction, 300 ml of distilled water and 100 ml of a saturated sodium chloride solution were added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (toluene:THF=85:15) to obtain 5.23 g of an intermediate J2 as a white solid (yield: 64.6%).

The structure of the target product was identified by $^1$H-NMR.

$^1$H-NMR (500 MHz, DMSO-$d_6$, TMS, δ ppm): 12.1 (s, 1H), 6.98 (dd, 2H, J=2.5 Hz, 9.0 Hz), 6.92 (dd, 2H, J=2.5 Hz, 8.0 Hz), 6.31 (dd, 1H, J=1.5 Hz, 17.5 Hz), 6.17 (dd, 1H, J=10.5 Hz, 17.5 Hz), 5.92 (dd, 1H, J=1.5 Hz, 10.5 Hz), 4.10 (t, 2H, J=6.5 Hz), 3.93 (t, 2H, J=6.5 Hz), 2.19-2.25 (m, 1H), 2.04-2.10 (m, 2H), 1.94-1.98 (m, 2H), 1.69 (tt, 2H, J=6.5 Hz, 6.5 Hz), 1.57-1.64 (m, 2H), 1.31-1.52 (m, 13H)

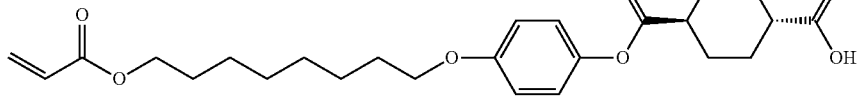

Intermediate J1

Step 4: Synthesis of Intermediate K1

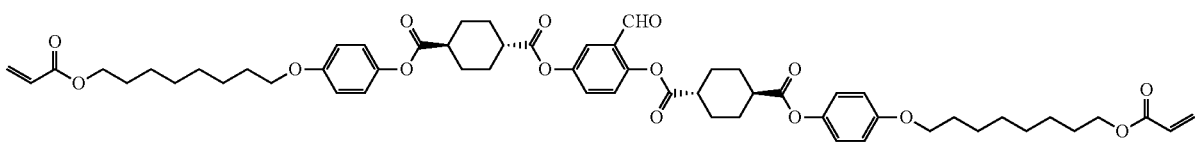

Intermediate K1

A three-necked reactor equipped with a thermometer was charged with 6.86 g (39.8 mmol) of trans-1,4-cyclohexanedicarboxylic acid, 70 ml of THF, and 14 ml of DMF under a nitrogen stream. After the addition of 2.28 g (19.9 mmol) of methanesulfonyl chloride to the mixture, the reactor was immersed in a water bath to adjust the temperature of the reaction mixture to 20° C. 2.20 g (21.7 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After the addition of 221 mg (1.81 mmol) of 4-(dimethylamino)pyridine and 5.30 g (18.1 mmol) of the intermediate I1 synthesized in the step 2 to the reaction mixture, the reactor was immersed in a water bath to adjust the temperature of the reaction mixture to 15° C. 2.20 g (21.7 mmol) of triethylamine was added dropwise to the reaction mixture A three-necked reactor equipped with a thermometer was charged with 4.00 g (8.96 mmol) of the intermediate J1 synthesized in the step 3 and 60 ml of THF under a nitrogen stream to prepare a solution. After the addition of 1.07 g (9.32 mmol) of methanesulfonyl chloride to the solution, the reactor was immersed in a water bath to adjust the temperature of the reaction mixture to 20° C. 944 mg (9.32 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After the addition of 92.0 mg (0.748 mmol) of 4-(dimethylamino)pyridine and 548 mg (3.97 mmol) of 2,5-dihydroxybenzaldehyde to the reaction mixture, the reactor was immersed in a water bath to adjust the temperature of the reaction mixture to 15° C. 944 mg (9.32 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After completion of the reaction, 350 ml of distilled water and 50 ml of a saturated sodium chloride solution were added to the reaction mixture, followed by extraction twice with 150 ml of chloroform. The organic layer was dried over anhydrous sodium sulfate, and sodium sulfate was separated by filtration. The filtrate was concentrated using a rotary evaporator, and the concentrate was dissolved in 15 ml of THF. 200 ml of methanol was added to the solution to precipitate crystals, which were filtered off. The crystals were washed with methanol, and dried under vacuum to obtain 2.85 g of an intermediate K1 as a white solid (yield: 72.3%).

The structure of the target product was identified by $^1$H-NMR.

$^1$H-NMR (500 MHz, CDCl$_3$, TMS, δ ppm): 10.1 (s, 1H), 7.61 (d, 1H, J=2.5 Hz), 7.37 (dd, 1H, J=2.5 Hz, 8.5 Hz), 7.20 (d, 1H, J=8.5 Hz), 6.97 (dd, 4H, J=2.0 Hz, 9.0 Hz), 6.88 (dd, 4H, J=2.0 Hz, 9.0 Hz), 6.40 (dd, 2H, J=1.5 Hz, 17.5 Hz), 6.12 (dd, 2H, J=10.5 Hz, 17.5 Hz), 5.82 (dd, 2H, J=1.5 Hz, 10.5 Hz), 4.16 (t, 4H, J=6.5 Hz), 3.93 (t, 4H, J=6.5 Hz), 2.57-2.74 (m, 4H), 2.26-2.37 (m, 8H), 1.65-1.80 (m, 16H), 1.35-1.48 (m, 16H)

Step 5: Synthesis of Compound 25

A three-necked reactor equipped with a thermometer was charged with 1.95 g (1.96 mmol) of the intermediate K1 synthesized in the step 4, 441 mg (1.76 mmol) of the intermediate J synthesized in the step 1 of Example 4 (see "Synthesis of compound 4"), 45.6 mg (0.196 mmol) of (±)-10-camphorsulfonic acid, 24 ml of THF, and 6 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The chloroform layer was dried over anhydrous sodium sulfate, and sodium sulfate was separated by filtration. Chloroform was evaporated from the filtrate under reduced pressure using a rotary evaporator to obtain a yellow solid. The yellow solid was purified by silica gel column chromatography (toluene:ethyl acetate=95:5) to obtain 1.56 g of a compound 25 as a light yellow solid (yield: 64.9%).

The structure of the target product was identified by $^1$H-NMR.

$^1$H-NMR (500 MHz, CDCl$_3$, TMS, δ ppm): 7.75 (d, 1H, J=1.5 Hz), 7.66-7.70 (m, 3H), 7.34 (dd, 1H, J=1.5 Hz, 7.8 Hz), 7.09-7.18 (m, 3H), 6.96-7.00 (m, 4H), 6.86-6.90 (m, 4H), 6.41 (dd, 2H, J=1.5 Hz, 17.5 Hz), 6.12 (dd, 2H, J=10.5 Hz, 17.5 Hz), 5.81 (dd, 2H, J=1.5 Hz, 10.5 Hz), 4.30 (t, 2H, J=7.5 Hz), 4.16 (t, 4H, J=6.5 Hz), 3.94 (t, 4H, J=6.5 Hz), 2.56-2.72 (m, 4H), 2.27-2.38 (m, 8H), 1.65-1.81 (m, 18H), 1.32-1.49 (m, 22H), 0.90 (t, 3H, J=7.5 Hz)

Example 39: Synthesis of Compound 26

Step 1: Synthesis of Intermediate L1

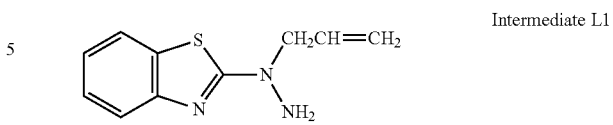

Intermediate L1

A four-necked reactor equipped with a thermometer was charged with 5.00 g (30.3 mmol) of 2-hydrazinobenzothiazole and 50 ml of DMF under a nitrogen stream to prepare a solution. After the addition of 14.8 g (45.5 mmol) of cesium carbonate and 3.1 ml (36.3 mmol) of allyl bromide to the solution, the mixture was stirred at 25° C. for 2 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (hexane:ethyl acetate=70:30) to obtain 1.82 g of an intermediate L1 as a white solid (yield: 29.0%).

The structure of the target product was identified by $^1$H-NMR.

$^1$H-NMR (500 MHz, CDCl$_3$, TMS, δ ppm): 7.62 (dd, 1H, J=1.0 Hz, 7.5 Hz), 7.54 (dd, 1H, J=1.0 Hz, 8.0 Hz), 7.29 (ddd, 1H, J=1.0 Hz, 7.0 Hz, 8.0 Hz), 7.08 (ddd, 1H, J=1.0 Hz, 7.0 Hz, 7.5 Hz), 5.90 (ddt, 1H, J=6.5 Hz, 10.5 Hz, 17.0 Hz), 5.38 (ddt, 1H, J=1.0 Hz, 2.5 Hz, 10.5 Hz), 5.34 (ddt, 1H, J=1.5 Hz, 2.5 Hz, 17.0 Hz), 4.42 (ddd, 2H, J=1.0 Hz, 1.5 Hz, 6.5 Hz), 4.18 (s, 2H)

Step 2: Synthesis of Compound 26

A four-necked reactor equipped with a thermometer was charged with 368 mg (1.77 mmol) of the intermediate L1 synthesized in the step 1, 1.50 g (1.60 mmol) of the intermediate B synthesized in the step 2 of Example 1 (see "Synthesis of compound 1"), 3 ml of ethanol, and 15 ml of THF under a nitrogen stream to prepare a solution. After the addition of 41.2 mg (0.18 mmol) of (±)-10-camphorsulfonic acid to the solution, the mixture was stirred at 40° C. for 5 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel

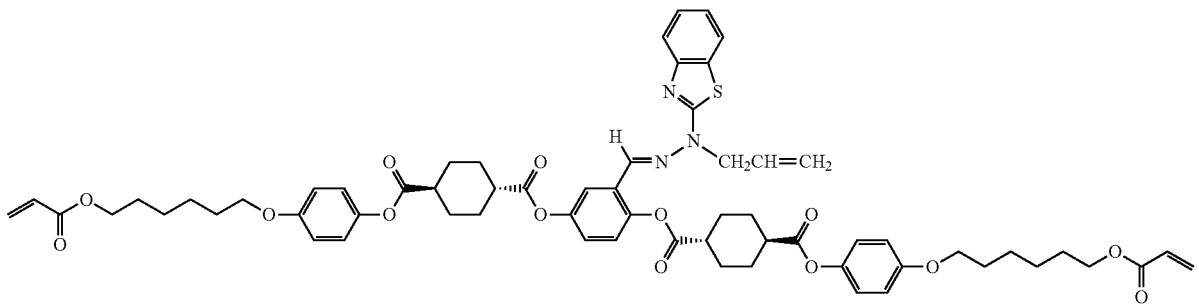

Compound 26 column chromatography (toluene:ethyl acetate=90:10) to obtain 1.61 g of a compound 26 as a yellow solid (yield: 89.6%).

The structure of the target product was identified by $^1$H-NMR.

$^1$H-NMR (500 MHz, CDCl$_3$, TMS, δ ppm): 7.74 (d, 1H, J=2.5 Hz), 7.70 (dd, 1H, J=1.0 Hz, 8.0 Hz), 7.64-7.69 (m, 2H), 7.35 (ddd, 1H, J=1.0 Hz, 7.5 Hz, 8.0 Hz), 7.18 (ddd, 1H, J=1.0 Hz, 7.5 Hz, 7.5 Hz), 7.09-7.13 (m, 2H), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.88 (ddt, 1H, J=4.5 Hz, 10.5 Hz, 17.5 Hz), 5.82 (dd, 2H, J=1.5 Hz, 10.5 Hz), 5.29 (dd, 1H, J=1.0 Hz, 10.5 Hz), 5.19 (dd, 1H, J=1.0 Hz, 17.5 Hz), 4.98-4.99 (m, 2H), 4.18 (t, 4H, J=6.5 Hz), 3.95 (t, 4H, J=6.5 Hz), 2.57-2.67 (m, 4H), 2.30-2.35 (m, 8H), 1.76-1.85 (m, 4H), 1.66-1.74 (m, 12H), 1.42-1.54 (m, 8H)

Example 40: Synthesis of Compound 27

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.54 (dd, 1H, J=1.0 Hz, 8.0 Hz), 7.28 (ddd, 1H, J=1.0 Hz, 7.5 Hz, 8.0 Hz), 7.06 (ddd, 1H, J=1.0 Hz, 7.5 Hz, 8.0 Hz), 5.89 (ddt, 1H, J=7.0 Hz, 10.5 Hz, 17.0 Hz), 5.17 (ddt, 1H, J=1.5 Hz, 3.0 Hz, 17.0 Hz), 5.09 (ddt, 1H, J=1.0 Hz, 3.0 Hz, 10.5 Hz), 4.26 (s, 2H), 3.85 (t, 2H, J=7.0 Hz), 2.52 (dddt, 2H, J=1.0 Hz, 1.5 Hz, 7.0 Hz, 7.0 Hz)

Step 2: Synthesis of Compound 27

A four-necked reactor equipped with a thermometer was charged with 195 mg (1.77 mmol) of the intermediate M1 synthesized in the step 1, 1.50 g (1.60 mmol) of the intermediate B synthesized in the step 2 of Example 1 (see "Synthesis of compound 1"), 3 ml of ethanol, and 15 ml of THF under a nitrogen stream to prepare a solution. After the addition of 41.2 mg (0.18 mmol) of (1)-10-camphorsulfonic Compound 27

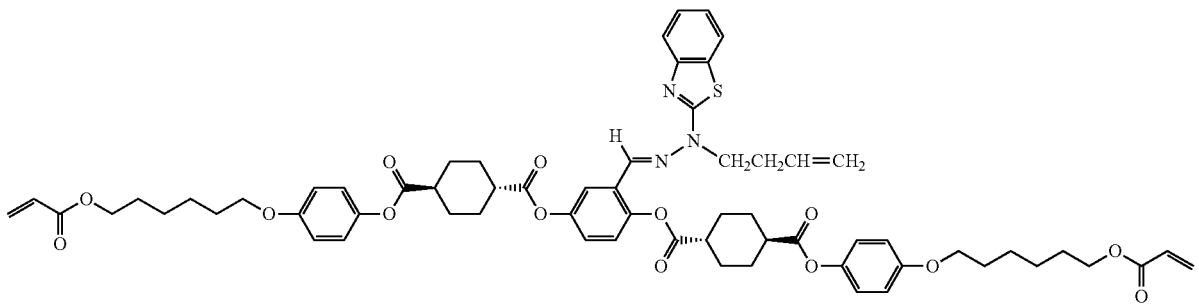

Step 1: Synthesis of Intermediate M1

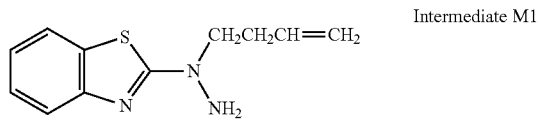

Intermediate M1

A four-necked reactor equipped with a thermometer was charged with 5.04 g (30.5 mmol) of 2-hydrazinobenzothiazole and 50 ml of DMF under a nitrogen stream to prepare a solution. After the addition of 14.9 g (45.8 mmol) of cesium carbonate and 4.94 g (36.6 mmol) of 4-bromo-1-butene to the solution, the mixture was stirred at 25° C. for 7 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (hexane:ethyl acetate=70:30) to obtain 4.40 g of an intermediate M1 as a white solid (yield: 49.5%).

acid to the solution, the mixture was stirred at 40° C. for 8 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.26 g of a compound 27 as a yellow solid (yield: 69.3%).

The structure of the target product was identified by $^1$H-NMR.

$^1$H-NMR (500 MHz, CDCl$_3$, TMS, δ ppm): 7.76 (d, 1H, J=2.5 Hz), 7.67-7.70 (m, 3H), 7.35 (ddd, 1H, J=1.5 Hz, 7.5 Hz, 8.0 Hz), 7.18 (ddd, 1H, J=1.5 Hz, 7.5 Hz, 8.0 Hz), 7.10-7.14 (m, 2H), 6.99 (d, 2H, J=9.5 Hz), 6.98 (d, 2H, J=9.5 Hz), 6.88 (d, 4H, J=9.5 Hz), 6.40 (dd, 2H, J=1.5 Hz, 17.5 Hz), 6.13 (dd, 2H, J=10.5 Hz, 17.5 Hz), 5.89 (ddt, 1H, J=6.5 Hz, 10.5 Hz, 17.0 Hz), 5.82 (dd, 2H, J=1.5 Hz, 10.5 Hz), 5.18 (dd, 1H, J=1.5 Hz, 17.0 Hz), 5.15 (dd, 1H, J=1.5 Hz, 10.5 Hz), 4.38 (t, 2H, J=7.0 Hz), 4.18 (t, 4H, J=6.5 Hz), 3.95 (t, 4H, J=6.5 Hz), 2.58-2.68 (m, 4H), 2.51 (dt, 2H, J=6.5 Hz, 7.0 Hz), 2.31-2.35 (m, 8H), 1.76-1.85 (m, 4H), 1.65-1.74 (m, 12H), 1.41-1.54 (m, 8H)

Example 41: Synthesis of Compound 28

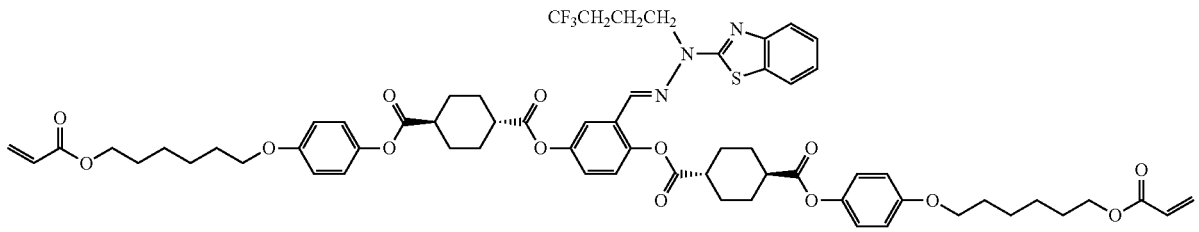

Compound 28

Step 1: Synthesis of Intermediate N1

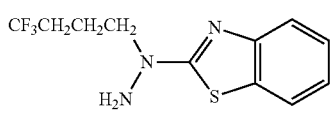

Intermediate N1

A four-necked reactor equipped with a thermometer was charged with 1.45 g (8.75 mmol) of 2-hydrazinobenzothiazole and 20 ml of DMF under a nitrogen stream to prepare a solution. After the addition of 3.63 g (26.3 mmol) of potassium carbonate and 2.50 g (10.5 mmol) of 1,1,1-trifluoro-4-iodobutane the solution, the mixture was stirred at 80° C. for 8 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (n-hexane:ethyl acetate=85:15) to obtain 961 mg of an intermediate N1 as a white solid (yield: 39.9%).

The structure of the target product was identified by $^1$H-NMR.

$^1$H-NMR (500 MHz, CDCl$_3$, TMS, δ ppm): 7.61 (d, 1H, J=8.0 Hz), 7.54 (d, 1H, J=7.8 Hz), 7.30 (dd, 1H, J=7.8 Hz, 7.8 Hz), 7.09 (dd, 1H, J=7.8 Hz, 8.0 Hz), 4.24 (s, 2H), 3.81 (t, 2H, J=7.0 Hz), 2.16-2.26 (m, 2H), 1.99-2.05 (m, 2H)

Step 2: Synthesis of Compound 28

A three-necked reactor equipped with a thermometer was charged with 1.50 g (1.60 mmol) of the intermediate B synthesized in the step 2 of Example 1 (see "Synthesis of compound 1"), 489 mg (1.78 mmol) of the intermediate N1 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (chloroform:THF=9:1) to obtain 1.47 g of a compound 28 as a light yellow solid (yield: 77.2%).

The structure of the target product was identified by $^1$H-NMR.

$^1$H-NMR (500 MHz, CDCl$_3$, TMS, δ ppm): 7.75 (s, 1H), 7.65-7.71 (m, 3H), 7.34 (ddd, 1H, J=1.0 Hz, 7.5 Hz, 7.5 Hz), 7.17 (ddd, 1H, J=1.0 Hz, 7.5 Hz, 7.5 Hz), 7.08-7.14 (m, 2H), 6.96-7.01 (m, 4H), 6.86-6.91 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.42 (t, 2H, J=7.5 Hz), 4.18 (t, 4H, J=6.5 Hz), 3.95 (t, 4H, J=6.5 Hz), 2.55-2.73 (m, 4H), 2.25-2.38 (m, 10H), 2.04 (tt, 2H, J=7.5 Hz, 7.5 Hz), 1.64-1.84 (m, 16H), 1.42-1.55 (m, 8H)

Example 42: Synthesis of Compound 29

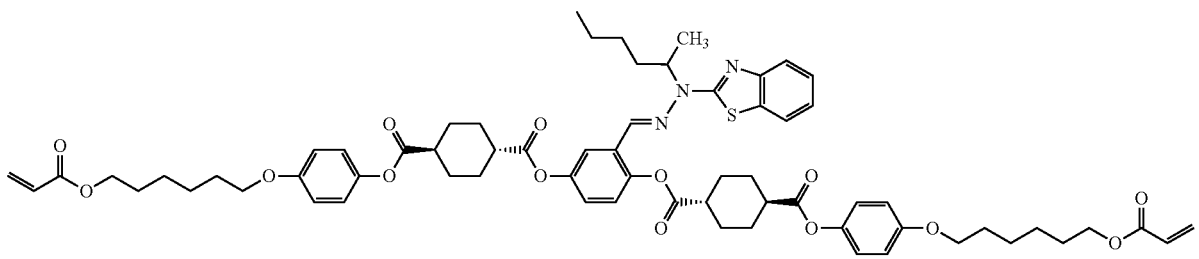

Compound 29

Step 1: Synthesis of Intermediate O1

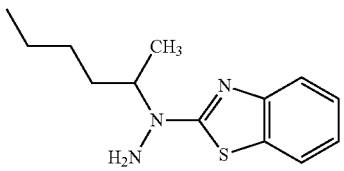

Intermediate O1

A three-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mol) of cesium carbonate to the solution, the mixture was cooled to 0° C. After the addition of 2.39 g (14.5 mmol) of 2-bromohexane to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (n-hexane: ethyl acetate=93:7) to obtain 1.61 g of an intermediate O1 as a white solid (yield: 53.4%).

The structure of the target product was identified by $^1$H-NMR.

$^1$H-NMR (400 MHz, CDCl$_3$, TMS, δ ppm): 7.59 (dd, 1H, J=1.0 Hz, 8.0 Hz), 7.52 (dd, 1H, J=1.0 Hz, 8.0 Hz), 7.24-7.30 (m, 1H), 7.05 (ddd, 1H, J=1.0 Hz, 8.0 Hz, 8.0 Hz), 3.97 (s, 2H), 1.47-1.74 (m, 3H), 1.20-1.41 (m, 7H), 0.89 (t, 3H, J=5.5 Hz)

Step 2: Synthesis of Compound 29

A three-necked reactor equipped with a thermometer was charged with 1.50 g (1.60 mmol) of the intermediate B synthesized in the step 2 of Example 1 (see "Synthesis of compound 1"), 444 mg (1.78 mmol) of the intermediate O1 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=92:8) to obtain 1.35 g of a compound 29 as a light yellow solid (yield: 72.4%).

The structure of the target product was identified by $^1$H-NMR.

$^1$H-NMR (500 MHz, CDCl$_3$, TMS, δ ppm): 8.04 (s, 1H), 7.73 (d, 1H, J=1.5 Hz), 7.69 (dd, 1H, J=1.5 Hz, 7.8 Hz), 7.65 (dd, 1H, J=1.5 Hz, 7.8 Hz), 7.33 (ddd, 1H, J=1.5 Hz, 7.8 Hz, 7.8 Hz), 7.07-7.19 (m, 3H), 6.95-7.01 (m, 4H), 6.85-6.91 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.18 (t, 4H, J=6.5 Hz), 3.95 (t, 4H, J=6.5 Hz), 2.54-2.73 (m, 4H), 2.25-2.40 (m, 8H), 1.65-1.83 (m, 16H), 1.60-1.62 (m, 2H), 1.57 (d, 3H, J=7.5 Hz), 1.24-1.55 (m, 13H), 0.87 (t, 3H, J=7.5 Hz)

Example 43: Synthesis of Compound 30

Step 1: Synthesis of Intermediate P1

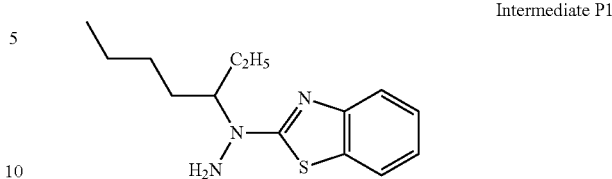

Intermediate P1

A three-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mol) of cesium carbonate to the solution, the mixture was cooled to 0° C. After the addition of 2.60 g (14.5 mmol) of 3-bromoheptane to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (n-hexane: ethyl acetate=9:1) to obtain 1.80 g of an intermediate P1 as a white solid (yield: 56.4%).

The structure of the target product was identified by $^1$H-NMR.

$^1$H-NMR (500 MHz, CDCl$_3$, TMS, δ ppm): 7.58 (dd, 1H, J=1.0 Hz, 7.5 Hz), 7.51 (dd, 1H, J=0.0 Hz, 7.5 Hz), 7.27 (ddd, 1H, J=1.0 Hz, 7.5 Hz, 7.5 Hz), 7.04 (ddd, 1H, J=1.0 Hz, 7.5 Hz, 7.5 Hz), 3.94 (s, 2H), 1.48-1.72 (m, 5H), 1.18-1.41 (m, 4H), 0.91 (t, 3H, J=7.5 Hz), 0.86 (t, 3H, J=7.5 Hz)

Step 2: Synthesis of Compound 30

A three-necked reactor equipped with a thermometer was charged with 1.50 g (1.60 mmol) of the intermediate B synthesized in the step 2 of Example 1 (see "Synthesis of compound 1"), 468 mg (1.78 mmol) of the intermediate P1 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography

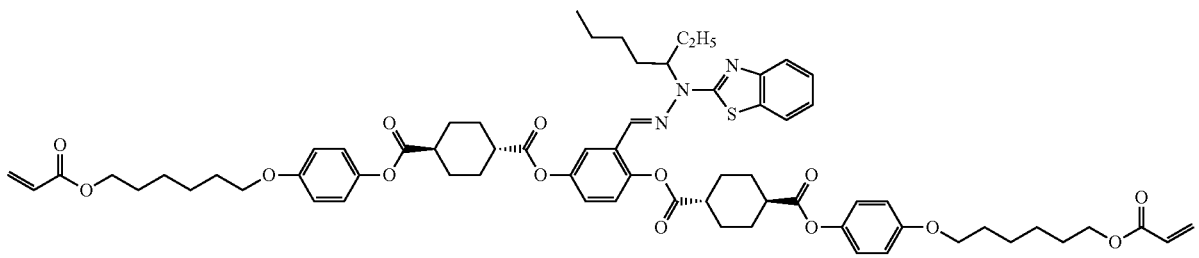

Compound 30

(toluene:ethyl acetate=9:1) to obtain 1.44 g of a compound 20 as a light yellow solid (yield: 76.3%).

The structure of the target product was identified by $^1$H-NMR.

$^1$H-NMR (500 MHz, CDCl$_3$, TMS, δ ppm): 8.03 (s, 1H), 7.74 (d, 1H, J=3.0 Hz), 7.69 (dd, 1H, J=1.0 Hz, 8.0 Hz), 7.64 (dd, 1H, J=1.0 Hz, 8.0 Hz), 7.33 (ddd, 1H, J=1.0 Hz, 8.0 Hz, 8.0 Hz), 7.16 (ddd, 1H, J=1.0 Hz, 8.0 Hz, 8.0 Hz), 7.07-7.14 (m, 2H), 6.96-7.01 (m, 4H), 6.86-6.91 (m, 4H), 6.40 (dd, 2H, J=1.5 Hz, 17.5 Hz), 6.12 (dd, 2H, J=10.5 Hz, 17.5 Hz), 5.82 (dd, 2H, J=1.5 Hz, 10.5 Hz), 4.18 (t, 4H, J=6.5 Hz), 3.95 (t, 4H, J=6.5 Hz), 2.55-2.72 (m, 4H), 2.26-2.40 (m, 8H), 1.65-1.91 (m, 19H), 1.23-1.55 (m, 14H), 0.94 (t, 3H, J=7.5 Hz), 0.86 (t, 3H, J=7.5 Hz)

Example 44: Synthesis of Compound 31

A three-necked reactor equipped with a thermometer was charged with 12.2 g (27.8 mmol) of the intermediate Q1 synthesized in the step 1, 2.22 g of 5% palladium-activated carbon, 50 ml of THF, and 200 ml of methanol. A hydrogen balloon was provided to the reactor, and the mixture was stirred at 25° C. for 21 hours in a hydrogen atmosphere. After completion of the reaction, 100 ml of chloroform was added to the reaction mixture, and palladium-activated carbon was separated by filtration. The organic layer was concentrated using a rotary evaporator to obtain 8.70 g of a brown powder. The brown powder was dissolved in 100 ml of toluene (20 g). After the addition of 2.34 g (32.6 mmol) of acrylic acid, 36.8 mg (0.296 mmol) of 4-methoxyphenol, and 284 mg (2.96 mmol) of methanesulfonic acid, the Compound 31

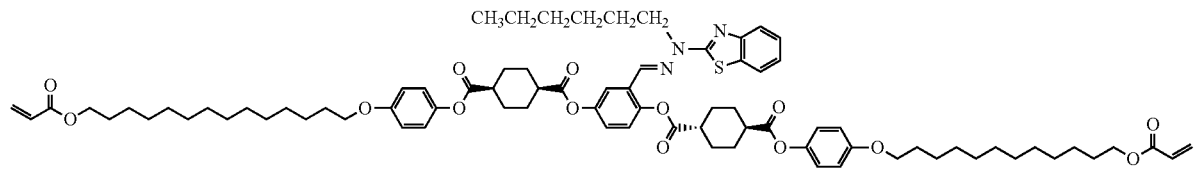

Step 1: Synthesis of Intermediate Q1

Intermediate Q1

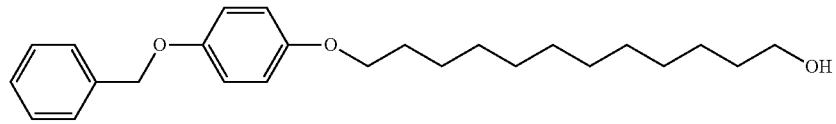

A three-necked reactor equipped with a thermometer was charged with 14.4 g (54.4 mmol) of 12-bromo-1-dodecanol, 12.0 g (59.8 mmol) of 4-(benzyloxy)phenol, 9.02 g (65.2 mmol) of potassium carbonate, 1.42 g (5.44 mmol) of 18-crown-6 ether, and 150 ml of acetone. The mixture was refluxed for 10 hours. After completion of the reaction, the reaction mixture was cooled to 25° C. 300 ml of distilled water was added to the reaction mixture, followed by extraction twice with 200 ml of ethyl acetate. The organic layer was dried over anhydrous sodium sulfate, and sodium sulfate was separated by filtration. The filtrate was concentrated using a rotary evaporator to obtain 12.2 g of an intermediate Q1 as a white solid (yield: 51.1%).

The structure of the target product was identified by $^1$H-NMR.

$^1$H-NMR (500 MHz, DMSO-d$_6$, TMS, δ ppm): 7.36-7.45 (m, 4H), 7.29-7.34 (m, 1H), 6.89-6.94 (m, 2H), 6.81-6.86 (m, 2H), 5.02 (s, 2H), 4.32 (t, 1H, J=5.0 Hz), 3.87 (t, 2H, J=7.5 Hz), 3.36 (t, 2H, J=7.5 Hz), 1.66 (tt, 2H, J=7.5 Hz, 7.5 Hz), 1.20-1.43 (m, 18H)

Step 2: Synthesis of Intermediate R1 mixture was refluxed for 10 hours. After completion of the reaction, the reaction mixture was cooled to 25° C., added to 300 ml of water, and extracted twice with 200 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=96:4) to obtain 5.94 g of an intermediate R1 as a white solid (yield: 57.6%).

The structure of the target product was identified by $^1$H-NMR.

$^1$H-NMR (500 MHz, DMSO-d$_6$, TMS, δ ppm): 8.87 (s, 1H), 6.69-6.74 (m, 2H), 6.62-6.67 (m, 2H), 6.31 (dd, 1H, J=1.5 Hz, 17.5 Hz), 6.16 (dd, 1H, J=10.5 Hz, 17.5 Hz), 5.93 (dd, 1H, J=1.5 Hz, 10.5 Hz), 4.09 (t, 2H, J=6.5 Hz), 3.82 (t, 2H, J=6.5 Hz), 1.55-1.68 (m, 4H), 1.21-1.42 (m, 16H)

Intermediate R1

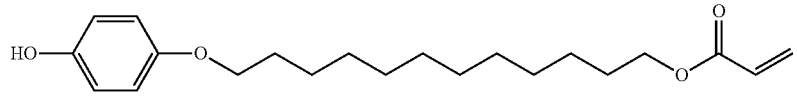

Step 3: Synthesis of Intermediate S1

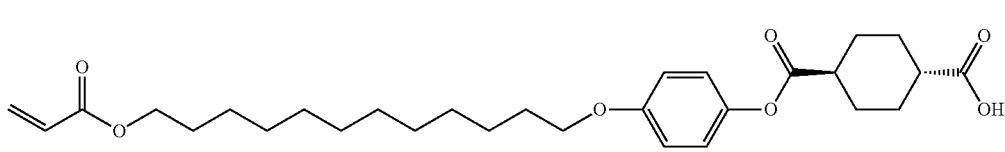

Intermediate S1

A three-necked reactor equipped with a thermometer was charged with 6.20 g (36.0 mmol) of trans-1,4-cyclohexanedicarboxylic acid, 40 ml of THF, and 8 ml of DMF under a nitrogen stream. After the addition of 2.06 g (18.0 mmol) of methanesulfonyl chloride to the mixture, the reactor was immersed in a water bath to adjust the temperature of the reaction mixture to 20° C. 1.99 g (19.6 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After the addition of 200 mg (1.64 mmol) of 4-(dimethylamino) pyridine and 5.70 g (16.4 mmol) of the intermediate R1 synthesized in the step 2 to the reaction mixture, the reactor was immersed in a water bath to adjust the temperature of the reaction mixture to 15° C. 1.99 g (19.6 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After completion of the reaction, 250 ml of distilled water and 100 ml of a saturated sodium chloride solution were added to the reaction mixture, followed by extraction twice with 200 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (toluene:THF=95:5) to obtain 3.90 g of an intermediate S1 as a white solid (yield: 47.4%).

The structure of the target product was identified by $^1$H-NMR.

$^1$H-NMR (500 MHz, DMSO-$d_6$, TMS, δ ppm): 12.1 (s, 1H), 6.96-7.01 (m, 2H), 6.89-6.94 (m, 2H), 6.31 (dd, 1H, J=1.5 Hz, 17.5 Hz), 6.16 (dd, 1H, J=10.0 Hz, 17.5 Hz), 5.93 (dd, 1H, J=1.5 Hz, 10.0 Hz), 4.09 (t, 2H, J=7.0 Hz), 3.93 (t, 2H, J=7.0 Hz), 2.18-2.26 (m, 1H), 2.04-2.10 (m, 2H), 1.93-2.00 (m, 2H), 1.69 (tt, 2H, J=7.0 Hz, 7.0 Hz), 1.59 (tt, 2H, J=7.0 Hz, 7.0 Hz), 1.20-1.52 (m, 21H)

Step 4: Synthesis of Intermediate T1

A three-necked reactor equipped with a thermometer was charged with 2.80 g (5.58 mmol) of the intermediate S1 synthesized in the step 3 and 40 ml of THF under a nitrogen stream to prepare a solution. After the addition of 664 mg (5.80 mmol) of methanesulfonyl chloride to the solution, the reactor was immersed in a water bath to adjust the temperature of the reaction mixture to 20° C. 586 mg (5.80 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After the addition of 56.6 mg (0.464 mmol) of 4-(dimethylamino) pyridine and 320 mg (2.32 mmol) of 2,5-dihydroxybenzaldehyde to the reaction mixture, the reactor was immersed in a water bath to adjust the temperature of the reaction mixture to 15° C. 586 mg (5.80 mmol) of triethylamine was added dropwise to the reaction mixture over 5 minutes while maintaining the temperature of the reaction mixture at 20 to 30° C. After the dropwise addition, the mixture was stirred at 25° C. for 2 hours. After completion of the reaction, 300 ml of distilled water and 50 ml of a saturated sodium chloride solution were added to the reaction mixture, followed by extraction twice with 150 ml of chloroform. The organic layer was dried over anhydrous sodium sulfate, and sodium sulfate was separated by filtration. The filtrate was concentrated using a rotary evaporator, and the resulting solid was dissolved in 20 ml of THF. 200 ml of methanol was added to the solution to precipitate crystals. The crystals were filtered off, washed with methanol, and dried under vacuum to obtain 1.84 g of an intermediate T1 as a white solid (yield: 71.6%).

The structure of the target product was identified by $^1$H-NMR.

$^1$H-NMR (500 MHz, CDCl$_3$, TMS, δ ppm): 10.1 (s, 1H), 7.61 (d, 1H, J=2.8 Hz), 7.37 (dd, 1H, J=2.8 Hz, 9.0 Hz), 7.20 (d, 1H, J=9.0 Hz), 6.94-7.01 (m, 4H), 6.85-6.91 (m, 4H), 6.40 (dd, 2H, J=1.5 Hz, 17.5 Hz), 6.12 (dd, 2H, J=10.5 Hz, 17.5 Hz), 5.81 (dd, 2H, J=1.5 Hz, 10.5 Hz), 4.15 (t, 4H, J=6.5 Hz), 3.93 (t, 4H, J=6.5 Hz), 2.54-2.75 (m, 4H), 2.24-2.39 (m, 8H), 1.62-1.81 (m, 14H), 1.24-1.48 (m, 34H)

Step 5: Synthesis of Compound 31

A three-necked reactor equipped with a thermometer was charged with 1.50 g (1.36 mmol) of the intermediate T1 synthesized in the step 4, 375 mg (1.51 mmol) of the intermediate J synthesized in the step 1 of Example 4 (see "Synthesis of compound 4"), 35.1 mg (0.151 mmol) of (±)-10-camphorsulfonic acid, 24 ml of THF, and 6 ml of ethanol under a nitrogen stream to prepare a homogeneous solution. The solution was stirred at 40° C. for 5 hours. After completion of the reaction, the reaction mixture was added to 150 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (chloroform:THF=97:3) to obtain 1.54 g of a compound 31 as a light yellow solid (yield: 84.6%).

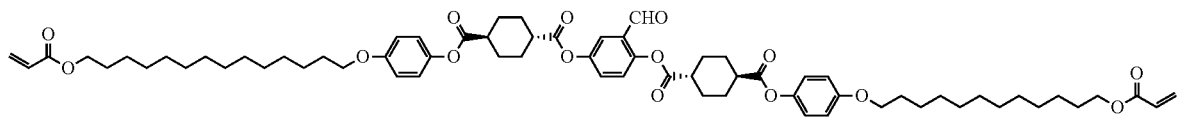

Intermediate T1

The structure of the target product was identified by ¹H-NMR.

1H-NMR (500 MHz, CDCl₃, TMS, δ ppm): 7.75 (d, 1H, J=2.0 Hz), 7.65-7.71 (m, 3H), 7.34 (ddd, 1H, J=1.0 Hz, 8.0 Hz, 8.0 Hz), 7.17 (ddd, 1H, J=1.0 Hz, 8.0 Hz, 8.0 Hz), 7.08-7.14 (m, 2H), 6.95-7.01 (m, 4H), 6.86-6.91 (m, 4H), 6.40 (dd, 2H, J=1.5 Hz, 17.5 Hz), 6.12 (dd, 2H, J=10.5 Hz, 17.5 Hz), 5.81 (dd, 2H, J=1.5 Hz, 10.5 Hz), 4.30 (t, 2H, J=7.0 Hz), 4.15 (t, 4H, J=7.0 Hz), 3.94 (t, 4H, J=7.0 Hz), 2.54-2.73 (m, 4H), 2.25-2.39 (m, 8H), 1.63-1.81 (m, 16H), 1.23-1.44 (m, 40H), 0.90 (t, 3H, J=7.0 Hz)

Example 45: Synthesis of Compound 32 of triethylamine was added dropwise to the reaction mixture over 10 minutes. After the dropwise addition, the mixture was stirred at 25° C. for 2 hours. After completion of the reaction, 1000 ml of distilled water and 100 ml of a saturated sodium chloride solution were added to the reaction mixture, followed by extraction twice with 400 ml of ethyl acetate. The organic layer was dried over anhydrous sodium sulfate, and sodium sulfate was separated by filtration. The reaction mixture was concentrated using a rotary evaporator, and the concentrate was purified by silica gel column chromatography (THF:chloroform=5:95) to obtain 9.66 g of an intermediate U1 as a white solid (yield: 53%).

Compound 32

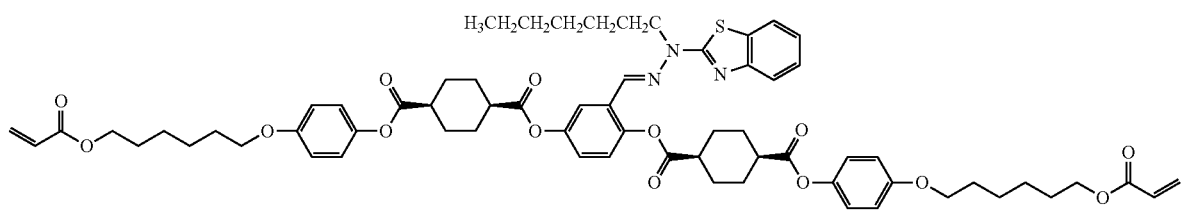

Step 1: Synthesis of Intermediate U1

Intermediate U1

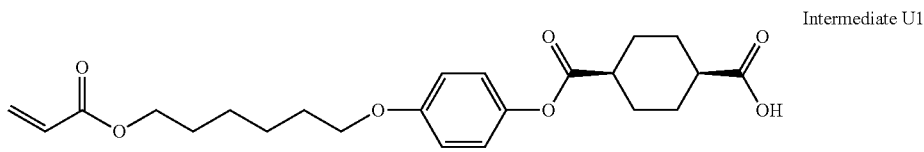 [SMILES: C=CC(=O)OCCCCCCOc1ccc(OC(=O)[C@H]2CC[C@@H](C(=O)O)CC2)cc1]

A three-necked reactor equipped with a thermometer was charged with 15.00 g (87.12 mmol) of cis-1,4-cyclohexanedicarboxylic acid and 150 ml of THF under a nitrogen stream. After the addition of 5.48 g (47.92 mmol) of methanesulfonyl chloride to the mixture, the reactor was immersed in a water bath to adjust the temperature of the reaction mixture to 15° C. After the addition of 5.07 g (50.09 mmol) of triethylamine dropwise to the reaction mixture over 10 minutes, the mixture was stirred at 25° C. for 2 hours. After the addition of 0.53 g (4.36 mmol) of 4-(dimethylamino)pyridine and 11.51 g (43.56 mmol) of 4-(6-acryloyloxyhex-1-yloxy)phenol to the reaction mixture, the reactor was immersed in a water bath to adjust the temperature of the reaction mixture to 15° C. 5.29 g (52.27 mmol)

The structure of the target product was identified by ¹H-NMR.

¹H-NMR (500 MHz, DMSO-d₆, TMS, δ ppm): 12.16 (s, 1H), 6.99 (d, 2H, J=9.0 Hz), 6.92 (d, 2H, J=9.0 Hz), 6.32 (dd, 1H, J=0.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.94 (t, 2H, J=6.5 Hz), 2.71-2.79 (m, 1H), 2.41-2.48 (m, 1H), 1.57-1.91 (m, 12H), 1.34-1.50 (m, 4H)

Step 2: Synthesis of Intermediate V1

Intermediate V1

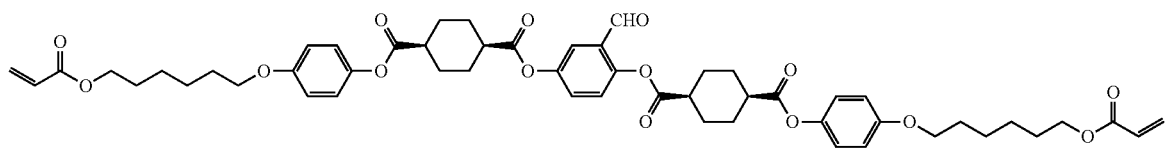

A three-necked reactor equipped with a thermometer was charged with 2.50 g (5.97 mmol) of the intermediate U1 synthesized in the step 1 and 30 ml of THF under a nitrogen stream to prepare a solution. After the addition of 0.70 g (6.10 mmol) of methanesulfonyl chloride to the solution, the reactor was immersed in a water bath to adjust the temperature of the reaction mixture to 15° C. After the addition of 0.63 g (6.22 mmol) of triethylamine dropwise to the reaction mixture over 5 minutes, the mixture was stirred at 25° C. for 2 hours. After the addition of 0.06 g (0.50 mmol) of 4-(dimethylamino)pyridine and 0.34 g (2.49 mmol) of 2,5-dihydroxybenzaldehyde to the reaction mixture, the reactor was immersed in a water bath to adjust the temperature of the reaction mixture to 15° C. 0.60 g (5.97 mmol) of triethylamine was added dropwise to the reaction mixture over 5 minutes. After the dropwise addition, the mixture was stirred at 25° C. for 2 hours. After completion of the reaction, 200 ml of distilled water and 20 ml of a saturated sodium chloride solution were added to the reaction mixture, followed by extraction twice with 100 ml of chloroform. The organic layer was dried over anhydrous sodium sulfate, and sodium sulfate was separated by filtration. The filtrate was concentrated using a rotary evaporator. After the addition of 100 ml of toluene to the concentrate, an insoluble solid was filtered off. The solid was washed with methanol, and dried under vacuum to obtain 1.32 g of an intermediate V1 as a white solid (yield: 56%).

The structure of the target product was identified by $^1$H-NMR.

$^1$H-NMR (500 MHz, DMSO-d$_6$, TMS, δ ppm): 10.02 (s, 1H), 7.67 (d, 1H, J=3.0 Hz), 7.55 (dd, 1H, J=3.0 Hz, 8.5 Hz), 7.39 (d, 1H, J=8.5 Hz), 7.01 (d, 4H, J=9.0 Hz), 6.93 (d, 4H, J=9.0 Hz), 6.31 (dd, 2H, J=1.5 Hz, 17.5 Hz), 6.17 (dd, 2H, J=10.0 Hz, 17.5 Hz), 5.93 (dd, 2H, J=1.5 Hz, 10.0 Hz), 4.11 (t, 4H, J=6.5 Hz), 3.94 (t, 4H, J=6.5 Hz), 2.78-3.02 (m, 4H), 1.79-2.05 (m, 16H), 1.55-1.76 (m, 8H), 1.33-1.49 (m, 8H)

Step 3: Synthesis of Compound 32

A three-necked reactor equipped with a thermometer was charged with 1.20 g (1.28 mmol) of the intermediate V1 synthesized in the step 2 and 30 ml of THF under a nitrogen stream to prepare a solution. After the addition of 0.26 ml (0.26 mmol) of 1 N hydrochloric acid and 0.48 g (1.92 mmol) of the intermediate J synthesized in the step 1 of Example 4 (see "Synthesis of compound 4") to the solution, the mixture was stirred at 40° C. for 7 hours. After completion of the reaction, the reaction mixture was concentrated using a rotary evaporator, and the concentrate was purified by silica gel column chromatography (chloroform:THF=98:2) to obtain 1.23 g of a compound 32 as a light yellow solid (yield: 82%).

The structure of the target product was identified by $^1$H-NMR.

$^1$H-NMR (500 MHz, CDCl$_3$, TMS, δ ppm): 7.74 (d, 1H, J=2.5 Hz), 7.68 (s, 1H), 7.64 (d, 1H, J=8.0 Hz), 7.58 (dt, 1H, J=1.0 Hz, 7.5 Hz), 7.31 (dt, 1H, J=1.0 Hz, 7.5 Hz), 7.05-7.14 (m, 3H), 6.98 (d, 2H, J=9.0 Hz), 6.96 (d, 2H, J=9.0 Hz), 6.86 (d, 2H, J=9.0 Hz), 6.84 (d, 2H, J=9.0 Hz), 6.39 (dd, 1H, J=1.5 Hz, 17.5 Hz), 6.39 (dd, 1H, J=1.5 Hz, 17.5 Hz), 6.12 (dd, 1H, J=10.5 Hz, 17.5 Hz), 6.12 (dd, 1H, J=10.5 Hz, 17.5 Hz), 5.81 (dd, 1H, J=1.5 Hz, 10.5 Hz), 5.81 (dd, 1H, J=1.5 Hz, 10.5 Hz), 4.28 (t, 2H, J=7.5 Hz), 4.17 (t, 2H, J=6.5 Hz), 4.16 (t, 2H, J=6.5 Hz), 3.87-3.96 (m, 4H), 2.75-2.90 (m, 4H), 2.08-2.26 (m, 8H), 1.85-2.03 (m, 8H), 1.65-1.82 (m, 10H), 1.24-1.54 (m, 14H), 0.87 (t, 3H, J=7.0 Hz)

Example 46: Synthesis of Compound 33

Compound 33

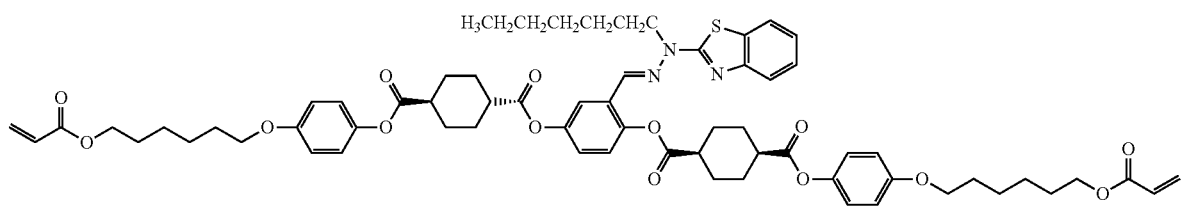

Step 1: Synthesis of Intermediate W1

Intermediate W1

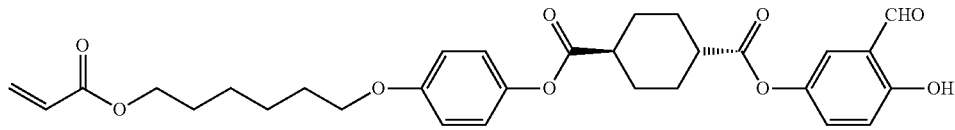

A three-necked reactor equipped with a thermometer was charged with 1.50 g (3.58 mmol) of the intermediate A synthesized in the step 1 of Example 1 (see "Synthesis of compound 1") and 30 ml of THF under a nitrogen stream to prepare a solution. After the addition of 0.43 g (3.76 mmol) of methanesulfonyl chloride to the solution, the reactor was immersed in a water bath to adjust the temperature of the reaction mixture to 15° C. After the addition of 0.40 g (3.94 mmol) of triethylamine dropwise to the reaction mixture over 5 minutes, the mixture was stirred at 25° C. for 2 hours. After the addition of 2.48 g (17.92 mmol) of 2,5-dihydroxybenzaldehyde and 0.04 g (0.36 mmol) of 4-(dimethylamino)pyridine to the reaction mixture, the reactor was immersed in a water bath to adjust the temperature of the reaction mixture to 15° C. 0.44 g (4.30 mmol) of triethylamine was added dropwise to the reaction mixture over 5 minutes. After the dropwise addition, the mixture was stirred at 25° C. for 2 hours. After completion of the reaction, 300 ml of distilled water and 50 ml of a saturated sodium chloride solution were added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator. After the addition of 100 ml of toluene to the concentrate, an insoluble solid was removed by filtration. The filtrate was concentrated using a rotary evaporator, and the concentrate was purified by silica gel column chromatography (THF:toluene=5:95) to obtain 0.80 g of an intermediate W1 as a white solid (yield: 41%).

The structure of the target product was identified by $^1$H-NMR.

$^1$H-NMR (500 MHz, CDCl$_3$, TMS, δ ppm): 10.91 (s, 1H), 9.86 (s, 1H), 7.32 (d, 1H, J=3.0 Hz), 7.25 (dd, 1H, J=3.0 Hz, 9.0 Hz), 7.01 (d, 1H, J=9.0 Hz), 6.97 (d, 2H, J=9.0 Hz), 6.87 (d, 2H, J=9.0 Hz), 6.40 (dd, 1H, J=1.5 Hz, 17.5 Hz), 6.12 (dd, 1H, J=10.0 Hz, 17.5 Hz), 5.82 (dd, 1H, J=1.5 Hz, 10.0 Hz), 4.17 (t, 2H, J=6.5 Hz), 3.94 (t, 2H, J=6.5 Hz), 2.53-2.65 (m, 2H), 2.23-2.35 (m, 4H), 1.75-1.84 (m, 2H), 1.62-1.75 (m, 6H), 1.41-1.55 (m, 4H)

Step 2: Synthesis of Intermediate X1

A three-necked reactor equipped with a thermometer was charged with 0.87 g (2.09 mmol) of the intermediate U1 synthesized in the step 1 of Example 45 (see "Synthesis of compound 32") and 30 ml of THF under a nitrogen stream to prepare a solution. After the addition of 0.25 g (2.16 mmol) of methanesulfonyl chloride to the solution, the reactor was immersed in a water bath to adjust the temperature of the reaction mixture to 15° C. 0.23 g (2.23 mmol) of triethylamine was added dropwise to the reaction mixture over 5 minutes. After the dropwise addition, the mixture was stirred at 25° C. for 2 hours. After the addition of 0.02 g (0.14 mmol) of 4-(dimethylamino)pyridine and 0.75 g (1.39 mmol) of the intermediate W1 synthesized in the step 1 to the reaction mixture, the reactor was immersed in a water bath to adjust the temperature of the reaction mixture to 15° C. 0.17 g (1.67 mmol) of triethylamine was added dropwise to the reaction mixture over 5 minutes. After the dropwise addition, the mixture was stirred at 25° C. for 2 hours. After completion of the reaction, 200 ml of distilled water and 20 ml of a saturated sodium chloride solution were added to the reaction mixture, followed by extraction twice with 100 ml of chloroform. The organic layer was dried over anhydrous sodium sulfate, and sodium sulfate was separated by filtration. The filtrate was concentrated using a rotary evaporator. After the addition of 100 ml of toluene to the concentrate, an insoluble solid was filtered off. The solid was washed with methanol, and dried under vacuum to obtain 0.98 g of an intermediate X1 as a white solid (yield: 75%).

The structure of the target product was identified by $^1$H-NMR.

$^1$H-NMR (500 MHz, CDCl$_3$, TMS, δ ppm): 10.09 (s, 1H), 7.61 (d, 1H, J=3.0 Hz), 7.36 (dd, 1H, J=3.0 Hz, 9.0 Hz), 7.21 (d, 1H, J=9.0 Hz), 6.97 (d, 2H, J=9.0 Hz), 6.97 (d, 2H, J=9.0 Hz), 6.87 (d, 2H, J=9.0 Hz), 6.87 (d, 2H, J=9.0 Hz), 6.40 (dd, 1H, J=1.5 Hz, 17.5 Hz), 6.40 (dd, 1H, J=1.5 Hz, 17.5 Hz), 6.12 (dd, 1H, J=10.0 Hz, 17.5 Hz), 6.12 (dd, 1H, J=10.0 Hz, 17.5 Hz), 5.82 (dd, 1H, J=1.5 Hz, 10.0 Hz), 5.82 (dd, 1H, J=1.5 Hz, 10.0 Hz), 4.17 (t, 2H, J=6.5 Hz), 4.17 (t, 2H, J=6.5 Hz), 3.94 (t, 2H, J=6.5 Hz), 3.94 (t, 2H, J=6.5 Hz), 2.77-2.93 (m, 2H), 2.52-2.66 (m, 2H), 2.09-2.37 (m, 8H), 1.85-2.04 (m, 4H), 1.58-1.84 (m, 12H), 1.38-1.56 (m, 8H)

Step 3: Synthesis of Compound 33

A three-necked reactor equipped with a thermometer was charged with 0.94 g (1.00 mmol) of the intermediate X1 synthesized in the step 2 and 15 ml of THF under a nitrogen stream to prepare a solution. After the addition of 0.20 ml (0.20 mmol) of 1 N hydrochloric acid and 0.37 g (1.49 mmol) of the intermediate J synthesized in the step 1 of Example 4 (see "Synthesis of compound 4") to the solution, the mixture was stirred at 60° C. for 10 hours, After completion of the reaction, the reaction mixture was concentrated using a rotary evaporator, and the concentrate was purified by silica gel column chromatography (chloroform:THF=98:2) to obtain 0.92 g of a compound 33 as a light yellow solid (yield: 79%).

Intermediate X1

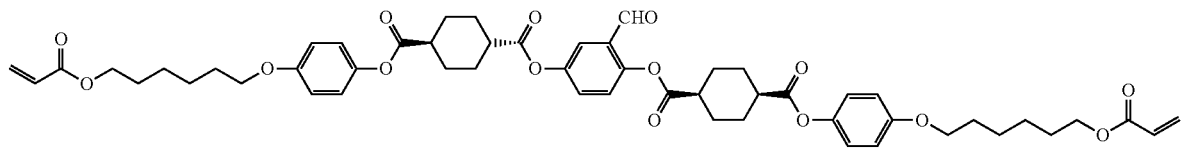

The structure of the target product was identified by $^1$H-NMR.

$^1$H-NMR (500 MHz, CDCl$_3$, TMS, δ ppm): 7.74 (d, 1H, J=2.5 Hz), 7.64-7.71 (m, 3H), 7.33 (dt, 1H, J=1.0 Hz, 7.5 Hz), 7.07-7.19 (m, 3H), 6.99 (d, 2H, J=9.0 Hz), 6.96 (d, 2H, J=9.0 Hz), 6.88 (d, 2H, J=9.0 Hz), 6.87 (d, 2H, J=9.0 Hz), 6.40 (dd, 1H, J=1.5 Hz, 17.5 Hz), 6.39 (dd, 1H, J=1.5 Hz, 17.5 Hz), 6.13 (dd, 1H, J=10.5 Hz, 17.5 Hz), 6.11 (dd, 1H, J=10.5 Hz, 17.5 Hz), 5.82 (dd, 1H, J=1.5 Hz, 10.5 Hz), 5.81 (dd, 1H, J=1.5 Hz, 10.5 Hz), 4.28 (t, 2H, J=7.5 Hz), 4.17 (t, 2H, J=6.5 Hz), 4.16 (t, 2H, J=6.5 Hz), 3.90-3.97 (m, 4H), 2.80-2.88 (m, 2H), 2.54-2.71 (m, 2H), 2.26-2.38 (m, 4H), 2.09-2.26 (m, 4H), 1.85-2.03 (m, 4H), 1.64-1.83 (m, 14H), 1.24-1.55 (m, 14H), 0.87 (t, 3H, J=7.0 Hz)

Phase Transition Temperature Measurement 2

10 mg of the compound (compounds 9 to 33) was weighed, and placed in a solid state between two glass substrates provided with a polyimide alignment film subjected to a rubbing treatment. The substrates were placed on a hot plate, heated from 40° C. to 250° C., and cooled to 40° C. A change in structure when the temperature was changed was observed using a polarizing microscope.

The phase transition temperature measurement results are shown in Table 3.

TABLE 3

| | Compound No. | Phase transition temperature |
|---|---|---|
| Example 22 | Compound 9 | C ⇌(144° C. / 110° C.) N →(250° C. or more) I |
| Example 23 | Compound 10 | C ⇌(128° C. / 85° C.) N →(250° C. or more) I |
| Example 24 | Compound 11 | C ⇌(142° C. / 114° C.) N ⇌(240° C. / 225° C.) I |

TABLE 3-continued

| Example | Compound No. | Phase transition temperature |
|---|---|---|
| Example 25 | Compound 12 | C ⇌ N (138°C / 100°C) → I (250°C or more) |
| Example 26 | Compound 13 | C ⇌ N (116°C / 40°C or less) → I (250°C or more) |
| Example 27 | Compound 14 | C ⇌ N (142°C / 88°C) → I (250°C or more) |
| Example 28 | Compound 15 | C ⇌ N (145°C / 105°C) → I (250°C or more) |
| Example 29 | Compound 16 | C ⇌ N (172°C / 40°C or less) → I (250°C or more) |
| Example 30 | Compound 17 | C ⇌ N (145°C / 118°C) → I (250°C or more) |
| Example 31 | Compound 18 | C ⇌ N (111°C / 40°C or less) → I (250°C or more) |
| Example 32 | Compound 19 | C ⇌ N (110°C / 40°C or less) → I (250°C or more) |
| Example 33 | Compound 20 | C ⇌ N (105°C / 40°C or less) ⇌ I (235°C / 226°C) |
| Example 34 | Compound 21 | C ⇌ N (112°C / 78°C) ⇌ I (215°C / 207°C) |
| Example 35 | Compound 22 | C ⇌ N (110°C / 40°C or less) ⇌ I (216°C / 210°C) |
| Example 36 | Compound 23 | C ⇌ N (114°C / 74°C) ⇌ I (200°C / 198°C) |
| Example 37 | Compound 24 | C ⇌ N (130°C / 40°C or less) ⇌ I (200°C / 196°C) |
| Example 38 | Compound 25 | C ⇌ N (95°C / 40°C or less) ⇌ I (218°C / 210°C) |
| Example 39 | Compound 26 | C ⇌ N (146°C / 80°C) ⇌ I (245°C / 237°C) |
| Example 40 | Compound 27 | C ⇌ N (120°C / 62°C) → I (250°C or more) |
| Example 41 | Compound 28 | C ⇌ N (142°C / 40°C or less) ⇌ I (238°C / 225°C) |
| Example 42 | Compound 29 | C ⇌ N (88°C / 40°C or less) ⇌ I (200°C / 193°C) |
| Example 43 | Compound 30 | C ⇌ N (115°C / 40°C or less) ⇌ I (185°C / 174°C) |
| Example 44 | Compound 31 | C ⇌ N (107°C / 52°C) ⇌ I (194°C / 186°C) |
| Example 45 | Compound 32 | C ⇌ I (100°C / 40°C or less) |
| Example 46 | Compound 33 | C ⇌ I (100°C / 40°C or less) |

Examples 47 and 48

1.0 g of the compound 9 obtained in Example 22 or the compound 10 obtained in Example 23, 30 mg of the photoinitiator A, and 100 mg of a 1% cyclopentanone solution of the surfactant A were dissolved in 2.3 g of cyclopentanone and 2.26 g of chloroform. The solution was filtered through a disposable filter having a pore size of 0.45 μm to obtain a polymerizable composition (polymerizable compositions 14 and 15).

Example 49

1.0 g of the compound 11 obtained in Example 24, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition 16.

Example 50

1.0 g of the compound 12 obtained in Example 25, 30 mg of the photoinitiator A, and 100 mg of a 1% cyclopentanone solution of the surfactant A were dissolved in 2.3 g of cyclopentanone and 1.7 g of chloroform. The solution was filtered through a disposable filter having a pore size of 0.45 μm to obtain a polymerizable composition 17.

Example 51

1.0 g of the compound 13 obtained in Example 26, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition 18.

Example 52

1.0 g of the compound 14 obtained in Example 27, 30 mg of the photoinitiator A, and 100 mg of a 1% cyclopentanone solution of the surfactant A were dissolved in 2.3 g of cyclopentanone and 1.7 g of chloroform. The solution was filtered through a disposable filter having a pore size of 0.45 μm to obtain a polymerizable composition 19.

Examples 53 and 54

1.0 g of the compound 15 obtained in Example 28 or the compound 16 obtained in Example 29, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition (polymerizable compositions 20 and 21).

Example 55

0.5 g of the compound 17 obtained in Example 30, 0.5 g of the compound 4 obtained in Example 4, 30 mg of the photoinitiator A, and 100 mg of a 1% cyclopentanone solution of the surfactant A were dissolved in 3.26 g of chloroform. The solution was filtered through a disposable filter having a pore size of 0.45 μm to obtain a polymerizable composition 22.

Examples 56 to 63

1.0 g of each of the compounds 18 to 25 respectively obtained in Examples 31 to 38, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition (polymerizable compositions 23 to 30).

Example 64

1.0 g of the compound 26 obtained in Example 39, 30 mg of the photoinitiator A, and 100 mg of a 1% cyclopentanone solution of the surfactant A were dissolved in 2.3 g of cyclopentanone and 0.7 g of chloroform. The solution was filtered through a disposable filter having a pore size of 0.45 m to obtain a polymerizable composition 31.

Example 65

1.0 g of the compound 27 obtained in Example 40, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition 32.

Example 66

1.0 g of the compound 28 obtained in Example 41, 30 mg of the photoinitiator A, and 100 mg of a 1% cyclopentanone solution of the surfactant A were dissolved in 2.3 g of cyclopentanone and 0.7 g of chloroform. The solution was filtered through a disposable filter having a pore size of 0.45 μm to obtain a polymerizable composition 33.

Examples 67 and 68

1.0 g of the compound 29 obtained in Example 42 or the compound 30 obtained in Example 43, 30 mg of the photoinitiator A, and 100 mg of a 1% cyclopentanone solution of the surfactant A were dissolved in 2.3 g of cyclopentanone. The solution was filtered through a disposable filter having a pore size of 0.45 m to obtain a polymerizable composition (polymerizable compositions 34 and 35).

Example 69

1.0 g of the compound 31 obtained in Example 44, 30 mg of the photoinitiator A, and 100 mg of a 1% cyclopentanone solution of the surfactant A were dissolved in 2.3 g of cyclopentanone and 0.7 g of chloroform. The solution was filtered through a disposable filter having a pore size of 0.45 μm to obtain a polymerizable composition 36.

Examples 70 and 71

1.0 g of the compound 32 obtained in Example 44 or the compound 33 obtained in Example 45, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition (polymerizable compositions 37 and 38).

The polymerizable compositions 14 to 38 were polymerized by the following method to obtain polymers. The retardation was measured, and the wavelength dispersion was evaluated using the resulting polymers.

Retardation Measurement and Wavelength Dispersion Evaluation II (i) Formation 1 of Liquid Crystal Layer Using Polymerizable Composition Each of the polymerizable compositions 16 to 18, 20 to 30, 32, and 34 to 38 was applied to a transparent glass substrate provided with a polyimide alignment film subjected to a rubbing treatment using a #4 wire bar. The resulting film was dried for 1 minute at the temperature shown in Table 4, and subjected to an alignment treatment for 1 minute at the temperature shown in Table 4 to form a liquid crystal layer. UV rays were applied to the liquid crystal layer at a dose of 2000 mJ/cm² at the temperature shown in Table 4 to effect polymerization to prepare a wavelength dispersion measurement sample.

(ii) Formation 2 of Liquid Crystal Layer Using Polymerizable Composition

Each of the polymerizable compositions 14, 15, 19, 31, and 33 was applied to a transparent glass substrate provided with a polyimide alignment film subjected to a rubbing treatment using a #6 wire bar. The resulting film was dried for 1 minute at the temperature shown in Table 4, and subjected to an alignment treatment for 1 minute at the temperature shown in Table 4 to form a liquid crystal layer. UV rays were applied to the liquid crystal layer at a dose of 2000 mJ/cm² at the temperature shown in Table 4 to effect polymerization to prepare a wavelength dispersion measurement sample.

(iii) Retardation Measurement and Wavelength Dispersion Evaluation

The retardation was measured, and the wavelength dispersion was evaluated in the same manner as described above using the resulting samples.

Table 4 shows the thickness (μm) of the liquid crystal polymer films obtained by polymerizing the polymerizable compositions, the retardation (Re) at a wavelength of 548.5 nm, and the values α and β.

TABLE 4

|  | Polymerizable composition | Polymerizable compound Type | Ratio (%) | Polymerizable compound Type | Ratio (%) | Drying temperature (°C.) | Alignment treatment temperature (°C.) | Exposure temperature (°C.) | Thickness (μm) | Re (548.5 nm) | α | β |
| --- | --- | --- | --- | --- | --- | --- | --- | --- | --- | --- | --- | --- |
| Example 47 | 14 | Compound 9 | 100 | — | — | 150 | 115 | 115 | 1.697 | 117.28 | 0.617 | 1.076 |
| Example 48 | 15 | Compound 10 | 100 | — | — | 140 | 90 | 90 | 1.872 | 144.39 | 0.829 | 1.033 |
| Example 49 | 16 | Compound 11 | 100 | — | — | 150 | 115 | 115 | 1.537 | 129.10 | 0.874 | 0.997 |
| Example 50 | 17 | Compound 12 | 100 | — | — | 145 | 105 | 105 | 1.201 | 95.65 | 0.854 | 1.043 |
| Example 51 | 18 | Compound 13 | 100 | — | — | 120 | 23 | 23 | 1.504 | 117.36 | 0.879 | 1.045 |
| Example 52 | 19 | Compound 14 | 100 | — | — | 150 | 90 | 90 | 1.881 | 175.24 | 0.863 | 1.026 |
| Example 53 | 20 | Compound 15 | 100 | — | — | 150 | 110 | 110 | 1.490 | 137.54 | 0.858 | 1.028 |
| Example 54 | 21 | Compound 16 | 100 | — | — | 175 | 23 | 23 | 1.477 | 115.05 | 0.787 | 1.031 |
| Example 55 | 22 | Compound 17 | 50 | Compound 4 | 50 | 150 | 23 | 23 | 1.818 | 69.40 | 0.972 | 0.995 |
| Example 56 | 23 | Compound 18 | 100 | — | — | 120 | 23 | 23 | 1.593 | 122.81 | 0.835 | 1.026 |
| Example 57 | 24 | Compound 19 | 100 | — | — | 130 | 23 | 23 | 1.620 | 124.28 | 0.848 | 1.057 |
| Example 58 | 25 | Compound 20 | 100 | — | — | 120 | 23 | 23 | 1.484 | 100.57 | 0.728 | 1.046 |
| Example 59 | 26 | Compound 21 | 100 | — | — | 120 | 80 | 80 | 1.514 | 105.37 | 0.814 | 1.039 |
| Example 60 | 27 | Compound 22 | 100 | — | — | 120 | 23 | 23 | 1.669 | 123.98 | 0.841 | 1.027 |
| Example 61 | 28 | Compound 23 | 100 | — | — | 120 | 75 | 75 | 1.454 | 109.76 | 0.759 | 1.055 |
| Example 62 | 29 | Compound 24 | 100 | — | — | 135 | 23 | 23 | 1.554 | 101.40 | 0.737 | 1.072 |
| Example 63 | 30 | Compound 25 | 100 | — | — | 120 | 23 | 23 | 1.486 | 112.87 | 0.824 | 1.058 |
| Example 64 | 31 | Compound 26 | 100 | — | — | 150 | 90 | 85 | 2.344 | 194.63 | 0.878 | 1.031 |
| Example 65 | 32 | Compound 27 | 100 | — | — | 130 | 70 | 65 | 1.519 | 122.28 | 0.847 | 1.023 |
| Example 66 | 33 | Compound 28 | 100 | — | — | 150 | 23 | 23 | 2.301 | 177.20 | 0.850 | 1.025 |
| Example 67 | 34 | Compound 29 | 100 | — | — | 130 | 23 | 23 | 1.486 | 113.07 | 0.838 | 1.022 |
| Example 68 | 35 | Compound 30 | 100 | — | — | 130 | 23 | 23 | 1.533 | 115.70 | 0.834 | 1.032 |
| Example 69 | 36 | Compound 31 | 100 | — | — | 130 | 65 | 55 | 2.287 | 162.31 | 0.825 | 1.041 |
| Example 70 | 37 | Compound 32 | 30 | Compound 4 | 70 | 130 | 23 | 23 | 1.504 | 121.64 | 0.834 | 1.017 |
| Example 71 | 38 | Compound 33 | 30 | Compound 4 | 70 | 130 | 23 | 23 | 1.616 | 111.36 | 0.827 | 1.047 |

As is clear from the results shown in Table 4, it was confirmed that the polymers obtained in Examples 47 to 71 using the compounds 9 to 33 according to the invention were an optically anisotropic article. The optically anisotropic articles showed ideal wideband wavelength dispersion in which the value α was smaller than 1, and the value β was larger than 1, or almost equal to 1.

Example 71: Compound 34

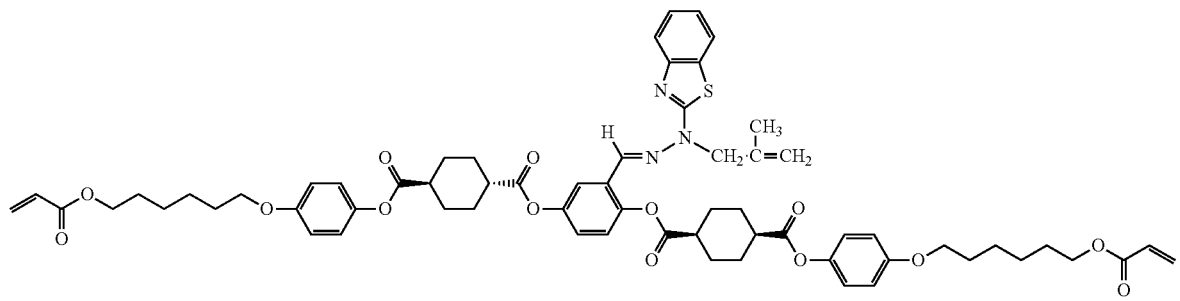

Compound 34

Step 1: Synthesis of Intermediate Y1

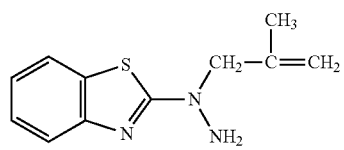

Intermediate Y1

A four-necked reactor equipped with a thermometer was charged with 2.50 g (15.1 mmol) of 2-hydrazinobenzothi- azole and 20 ml of DMF under a nitrogen stream to prepare a solution. After the addition of 7.38 g (22.7 mmol) of cesium carbonate and 2.45 g (18.2 mmol) of 3-bromo-2-methyl-1-propene to the solution, the mixture was stirred at 25° C. for 18 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (hexane:ethyl acetate=80:20) to obtain 368 mg of an intermediate Y1 as a white solid (yield: 11.1%).

The structure of the target product was identified by $^1$H-NMR.

$^1$H-NMR (500 MHz, CDCl$_3$, TMS, δ ppm): 7.59 (dd, 1H, J=1.0 Hz, 8.0 Hz), 7.52 (dd, 1H, J=1.5 Hz, 8.0 Hz), 7.26 (ddd, 1H, J=1.0 Hz, 7.5 Hz, 8.0 Hz), 7.05 (ddd, 1H, J=1.5 Hz, 7.5 Hz, 8.0 Hz), 4.98 (s, 1H), 4.86 (s, 1H), 4.29 (s, 2H), 4.12 (s, 2H), 1.71 (s, 3H)

Step 2: Synthesis of Compound 34

A four-necked reactor equipped with a thermometer was charged with 368 mg (1.68 mmol) of the intermediate Y1 synthesized in the step 1, 1.00 g (1.06 mmol) of the intermediate B synthesized in the step 2 of Example 1 (see "Synthesis of compound 1"), 3 ml of ethanol, and 15 ml of THF under a nitrogen stream to prepare a solution. After the addition of 49.2 mg (0.21 mmol) of (±)-10-camphorsulfonic acid to the solution, the mixture was stirred at 40° C. for 5 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.07 g of a compound 34 as a white solid (yield: 88.5%).

The structure of the target product was identified by $^1$H-NMR.

$^1$H-NMR (500 MHz, CDCl$_3$, TMS, δ ppm): 7.74 (d, 1H, J=2.5 Hz), 7.70 (d, 1H, J=7.5 Hz), 7.67 (d, 1H, J=8.0 Hz), 7.63 (s, 1H), 7.34 (dd, 1H, J=7.5 Hz, 8.0 Hz), 7.18 (dd, 1H, J=7.5 Hz, 7.5 Hz), 7.12 (d, 1H, J=9.0 Hz), 7.10 (dd, 1H, J=2.5 Hz, 9.0 Hz), 6.99 (d, 2H, J=9.0 Hz), 6.98 (d, 2H, J=9.0 Hz), 6.88 (d, 4H, J=9.0 Hz), 6.40 (dd, 2H, J=0.5 Hz, 17.5 Hz), 6.13 (dd, 2H, J=10.5 Hz, 17.5 Hz), 5.82 (dd, 2H, J=1.5 Hz, 10.5 Hz), 4.98 (s, 1H), 4.90 (s, 2H), 4.83 (s, 1H), 4.18 (t, 4H, J=6.5 Hz), 3.95 (t, 4H, J=6.5 Hz), 2.56-2.66 (m, 4H), 2.31-2.36 (m, 8H), 1.76-1.82 (m, 7H), 1.64-1.74 (m, 12H), 1.40-1.55 (m, 8H)

Example 73: Compound 35

C. for 24 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (n-hexane:ethyl acetate=85:15) to obtain 3.28 g of an intermediate Z1 as a white solid (yield: 48.9%).

The structure of the target product was identified by $^1$H-NMR.

$^1$H-NMR (500 MHz, CDCl$_3$, TMS, δ ppm): 7.60 (dd, 1H, J=1.0 Hz, 7.5 Hz), 7.52 (dd, 1H, J=1.0 Hz, 8.5 Hz), 7.27 (ddd, 1H, J=1.0 Hz, 7.5 Hz, 8.5 Hz), 7.06 (ddd, 1H, J=1.0 Hz, 7.5 Hz, 7.5 Hz), 4.24 (s, 2H), 3.57 (d, 2H, J=6.5 Hz), 2.14-2.25 (triplet of septets, 1H, J=6.5 Hz, 6.5 Hz), 1.00 (d, 6H, J=6.5 Hz)

Step 2: Synthesis of Compound 35

A four-necked reactor equipped with a thermometer was charged with 518 mg (2.34 mmol) of the intermediate Z1 synthesized in the step 1, 2.00 g (2.12 mmol) of the intermediate B synthesized in the step 2 of Example 1 (see "Synthesis of compound 1"), 3 ml of ethanol, and 20 ml of THF under a nitrogen stream to prepare a solution. After the addition of 54.4 mg (0.24 mmol) of (±)-10-camphorsulfonic acid to the solution, the mixture was stirred at 40° C. for 7 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a

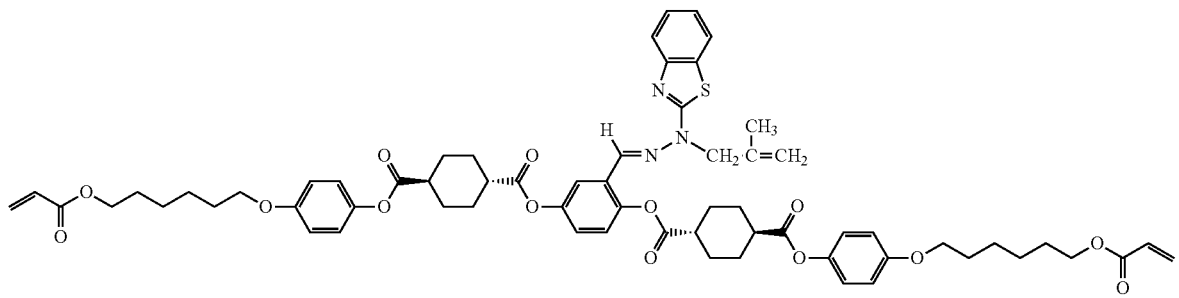

Compound 35

Step 1: Synthesis of Intermediate Z1

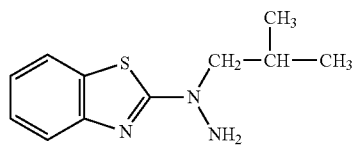

Intermediate Z1

A four-necked reactor equipped with a thermometer was charged with 5.00 g (30.3 mmol) of 2-hydrazinobenzothiazole and 50 ml of DMF under a nitrogen stream to prepare a solution. After the addition of 14.8 g (45.5 mmol) of cesium carbonate and 4.98 g (36.4 mmol) of 4-bromo-2-methylpropane to the solution, the mixture was stirred at 25° yellow solid. The yellow solid was purified by silica gel column chromatography (toluene:ethyl acetate=90:10) to obtain 1.83 g of a compound 35 as a white solid (yield: 75.7%).

The structure of the target product was identified by $^1$H-NMR.

$^1$H-NMR (500 MHz, CDCl$_3$, TMS, δ ppm): 7.76 (d, 1H, J=2.5 Hz), 7.692 (s, 1H), 7.690 (d, 1H, J=7.5 Hz), 7.66 (d, 1H, J=8.0 Hz), 7.34 (dd, 1H, J=7.5 Hz, 8.0 Hz), 7.17 (dd, 1H, J=7.5 Hz, 7.5 Hz), 7.12 (d, 1H, J=9.0 Hz), 7.10 (dd, 1H, J=2.5 Hz, 9.0 Hz), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.16-4.19 (m, 6H), 3.95 (t, 4H, J=6.5 Hz), 2.59-2.68 (m, 4H), 2.23-2.35 (m, 9H), 1.76-1.82 (m, 4H), 1.66-1.74 (m, 12H), 1.42-1.54 (m, 8H), 1.03 (d, 6H, J=6.5 Hz)

Example 74: Compound 36

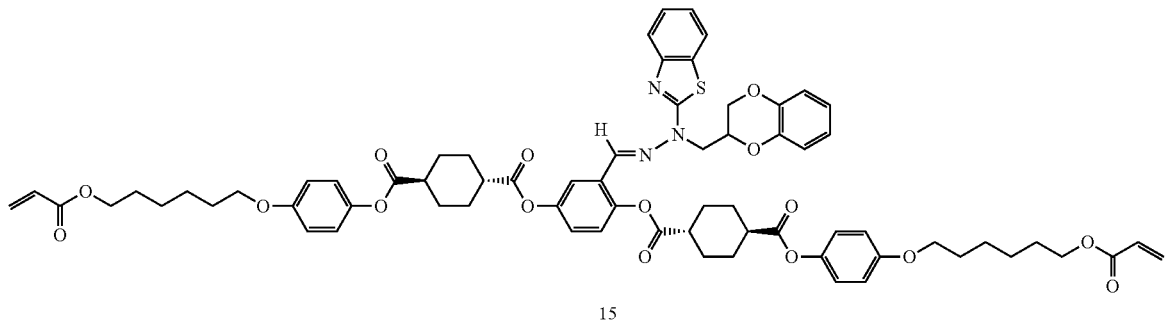

Compound 36

Step 1: Synthesis of Intermediate A2

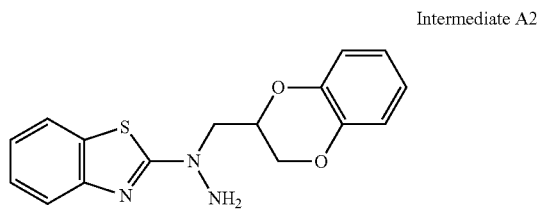 [SMILES: NN(CC1COc2ccccc2O1)c1nc2ccccc2s1]

Intermediate A2

A four-necked reactor equipped with a thermometer was charged with 2.50 g (15.1 mmol) of 2-hydrazinobenzothiazole and 20 ml of DMF under a nitrogen stream to prepare a solution. After the addition of 7.38 g (22.7 mmol) of cesium carbonate and 4.17 g (18.2 mmol) of 2-bromomethyl-1,4-benzodioxane to the solution, the mixture was stirred at 25° C. for 6 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (n-hexane:ethyl acetate=70:30) to obtain 2.39 g of an intermediate A2 as a white solid (yield: 53.7%).

The structure of the target product was identified by $^1$H-NMR.

$^1$H-NMR (500 MHz, CDCl$_3$, TMS, δ ppm): 7.62 (dd, 1H, J=1.0 Hz, 8.0 Hz), 7.51 (dd, 1H, J=1.0 Hz, 8.0 Hz), 7.28 (ddd, 1H, J=1.0 Hz, 7.5 Hz, 8.0 Hz), 7.08 (ddd, 1H, J=1.0 Hz, 7.5 Hz, 8.0 Hz), 6.83-6.90 (m, 4H), 4.72 (dddd, 1H, J=2.5 Hz, 3.0 Hz, 7.0 Hz, 7.0 Hz), 4.64 (s, 2H), 4.39 (dd, 1H, J=2.5 Hz, 12.5 Hz), 4.25 (dd, 1H, J=3.0 Hz, 15.0 Hz), 4.07 (dd, 1H, J=7.0 Hz, 12.0 Hz), 3.98 (dd, 1H, J=7.0 Hz, 15.0 Hz)

Step 2: Synthesis of Compound 36

A four-necked reactor equipped with a thermometer was charged with 627 mg (2.13 mmol) of the intermediate A2 synthesized in the step 1, 1.00 g (1.06 mmol) of the intermediate B synthesized in the step 2 of Example 1 (see "Synthesis of compound 1"), 3 ml of ethanol, and 15 ml of THF under a nitrogen stream to prepare a solution. After the addition of 49.2 mg (0.21 mmol) of (±)-10-camphorsulfonic acid to the solution, the mixture was stirred at 40° C. for 4 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.11 g of a compound 36 as a white solid (yield: 84.8%).

The structure of the target product was identified by $^1$H-NMR.

$^1$H-NMR (500 MHz, CDCl$_3$, TMS, δ ppm): 8.02 (s, 1H), 7.76 (d, 1H, J=2.0 Hz), 7.71 (d, 1H, J=7.5 Hz), 7.67 (d, 1H, J=8.0 Hz), 7.36 (dd, 1H, J=7.5 Hz, 8.0 Hz), 7.20 (dd, 1H, J=7.5 Hz, 7.5 Hz), 7.13 (dd, 1H, J=2.0 Hz, 9.0 Hz), 7.11 (d, 1H, J=9.0 Hz), 6.99 (d, 2H, J=9.0 Hz), 6.97 (d, 2H, J=9.0 Hz), 6.88 (d, 4H, J=9.0 Hz), 6.85-6.87 (m, 4H), 6.40 (dd, 2H, J=1.0 Hz, 17.5 Hz), 6.13 (dd, 2H, J=10.5 Hz, 17.5 Hz), 5.82 (dd, 2H, J=1.0 Hz, 10.5 Hz), 4.75 (dd, 1H, J=6.0 Hz, 15.0 Hz), 4.68 (dddd, 1H, J=2.0 Hz, 5.5 Hz, 6.0 Hz, 7.0 Hz), 4.47 (dd, 1H, J=2.0 Hz, 11.5 Hz), 4.42 (dd, 1H, J=5.5 Hz, 15.0 Hz), 4.18 (t, 4H, J=7.0 Hz), 4.08 (dd, 1H, J=7.5 Hz, 11.5 Hz), 3.95 (t, 4H, J=6.0 Hz), 2.57-2.68 (m, 3H), 2.41-2.47 (m, 1H), 2.24-2.36 (m, 6H), 2.17-2.20 (m, 2H), 1.77-1.82 (m, 4H), 1.69-1.74 (m, 8H), 1.56-1.65 (m, 4H), 1.42-1.54 (m, 8H)

Example 75: Compound 37

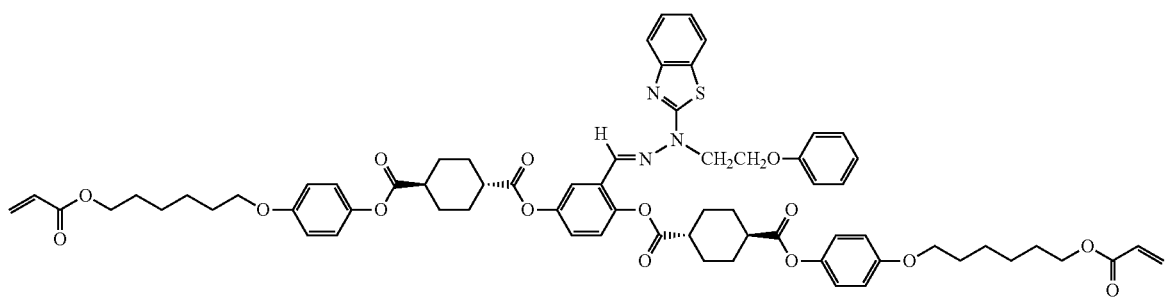

Compound 37

Step 1: Synthesis of Intermediate B2

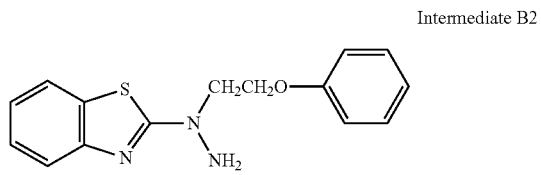

Intermediate B2

A four-necked reactor equipped with a thermometer was charged with 5.00 g (30.3 mmol) of 2-hydrazinobenzothiazole and 50 ml of DMF under a nitrogen stream to prepare a solution. After the addition of 14.8 g (45.5 mmol) of cesium carbonate and 7.30 g (36.6 mmol) of β-bromophenetole to the solution, the mixture was stirred at 25° C. for 24 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (n-hexane:ethyl acetate=70:30) to obtain 2.26 g of an intermediate B2 as a white solid (yield: 28.1%).

The structure of the target product was identified by $^1$H-NMR.

$^1$H-NMR (500 MHz, CDCl$_3$, TMS, δ ppm): 7.61 (dd, 1H, J=1.0 Hz, 7.5 Hz), 7.53 (dd, 1H, J=1.0 Hz, 8.0 Hz), 7.26-7.31 (m, 3H), 7.07 (ddd, 1H, J=1.0 Hz, 7.5 Hz, 8.0 Hz), 6.97 (ddd, 1H, J=1.0 Hz, 7.5 Hz, 7.5 Hz), 6.90 (dd, 2H, J=1.0 Hz, 8.5 Hz), 4.70 (s, 2H), 4.39 (t, 2H, J=4.5 Hz), 4.23 (t, 2H, J=4.5 Hz)

Step 2: Synthesis of Compound 37

A four-necked reactor equipped with a thermometer was charged with 312 mg (1.77 mmol) of the intermediate B2 synthesized in the step 1, 1.00 g (1.06 mmol) of the intermediate B synthesized in the step 2 of Example 1 (see "Synthesis of compound 1"), 3 ml of ethanol, and 15 ml of THF under a nitrogen stream to prepare a solution. After the addition of 27.1 mg (0.12 mmol) of (±)-10-camphorsulfonic acid to the solution, the mixture was stirred at 40° C. for 7 hours. After completion of the reaction, the reaction mixture was added to 150 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (toluene:ethyl acetate=90:10) to obtain 1.18 g of a compound 37 as a white solid (yield: 92.3%).

The structure of the target product was identified by $^1$H-NMR.

$^1$H-NMR (500 MHz, CDCl$_3$, TMS, δ ppm): 8.14 (s, 1H), 7.78 (d, 1H, J=1.0 Hz), 7.70 (d, 1H, J=8.0 Hz), 7.67 (d, 1H, J=8.0 Hz), 7.35 (dd, 1H, J=7.5 Hz, 8.0 Hz), 7.24-7.27 (m, 2H), 7.18 (dd, 1H, J=7.5 Hz, 8.0 Hz), 7.14 (dd, 1H, J=1.0 Hz, 7.5 Hz), 7.12 (d, 1H, J=7.5 Hz), 6.93-7.00 (m, 5H), 6.87-6.90 (m, 6H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.69 (t, 2H, J=6.0 Hz), 4.36 (t, 2H, J=6.0 Hz), 4.17 (t, 4H, J=6.5 Hz), 3.95 (t, 2H, J=6.5 Hz), 3.94 (t, 2H, J=6.5 Hz), 2.56-2.68 (m, 3H), 2.31-2.39 (m, 5H), 2.23-2.27 (m, 2H), 2.11-2.14 (m, 2H), 1.77-1.85 (m, 4H), 1.69-1.74 (m, 8H), 1.42-1.65 (m, 12H)

Example 76: Compound 38

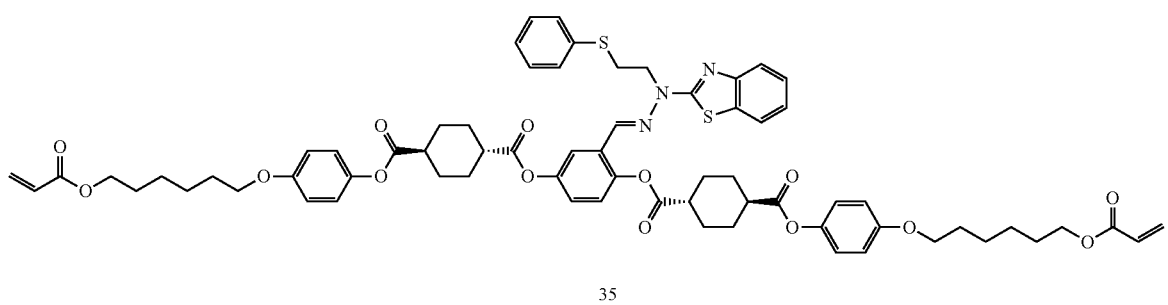

Compound 38

Step 1: Synthesis of Intermediate C2

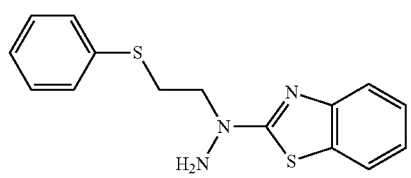

Intermediate C2

A three-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mmol) of cesium carbonate and 3.15 g (14.5 mmol) of 2-bromoethylphenyl sulfide to the solution, the mixture was stirred at 25° C. for 3 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a yellow solid. The yellow solid was purified by silica gel column chromatography (n-hexane:ethyl acetate=80:20) to obtain 1.55 g of an intermediate C2 as a white solid (yield: 42.5%).

The structure of the target product was identified by $^1$H-NMR.

$^1$H-NMR (500 MHz, CDCl$_3$, TMS, δ ppm): 7.61 (dd, 1H, J=1.3 Hz, 8.0 Hz), 7.53 (dd, 1H, J=1.3 Hz, 8.0 Hz), 7.38-7.43 (m, 2H), 7.27-7.32 (m, 3H), 7.21 (ddd, 1H, J=1.3 Hz, 8.0 Hz, 8.0 Hz), 7.08 (ddd, 1H, J=1.3 Hz, 8.0 Hz, 8.0 Hz), 4.44 (s, 2H), 4.00 (t, 2H, J=6.5 Hz), 3.36 (t, 2H, J=6.5 Hz)

Step 2: Synthesis of Compound 38

A three-necked reactor equipped with a thermometer was charged with 1.50 g (1.60 mmol) of the intermediate B synthesized in the step 2 of Example 1 (see "Synthesis of compound 1"), 534 mg (1.78 mmol) of the intermediate C2 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=9:1) to obtain 1.67 g of a compound 38 as a light yellow solid (yield: 86.9%).

The structure of the target product was identified by $^1$H-NMR.

$^1$H-NMR (500 MHz, CDCl$_3$, TMS, δ ppm): 7.74 (s, 1H), 7.65-7.72 (m, 3H), 7.44-7.49 (m, 2H), 7.30-7.39 (m, 3H), 7.23 (ddd, 1H, J=1.0 Hz, 7.0 Hz, 7.0 Hz), 7.19 (ddd, 1H, J=1.0 Hz, 7.0 Hz, 7.0 Hz), 7.10-7.14 (m, 2H), 6.96-7.01 (m, 4H), 6.86-6.91 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 5.22 (t, 2H, J=8.0 Hz), 4.18 (t, 4H, J=6.5 Hz), 3.95 (t, 4H, J=6.5 Hz), 3.28 (t, 2H, J=8.0 Hz), 2.52-2.73 (m, 4H), 2.24-2.40 (m, 8H), 1.62-1.84 (m, 16H), 1.41-1.56 (m, 8H)

Example 77: Compound 39 a solution. After the addition of 7.88 g (24.2 mol) of cesium carbonate to the solution, the mixture was cooled to 0° C. After the addition of 2.83 g (14.5 mmol) of 2-(2-bromo-ethyl)-1,3-dioxane to the mixture over 5 minutes, the mixture was stirred at 25° C. for 25 hours. After completion of the reaction, 200 ml of water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the resulting white solid was washed with 50 ml of toluene, and dried under vacuum to obtain 1.45 g of an intermediate D2 as a white solid (yield: 42.9%).

The structure of the target product was identified by $^1$H-NMR.

$^1$H-NMR (400 MHz, CDCl$_3$, TMS, δ ppm): 7.59 (dd, 1H, J=1.3 Hz, 7.5 Hz), 7.52 (dd, 1H, J=1.3 Hz, 7.5 Hz), 7.27 (ddd, 1H, J=1.3 Hz, 7.5 Hz, 7.5 Hz), 7.05 (ddd, 1H, J=1.3 Hz, 7.5 Hz, 7.5 Hz), 4.70 (t, 1H, J=4.5 Hz), 4.47 (s, 2H), 4.00-4.12 (m, 2H), 3.93 (t, 2H, J=6.5 Hz), 3.68-3.76 (m, 2H), 1.98-2.11 (m, 3H), 1.29-1.36 (m, 1H)

Step 2: Synthesis of Compound 39

A three-necked reactor equipped with a thermometer was charged with 1.50 g (1.60 mmol) of the intermediate B synthesized in the step 2 of Example 1 (see "Synthesis of compound 1"), 495 mg (1.78 mmol) of the intermediate D2 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 3 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate Compound 39

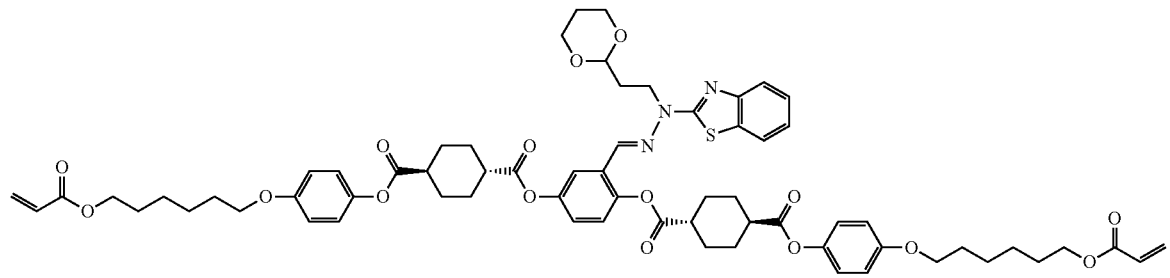

Step 1: Synthesis of Intermediate D2

Intermediate D2

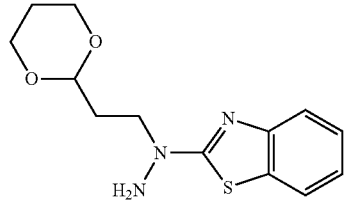

A three-necked reactor equipped with a thermometer was charged with 2.00 g (12.1 mmol) of 2-hydrazinobenzothiazole and 30 ml of DMF under a nitrogen stream to prepare was concentrated using a rotary evaporator, and the concentrate was purified by silica gel column chromatography (toluene:ethyl acetate=92:8) to obtain 1.61 g of a compound 39 as a light yellow solid (yield: 83.8%).

The structure of the target product was identified by $^1$H-NMR.

$^1$H-NMR (500 MHz, CDCl$_3$, TMS, δ ppm): 7.79 (s, 1H), 7.74 (d, 1H, J=1.5 Hz), 7.69 (dd, 1H, J=1.3 Hz, 6.5 Hz), 7.67 (dd, 1H, J=1.3 Hz, 6.5 Hz), 7.34 (ddd, 1H, J=1.3 Hz, 6.5 Hz, 6.5 Hz), 7.16 (ddd, 1H, J=1.3 Hz, 6.5 Hz, 6.5 Hz), 7.08-7.13 (m, 2H), 6.95-7.01 (m, 4H), 6.85-6.91 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.68 (t, 1H, J=5.0 Hz), 4.41 (t, 2H, J=7.5 Hz), 4.18 (t, 4H, J=6.5 Hz), 4.07-4.14 (m, 2H), 3.94 (t, 4H, J=6.5 Hz), 3.71-3.79 (m, 2H), 2.55-2.75 (m, 4H), 2.25-2.41 (m, 8H), 2.01-2.15 (m, 3H), 1.64-1.84 (m, 16H), 1.41-1.56 (m, 8H), 1.32-1.38 (m, 1H)

Example 78: Compound 40

Step 2: Synthesis of Compound 40

A three-necked reactor equipped with a thermometer was charged with 1.50 g (1.60 mmol) of the intermediate B synthesized in the step 2 of Example 1 (see "Synthesis of compound 1"), 447 mg (1.78 mmol) of the intermediate E2

Compound 40

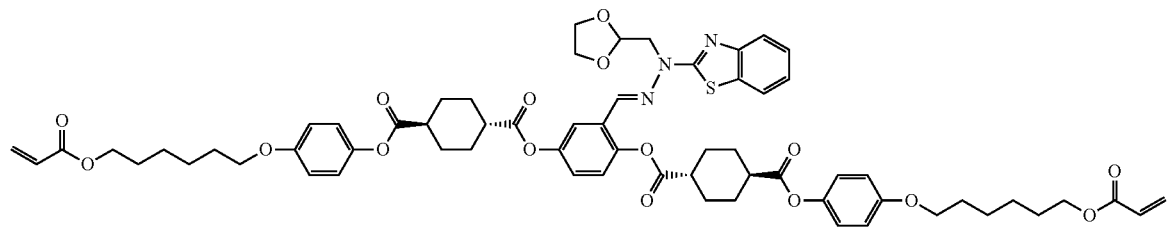

Step 1: Synthesis of Intermediate E2

Intermediate E2

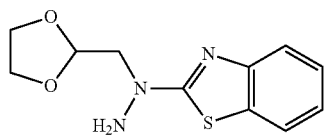

A three-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mol) of cesium carbonate to the solution, the mixture was cooled to 0° C. After the addition of 2.42 g (14.5 mmol) of 2-bromomethyl-1,3-dioxolane to the mixture over 5 minutes, the mixture was stirred at 25° C. for 3 hours. After completion of the reaction, 200 ml of water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (n-hexane:ethyl acetate=55:45) to obtain 1.31 g of an intermediate E2 as a white solid (yield: 43.1%).

The structure of the target product was identified by $^1$H-NMR.

$^1$H-NMR (500 MHz, CDCl$_3$, TMS, δ ppm): 7.60 (dd, 1H, J=1.0 Hz, 7.5 Hz), 7.53 (dd, 1H, J=1.0 Hz, 7.5 Hz), 7.27 (ddd, 1H, J=1.0 Hz, 7.5 Hz, 7.5 Hz), 7.06 (ddd, 1H, J=1.0 Hz, 7.5 Hz, 7.5 Hz), 5.19 (t, 1H, J=4.5 Hz), 4.63 (s, 2H), 3.93-4.05 (m, 4H), 3.86-3.94 (m, 2H)

synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over sodium sulfate, and concentrated using a rotary evaporator. The concentrate was purified by silica gel column chromatography (toluene:ethyl acetate=85:15) to obtain 1.60 g of a compound 40 as a light yellow solid (yield: 85.7%).

The structure of the target product was identified by $^1$H-NMR.

$^1$H-NMR (500 MHz. CDCl$_3$. TMS. δ ppm): 8.11 (s. 1H). 7.76 (d. 1H. J=1.5 Hz). 7.71 (dd. 1H. J=1.0 Hz, 7.5 Hz). 7.69 (dd. 1H. J=1.0 Hz. 7.5 Hz). 7.39 (ddd. 1H. J=1.0 Hz. 7.5 Hz. 7.5 Hz). 7.17 (ddd. 1H. J=1.0 Hz, 7.5 Hz. 7.5 Hz). 7.09-7.13 (m. 2H). 6.96-7.01 (m, 4H). 6.86-6.91 (m. 4H). 6.40 (dd. 2H. J=1.5 Hz. 17.5 Hz). 6.13 (dd. 2H. J=10.5 Hz. 17.5 Hz). 5.82 (dd. 2H, J=1.5 Hz. 10.5 Hz). 5.24 (t. 1H. J=3.5 Hz). 4.57 (d. 2H. J=3.5 Hz). 4.18 (t. 4H. J=6.5 Hz). 3.97-4.01 (m. 2H). 3.95 (t. 4H. J=6.5 Hz). 3.86-3.90 (m. 2H). 2.55-2.74 (m. 4H). 2.25-2.41 (m. 8H). 1.64-1.84 (m. 16H). 1.40-1.55 (m. 8H)

Example 79: Compound 41

Compound 41

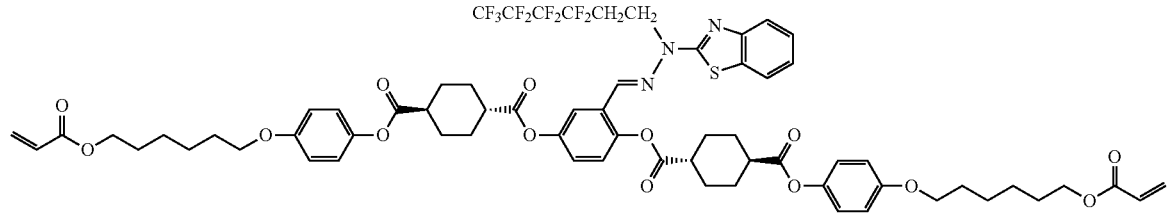

Step 1: Synthesis of Intermediate F2

Intermediate F2

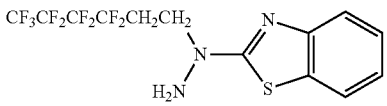

A four-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mmol) of cesium carbonate and 5.00 g (14.5 mmol) of 2-(nonafluorobutyl)ethyl iodide to the solution, the mixture was stirred at 25° C. for 20 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a brown solid. The brown solid was purified by silica gel column chromatography (n-hexane:ethyl acetate=9:1) to obtain 1.15 g of an intermediate F2 as a white solid (yield: 22.9%).

The structure of the target product was identified by $^1$H-NMR.

$^1$H-NMR (500 MHz, CDCl$_3$, TMS, δ ppm): 7.63 (dd, 1H, J=1.0 Hz, 7.5 Hz), 7.57 (dd, 1H, J=1.0 Hz, 7.5 Hz), 7.32 (ddd, 1H, J=1.0 Hz, 7.5 Hz, 7.5 Hz), 7.11 (ddd, 1H, J=1.0 Hz, 7.5 Hz, 7.5 Hz), 4.35 (s, 2H), 4.08 (t, 2H, J=7.5 Hz), 2.56-2.70 (m, 2H)

Step 2: Synthesis of Compound 41

A three-necked reactor equipped with a thermometer was charged with 1.35 g (1.44 mmol) of the intermediate B synthesized in the step 2 of Example 1 (see "Synthesis of compound 1"), 654 mg (1.59 mmol) of the intermediate F2 synthesized in the step 1, 38.4 mg (0.165 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=92:8) to obtain 1.41 g of a compound 41 as a light yellow solid (yield: 73.6%).

The structure of the target product was identified by $^1$H-NMR.

$^1$H-NMR (500 MHz, CDCl$_3$, TMS, δ ppm): 7.74-7.78 (m, 2H), 7.69-7.73 (m, 2H), 7.38 (ddd, 1H, J=1.0 Hz, 7.5 Hz, 7.5 Hz), 7.21 (ddd, 1H, J=1.0 Hz, 7.5 Hz, 7.5 Hz), 7.11-7.17 (m, 2H), 6.95-7.01 (m, 4H), 6.85-6.91 (m, 4H), 6.40 (dd, 2H, J=1.5 Hz, 17.5 Hz), 6.13 (dd, 2H, J=10.0 Hz, 17.5 Hz), 5.82 (dd, 2H, J=1.5 Hz, 10.0 Hz), 4.61-4.69 (m, 2H), 4.18 (t, 4H, J=6.5 Hz), 3.95 (t, 4H, J=6.5 Hz), 2.52-2.71 (m, 6H), 2.25-2.40 (m, 8H), 1.61-1.84 (m, 16H), 1.41-1.55 (m, 8H)

Example 80: Compound 42

Step 1: Synthesis of Intermediate G2

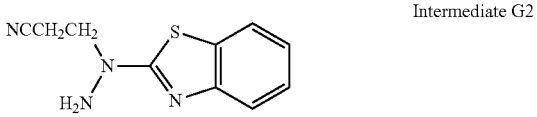

Intermediate G2

A three-necked reactor equipped with a thermometer was charged with 2.00 g (12.11 mmol) of 2-hydrazinobenzothiazole and 40 ml of DMF under a nitrogen stream to prepare a solution. After the addition of 7.89 g (24.21 mmol) of cesium carbonate and 1.95 g (14.53 mmol) of 3-bromopropionitrile to the solution, the mixture was stirred at 25° C. for 15 hours. After completion of the reaction, 500 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator. After the addition of 20 ml of toluene to the concentrate, the mixture was cooled to 0° C. to precipitate crystals. The crystals were filtered off, and dried under vacuum to obtain 1.12 g of an intermediate G2 as a white solid (yield: 42%).

The structure of the target product was identified by $^1$H-NMR, $^1$H-NMR (500 MHz, DMSO-d$_6$, TMS, δ ppm): 7.70 (dd, 1H, J=1.0 Hz, 8.0 Hz), 7.42 (dd, 1H, J=1.0 Hz, 8.0 Hz), 7.24 (dt, 1H, J=1.0 Hz, 7.5 Hz), 7.03 (dt, 1H, J=1.0 Hz, 7.5 Hz), 5.47 (s, 2H), 3.99 (t, 2H, J=6.5 Hz), 2.97 (t, 2H, J=6.5 Hz)

Step 2: Synthesis of Compound 42

A three-necked reactor equipped with a thermometer was charged with 1.00 g (1.06 mmol) of the intermediate B synthesized in the step 2 of Example 1 (see "Synthesis of compound 1") and 30 ml of THF under a nitrogen stream to prepare a solution. After the addition of 0.44 ml (0.44 mmol) of 1 N hydrochloric acid and 1.12 g (5.13 mmol) of the intermediate G2 synthesized in the step 1 to the solution, the mixture was stirred at 60° C. for 20 hours. After completion of the reaction, the reaction mixture was concentrated using a rotary evaporator, and the concentrate was purified by silica gel column chromatography (chloroform:THF=40:1) to obtain 0.55 g of a compound 42 as a light yellow solid (yield: 91%).

The structure of the target product was identified by $^1$H-NMR.

$^1$H-NMR (500 MHz, CDCl$_3$, TMS, δ ppm): 7.84 (s, 1H), 7.66-7.76 (m, 3H), 7.38 (dt, 1H, J=1.0 Hz, 7.5 Hz), 7.22 (dt, 1H, J=1.0 Hz, 7.5 Hz), 7.13-7.16 (m, 2H), 6.99 (d, 2H, J=9.0 Hz), 6.98 (d, 2H, J=9.0 Hz), 6.88 (d, 2H, J=9.0 Hz), 6.87 (d, 2H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), Compound 42

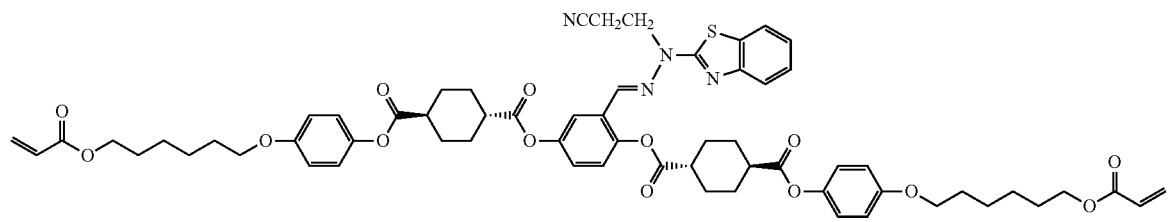

4.62 (t, 2H, J=7.0 Hz), 4.17 (t, 4H, J=6.5 Hz), 3.94 (t, 2H, J=6.5 Hz), 3.94 (t, 2H, J=6.5 Hz), 2.85 (t, 2H, J=7.0 Hz), 2.70-2.80 (m, 1H), 2.54-2.70 (m, 3H), 2.25-2.41 (m, 8H), 1.64-1.85 (m, 16H), 1.41-1.55 (m, 8H)

Example 81: Compound 43

Compound 43

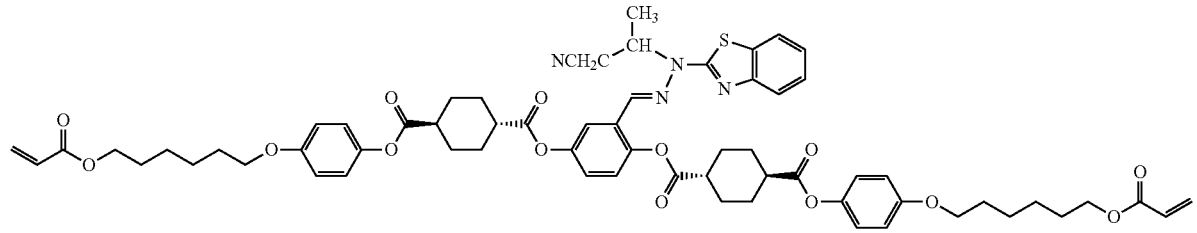

Step 1: Synthesis of Intermediate H2

Intermediate H2

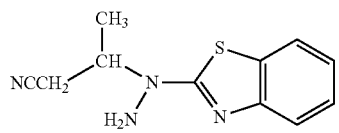

A three-necked reactor equipped with a thermometer was charged with 2.00 g (12.11 mmol) of 2-hydrazinobenzothiazole and 40 ml of DMF under a nitrogen stream to prepare a solution. After the addition of 7.89 g (24.21 mmol) of cesium carbonate and 2.15 g (14.53 mmol) of 3-bromobutyronitrile to the solution, the mixture was stirred at 25° C. for 15 hours. After completion of the reaction, 500 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=1:9) to obtain 2.03 g of an intermediate H2 as a white solid (yield: 72%).

The structure of the target product was identified by $^1$H-NMR.

$^1$H-NMR (500 MHz, DMSO-d$_6$, TMS, δ ppm): 7.70 (dd, 1H, J=1.0 Hz, 8.0 Hz), 7.41 (dd, 1H, J=1.0 Hz, 8.0 Hz), 7.24 (dt, 1H, J=1.0 Hz, 7.5 Hz), 7.03 (dt, 1H, J=1.0 Hz, 7.5 Hz), 5.24 (s, 2H), 4.86-4.96 (m, 1H), 2.80-2.96 (m, 2H), 1.27 (d, 3H, J=6.5 Hz)

Step 2: Synthesis of Compound 43

A three-necked reactor equipped with a thermometer was charged with 1.00 g (1.06 mmol) of the intermediate B synthesized in the step 2 of Example 1 (see "Synthesis of compound 1") and 30 ml of THF under a nitrogen stream to prepare a solution. After the addition of 0.44 ml (0.44 mmol) of 1 N hydrochloric acid and 0.74 g (3.20 mmol) of the intermediate H2 synthesized in the step 1 to the solution, the mixture was stirred at 60° C. for 15 hours. After completion of the reaction, the reaction mixture was concentrated using a rotary evaporator, and the concentrate was purified by silica gel column chromatography (chloroform:THF=40:1) to obtain 1.04 g of a compound 43 as a light yellow solid (yield: 85%).

The structure of the target product was identified by $^1$H-NMR.

$^1$H-NMR (500 MHz, CDCl$_3$, TMS, δ ppm): 8.18 (s, 1H), 7.65-7.76 (m, 3H), 7.37 (dt, 1H, J=1.0 Hz, 7.5 Hz), 7.21 (dt, 1H, J=1.0 Hz, 7.5 Hz), 7.13-7.16 (m, 2H), 6.98 (d, 2H, J=9.0 Hz), 6.98 (d, 2H, J=9.0 Hz), 6.88 (d, 2H, J=9.0 Hz), 6.88 (d, 2H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.85-4.94 (m, 1H), 4.17 (t, 4H, J=6.5 Hz), 3.94 (t, 2H, J=6.5 Hz), 3.94 (t, 2H, J=6.5 Hz), 3.28-3.46 (m, 2H), 2.53-2.80 (m, 4H), 2.23-2.41 (m, 8H), 1.64-1.84 (m, 19H), 1.41-1.55 (m, 8H)

Example 82: Compound 44

Compound 44

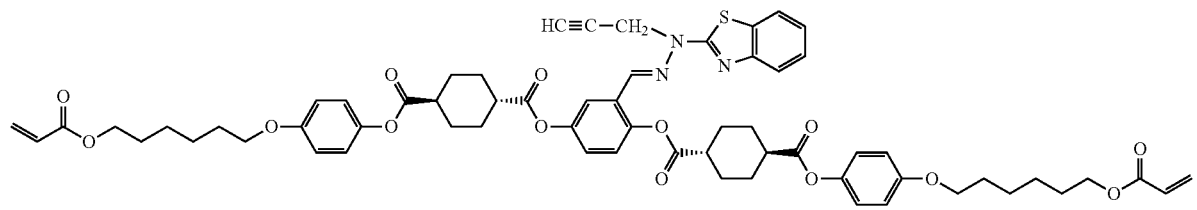

Step 1: Synthesis of Intermediate I2

Intermediate I2

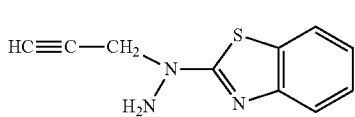

A three-necked reactor equipped with a thermometer was charged with 2.00 g (12.11 mmol) of 2-hydrazinobenzothiazole and 40 ml of DMF under a nitrogen stream to prepare a solution. After the addition of 7.89 g (24.21 mmol) of cesium carbonate and 1.73 g (14.53 mmol) of propargyl bromide to the solution, the mixture was stirred at 25° C. for 15 hours. After completion of the reaction, 500 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=1:19) to obtain 0.69 g of an intermediate 12 as a white solid (yield: 28%).

The structure of the target product was identified by $^1$H-NMR.

$^1$H-NMR (500 MHz, DMSO-$d_6$, TMS, δ ppm): 7.73 (dd, 1H, J=1.0 Hz, 8.0 Hz), 7.44 (dd, 1H, J=1.0 Hz, 8.0 Hz), 7.26 (dt, 1H, J=1.0 Hz, 7.5 Hz), 7.06 (dt, 1H, J=1.0 Hz, 7.5 Hz), 5.31 (s, 2H), 4.52 (d, 2H, J=2.5 Hz), 3.35 (t, 1H, J=2.5 Hz)

Step 2: Synthesis of Compound 44

A three-necked reactor equipped with a thermometer was charged with 1.00 g (1.06 mmol) of the intermediate B synthesized in the step 2 of Example 1 (see "Synthesis of compound 1") and 30 ml of THF under a nitrogen stream to prepare a solution. After the addition of 0.44 ml (0.44 mmol) of 1 N hydrochloric acid and 0.64 g (3.20 mmol) of the intermediate 12 synthesized in the step 1 to the solution, the mixture was stirred at 50° C. for 15 hours. After completion of the reaction, the reaction mixture was concentrated using a rotary evaporator, and the concentrate was purified by silica gel column chromatography (chloroform:THF=40:1) to obtain 1.10 g of a compound 44 as a light yellow solid (yield: 92%).

The structure of the target product was identified by $^1$H-NMR.

$^1$H-NMR (500 MHz, CDCl$_3$, TMS, δ ppm): 7.92 (s, 1H), 7.67-7.78 (m, 3H), 7.36 (dt, 1H, J=1.0 Hz, 7.5 Hz), 7.20 (dt, 1H, J=1.0 Hz, 7.5 Hz), 7.11-7.17 (m, 2H), 6.99 (d, 2H, J=9.0 Hz), 6.98 (d, 2H, J=9.0 Hz), 6.88 (d, 2H, J=9.0 Hz), 6.88 (d, 2H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 5.14 (d, 2H, J=2.0 Hz), 4.17 (t, 4H, J=6.5 Hz), 3.94 (t, 4H, J=6.5 Hz), 2.54-2.76 (m, 4H), 2.24-2.42 (m, 9H), 1.64-1.84 (m, 16H), 1.41-1.56 (m, 8H)

Example 83: Compound 45

A three-necked reactor equipped with a thermometer was charged with 2.00 g (12.11 mmol) of 2-hydrazinobenzothiazole and 40 ml of DMF under a nitrogen stream to prepare a solution. After the addition of 7.89 g (24.21 mmol) of cesium carbonate and 1.93 g (14.53 mmol) 4-bromo-1-butyne to the solution, the mixture was stirred at 25° C. for 15 hours. The reaction mixture was heated to 60° C., and stirred for 3 hours. After completion of the reaction, 500 ml of distilled water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=1:19) to obtain 0.98 g of an intermediate J2 as a white solid (yield: 37%).

The structure of the target product was identified by $^1$H-NMR.

$^1$H-NMR (500 MHz, DMSO-$d_6$, TMS, δ ppm): 7.68 (dd, 1H, J=1.0 Hz, 8.0 Hz), 7.39 (dd, 1H, J=1.0 Hz, 8.0 Hz), 7.22 (dt, 1H, J=1.0 Hz, 7.5 Hz), 7.01 (dt, 1H, J=1.0 Hz, 7.5 Hz), 5.33-5.40 (m, 1H), 5.29 (s, 2H), 4.91-4.97 (m, 2H), 4.32-4.37 (m, 2H)

Step 2: Synthesis of Compound 45

A three-necked reactor equipped with a thermometer was charged with 1.00 g (1.06 mmol) of the intermediate B synthesized in the step 2 of Example 1 (see "Synthesis of compound 1") and 30 ml of THF under a nitrogen stream to prepare a solution. After the addition of 0.44 ml (0.44 mmol) of 1 N hydrochloric acid and 0.7 g (3.20 mmol) of the intermediate J2 synthesized in the step 1 to the solution, the mixture was stirred at 50° C. for 15 hours. After completion of the reaction, the reaction mixture was concentrated using a rotary evaporator, and the concentrate was purified by silica gel column chromatography (chloroform:THF=40:1) to obtain 1.08 g of a compound 45 as a light yellow solid (yield: 89%).

The structure of the target product was identified by $^1$H-NMR.

Compound 45

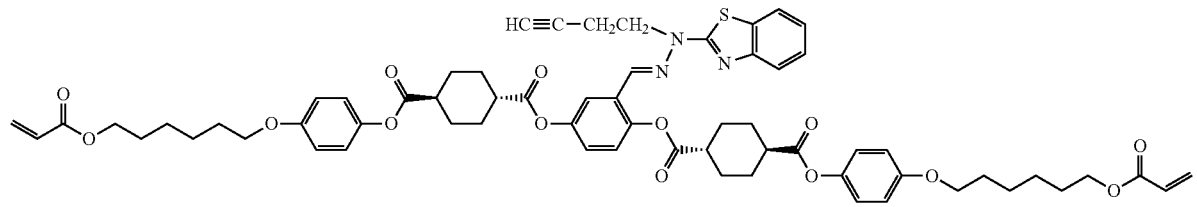

Step 1: Synthesis of Intermediate J2

Intermediate J2

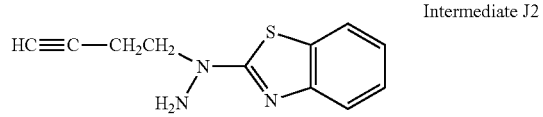

$^1$H-NMR (500 MHz, CDCl$_3$, TMS, δ ppm): 7.76 (s, 1H), 7.66-7.76 (m, 3H), 7.35 (dt, 1H, J=1.0 Hz, 7.5 Hz), 7.18 (dt, 1H, J=1.0 Hz, 7.5 Hz), 7.09-7.13 (m, 2H), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 5.19-5.27 (m, 1H), 4.93-4.99 (m, 2H), 4.83-4.89 (m, 2H), 4.18 (t, 4H, J=6.5 Hz), 3.95 (t, 4H, J=6.5 Hz), 2.54-2.74 (m, 4H), 2.24-2.40 (m, 8H), 1.63-1.84 (m, 16H), 1.41-1.56 (m, 8H)

Example 84: Compound 46

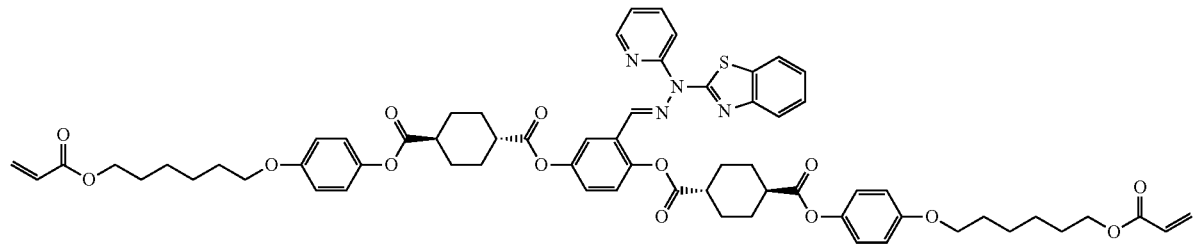

Compound 46

Step 1: Synthesis of Intermediate K2

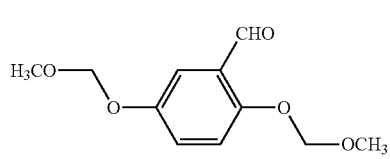

Intermediate K2

A three-necked reactor equipped with a thermometer was charged with 10.0 g (72.4 mmol) of 2,5-dihydroxybenzaldehyde and 200 ml of dichloromethane under a nitrogen stream to prepare a solution. The solution was cooled to 0° C. After the addition of 35.06 g (0.27 mol) of diisopropylethylamine to the solution, 23.32 g (0.29 mmol) of chloromethyl methyl ether was added to the mixture over 10 minutes. After the dropwise addition, the reaction mixture was heated to 25° C., and stirred for 15 hours. After completion of the reaction, 1000 ml of distilled water was added to the reaction mixture, followed by extraction twice with 200 ml of dichloromethane. The organic layer was dried over anhydrous sodium sulfate, and sodium sulfate was separated by filtration. The filtrate was concentrated using a rotary evaporator, and the concentrate was purified by silica gel column chromatography (THF:toluene=1:19) to obtain 13.26 g of an intermediate K2 as a colorless oil (yield: 81%).

The structure of the target product was identified by $^1$H-NMR.

$^1$H-NMR (500 MHz, CDCl$_3$, TMS, δ ppm): 10.46 (s, 1H), 7.49 (d, 1H, J=3.0 Hz), 7.23 (dd, 1H, J=3.0 Hz, 9.0 Hz), 7.17 (d, 1H, J=9.0 Hz), 5.25 (s, 2H), 5.15 (s, 2H), 3.52 (s, 3H), 3.47 (s, 3H)

Step 2: Synthesis of Intermediate L2

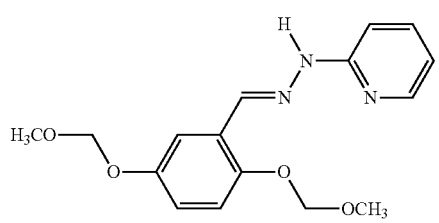

Intermediate L2

A three-necked reactor equipped with a thermometer was charged with 11.04 g (48.8 mmol) of the intermediate K2 synthesized in the step 1 and 400 ml of ethanol under a nitrogen stream to prepare a solution. After the addition of 6.40 g (58.56 mol) of 2-hydrazinopyridine to the solution, the mixture was stirred at 25° C. for 3 hours. After completion of the reaction, 400 ml of distilled water was added to the reaction mixture to precipitate crystals. The crystals were filtered off, washed with distilled water, and dried under vacuum to obtain 11.16 g of an intermediate L2 as a light yellow solid (yield: 72%).

The structure of the target product was identified by $^1$H-NMR.

$^1$H-NMR (500 MHz, DMSO-d$_6$, TMS, δ ppm): 10.93 (s, 1H), 8.34 (s, 1H), 8.07-8.12 (m, 1H), 7.61-7.67 (m, 1H), 7.52 (d, 1H, J=3.0 Hz), 7.23 (d, 1H, J=8.5 Hz), 7.09 (d, 1H, J=9.0 Hz), 6.96 (dd, 1H, J=3.0 Hz, 9.0 Hz), 6.73-6.78 (m, 1H), 5.20 (s, 2H), 5.18 (s, 2H), 3.42 (s, 3H), 3.40 (s, 3H)

Step 3: Synthesis of Intermediate M2

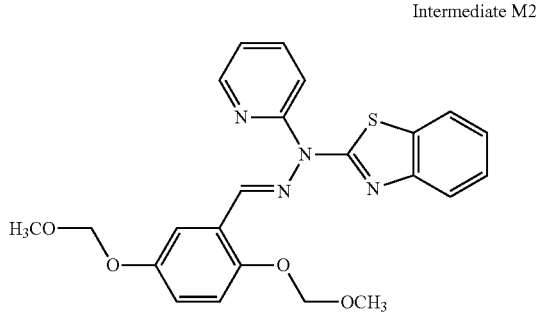 [SMILES: COCOc1ccc(OCOC)c(/C=N/N(c2ccccn2)c2nc3ccccc3s2)c1]

Intermediate M2

A three-necked reactor equipped with a thermometer was charged with 10.0 g (31.5 mmol) of the intermediate L2 synthesized in the step 2 and 300 ml of THF under a nitrogen stream to prepare a solution. After the addition of 14.0 g (34.7 mmol) of sodium hydride (50 to 72%, in oil) to the solution over 30 minutes, the mixture was stirred at 25° C. for 30 minutes. After the addition of 5.9 g (34.7 mmol) of 2-chlorobenzothiazole, the reaction mixture was stirred for 8 hours under reflux with heating. 2000 ml of distilled water and 500 ml of a saturated sodium chloride solution were added to the reaction mixture, followed by extraction twice with 1000 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=1:19) to obtain 8.8 g of an intermediate M2 as a light yellow solid (yield: 62%).

The structure of the target product was identified by $^1$H-NMR.

¹H-NMR (500 MHz, CDCl₃, TMS, δ ppm): 8.69-8.75 (m, 1H), 8.19 (s, 1H), 7.99 (dt, 1H, J=2.0 Hz, 7.5 Hz), 7.71-7.79 (m, 2H), 7.59-7.67 (m, 2H), 7.37-7.43 (m, 1H), 7.28-7.33 (m, 1H), 7.15-7.21 (m, 2H), 7.01-7.04 (m, 1H), 5.22 (s, 2H), 5.03 (s, 2H), 3.54 (s, 3H), 3.36 (s, 3H)

Step 4: Synthesis of Intermediate N2

Intermediate N2

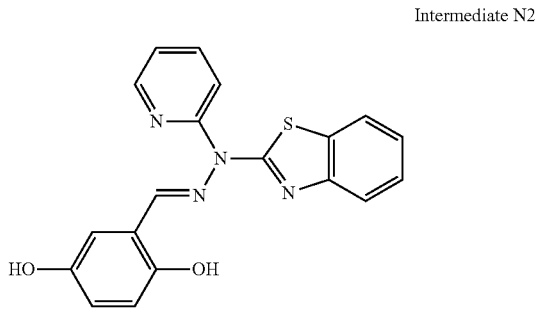 [SMILES: Oc1ccc(O)c(/C=N/N(c2ccccn2)c2nc3ccccc3s2)c1]

A three-necked reactor equipped with a thermometer was charged with 8.4 g (18.7 mmol) of the intermediate M2 synthesized in the step 3 and 300 ml of ethanol under a nitrogen stream to prepare a solution. After the addition of 17.7 g (93.2 mmol) of p-toluenesulfonic acid monohydrate, the mixture was stirred at 25° C. for 15 hours. 2000 ml of distilled water and 500 ml of a saturated sodium chloride solution were added to the reaction mixture, followed by extraction twice with 1500 ml of ethyl acetate. The organic layer was dried over anhydrous sodium sulfate, and sodium sulfate was separated by filtration. The filtrate was concentrated using a rotary evaporator, and 150 ml of methanol was added to the concentrate. Insoluble crystals were filtered off, washed with methanol, and dried under vacuum to obtain 3.1 g of an intermediate N2 as a yellow solid (yield: 46%).

The structure of the target product was identified by ¹H-NMR.

¹H-NMR (500 MHz, DMSO-d₆, TMS, δ ppm): 9.28 (s, 1H), 9.01 (s, 1H), 8.74-8.78 (m, 1H), 8.17 (dt, 1H, J=2.0 Hz, 7.5 Hz), 7.92 (dd, 1H, J=1.0 Hz, 8.0 Hz), 7.86 (s, 1H), 7.72-7.76 (m, 1H), 7.58-7.63 (m, 1H), 7.51 (d, 1H, J=8.0 Hz), 7.32 (dt, 1H, J=1.0 Hz, 7.5 Hz), 7.25-7.28 (m, 1H), 7.21 (dt, 1H, J=1.0 Hz, 7.5 Hz), 6.70-6.72 (m, 2H)

Step 5: Synthesis of Compound 46

A three-necked reactor equipped with a thermometer was charged with 10.4 g (24.8 mmol) of the intermediate A synthesized in the step 1 of Example 1 (see "Synthesis of compound 1") and 150 ml of THF under a nitrogen stream to prepare a solution. After the addition of 2.9 g (25.7 mmol) of methanesulfonyl chloride to the solution, the reactor was immersed in a water bath to adjust the temperature of the reaction mixture to 20° C. 2.7 g (26.5 mmol) of triethylamine was added dropwise to the reaction mixture over 10 minutes. After the dropwise addition, the water bath was removed, and the mixture was stirred at 25° C. for 2 hours. After the addition of 0.2 g (1.7 mmol) of 4-(dimethylamino) pyridine and 3.0 g (8.3 mmol) of the intermediate N2 synthesized in the step 4 to the mixture, 2.5 g (24.8 mmol) of triethylamine was added dropwise to the mixture over 10 minutes. After the dropwise addition, the mixture was stirred at 25° C. for 2 hours. After completion of the reaction, 2000 ml of distilled water and 500 ml of a saturated sodium chloride solution were added to the reaction mixture, followed by extraction twice with 1000 ml of chloroform. The organic layer was dried over anhydrous sodium sulfate, and sodium sulfate was separated by filtration. The filtrate was concentrated using a rotary evaporator, and the concentrate was purified by silica gel column chromatography (chloroform:THF=25:1) to obtain 1.8 g of a compound 46 as a light yellow solid (yield: 19%).

The structure of the target product was identified by ¹H-NMR.

¹H-NMR (500 MHz, CDCl₃, TMS, δ ppm): 8.70-8.74 (m, 1H), 8.02 (dt, 1H, J=2.0 Hz, 7.5 Hz), 7.87 (s, 1H), 7.83 (d, 1H, J=2.5 Hz), 7.74-7.78 (m, 1H), 7.62-7.67 (m, 2H), 7.42-7.46 (m, 1H), 7.34 (dt, 1H, J=1.0 Hz, 7.5 Hz), 7.22 (dt, 1H, J=1.0 Hz, 7.5 Hz), 7.07-7.15 (m, 2H), 6.96-7.01 (m, 4H), 6.90 (d, 2H, J=9.0 Hz), 6.88 (d, 2H, J=9.0 Hz), 6.41 (dd, 1H, J=1.5 Hz, 17.5 Hz), 6.41 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.18 (t, 2H, J=6.5 Hz), 3.95 (t, 2H, J=6.5 Hz), 3.95 (t, 2H, J=6.5 Hz), 2.56-2.71 (m, 2H), 2.25-2.50 (m, 6H), 2.12-2.21 (m, 2H), 1.93-2.01 (m, 2H), 1.65-1.85 (m, 12H), 1.31-1.61 (m, 12H)

Example 85: Compound 47

Compound 47

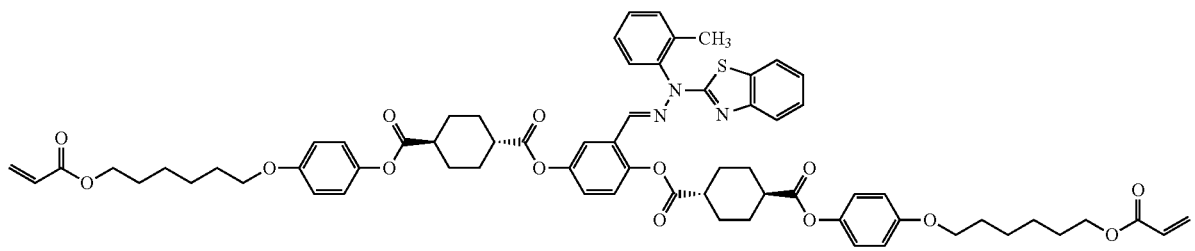

Step 1: Synthesis of Intermediate O2

Intermediate O2

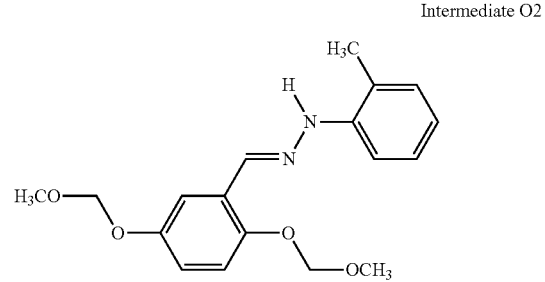 [SMILES: COCOc1ccc(OCOC)c(/C=N/Nc2ccccc2C)c1]

A three-necked reactor equipped with a thermometer was charged with 1.68 g (10.61 mol) of o-tolylhydrazine and 50 ml of ethanol under a nitrogen stream to prepare a solution. After the addition of 1.34 g (13.26 mmol) of triethylamine to the solution, the mixture was stirred at 25° C. for 10 minutes. After the addition of 2.00 g (8.84 mol) of the intermediate K2 synthesized in the step 1 of Example 84 (see "Synthesis of compound 46") to the mixture, the mixture was stirred at 25° C. for 1 hour. After completion of the reaction, 300 ml of distilled water and 50 ml of a saturated sodium chloride solution were added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=1:25) to obtain 2.81 g of an intermediate O2 as a light yellow solid (yield: 96%).

The structure of the target product was identified by $^1$H-NMR.

$^1$H-NMR (500 MHz, CDCl$_3$, TMS, δ ppm): 8.16 (s, 1H), 7.69 (d, 1H, J=3.0 Hz), 7.57 (dd, 1H, J=1.0 Hz, 8.0 Hz), 7.14-7.26 (m, 2H), 7.03-7.11 (m, 2H), 6.95 (dd, 1H, J=3.0 Hz, 9.0 Hz), 6.81 (dt, 1H, J=1.0 Hz, 7.5 Hz), 5.18 (s, 2H), 5.18 (s, 2H), 3.51 (s, 3H), 3.50 (s, 3H), 2.24 (s, 3H)

Step 2: Synthesis of Intermediate P2

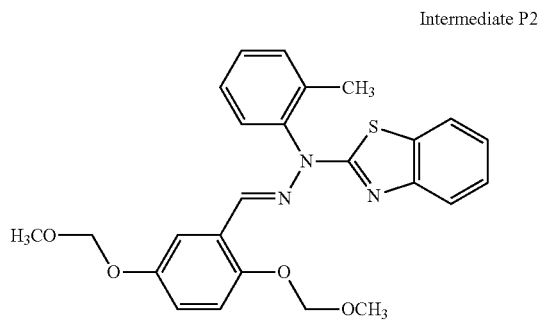 [SMILES: COCOc1ccc(OCOC)c(/C=N/N(c2nc3ccccc3s2)c2ccccc2C)c1]

Intermediate P2

A three-necked reactor equipped with a thermometer was charged with 2.78 g (8.42 mol) of the intermediate O2 synthesized in the step 1 and 50 ml of THF under a nitrogen stream to prepare a solution. After the addition of 0.54 g (13.46 mmol) of sodium hydride (50 to 72%, in oil) to the solution at 25° C. over 15 minutes, the mixture was stirred for 30 minutes. After the addition of 2.14 g (12.62 mmol) of 2-chlorobenzothiazole, the reaction mixture was stirred for 2 hours under reflux with heating. After completion of the reaction, 400 ml of distilled water and 50 ml of a saturated sodium chloride solution were added to the reaction mixture, followed by extraction twice with 150 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (THF:toluene=3:100) to obtain 2.66 g of an intermediate P2 as a light yellow solid (yield: 68%).

The structure of the target product was identified by $^1$H-NMR.

$^1$H-NMR (500 MHz, CDCl$_3$, TMS, δ ppm): 7.76 (d, 1H, J=3.0 Hz), 7.72 (dd, 1H, J=1.0 Hz, 8.0 Hz), 7.60 (dd, 1H, J=1.0 Hz, 8.0 Hz), 7.54 (s, 1H), 7.41-7.48 (m, 3H), 7.25-7.34 (m, 2H), 7.11-7.21 (m, 1H), 6.95-7.03 (m, 2H), 5.22 (s, 2H), 4.98 (s, 2H), 3.55 (s, 3H), 3.26 (s, 3H), 2.16 (s, 31H)

Step 3: Synthesis of Intermediate Q2

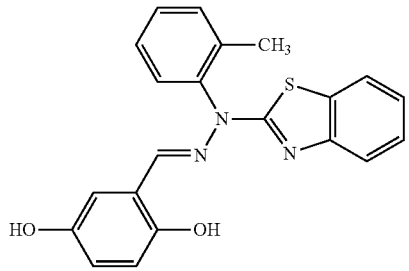

Intermediate Q2

A three-necked reactor equipped with a thermometer was charged with 2.65 g (5.72 mmol) of the intermediate P2 synthesized in the step 2 and 80 ml of ethanol under a nitrogen stream to prepare a solution. After the addition of 5.44 mg (28.58 mmol) of p-toluenesulfonic acid monohydrate to the solution, the mixture was stirred for 15 hours. After completion of the reaction, the reaction mixture was concentrated using a rotary evaporator, and 40 ml of methanol was added to the concentrate. Insoluble crystals were filtered off, washed with methanol, and dried under vacuum to obtain 1.88 g of an intermediate Q2 as a yellow solid (yield: 88%).

The structure of the target product was identified by $^1$H-NMR.

$^1$H-NMR (500 MHz, DMSO-d$_6$, TMS, δ ppm): 7.90 (dd, 1H, J=1.0 Hz, 8.0 Hz), 7.46-7.58 (m, 5H), 7.39-7.42 (m, 1H), 7.25-7.33 (m, 2H), 7.18 (dt, 1H, J=1.0 Hz, 7.5 Hz), 7.10-7.15 (m, 2H), 6.69 (s, 1H), 6.69 (s, 1H), 2.29 (s, 3H)

Step 4: Synthesis of Compound 47

A three-necked reactor equipped with a thermometer was charged with 5.36 g (12.78 mmol) of the intermediate A synthesized in the step 1 of Example 1 (see "Synthesis of compound 1") and 60 ml of THF under a nitrogen stream to prepare a solution. After the addition of 1.52 g (13.22 mmol) of methanesulfonyl chloride to the solution, the reactor was immersed in a water bath to adjust the temperature of the reaction mixture to 20° C. 1.38 g (13.7 mmol) of triethylamine was added dropwise to the reaction mixture over 5 minutes. After removing the water bath, the mixture was stirred at 25° C. for 2 hours. After the addition of 0.1 g (0.82 mmol) of 4-(dimethylamino)pyridine and 1.60 g (4.26 mmol) of the intermediate Q2 synthesized in the step 3 to the mixture, 1.30 g (12.78 mmol) of triethylamine was added dropwise to the mixture over 5 minutes. After the dropwise addition, the mixture was stirred at 25° C. for 2 hours. After completion of the reaction, 400 ml of distilled water and 100 ml of a saturated sodium chloride solution were added to the reaction mixture, followed by extraction twice with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (chloroform:THF=40:1) to obtain 1.04 g of a compound 47 as a light yellow solid (yield: 21%).

The structure of the target product was identified by $^1$H-NMR.

$^1$H-NMR (500 MHz, CDCl$_3$, TMS, δ ppm): 7.84 (d, 1H, J=3.0 Hz), 7.73 (dt, 1H, J=1.0 Hz, 8.0 Hz), 7.61 (d, 1H, J=8.0 Hz), 7.44-7.52 (m, 3H), 7.27-7.34 (m, 2H), 7.15-7.20 (m, 2H), 7.10 (dd, 1H, J=3.0 Hz, 9.0 Hz), 7.05 (d, 1H, J=9.0 Hz), 7.01 (d, 2H, J=9.0 Hz), 6.99 (d, 2H, J=9.0 Hz), 6.90 (d, 2H, J=9.0 Hz), 6.89 (d, 2H, J=9.0 Hz), 6.41 (dd, 1H, J=1.5 Hz, 17.5 Hz), 6.41 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.18 (t, 2H, J=6.5 Hz), 3.96 (t, 2H, J=6.5 Hz), 3.95 (t, 2H, J=6.5 Hz), 2.56-2.72 (m, 2H), 2.42-2.51 (m, 1H), 2.28-2.40 (m, 5H), 2.14-2.22 (m, 2H), 2.14 (s, 3H), 1.65-1.91 (m, 14H), 1.41-1.57 (m, 10H), 1.19-1.31 (m, 2H)

Phase Transition Temperature Measurement 3

10 mg of the compound (compounds 34 to 47) was weighed, and placed in a solid state between two glass substrates provided with a polyimide alignment film subjected to a rubbing treatment. The substrates were placed on a hot plate, heated from 40° C. to 250° C., and cooled to 40° C. A change in structure when the temperature was changed was observed using a polarizing microscope.

The phase transition temperature measurement results are shown in Table 5.

TABLE 5

| | Compound No. | Phase transition temperature |
|---|---|---|
| Example 72 | Compound 34 | C ⇌ (144° C. / 110° C.) N ⇌ (247° C. / 232° C.) I |
| Example 73 | Compound 35 | C ⇌ (134° C. / 97° C.) N → (250° C. or more) I |
| Example 74 | Compound 36 | C ⇌ (144° C. / 40° C. or less) N ⇌ (230° C. / 223° C.) I |
| Example 75 | Compound 37 | C ⇌ (102° C. / 40° C. or less) N ⇌ (227° C. / 218° C.) I |
| Example 76 | Compound 38 | C ⇌ (124° C. / 40° C. or less) N ⇌ (230° C. / 220° C.) I |
| Example 77 | Compound 39 | C ⇌ (115° C. / 40° C. or less) N ⇌ (233° C. / 220° C.) I |
| Example 78 | Compound 40 | C ⇌ (130° C. / 40° C. or less) N ⇌ (234° C. / 219° C.) I |
| Example 79 | Compound 41 | C ⇌ (143° C. / 40° C. or less) N ⇌ (230° C. / 223° C.) I |
| Example 80 | Compound 42 | C ⇌ (166° C. / 100° C.) N → (250° C. or more) I |
| Example 81 | Compound 43 | C ⇌ (125° C. / 40° C. or less) N → (250° C. or more) I |
| Example 82 | Compound 44 | C ⇌ (162° C. / 40° C. or less) N ⇌ (221° C. / 194° C.) I |

TABLE 5-continued

| | Compound No. | Phase transition temperature |
|---|---|---|
| Example 83 | Compound 45 | C ⇌ (128° C. / 60° C.) N ⇌ (228° C. / 203° C.) I |
| Example 84 | Compound 46 | C ⇌ (113° C. / 65° C.) N → (250° C. or more) I |
| Example 85 | Compound 47 | C ⇌ (148° C. / 113° C.) N → (250° C. or more) I |

Examples 86 to 88

1.0 g of each of the compounds 34 to 36 respectively obtained in Examples 72 to 74, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition (polymerizable compositions 39 to 41).

Example 89

1.0 g of the compound 37 obtained in Example 75, 30 mg of the photoinitiator A, and 100 mg of a 1% cyclopentanone solution of the surfactant A were dissolved in 3.0 g of chloroform. The solution was filtered through a disposable filter having a pore size of 0.45 μm to obtain a polymerizable composition 42.

Examples 90 to 93

1.0 g of each of the compounds 38 to 41 respectively obtained in Examples 76 to 79, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition (polymerizable compositions 43 to 46).

Example 94

1.0 g of the compound 42 obtained in Example 80, 30 mg of the photoinitiator A, and 100 mg of a 1% cyclopentanone solution of the surfactant A were dissolved in 3.0 g of chloroform. The solution was filtered through a disposable filter having a pore size of 0.45 μm to obtain a polymerizable composition 47.

Examples 95 to 97

1.0 g of each of the compounds 43 to 45 respectively obtained in Examples 81 to 83, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition (polymerizable compositions 48 to 50).

Example 98

1.0 g of the compound 46 obtained in Example 84, 30 mg of the photoinitiator A, and 100 mg of a 1% cyclopentanone solution of the surfactant A were dissolved in 2.3 g of chloroform. The solution was filtered through a disposable filter having a pore size of 0.45 μm to obtain a polymerizable composition 51.

at the temperature shown in Table 6 to effect polymerization to prepare a wavelength dispersion measurement sample.

(ii) Retardation Measurement and Wavelength Dispersion Evaluation

The retardation was measured, and the wavelength dispersion was evaluated in the same manner as described above using the resulting samples.

Table 6 shows the thickness (μm) of the liquid crystal polymer films obtained by polymerizing the polymerizable compositions, the retardation (Re) at a wavelength of 548.5 nm, and the values α and β.

TABLE 6

| | Polymerizable composition | Polymerizable compound Type | Ratio (%) | Drying temperature (° C.) | Alignment treatment temperature (° C.) | Exposure temperature (° C.) | Thickness (μm) | Re (548.5 nm) | α | β |
|---|---|---|---|---|---|---|---|---|---|---|
| Example 86 | 39 | Compound 34 | 100 | 150 | 150 | 145 | 2.189 | 170.668 | 0.868 | 1.025 |
| Example 87 | 40 | Compound 35 | 100 | 140 | 140 | 100 | 1.610 | 119.785 | 0.810 | 1.036 |
| Example 88 | 41 | Compound 36 | 100 | 150 | 23 | 23 | 1.493 | 131.210 | 0.893 | 1.002 |
| Example 89 | 42 | Compound 37 | 100 | 120 | 23 | 23 | 1.810 | 145.979 | 0.863 | 1.018 |
| Example 90 | 43 | Compound 38 | 100 | 130 | 23 | 23 | 1.525 | 111.539 | 0.885 | 1.048 |
| Example 91 | 44 | Compound 39 | 100 | 130 | 23 | 23 | 1.660 | 118.003 | 0.817 | 1.011 |
| Example 92 | 45 | Compound 40 | 100 | 140 | 23 | 23 | 1.763 | 136.324 | 0.891 | 1.022 |
| Example 93 | 46 | Compound 41 | 100 | 150 | 23 | 23 | 1.304 | 91.456 | 0.903 | 1.010 |
| Example 94 | 47 | Compound 42 | 100 | 170 | 110 | 105 | 1.237 | 132.494 | 0.910 | 1.019 |
| Example 95 | 48 | Compound 43 | 100 | 130 | 23 | 23 | 1.501 | 136.780 | 0.917 | 0.999 |
| Example 96 | 49 | Compound 44 | 100 | 165 | 23 | 23 | 1.498 | 127.091 | 0.887 | 1.012 |
| Example 97 | 50 | Compound 45 | 100 | 130 | 65 | 65 | 1.511 | 129.743 | 0.903 | 1.011 |
| Example 98 | 51 | Compound 46 | 100 | 120 | 70 | 70 | 1.984 | 197.529 | 0.957 | 1.000 |
| Example 99 | 52 | Compound 47 | 100 | 150 | 120 | 115 | 1.531 | 107.094 | 0.899 | 1.020 |

Example 99

1.0 g of the compound 47 obtained in Example 85, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition 52.

As is clear from the results shown in Table 6, it was confirmed that the polymers obtained in Examples 86 to 99 using the compounds 34 to 47 according to the invention were an optically anisotropic article. The optically anisotropic articles showed ideal wideband wavelength dispersion in which the value α was smaller than 1, and the value β was larger than 1, or almost equal to 1.

Example 100: Synthesis of Compound 48

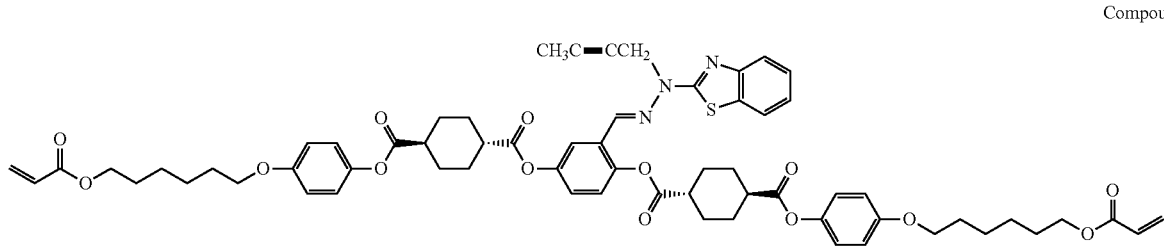

Compound 48

Retardation Measurement and Wavelength Dispersion Evaluation III (i) Formation of Liquid Crystal Layer Using Polymerizable Composition Each of the polymerizable compositions 39 to 52 was applied to a transparent glass substrate provided with a polyimide alignment film subjected to a rubbing treatment using a #4 wire bar. The resulting film was dried for 1 minute at the temperature shown in Table 6, and subjected to an alignment treatment for 1 minute at the temperature shown in Table 6 to form a liquid crystal layer. UV rays were applied to the liquid crystal layer at a dose of 2000 mJ/cm$^2$ Step 1: Synthesis of Intermediate R2

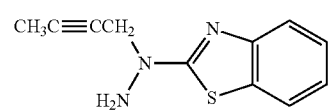

Intermediate R2

A four-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mmol) of cesium carbonate and 1.93 g (14.5 mmol) of 1-bromo-2-butyne to the solution, the mixture was stirred at 25° C. for 204 hours, After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a brown solid. The brown solid was purified by silica gel column chromatography (n-hexane:ethyl acetate=85:15) to obtain 1.25 g of an intermediate R2 as a white solid (yield: 47.5%).

The structure of the target product was identified by $^1$H-NMR.

$^1$H-NMR (500 M Hz, CDCl$_3$, TMS, δ ppm): 7.63 (dd, 1H, J=1.3 Hz, 7.8 Hz), 7.58 (dd, 1H, J=1.3 Hz, 7.8 Hz), 7.29 (ddd, 1H, J=1.3 Hz, 7.8 Hz, 7.8 Hz), 7.10 (ddd, 1H, J=1.3 Hz, 7.8 Hz, 7.8 Hz), 4.56 (q, 2H, J=2.5 Hz), 4.36 (s, 2H), 1.84 (t, 3H, J=2.5 Hz)

Step 2: Synthesis of Compound 48

A three-necked reactor equipped with a thermometer was charged with 1.50 g (1.60 mmol) of the intermediate B synthesized in the step 2 of Example 1 (see "Synthesis of compound 1"), 387 mg (1.78 mmol) of the intermediate R2 synthesized in the step 1, 41.4 mg (0.165 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=9:1) to obtain 1.54 g of a compound 48 as a light yellow solid (yield: 84.9%).

The structure of the target product was identified by $^1$H-NMR.

$^1$H-NMR (500 MHz, CDCl$_3$, TMS, δ ppm): 7.90 (s, 1H), 7.78 (d, 1H, J=1.3 Hz), 7.67-7.73 (m, 2H), 7.35 (ddd, 1H, J=1.3 Hz, 7.5 Hz, 7.5 Hz), 7.18 (ddd, 1H, J=1.3 Hz, 7.5 Hz, 7.5 Hz), 7.09-7.15 (m, 2H), 6.95-7.01 (m, 4H), 6.85-6.91 (m, 4H), 6.40 (dd, 2H, J=1.5 Hz, 17.0 Hz), 6.13 (dd, 2H, J=10.5 Hz, 17.0 Hz), 5.82 (dd, 2H, J=1.5 Hz, 10.5 Hz), 5.06 (d, 2H, J=2.0 Hz), 4.18 (t, 4H, J=6.0 Hz), 3.95 (t, 4H, J=6.0 Hz), 2.55-2.76 (m, 4H), 2.26-2.43 (m, 8H), 1.64-1.83 (m, 19H), 1.41-1.55 (m, 8H)

Example 101: Synthesis of Compound 49

Step 1: Synthesis of Intermediate S2

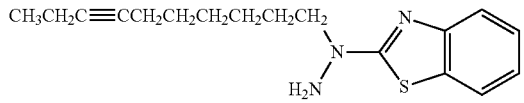

Intermediate S2

A three-necked reactor equipped with a thermometer was charged with 2.00 g (12.1 mmol) of 2-hydrazinobenzothiazole and 30 ml of DMF under a nitrogen stream to prepare a solution. After the addition of 7.88 g (24.2 mol) of cesium carbonate to the solution, the mixture was cooled to 0° C. 2.50 g (14.5 mmol) of 10-chloro-3-decyne was added dropwise to the mixture over 5 minutes. After the dropwise addition, the mixture was stirred at 25° C. for 5 hours. After completion of the reaction, the reaction mixture was added to 200 ml of water, and extracted with 300 ml of ethyl acetate. After drying the ethyl acetate layer over anhydrous sodium sulfate, sodium sulfate was separated by filtration. Ethyl acetate was evaporated from the filtrate under reduced pressure using a rotary evaporator to obtain a brown solid. The brown solid was purified by silica gel column chromatography (n-hexane:ethyl acetate=85:15) to obtain 1.51 g of an intermediate S2 as a white solid (yield: 41.4%).

The structure of the target product was identified by $^1$H-NMR.

$^1$H-NMR (500 MHz, CDCl$_3$, TMS, δ ppm): 7.60 (dd, 1H, J=1.5 Hz, 7.5 Hz), 7.53 (dd, 1H, J=1.5 Hz, 7.5 Hz), 7.28 (ddd, 1H, J=1.5 Hz, 7.5 Hz, 7.5 Hz), 7.06 (ddd, 1H, J=1.5 Hz, 7.5 Hz, 7.5 Hz), 4.23 (s, 2H), 3.75 (t, 2H, J=7.5 Hz), 2.09-2.21 (m, 4H), 1.75 (tt, 2H, J=7.5 Hz, 7.5 Hz), 1.35-1.54 (m, 6H), 1.11 (t, 3H, J=7.5 Hz)

Step 2: Synthesis of Compound 49

A three-necked reactor equipped with a thermometer was charged with 1.50 g (1.60 mmol) of the intermediate B synthesized in the step 2 of Example 1 (see "Synthesis of compound 1"), 534 mg (1.78 mmol) of the intermediate S2 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 3 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=92:8) to obtain 1.62 g of a compound 49 as a light yellow solid (yield: 83.8%).

The structure of the target product was identified by $^1$H-NMR.

$^1$H-NMR (500 MHz, CDCl$_3$, TMS, δ ppm): 7.75 (d, 1H, J=1.5 Hz), 7.65-7.71 (m, 3H), 7.34 (ddd, 1H, J=1.5 Hz, 7.8 Hz, 7.8 Hz), 7.17 (ddd, 1H, J=1.5 Hz, 7.8 Hz, 7.8 Hz), 7.08-7.14 (m, 2H), 6.95-7.01 (m, 4H), 6.85-6.91 (m, 4H), Compound 49

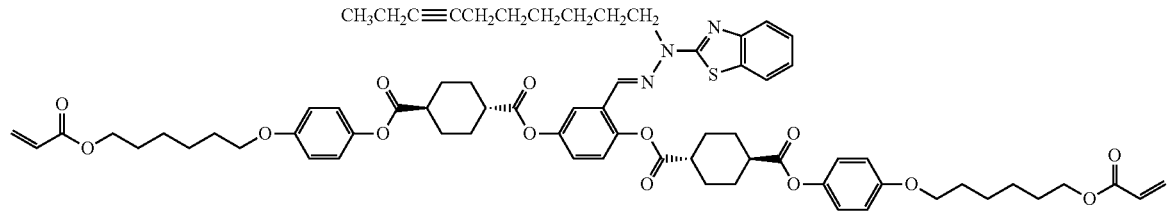

6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.31 (t, 2H, J=7.5 Hz), 4.18 (t, 4H, J=6.5 Hz), 3.94 (t, 4H, J=6.5 Hz), 2.54-2.74 (m, 4H), 2.25-2.40 (m, 8H), 2.09-2.19 (m, 4H), 1.63-1.85 (m, 18H), 1.38-1.55 (m, 14H), 1.09 (t, 3H, J=7.5 Hz)

Example 102: Synthesis of Compound 50

Step 1: Synthesis of Intermediate T2

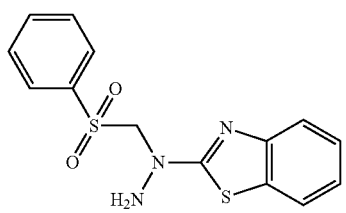

Intermediate T2

A three-necked reactor equipped with a thermometer was charged with 3.00 g (18.2 mmol) of 2-hydrazinobenzothiazole and 40 ml of DMF under a nitrogen stream to prepare a solution. After the addition of 11.9 g (36.4 mol) of cesium carbonate to the solution, the mixture was cooled to 0° C. 41.5 g (21.8 mmol) of chloromethylphenylsulfone was added dropwise to the mixture over 5 minutes. After the dropwise addition, the mixture was stirred at 25° C. for 6 hours. After completion of the reaction, 300 ml of water was added to the reaction mixture, followed by extraction twice with 200 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (n-hexane:ethyl acetate=75:25) to obtain 1.81 g of an intermediate T2 as a white solid (yield: 31.2%).

The structure of the target product was identified by $^1$H-NMR.

$^1$H-NMR (500 MHz, CDCl$_3$, TMS, δ ppm): 7.85-7.90 (m, 2H), 7.55 (dd, 1H, J=1.5 Hz, 7.3 Hz), 7.32-7.43 (m, 3H), 7.13-7.21 (m, 2H), 7.05 (ddd, 1H, J=1.5 Hz, 7.3 Hz, 7.3 Hz), 5.25 (s, 2H), 4.99 (s, 2H)

Step 2: Synthesis of Compound 50

A three-necked reactor equipped with a thermometer was charged with 1.50 g (1.60 mmol) of the intermediate B synthesized in the step 2 of Example 1 (see "Synthesis of Compound 50

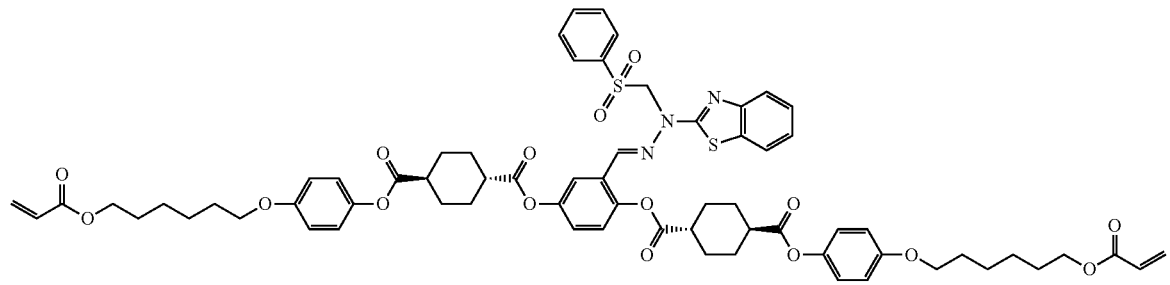

compound 1"), 567 mg (1.78 mmol) of the intermediate T2 synthesized in the step 1, 41.4 mg (0,178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=9:1) to obtain 1.53 g of a compound 50 as a light yellow solid (yield: 77.3%).

The structure of the target product was identified by $^1$H-NMR.

$^1$H-NMR (500 MHz, CDCl$_3$, TMS, δ ppm): 8.50 (s, 1H), 7.87-7.95 (m, 2H), 7.72 (d, 1H, J=1.3 Hz), 7.61 (d, 1H, J=7.5 Hz), 7.33-7.45 (m, 4H), 7.27 (ddd, 1H, J=1.3 Hz, 7.5 Hz, 7.5 Hz), 7.16-7.20 (m, 2H), 7.15 (ddd, 1H, J=1.3 Hz, 7.5 Hz, 7.5 Hz), 6.94-7.01 (m, 4H), 6.84-6.91 (m, 4H), 6.40 (dd, 2H, J=1.5 Hz, 17.5 Hz), 6.12 (dd, 2H, J=10.0 Hz, 17.5 Hz), 5.82 (dd, 2H, J=1.5 Hz, 10.0 Hz), 5.61 (s, 2H), 4.17 (t, 4H, J=6.5 Hz), 3.94 (t, 4H, J=6.5 Hz), 2.73-2.86 (m, 1H), 2.54-2.71 (m, 3H), 2.40-2.49 (m, 2H), 2.29-2.39 (m, 6H), 1.62-1.84 (m, 16H), 1.40-1.54 (m, 8H)

Example 103: Synthesis of Compound 51

Compound 51

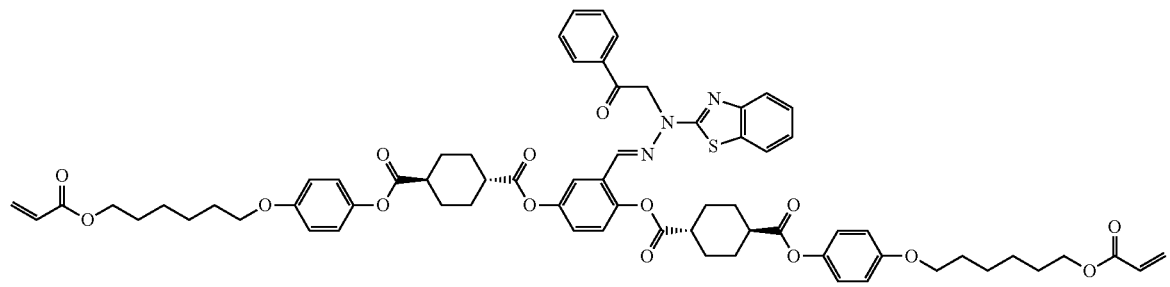

Step 1: Synthesis of Intermediate U2

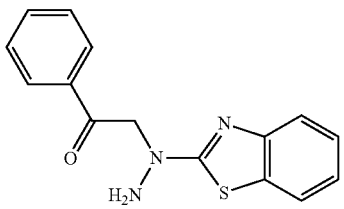

Intermediate U2

A three-necked reactor equipped with a thermometer was charged with 3.00 g (18.2 mmol) of 2-hydrazinobenzothiazole and 40 ml of DMF under a nitrogen stream to prepare a solution. After the addition of 11.9 g (36.4 mol) of cesium carbonate to the solution, the mixture was cooled to 0° C. 4.34 g (21.8 mmol) of phenacyl bromide was added dropwise to the mixture over 5 minutes. After the dropwise addition, the mixture was stirred at 25° C. for 5 hours. After completion of the reaction, 250 ml of water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (n-hexane:ethyl acetate=75:25) to obtain 1.79 g of an intermediate U2 as a white solid (yield: 34.7%).

The structure of the target product was identified by $^1$H-NMR.

$^1$H-NMR (500 MHz, CDCl$_3$, TMS, δ ppm): 7.99 (dd, 2H, J=1.3 Hz, 7.5 Hz), 7.59-7.66 (m, 2H), 7.44-7.53 (m, 3H), 7.25 (ddd, 1H, J=1.3 Hz, 7.5 Hz, 7.5 Hz), 7.08 (ddd, 1H, J=1.3 Hz, 7.5 Hz, 7.5 Hz), 5.31 (s, 2H), 4.65 (s, 2H)

Step 2: Synthesis of Compound 51

A three-necked reactor equipped with a thermometer was charged with 1.50 g (1.60 mmol) of the intermediate B synthesized in the step 2 of Example 1 (see "Synthesis of compound 1"), 504 mg (1.78 mmol) of the intermediate U2 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=85:15) to obtain 1.59 g of a compound 51 as a light yellow solid (yield: 82.9%).

The structure of the target product was identified by $^1$H-NMR.

$^1$H-NMR (500 MHz, CDCl$_3$, TMS, δ ppm): 8.12 (dd, 2H, J=1.0 Hz, 7.5 Hz), 7.76 (d, 1H, J=2.5 Hz), 7.72 (dd, 1H, J=1.0 Hz, 7.5 Hz), 7.60-7.69 (m, 2H), 7.53-7.59 (m, 2H), 7.42 (s, 1H), 7.34 (ddd, 1H, J=1.0 Hz, 7.5 Hz, 7.5 Hz), 7.19 (ddd, 1H, J=1.0 Hz, 7.5 Hz, 7.5 Hz), 7.06-7.12 (m, 2H), 6.95-7.01 (m, 4H), 6.86-6.93 (m, 4H), 6.40 (dd, 2H, J=1.5 Hz, 17.5 Hz), 6.13 (dd, 2H, J=10.5 Hz, 17.5 Hz), 5.83 (dd, 2H, J=1.5 Hz, 10.5 Hz), 5.82 (s, 2H), 4.18 (t, 4H, J=6.5 Hz), 3.95 (t, 4H, J=6.5 Hz), 2.55-2.72 (m, 2H), 2.20-2.42 (m, 6H), 1.87-2.09 (m, 4H), 1.64-1.85 (m, 12H), 1.32-1.56 (m, 12H)

Example 104: Synthesis of Compound 52

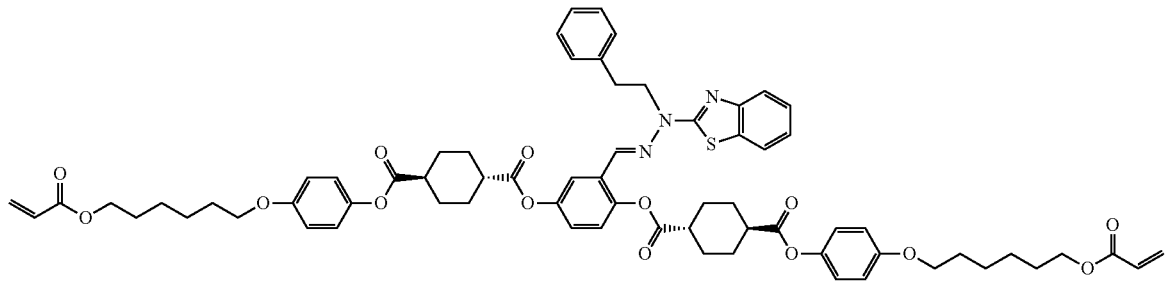

Compound 52

Step 1: Synthesis of Intermediate V2

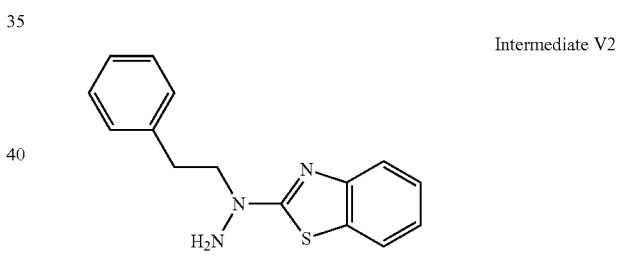

Intermediate V2

A three-necked reactor equipped with a thermometer was charged with 3.00 g (18.2 mmol) of 2-hydrazinobenzothiazole and 30 ml of DMF under a nitrogen stream to prepare a solution. After the addition of 11.9 g (36.4 mol) of cesium carbonate to the solution, the mixture was cooled to 0° C. 4.03 g (21.8 mmol) of 2-phenylethyl bromide was added dropwise to the mixture over 5 minutes. After the dropwise addition, the mixture was stirred at 25° C. for 25 hours. After completion of the reaction, 250 ml of water was added to the reaction mixture, followed by extraction twice with 100 ml of ethyl acetate. The organic layer was dried over anhydrous sodium sulfate, and sodium sulfate was separated by filtration. The filtrate was concentrated using a rotary evaporator, and the concentrate was purified by silica gel column chromatography (n-hexane:ethyl acetate=78:22) to obtain 2.10 g of an intermediate V2 as a white solid (yield: 42.9%).

The structure of the target product was identified by $^1$H-NMR.

$^1$H-NMR (500 MHz, CDCl$_3$, TMS, δ ppm): 7.60 (dd, 1H, J=1.3 Hz, 7.8 Hz), 7.56 (dd, 1H, J=1.3 Hz, 7.8 Hz), 7.20-7.36 (m, 6H), 7.07 (ddd, 1H, J=1.3 Hz, 7.8 Hz, 7.8 Hz), 4.05 (s, 2H), 4.01 (t, 2H, J=7.3 Hz), 3.07 (t, 2H, J=7.3 Hz)

Step 2: Synthesis of Compound 52

A three-necked reactor equipped with a thermometer was charged with 1.50 g (1.60 mmol) of the intermediate B synthesized in the step 2 of Example 1 (see "Synthesis of compound 1"), 477 mg (1.78 mmol) of the intermediate V2 synthesized in the step 1, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of chloroform. The organic layer was dried over anhydrous sodium sulfate, and sodium sulfate was separated by filtration. The filtrate was concentrated using a rotary evaporator, and the concentrate was purified by silica gel column chromatography (toluene:ethyl acetate=92:8) to obtain 1.56 g of a compound 52 as a light yellow solid (yield: 82.3%).

The structure of the target product was identified by $^1$H-NMR.

1H-NMR (500 MHz, CDCl$_3$, TMS, δ ppm): 7.76 (d, 1H, J=1.5 Hz), 7.68-7.73 (m, 3H), 7.29-7.39 (m, 5H), 7.22-7.26 (m, 1H), 7.19 (ddd, 1H, J=1.5 Hz, 8.5 Hz, 8.5 Hz), 7.08-7.14 (m, 2H), 6.95-7.02 (m, 4H), 6.86-6.92 (m, 4H), 6.40 (dd, 2H, J=1.5 Hz, 17.0 Hz), 6.13 (dd, 2H, J=10.5 Hz, 17.0 Hz), 5.82 (dd, 2H, J=1.5 Hz, 10.5 Hz), 4.54 (t, 2H, J=5.5 Hz), 4.18 (t, 4H, J=6.5 Hz), 3.95 (t, 4H, J=6.5 Hz), 3.06 (t, 2H, J=5.5 Hz), 2.56-2.71 (m, 3H), 2.42-2.53 (m, 1H), 2.13-2.40 (m, 8H), 1.59-1.84 (m, 16H), 1.41-1.56 (m, 8H)

Phase Transition Temperature Measurement 4

10 mg of the compound (compounds 48 to 52) was weighed, and placed in a solid state between two glass substrates provided with a polyimide alignment film subjected to a rubbing treatment. The substrates were placed on a hot plate, heated from 40° C. to 250° C., and cooled to 40° C. A change in structure when the temperature was changed was observed using a polarizing microscope.

The phase transition temperature measurement results are shown in Table 7.

TABLE 7

| | Compound No. | Phase transition temperature |
|---|---|---|
| Example 100 | Compound 48 | C ⇌(134° C. / 40° C. or less) N ⇌(204° C. / 194° C.) I |
| Example 101 | Compound 49 | C ⇌(119° C. / 65° C.) N ⇌(216° C. / 194° C.) I |

TABLE 7-continued

| | Compound No. | Phase transition temperature |
|---|---|---|
| Example 102 | Compound 50 | C ⇌(145° C. / 85° C.) N ⇌(220° C. / 198° C.) I |
| Example 103 | Compound 51 | C ⇌(150° C. / 115° C.) N →(250° C. or more) I |
| Example 104 | Compound 52 | C ⇌(98° C. / 40° C. or less) N →(250° C. or more) I |

Examples 105 to 109

1.0 g of each of the compounds 48 to 52 respectively obtained in Examples 100 to 104, 30 mg of the photoinitiator A, and 100 mg of a 1% cyclopentanone solution of the surfactant A were dissolved in 2.3 g of cyclopentanone. The solution was filtered through a disposable filter having a pore size of 0.45 μm to obtain a polymerizable composition (polymerizable compositions 53 to 57).

Retardation Measurement and Wavelength Dispersion Evaluation IV
(i) Formation of Liquid Crystal Layer Using Polymerizable Composition Each of the polymerizable compositions 53 to 57 was applied to a transparent glass substrate provided with a polyimide alignment film subjected to a rubbing treatment using a #4 wire bar. The resulting film was dried for 1 minute at the temperature shown in Table 8, and subjected to an alignment treatment for 1 minute at the temperature shown in Table 8 to form a liquid crystal layer. UV rays were applied to the liquid crystal layer at a dose of 2000 mJ/cm$^2$ at the temperature shown in Table 8 to effect polymerization to prepare a wavelength dispersion measurement sample.
(ii) Retardation Measurement and Wavelength Dispersion Evaluation The retardation was measured, and the wavelength dispersion was evaluated in the same manner as described above using the resulting samples.

Table 8 shows the thickness (km) of the liquid crystal polymer films obtained by polymerizing the polymerizable compositions, the retardation (Re) at a wavelength of 548.5 nm, and the values α and β.

TABLE 8

| | Polymerizable composition | Polymerizable compound Type | Ratio (%) | Drying temperature (° C.) | Alignment treatment temperature (° C.) | Exposure temperature (° C.) | Thickness (μm) | Re (548.5 nm) | α | β |
|---|---|---|---|---|---|---|---|---|---|---|
| Example 105 | 53 | Compound 48 | 100 | 130 | 23 | 23 | 1.466 | 123.35 | 0.898 | 1.037 |
| Example 106 | 54 | Compound 49 | 100 | 130 | 23 | 23 | 1.671 | 120.22 | 0.830 | 1.042 |
| Example 107 | 55 | Compound 50 | 100 | 155 | 100 | 90 | 1.406 | 112.79 | 0.932 | 1.002 |
| Example 108 | 56 | Compound 51 | 100 | 155 | 120 | 120 | 1.774 | 104.85 | 0.886 | 1.016 |
| Example 109 | 57 | Compound 52 | 100 | 110 | 23 | 23 | 1.435 | 126.26 | 0.854 | 1.012 |

As is clear from the results shown in Table 8, it was confirmed that the polymers obtained in Examples 105 to 109 using the compounds 48 to 52 according to the invention were an optically anisotropic article. The optically anisotropic articles showed ideal wideband wavelength dispersion in which the value α was smaller than 1, and the value β was larger than 1.

Example 110

19.3 parts of the compound 4 obtained in Example 4, 0.6 parts of a photoinitiator B ("Irgacure 379" manufactured by BASF Japan Ltd.), and 5.8 parts of a 1% cyclopentanone solution of a surfactant B ("Surflon S-420" manufactured by AGC Seimi Chemical Co., Ltd.) were dissolved in 74.2 parts of cyclopentanone. The solution was filtered through a disposable filter having a pore size of 0.6 μm to obtain a polymerizable composition 58.

Example 111

A polymerizable composition 59 was obtained in the same manner as in Example 110, except that the compound 13 obtained in Example 26 was used instead of the compound 4 obtained in Example 4.

Example 112

A polymerizable composition 60 was obtained in the same manner as in Example 110, except that the compound 22 obtained in Example 35 was used instead of the compound 4 obtained in Example 4.

Comparative Example 3

A polymerizable composition 61 was obtained in the same manner as in Example 110, except that the compound A obtained in Synthesis Example 1 was used instead of the compound 4 obtained in Example 4.

Retardation Measurement and Reflected Luminance Evaluation

The polymerizable compositions 58 to 61 were polymerized by the following method to obtain polymers. The retardation was measured, and the reflected luminance was evaluated using the resulting polymers.

Production of Retardation Film

One side of a support ("Zeonor Film ZF16" manufactured by Zeon Corporation) was subjected to an alignment treatment by rubbing. Each of the polymerizable compositions 58 to 61 was applied to the side of the support subjected to the alignment treatment using a spin coater so that the thickness after drying was 2.5 μm, 1.9 μm, 1.9 μm, or 1.4 μm, respectively. The polymerizable composition layer was dried by heating the polymerizable composition layer at 130° C. for 2 minutes using an oven. Note that the polymerizable composition 60 was heated at 105° C. A laminate consisting of the support and the dried polymerizable composition layer formed on the support was thus obtained.

UV rays were applied to the laminate using a metal halide lamp to polymerize the polymerizable composition. UV rays were applied at an illuminance of 16 mW/cm$^2$ and a dose of 100 mJ/cm$^2$. A retardation film consisting of the support and an optically anisotropic article layer provided on the support was thus obtained. The thickness of the resulting optically anisotropic article layer was 2.5 μm, 1.9 μm, 1.9 μm, or 1.4 μm, respectively.

The retardation Re (550) of the retardation film at a wavelength λ of 550 nm was measured using a retardation analyzer ("AxoScan" manufactured by AXOMETRICS), The results are shown in Table 9.

Production of Circular Polarizer

The retardation film and a linear polarizer ("HLC2-5618" manufactured by SANRITZ Corporation) were bonded using an optical transparent adhesive ("LUCIACS" manufactured by Nitto Denko Corporation) to produce a circular polarizer. The relative angle formed by the absorption axis direction of the linear polarizer and the slow axis direction (direction parallel to the rubbing direction) of the retardation film was set to 45°.

Calculation of Reflected Luminance of Circular Polarizer

An aluminum-deposited PET film ("Metalumy TS #50" manufactured by Toray Advanced Film Co., Ltd.) was bonded to the retardation film of the circular polarizer using the optical transparent adhesive to obtain a measurement sample. The reflection spectrum of the sample (5° reflection) was measured using a spectrophotometer ("V7200" manufactured by JASCO Corporation). The measurement wavelength was 380 to 780 nm.

The resulting reflection spectrum was multiplied by a color-matching function y(λ), and the resulting values were integrated to calculate the reflected luminance Y. A reference white light source was a D65 light source. The results are shown in Table 9.

TABLE 9

| | Polymerizable composition | Polymerizable compound | | | | Reflected luminance Y (%) |
| | | Type | Ratio (%) | Thickness (μm) | Retardation (550 nm) | |
| --- | --- | --- | --- | --- | --- | --- |
| Example 110 | 58 | Compound 4 | 100 | 2.5 | 141 | 1.44 |
| Example 111 | 59 | Compound 13 | 100 | 1.9 | 141 | 1.55 |
| Example 112 | 60 | Compound 22 | 100 | 1.9 | 139 | 1.65 |
| Comparative Example 3 | 61 | Compound A | 100 | 1.4 | 140 | 1.70 |

As is clear from the results shown in Table 9, it was confirmed that the circular polarizers obtained in Examples 110 to 112 showed a reflected luminance lower than that of the circular polarizer obtained in Comparative Example 3 (i.e., the circular polarizers obtained in Examples 110 to 112 exhibited excellent performance).

The invention claimed is:
1. A polymer obtained by polymerizing a polymerizable compound represented by a formula (I),

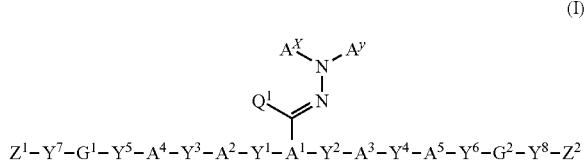

$Z^1-Y^7-G^1-Y^5-A^4-Y^3-A^2-Y^1-A^1-Y^2-A^3-Y^4-A^5-Y^6-G^2-Y^8-Z^2$ or a polymerizable composition comprising at least one polymerizable compound represented by a formula (I) and an initiator; wherein $Y^1$ to $Y^8$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ is a hydrogen atom or an alkyl group having 1 to 6 carbon atoms, $G^1$ and $G^2$ are independently a substituted or unsubstituted divalent linear aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more contiguous —O— or —S— is excluded, R$^2$ is a hydrogen atom or an alkyl group having 1 to 6 carbon atoms, $Z^1$ and $Z^2$ are independently an alkenyl group having 2 to 10 carbon atoms that is unsubstituted, or substituted with a halogen atom, $A^x$ is an organic group having 2 to 30 carbon atoms that includes at least one aromatic ring selected from a group consisting of an aromatic hydrocarbon ring and a heteroaromatic ring, $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted alkynyl group having 1 to 20 carbon atoms, a substituted or unsubstituted cycloalkyl group having 3 to 12 carbon atoms, —C(=O)—R$^3$, —SO$_2$—R$^4$, —C(=S)NH—R$^9$, or an organic group having 2 to 30 carbon atoms that includes at least one aromatic ring selected from a group consisting of an aromatic hydrocarbon ring and a heteroaromatic ring, R$^3$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or an aromatic hydrocarbon group having 5 to 12 carbon atoms, R$^4$ is an alkyl group having 1 to 20 carbon atoms, an alkenyl group having 2 to 20 carbon atoms, a phenyl group, or a 4-methylphenyl group, R$^9$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or a substituted or unsubstituted aromatic group having 5 to 20 carbon atoms, provided that the aromatic ring included in A$^x$ and A$^y$ is substituted or unsubstituted, and A$^x$ and A$^y$ are optionally bonded to each other to form a ring, $A^1$ is a substituted or unsubstituted trivalent aromatic group, $A^2$ and $A^3$ are independently a substituted or unsubstituted divalent alicyclic hydrocarbon group having 3 to 30 carbon atoms, $A^4$ and $A^5$ are independently a substituted or unsubstituted divalent aromatic group having 6 to 30 carbon atoms, and $Q^1$ is a hydrogen atom, or a substituted or unsubstituted alkyl group having 1 to 6 carbon atoms.

2. The polymer according to claim 1, the polymer being a liquid crystalline polymer.

3. An optically anisotropic article comprising the polymer according to claim 2.

4. A method comprising:
reacting a raw material comprising a carbonyl compound to produce a polymerizable compound; wherein
the carbonyl compound is represented by a formula (4):

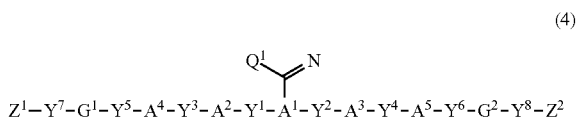

$Z^1-Y^7-G^1-Y^5-A^4-Y^3-A^2-Y^1-A^1-Y^2-A^3-Y^4-A^5-Y^6-G^2-Y^8-Z^2$ where $Y^1$ to $Y^8$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, R$^1$ is a hydrogen atom or an alkyl group having 1 to 6 carbon atoms, $G^1$ and $G^2$ are independently a substituted or unsubstituted divalent linear aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more contiguous —O— or —S— is excluded, R$^2$ is a hydrogen atom or an alkyl group having 1 to 6 carbon atoms, $Z^1$ and $Z^2$ are independently an alkenyl group having 2 to 10 carbon atoms that is unsubstituted, or substituted with a halogen atom, $A^1$ is a substituted or unsubstituted trivalent aromatic group, $A^2$ and $A^3$ are independently a substituted or unsubstituted divalent alicyclic hydrocarbon group having 3 to 30 carbon atoms, $A^4$ and $A^5$ are independently a substituted or unsubstituted divalent aromatic group having 6 to 30 carbon atoms, and $Q^1$ is a hydrogen atom, or a substituted or unsubstituted alkyl group having 1 to 6 carbon atoms; and the polymerizable compound is represented by a formula (I):

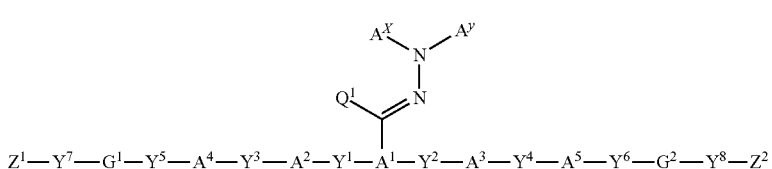

$$Z^1-Y^7-G^1-Y^5-A^4-Y^3-A^2-Y^1-A^1-Y^2-A^3-Y^4-A^5-Y^6-G^2-Y^8-Z^2$$

where
- $A^x$ is an organic group having 2 to 30 carbon atoms that includes at least one aromatic ring selected from a group consisting of an aromatic hydrocarbon ring and a heteroaromatic ring,
- $A^y$ is a hydrogen atom, a substituted or unsubstituted alkyl group having 1 to 20 carbon atoms, a substituted or unsubstituted alkenyl group having 2 to 20 carbon atoms, a substituted or unsubstituted alkynyl group having 1 to 20 carbon atoms, a substituted or unsubstituted cycloalkyl group having 3 to 12 carbon atoms, —C(=O)—R$^3$, —SO$_2$—R$^4$, —C(=S)NH—R$^9$, or an organic group having 2 to 30 carbon atoms that includes at least one aromatic ring selected from a group consisting of an aromatic hydrocarbon ring and a heteroaromatic ring, R$^3$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or an aromatic hydrocarbon group having 5 to 12 carbon atoms, R$^4$ is an alkyl group having 1 to 20 carbon atoms, an alkenyl group having 2 to 20 carbon atoms, a phenyl group, or a 4-methylphenyl group, R$^9$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or a substituted or unsubstituted aromatic group having 5 to 20 carbon atoms, provided that the aromatic ring included in $A^x$ and $A^y$ is substituted or unsubstituted, and $A^x$ and $A^y$ are optionally bonded to each other to form a ring, and
- $Y^1$ to $Y^8$, $G^1$, $G^2$, $Z^1$, $Z^2$, $A^1$, $A^2$, $A^3$, $A^4$, $A^5$ and $Q^1$ are the same as defined above in connection with formula (4).

5. The method according claim 4, wherein $A^1$ of the carbonyl compound represented by formula (4) is a substituted or unsubstituted trivalent benzene ring group, or a substituted or unsubstituted trivalent naphthalene ring group.

6. The method according claim 4, wherein $A^2$ and $A^3$ of the carbonyl compound represented by formula (4) are independently a substituted or unsubstituted divalent cyclohexyl group.

7. The method according claim 4, wherein $Z^1$ and $Z^2$ of the carbonyl compound represented by formula (4) are independently CH$_2$=CH—, CH$_2$=C(CH$_3$)—, or CH$_2$=C(Cl)—.

* * * * *

UNITED STATES PATENT AND TRADEMARK OFFICE
CERTIFICATE OF CORRECTION

| | | |
|---|---|---|
| PATENT NO. | : 10,173,992 B2 | Page 1 of 1 |
| APPLICATION NO. | : 15/179145 | |
| DATED | : January 8, 2019 | |
| INVENTOR(S) | : Kei Sakamoto et al. | |

It is certified that error appears in the above-identified patent and that said Letters Patent is hereby corrected as shown below:

In the Claims

In Claim 4 (Column 154, Lines 28-31), change:

"$Z^1-Y^7-G^1-Y^5-A^4-Y^3-A^2-Y^1-\overset{\overset{Q^1\diagdown\!\!\diagup N}{|}}{A^1}-Y^2-A^3-Y^4-A^5-Y^6-G^2-Y^8-Z^2$", To:

--$Z^1-Y^7-G^1-Y^5-A^4-Y^3-A^2-Y^1-\overset{\overset{Q^1\diagdown\!\!\diagup O}{|}}{A^1}-Y^2-A^3-Y^4-A^5-Y^6-G^2-Y^8-Z^2$--.

Signed and Sealed this
Twenty-sixth Day of November, 2019

Andrei Iancu
*Director of the United States Patent and Trademark Office*